United States Patent
Angbrant et al.

(10) Patent No.: US 7,812,017 B2
(45) Date of Patent: Oct. 12, 2010

(54) 4-SUBSTITUTED INDOLE AND INDOLINE COMPOUNDS

(75) Inventors: Johan Angbrant, Stockholm (SE); Rune Ringom, Uppsala (SE); Kristin Hammer, Sollentuna (SE); Erik Ringberg, Uppsala (SE); Bengt Lindqvist, Uppsala (SE); Gary Johansson, Solna (SE); Peter Brandt, Uppsala (SE); Katarina Beierlein, Uppsala (SE); Björn M Nilsson, Stockholm (SE)

(73) Assignee: Biovitrum AB (publ.), Stockholm (SE)

( * ) Notice: Subject to any disclaimer, the term of this patent is extended or adjusted under 35 U.S.C. 154(b) by 68 days.

(21) Appl. No.: 11/824,939

(22) Filed: Jul. 3, 2007

(65) Prior Publication Data

US 2008/0032968 A1 Feb. 7, 2008

Related U.S. Application Data

(60) Provisional application No. 60/861,146, filed on Nov. 27, 2006.

(30) Foreign Application Priority Data

Jul. 3, 2006 (SE) .................................. 0601459

(51) Int. Cl.
- *A61K 31/404* (2006.01)
- *A61K 31/435* (2006.01)
- *A61K 31/496* (2006.01)
- *A61K 31/5355* (2006.01)
- *C07D 265/30* (2006.01)
- *C07D 403/02* (2006.01)
- *C07D 211/06* (2006.01)
- *C07D 209/04* (2006.01)

(52) U.S. Cl. .................. 514/231.2; 514/252.1; 514/315; 514/412; 544/106; 544/359; 546/184; 548/466; 548/467; 548/469

(58) Field of Classification Search .................. 548/466, 548/467, 469
See application file for complete search history.

(56) References Cited

FOREIGN PATENT DOCUMENTS

| | | |
|---|---|---|
| GB | 2341549 | 3/2000 |
| WO | WO 96/03400 | 2/1996 |
| WO | WO 02/32863 | 4/2002 |
| WO | WO 02/41889 | 5/2002 |
| WO | WO 02/102774 | 12/2002 |
| WO | WO 03/104193 | 12/2003 |
| WO | WO 2005/037834 | 4/2005 |

OTHER PUBLICATIONS

Russell, et al. J. Med. Chem. 2001, 44, pp. 3881-3895.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2009]. Retrieved from the Internet, URL; http://www.cnn.com/2003/HEALTH/conditions/09/24/alzheimers.drug.ap/indexhtml>.*
Type 2 diabetes cure [online], [retrieved on Dec. 30, 2009]. Retrieved from the Internet, URL; http://www.ehow.com/about_5438387_type-diabetes-cure.html?ref=Track2&utm_source=ask.*

* cited by examiner

*Primary Examiner*—Rebecca L Anderson
*Assistant Examiner*—Shawquia Young
(74) *Attorney, Agent, or Firm*—Fish & Richardson P.C.

(57) ABSTRACT

The present invention relates to novel compounds of formula (I):

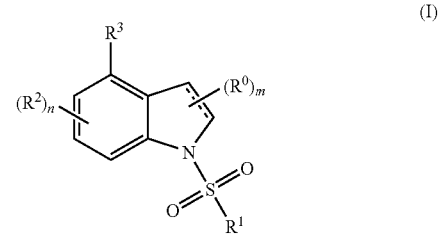

wherein m, n, $R^0$, $R^1$, $R^2$, $R^3$ and $R^4$ are as described herein, to pharmaceutical compositions comprising the compounds, to processes for their preparation, as well as to the use of the compounds for the preparation of a medicament against $5\text{-HT}_6$ receptor-related disorders.

27 Claims, No Drawings

4-SUBSTITUTED INDOLE AND INDOLINE COMPOUNDS

CROSS REFERENCE TO RELATED APPLICATIONS

This application claims the benefit of Swedish Patent Application No.: SE 0601459-1, filed on Jul. 3, 2006 and U.S. Provisional Application No. 60/861,146, filed on Nov. 27, 2006, both of these prior applications are incorporated herein by reference in their entireties.

TECHNICAL FIELD

The invention relates to novel compounds, to pharmaceutical compositions comprising the compounds, to processes for their preparation, as well as to the use of the compounds for the preparation of a medicament against $5\text{-HT}_6$ receptor-related disorders.

BACKGROUND OF THE INVENTION

Obesity is a condition characterized by an increase in body fat content resulting in excess body weight above accepted norms. Obesity is among the most important nutritional disorders in the western world and represents a major health problem in many industrialized countries. This disorder can lead to increased mortality due to increased incidences of diseases such as cardiovascular disease, digestive disease, respiratory disease, cancer and type 2 diabetes. Searching for compounds that reduce body weight has been going on for many decades. One line of research includes the activation of serotoninergic systems, either by direct activation of serotonin receptor subtypes or by inhibiting serotonin reuptake. The exact receptor subtype profile required is however not believed to be known.

Serotonin (5-hydroxytryptamine or 5-HT) is considered to be a key transmitter of the peripheral and central nervous system and is believed to modulate a wide range of physiological and pathological functions, including, for example, anxiety, sleep regulation, aggression, feeding and depression. The identification and cloning of multiple serotonin receptor subtypes have been reported. The cloning of the $5\text{-HT}_6$ receptor was reported by several groups in 1993. See, e.g., (Ruat, M. et al. (1993) Biochem. Biophys. Res. Commun. 193: 268-276; Sebben, M. et al. (1994) NeuroReport 5: 2553-2557). This receptor is believed to be positively coupled to adenylyl cyclase and has been shown to display affinity for neuroleptics such as clozapine. Recently, the effect of $5\text{-HT}_6$ antagonist and $5\text{-HT}_6$ antisense oligonucleotides to reduce food intake in rats has been reported. See, e.g., (Bentley, J. C. et al. (1999) Br J. Pharmacol. Suppl. 126, P66; Bentley, J. C. et al. (1997) J. Psychopharmacol. Suppl. A64, 255; Woolley M. L. et al. (2001) Neuropharmacology 41: 210-219).

Compounds with enhanced affinity and selectivity for the $5\text{-HT}_6$ receptor have been identified, e.g. in WO 00/34242 and by Isaac, M. et al. (2000) 6-*Bicyclopiperazinyl*-1-*arylsulphonylindoles* and 6-*Bicyclopiperidinyl*-1-*arylsulphonylindoles derivatives as novel, potent and selective* $5\text{-HT}_6$ *receptor antagonists*. Bioorganic & Medicinal Chemistry Letters 10: 1719-1721 (2000), Bioorganic & Medicinal Chemistry Letters 13: 3355-3359 (2003), Expert Opinion Therapeutic Patents 12(4) 513-527 (2002).

DISCLOSURE OF THE INVENTION

This invention relates generally to certain indole and indoline compounds that show affinity for the $5\text{-HT}_6$ receptor.

It has surprisingly been found that certain indole and indoline compounds show affinity for the $5\text{-HT}_6$ receptor at nanomolar range. In general, the preferred compounds described herein feature a benzylic amino function at the indole or indoline 4-position, preferably a benzylic amino function at the indole 4-position. This class of amines has improved in vivo properties and is not expected to be metabolized into non-desired metabolites. In some embodiments, the compounds described herein (e.g., the indole compounds) and their pharmaceutically acceptable salts can have $5\text{-HT}_6$ receptor antagonist activity. In some embodiments, the compounds described herein (e.g., the indole compounds) and their pharmaceutically acceptable salts can have $5\text{-HT}_6$ receptor agonist and partial agonist activity. Preferred compounds can include those compounds having antagonist activity. As such, the compounds described herein are believed to be useful for one or more of the following: the treatment or prophylaxis of obesity and type 2 diabetes, reduction of body weight and of body weight gain, as well as in the treatment or prophylaxis of disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea and/or schizophrenia, panic attacks, Attention Deficit Hyperactive Disorder (ADHD), withdrawal from drug abuse (e.g. abuse of amphetamine, cocain abuse and/or nicotine), neurodegenerative diseases characterized by impaired neuronal growth, and pain. In certain embodiments, the reduction of body weight and of body weight gain (e.g. treating body-weight disorders) can be achieved inter alia by reduction of food intake. As used herein, the term "body weight disorders" refers to the disorders caused by an imbalance between energy intake and energy expenditure, resulting in abnormal (e.g., excessive) body weight. Such body weight disorders include obesity.

In one aspect, this invention relates to a compound of the formula (I)

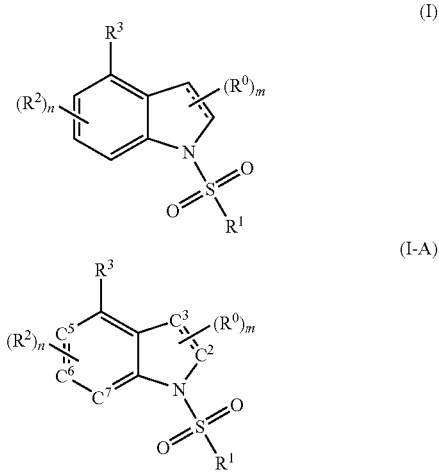

wherein:
═ represents a single bond or a double bond;
m is 0, 1 or 2 (e.g., 2);
n is 0, 1, 2 or 3 (e.g., 3);
in embodiments, when m is 1, then one of $C^2$ and $C^3$ (see formula I-A) of the indole/indoline ring system is substituted with hydrogen, and the other of $C^2$ and $C^3$ of the indole/ indoline ring system is substituted with either hydrogen or one of the non-hydrogen possibilities set forth in the definition of $R^0$;

in embodiments, when m is 0, then each of $C^2$ and $C^3$ of the indole/indoline ring system is substituted with hydrogen;

in embodiments, when n is 2, then one of $C^5$, $C^6$ and $C^7$ (see formula I-A) of the indole/indoline ring system is substituted with hydrogen, and the other two of $C^5$, $C^6$ and $C^7$ of the indole/indoline ring system are each, independently, substituted with hydrogen or one of the non-hydrogen possibilities set forth in the definition of $R^2$;

in embodiments, when n is 1, then two of $C^5$, $C^6$ and $C^7$ of the indole/indoline ring system are substituted with hydrogen, the other of $C^5$, $C^6$ and $C^7$ of the indole/indoline ring system is substituted with either hydrogen or one of the non-hydrogen possibilities set forth in the definition of $R^2$;

in embodiments, when n is 0, then each of $C^5$, $C^6$ and $C^7$ of the indole/indoline ring system is substituted with hydrogen;

each $R^0$ is, independently, selected from:
(a) hydrogen,
(b) halogen, preferably chlorine,
(c) $C_{1-6}$-alkyl,
(d) $C_{3-7}$-cycloalkyl,
(e) hydroxy-$C_{1-4}$-alkyl.
(f) —$COOR^6$.
(g) —$CONR^5R^5$,
(h) —CO—$R^8$,
(i) —CN,
(j) aryl, and
(k) heteroaryl, wherein when $R^0$ is or includes a heteroaryl or aryl residue, each heteroaryl or aryl residue can be optionally substituted in one or more (e.g., 1-5, 14, 1-3, 1-2, or 1) positions with a substituent independently selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;

$R^1$ is a group selected from:
(a) $C_{1-6}$-alkyl,
(b) $C_{3-7}$-cycloalkyl,
(c) $C_{3-6}$-alkenyl,
(d) aryl,
(e) aryl-$C_{2-6}$-alkenyl,
(f) aryl-$C_{1-6}$-alkyl,
(g) heteroaryl,
(h) heteroaryl-$C_{2-6}$-alkenyl, and
(i) heteroaryl-$C_{1-6}$-alkyl, wherein when $R^1$ is or includes any heteroaryl or aryl residue, alone or as part of another group, the heteroaryl or aryl residue is optionally independently substituted in one or more (e.g., 1-5, 1-4, 1-3, 1-2, or 1) positions with a substituent independently selected from:
(a) halogen,
(b) $C_{1-6}$-alkyl,
(c) fluoro-$C_{1-6}$-alkyl,
(d) $C_{3-7}$-cycloalkyl,
(e) $C_{2-6}$-alkenyl,
(f) fluoro-$C_{2-6}$-alkenyl,
(g) ethynyl,
(h) hydroxy-$C_{1-4}$-alkyl,
(i) hydroxy,
j) $C_{1-6}$-alkoxy,
(k) fluoro-$C_{1-6}$-alkoxy,
(l) —$SCF_3$,
(m) —$SCF_2H$,
(n) —$SO_2NR^5R^5$,
(o) —$S(O)_eR^8$, wherein e is 0, 1, 2 or 3,
(p) —CN,
(q) —$NR^5R^5$,
(r) —$NHSO_2R^8$,
(s) —$NR^6COR^8$,
(t) —$NO_2$,
(u) —$CONR^5R^5$,
(v) —C(=O)$R^8$,
(w) —COOH,
(x) $C_{1-6}$-alkoxycarbonyl,
(y) $C_{3-7}$-cycloalkoxy
(z) phenyl, optionally substituted with one or more of halogen, $C_{1-4}$-alkyl, $C_{1-4}$-alkylthio, $C_{1-4}$-alkoxy, cyano, or trifluoromethyl,
(aa) phenoxy, optionally substituted with one or more of halogen, $C_{1-4}$-alkyl, $C_{1-4}$-alkylthio, $C_{1-4}$-alkoxy, cyano, or trifluoromethyl,
(ab) benzyloxy, optionally substituted with one or more of halogen, $C_{1-4}$-alkyl, $C_{1-4}$-alkylthio, $C_{1-4}$-alkoxy, cyano, or trifluoromethyl,
(ac) benzoyl, optionally substituted with one or more of halogen, $C_{1-4}$-alkyl, $C_{1-4}$-alkylthio, $C_{1-4}$-alkoxy, cyano, or trifluoromethyl, and
(ad) heteroaryl, optionally substituted with trifluoromethyl and methyl;

each $R^2$ is independently selected from:
(a) hydrogen
(b) halogen,
(c) $C_{1-6}$-alkyl,
(d) fluoro-$C_{1-6}$-alkyl,
(e) $C_{3-7}$-cycloalkyl,
(f) $C_{2-6}$-alkenyl,
(g) fluoro-$C_{2-6}$-alkenyl,
(h) ethynyl,
(i) hydroxy-$C_{1-4}$-alkyl,
(j) hydroxy,
(k) $C_{1-6}$-alkoxy,
(l) fluoro-$C_{1-6}$-alkoxy,
(m) $C_{3-7}$-cycloalkoxy,
(n) fluoro-$C_{3-7}$-cycloalkoxy,
(o) —$SCF_3$,
(p) —$SCF_2H$,
(q) —$SO_2NR^5R^5$,
(r) —$S(O)_eR^8$, wherein e is 0, 1, 2 or 3,
(s) —CN,
(t) —$NR^5R^5$,
(u) —$NHSO_2R^8$,
(v) —$NR^6COR^8$,
(w) —$NO_2$,
(x) —$CONR^5R^5$,
(y) —$OCONR^5R^5$,
(z) —C(=O)$R^8$,
(aa) —COOH,
(ab) $C_{1-6}$-alkoxycarbonyl, and
(ac) —$OR^{11}$;

$R^3$ is a group selected from:

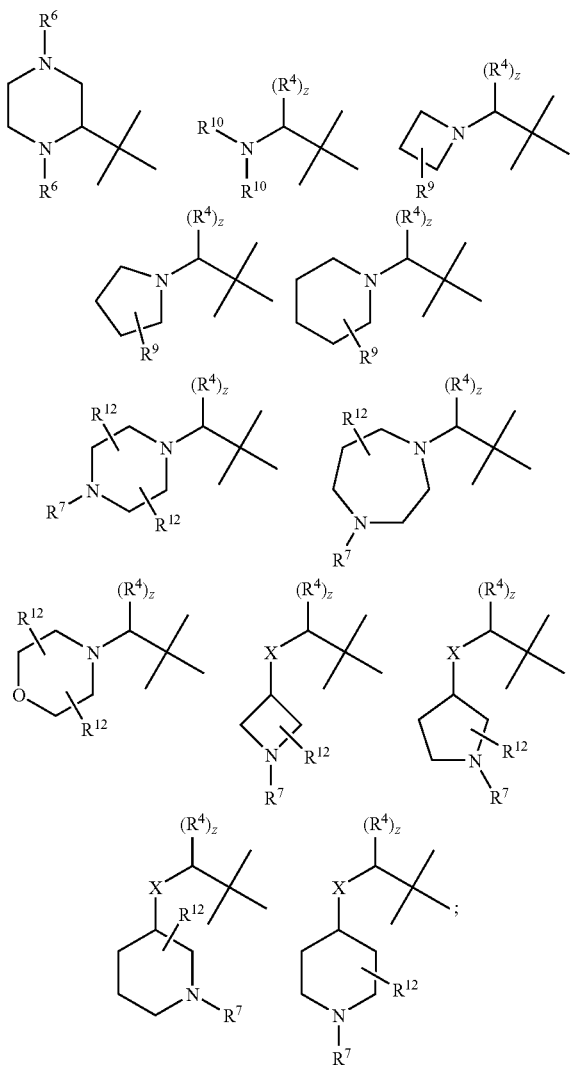

wherein

X is selected from O or —$NR^6$;

$R^4$ at each occurrence can be, independently, hydrogen, $C_{1-4}$-alkyl, fluoro-$C_{1-4}$-alkyl, hydroxy-$C_{1-4}$-alkyl, or cyano; z can be 0, 1, or 2 (e.g., 2); in embodiments, it is provided that when z is 2, and each of the two $R^4$ substituents is the same substituent, then each of the two $R^4$ substituents is hydrogen or each of the two $R^4$ substituents is methyl;

in some embodiments:

z can be 2 (i.e., there are two germinal $R^4$ substitutents attached to the carbon atom that serves as the point of attachment of the $R^3$ substitutent to the indole/indoline ring system); and (i) both of the $R^4$ substituents can be hydrogen; or (ii) one of the two $R^4$ substituents can be hydrogen, and the other of the two $R^4$ substituents can be $C_{1-4}$ alkyl, fluoro-$C_{1-4}$-alkyl, hydroxy-$C_{1-4}$-alkyl, or cyano; or (iii) both of the $R^4$ substituents can be $CH_3$.

Some of the $R^3$ formulae delineated herein include the following substructure:

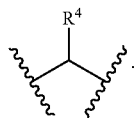

It is understood that this substructure is intended to represent the following substitution on the carbon atom:

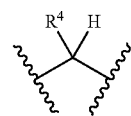

(i.e., an $R^4$ substituent is attached to the carbon atom that serves as the point of attachment for $R^3$, and a hydrogen atom is attached to the carbon atom that serves as the point of attachment for $R^3$). In these embodiments, $R^4$ can be any one of hydrogen, $C_{1-4}$-alkyl, fluoro-$C_{1-4}$-alkyl, hydroxy-$C_{1-4}$-alkyl, or cyano;

$R^5$ is each independently selected from:
(a) hydrogen,
(b) $C_{1-6}$-alkyl,
(c) fluoro-$C_{1-6}$-alkyl,
(d) heteroaryl-$C_{1-2}$-alkyl
(e) $C_{3-7}$-cycloalkyl, or
two $R^5$ groups together with the nitrogen to which they are attached form a heterocyclic ring;

$R^6$ is each independently selected from:
(a) hydrogen,
(b) $C_{1-4}$-alkyl,
(c) fluoro-$C_{2-4}$-alkyl, and
(d) hydroxy-$C_{1-3}$-alkyl;

$R^7$ is selected from:
(a) hydrogen,
(b) $C_{1-4}$-alkyl,
(c) fluoro-$C_{2-4}$-alkyl,
(d) 2-cyanoethyl,
(e) hydroxy-$C_{2-4}$-alkyl,
(f) $C_{3-4}$-alkenyl,
(g) $C_{3-4}$-alkynyl,
(h) $C_{3-7}$-cycloalkyl,
(i) $C_{3-4}$-cycloalkyl-$C_{1-4}$-alkyl, and
(j) $C_{1-4}$-alkoxy-$C_{2-4}$-alkyl;

$R^8$ is each independently selected from:
(a) $C_{1-6}$-alkyl,
(b) fluoro-$C_{1-6}$-alkyl,
(c) $C_{3-7}$-cycloalkyl,
(d) aryl, and
(e) heteroaryl,
wherein when $R^8$ is a heteroaryl or aryl residue, each heteroaryl or aryl residue is optionally independently substituted in one or more (e.g., 1-5, 1-4, 1-3, 1-2, or 1) positions with a substituent independently selected from:
(a) halogen,
(b) $C_{1-4}$-alkyl,
(c) $C_{1-4}$-alkylthio,
(d) $C_{1-4}$-alkoxy,
(e) —$CF_3$,
(f) —$OCF_3$, (g) —CN, and
(h) hydroxymethyl;
$R^9$ is selected from:
(a) hydrogen,
(b) fluorine, provided that the said fluorine is not attached to a carbon atom adjacent to a ring nitrogen atom,
(c) $C_{1-4}$-alkyl,
(d) —$NR^6R^6$, provided that the said —$NR^6R^6$ group is not attached to a carbon atom adjacent to a ring nitrogen atom,
(e) hydroxy, provided that the said hydroxy group is not attached to a carbon atom adjacent to a ring nitrogen atom, and
(f) hydroxy-$C_{1-4}$-alkyl;
$R^{10}$ is each independently selected from:
(a) hydrogen,
(b) hydroxy-$C_{2-4}$-alkyl,
(c) $C_{1-3}$-alkoxy-$C_{2-4}$-alkyl,
(d) cyclopropyl;
(e) cyclobutyl,
(f) benzyl, and
(g) $C_{1-4}$-alkyl, provided that when both $R^{10}$ represent ethyl, then ≡ represents a double bond;
$R^{11}$ is selected from
(a) —$CH_2CN$
(b) benzyl;
$R^{12}$ is each independently selected from:
(a) hydrogen,
(b) $C_{1-4}$-alkyl,
(c) fluoro-$C_{1-4}$-alkyl,
(d) hydroxy-$C_{1-3}$-alkyl, and
(e) $C_{1-6}$-alkoxycarbonyl; and
pharmaceutically acceptable salts, hydrates, solvates, geometrical isomers, tautomers, optical isomers, and metabolites, (e.g., pharmaceutically acceptable salts) in particular N-oxides of tertiary amines, demethylated amines, and N-oxidized heteroaromatic rings, thereof.

In some embodiments, it is provided that the compound of formula (I) is not N-methyl-1-(phenylsulfonyl)-1H-indole-4-methanamine.

In another aspect, this invention relates to a compound of the formula (I), wherein:
≡ represents a single bond or a double bond;
m is 1;
n is 1;
$R^0$ is a group selected from:
(a) hydrogen,
(b) $C_{1-6}$-alkyl,
(c) $C_{3-7}$-cycloalkyl,
(d) hydroxy-$C_{1-4}$-alkyl,
(e) —$COOR^6$,
(f) —$CONR^5R^5$,
(g) —CO—$R^8$,
(h) —CN,
(i) aryl, and
(j) heteroaryl,
wherein when $R^0$ is or includes a heteroaryl or aryl residue, each heteroaryl or aryl residue can be optionally substituted in one or more (e.g., 1-5, 1-4, 1-3, 1-2, or 1) positions with a substituent independently selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;

$R^3$ is a group selected from:

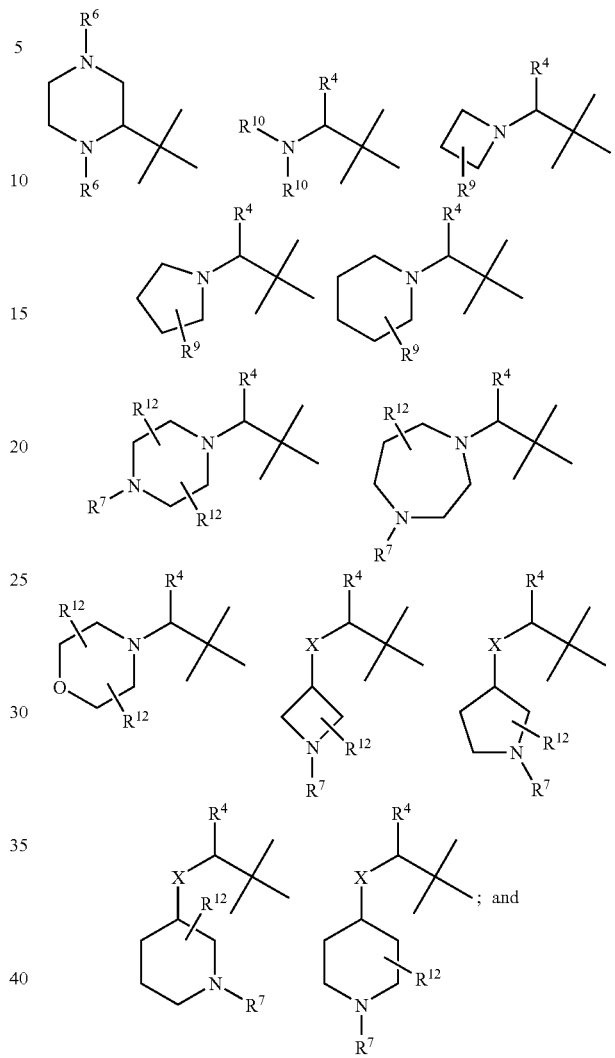

X, $R^1$, $R^2$, $R^4$, $R^6$, $R^7$, $R^9$, $R^{10}$, $R^{11}$, and $R^{12}$ are as defined for formula (I).

It is preferred in formula (I) that X is —$NR^6$. More preferably, X is —$NR^6$, wherein $R^6$ is H.

It is also preferred in formula (I) that:
≡ represents a double bond;
$R^0$ is a group selected from:
(a) hydrogen,
(b) $C_{1-6}$-alkyl,
(c) $C_{3-7}$-cycloalkyl,
(d) hydroxy-$C_{1-4}$-alkyl,
(e) —CO—$R^8$,
(f) —CN,
(g) aryl, and
(h) heteroaryl,
wherein any heteroaryl or aryl residue is optionally independently substituted in or more positions with a substituent selected from:
(a) halogen,
(b) $C_{1-4}$-alkyl,
(c) $C_{1-4}$-alkylthio,
(d) $C_{1-4}$-alkoxy, (e) —CF$_3$,
(f) —CN, and
(g) hydroxymethyl;
R$^1$ is a group selected from:
(a) aryl,
(b) heteroaryl,
wherein any heteroaryl or aryl residue is optionally independently substituted in one or more positions with a substituent selected from:
(a) halogen,
(b) C$_{1-6}$-alkyl,
(c) fluoro-C$_{1-6}$-alkyl,
(d) C$_{3-7}$-cycloalkyl,
(e) C$_{2-6}$-alkenyl,
(f) fluoro-C$_{2-6}$-alkenyl,
(g) ethynyl,
(h) hydroxy-C$_{1-4}$-alkyl,
(i) hydroxy,
(j) C$_{1-6}$-alkoxy,
(k) fluoro-C$_{1-6}$-alkoxy,
(l) —SCF$_3$,
(m) —SCF$_2$H,
(n) —SO$_2$NR$^5$R$^5$,
(o) —S(O)$_e$R$^8$, wherein e is 0, 1, or 2,
(p) —CN,
(q) —NR$^5$R$^5$,
(r) —NHSO$_2$R$^8$,
(s) —NR$^6$COR$^8$,
(t) —NO$_2$,
(u) —CONR$^5$R$^5$, and
(v) —C(=O)R$^8$;
R$^2$ is a group selected from:
(a) hydrogen,
(b) halogen,
(c) C$_{1-6}$-alkyl,
(d) C$_{3-7}$-cycloalkyl,
(e) hydroxy-C$_{1-4}$-alkyl,
(f) hydroxy,
(g) C$_{1-6}$-alkoxy,
(h) —SCF$_3$,
(i) —SCF$_2$H,
(j) —SO$_2$NR$^5$R$^5$,
(k) —S(O)$_e$R$^8$, wherein e is 0, 1, 2 or 3,
(l) —CN,
(m) —NR$^5$R$^5$,
(n) —NHSO$_2$R$^8$,
(o) —NR$^6$COR$^8$,
(p) —CONR$^5$R$^5$,
(q) —OCONR$^5$R$^5$,
(r) —C(=O)R$^8$, and
(s) —OR$^{11}$;
R$^3$ is a group selected from:

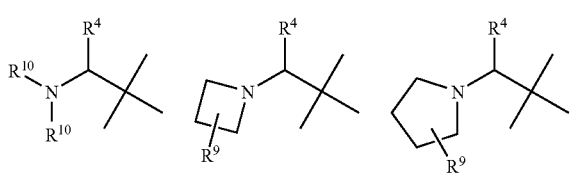

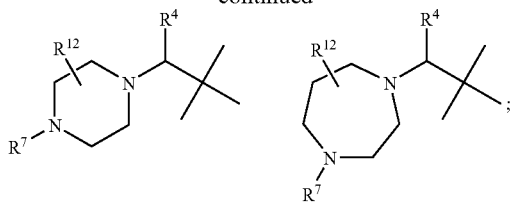

R$^4$ is a group selected from:
(a) hydrogen,
(b) C$_{1-4}$-alkyl, and
(c) hydroxy-C$_{1-4}$-alkyl;
R$^5$ is each independently selected from:
(a) hydrogen, and
(b) C$_{1-3}$-alkyl,
or two R$^5$ groups together with the nitrogen to which they are attached form a heterocyclic ring;
R$^6$ is each independently selected from:
(a) hydrogen,
(b) methyl, and
(c) ethyl;
R$^7$ is selected from:
(a) hydrogen,
(b) C$_{1-4}$-alkyl,
(c) 2-cyanoethyl,
(d) 2-hydroxyethyl,
(e) C$_{3-4}$-alkenyl,
(f) C$_{3-7}$-cycloalkyl,
(h) C$_{3-4}$-cycloalkyl-C$_{1-4}$-alkyl, and
(i) C$_{1-4}$-alkoxy-C$_{2-4}$-alkyl;
R$^8$ is each independently selected from:
(a) C$_{1-3}$-alkyl,
(b) C$_{3-7}$-cycloalkyl,
(c) aryl, and
(d) heteroaryl,
wherein any heteroaryl or aryl residue is optionally independently substituted in one or more positions with a substituent selected from:
(a) fluorine,
(b) chlorine
(c) bromine,
(d) C$_{1-4}$-alkyl,
(e) C$_{1-4}$-alkylthio,
(f) C$_{1-4}$-alkoxy,
(g) —CF$_3$,
(h) —CN, and
(i) hydroxymethyl;
R$^9$ is selected from:
(a) hydrogen,
(b) C$_{1-4}$-alkyl,
(c) —NR$^6$R$^6$, provided that the said —NR$^6$R$^6$ group is not attached to a carbon atom adjacent to a ring nitrogen atom,
(d) hydroxy, provided that the said hydroxy group is not attached to a carbon atom adjacent to a ring nitrogen atom, and
(e) hydroxymethyl;
R$^{10}$ is each independently selected from:
(a) hydrogen,
(b) hydroxy-C$_{2-4}$-alkyl,
(c) C$_{1-3}$-alkoxy-C$_{2-4}$-alkyl,
(d) C$_{1-4}$-alkyl
(e) cyclopropyl, and
(f) cyclobutyl;

$R^{11}$ is selected from
(a) —$CH_2CN$
(b) benzyl;
$R^{12}$ is each independently selected from:
(a) hydrogen,
(b) $C_{1-2}$-alkyl, and
(c) hydroxy-$C_{1-2}$-alkyl.
It is further preferred in formula (I) that:
= represents a double bond;
$R^0$ is a group selected from:
(a) hydrogen,
(b) methyl, and
(c) hydroxymethyl;
$R^1$ is a group selected from:
(a) aryl, and
(b) heteroaryl;
wherein any heteroaryl or aryl residue is optionally independently substituted in one or more positions with a substituent selected from:
(a) halogen,
(b) methyl,
(c) trifluoromethyl,
(d) methoxy,
(e) t-butyl, and
(f) —CN;
$R^2$ is a group selected from:
(a) hydrogen,
(b) fluorine,
(c) chlorine,
(d) bromine,
(e) hydroxy,
(f) methoxy,
(g) ethoxy,
(h) iso-propoxy,
(i) —$OCON(Me)_2$, and
(j) —$OR^{11}$;
$R^3$ is a group selected from:

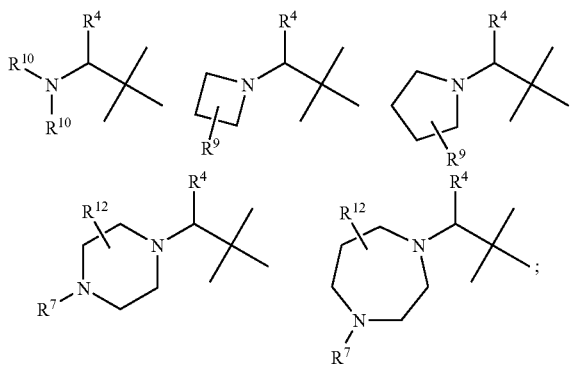

$R^4$ is hydrogen;
$R^7$ is selected from:
(a) hydrogen,
(b) methyl,
(c) n-propyl,
(d) i-propyl, and
(e) 2-methoxyethyl;
$R^9$ is selected from:
(a) hydrogen,
(b) methyl,
(c) —$NH_2$, provided that the said —$NH_2$ group is not attached to a carbon atom adjacent to a ring nitrogen atom,
(d) hydroxy, provided that the said hydroxy group is not attached to a carbon atom adjacent to a ring nitrogen atom, and
(e) hydroxymethyl;
$R^{10}$ is each independently selected from:
(a) hydrogen,
(b) methyl,
(c) ethyl,
(d) i-propyl,
(e) 2-hydroxyethyl,
(f) 2-methoxyethyl
(g) cyclopropyl, and
(h) cyclobutyl;
$R^{11}$ is selected from
(a) —$CH_2CN$,
(b) benzyl;
$R^{12}$ is each independently selected from:
(a) hydrogen,
(b) methyl, and
(c) hydroxymethyl.
In more preferred compounds of formula (I):
= represents a double bond;
$R^0$ is a group selected from:
(a) hydrogen,
(b) methyl, and
(c) hydroxymethyl;
$R^1$ is a group selected from:
(a) phenyl,
(b) pyridyl, and
(c) 2-thienyl,
wherein any heteroaryl or aryl residue is optionally independently substituted in one or more positions with a substituent selected from:
(a) chlorine,
(b) fluorine,
(c) methyl,
(d) trifluoromethyl,
(e) methoxy, and
(f) —CN;
$R^2$ is a group selected from:
(a) hydrogen,
(b) fluorine,
(c) hydroxy,
(d) methoxy,
(e) ethoxy,
(f) iso-propoxy,
(g) —$OCON(Me)_2$, and
(h) —$OR^{11}$;
$R^3$ is a group selected from:

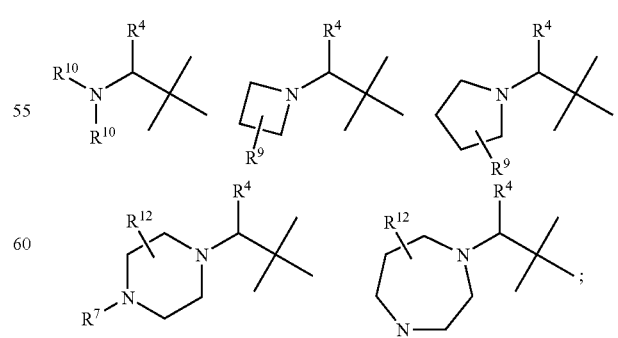

$R^4$ is hydrogen;

$R^7$ is selected from:
(a) hydrogen,
(b) methyl,
(c) n-propyl,
(d) i-propyl, and
(e) 2-methoxyethyl;
$R^9$ is selected from:
(a) hydrogen,
(b) methyl,
(c) —NH$_2$, provided that the said —NH$_2$ group is not attached to a carbon atom adjacent to a ring nitrogen atom,
(d) hydroxy, provided that the said hydroxy group is not attached to a carbon atom adjacent to a ring nitrogen atom, and
(e) hydroxymethyl;
$R^{10}$ is each independently selected from:
(a) hydrogen,
(b) methyl,
(c) ethyl,
(d) i-propyl,
(e) 2-hydroxyethyl,
(f) 2-methoxyethyl; and
$R^{11}$ is selected from
(a) —CH$_2$CN,
(b) benzyl;
$R^{12}$ is each independently selected from:
(a) hydrogen,
(b) methyl, and
(c) hydroxymethyl.

Other preferred compounds of formula (I) are those wherein $R^1$ is selected from the group consisting of:
(a) chloroimidazo[2,1-b][1,3]thiazolyl, preferably 6-chloroimidazo[2,1-b][1,3]thiazol-5-yl,
(b) 3,4-dihydro-2H-1,5-benzodioxepinyl, preferably 3,4-dihydro-2H-1,5-benzodioxepin-7-yl,
(c) 2,1,3-benzothiadiazolyl, preferably 2,1,3-benzothiadiazol-4-yl,
(d) trifluoromethoxyphenyl, preferably 4-trifluoromethoxyphenyl,
(e) methyl-1-benzothienyl, preferably 5-methyl-1-benzothien-2-yl,
(f) dimethyl-1H-imidazolyl, preferably 1,2-dimethyl-1H-imidazol-4-yl,
(g) quinolinyl, preferably quinolin-8-yl,
(h) [methyl(trifluoromethyl)-1H-pyrazolyl]thienyl, preferably 5-[1-methyl-3-(trifluoromethyl)-1H-pyrazol-5-yl]-2-thienyl,
(i) 1-naphthyl,
(j) 2-naphthyl, and
(k) methyl; and each of $R^0$ and $R^2$—$R^{12}$ can be, independently of one another, as defined anywhere herein.

Also preferred are compounds of formula (I) wherein:
$R^3$ is a group selected from:

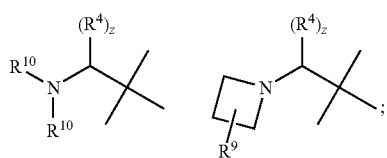

wherein z, $R^4$, $R^9$ and $R^{10}$ are as defined for formula (I).

Further preferred are compounds of formula (I) wherein $R^3$ is a group selected from:

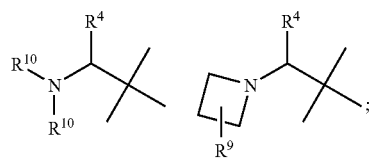

$R^4$ is hydrogen or methyl;
$R^9$ is hydrogen,
$R^{10}$ is each independently selected from:
(a) hydrogen, and
(b) methyl.
Preferably $R^3$ is

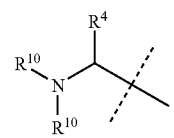

in compounds of formula (I), $R^4$ is hydrogen or methyl; and
$R^{10}$ is each, independently, selected from:
(a) hydrogen, and
(b) methyl.
One preferred sub-class of compounds is represented by the compounds of formula (Ib):

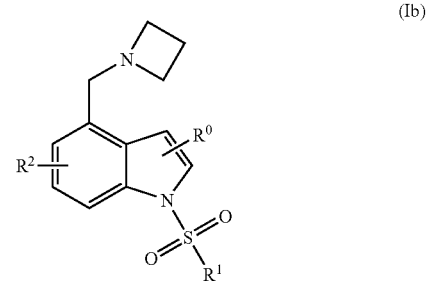

(Ib)

wherein:
$R^0$ is a group selected from:
(a) hydrogen,
(b) methyl, and
(c) hydroxymethyl;
$R^1$ is a group selected from:
(a) phenyl,
(b) 2-naphthyl,
(c) 2-thienyl, and
(d) 6-chloroimidazo[2,1-b][1,3]thiazol-5-yl
wherein any heteroaryl or aryl residue is optionally independently substituted in one or more positions with a substituent selected from:
(a) chlorine,
(b) fluorine,
(c) bromine,
(d) methyl,
(e) trifluoromethyl,
(f) methoxy, and
(g) —CN;

R² is a group selected from:
(a) hydrogen,
(b) fluorine,
(c) hydroxy,
(d) methoxy,
(e) ethoxy,
(f) iso-propoxy,
(g) —OCON(Me)₂, and
(h) —OR¹¹.

In another aspect, this invention features compounds of formula (I) in which:
═ represents a single bond;
R¹ is a group selected from:
(a) phenyl,
(b) pyridyl, and
(c) 2-thienyl,
in which any heteroaryl or aryl residue is optionally independently substituted in one or more positions with a substituent selected from:
(a) chlorine,
(b) fluorine,
(c) methyl,
(d) trifluoromethyl,
(e) methoxy, and
(f) —CN;
R² is a group selected from:
(a) hydrogen,
(b) fluorine,
(c) hydroxy,
(d) methoxy,
(e) ethoxy,
(f) iso-propoxy,
(g) —OCON(Me)₂, and
(h) —OR¹¹; and
R¹¹ is selected from
(a) —CH₂CN and
(b) benzyl.

Other embodiments can include one or more of the features described above.

Preferred compounds include:
1-(Phenylsulfonyl)-4-(piperazin-1-ylmethyl)-1H-indole,
4-(1,4-Diazepan-1-ylmethyl)-1-(phenylsulfonyl)-1H-indole,
1-{[1-(Phenylsulfonyl)-1H-indol-4-yl]methyl}pyrrolidin-3-amine,
1-{[1-(Phenylsulfonyl)-1H-indol-4-yl]methyl}pyrrolidin-3-amine,
1-[(4-Methylphenyl)sulfonyl]-4-(piperazin-1-ylmethyl)-1H-indole,
1-[(4-Methylphenyl)sulfonyl]-4-[(3-methylpiperazin-1-yl)methyl]-1H-indole,
4-(1,4-Diazepan-1-ylmethyl)-1-[(4-methylphenyl)sulfonyl]-1H-indole,
4-[(4-Methyl-1,4-diazepan-1-yl)methyl]-1-[(4-methylphenyl)sulfonyl]-1H-indole,
1-[(4-Methylphenyl)sulfonyl]-4-[(4-methylpiperazin-1-yl)methyl]-1H-indole,
4-[(4-Isopropylpiperazin-1-yl)methyl]-1-[(4-methylphenyl)sulfonyl]-1H-indole,
1-[(4-Methylphenyl)sulfonyl]-4-[(4-propylpiperazin-1-yl)methyl]-1H-indole,
1-[(4-Methylphenyl)sulfonyl]-4-(pyrrolidin-1-ylmethyl)-1H-indole,
1-[(2-Methoxy-5-methylphenyl)sulfonyl]-4-(piperazin-1-ylmethyl)-1H-indole,
1-[(2-Methoxy-5-methylphenyl)sulfonyl]-4-[(3-methylpiperazin-1-yl)methyl]-1H-indole,
N-({1-[(2-Methoxy-5-methylphenyl)sulfonyl]-1H-indol-4-yl}methyl)piperidin-4-amine,
1-Isopropyl-N-({1-[(2-methoxy-5-methylphenyl)sulfonyl]-1H-indol-4-yl}methyl)piperidin-4-amine,
1-[(2-Methoxy-5-methylphenyl)sulfonyl]-4-[(2-methylpyrrolidin-1-yl)methyl]-1H-indole,
1-[(2-Methoxy-5-methylphenyl)sulfonyl]-4-[(3-methylpiperazin-1-yl)methyl]indoline,
1-[(2-Methoxy-5-methylphenyl)sulfonyl]-4-[(4-methylpiperazin-1-yl)methyl]indoline,
1-[(2-Methoxy-5-methylphenyl)sulfonyl]-4-(pyrrolidin-1-ylmethyl)indoline,
({1-[(2-Methoxy-5-methylphenyl)sulfonyl]-2,3-dihydro-1H-indol-4-yl}methyl)dimethylamine,
1-[(4-Fluorophenyl)sulfonyl]-4-[(3-methylpiperazin-1-yl)methyl]-1H-indole,
4-(1,4-Diazepan-1-ylmethyl)-1-[(4-fluorophenyl)sulfonyl]-1H-indole,
1-[(4-Fluorophenyl)sulfonyl]-4-(pyrrolidin-1-ylmethyl)-1H-indole,
({1-[(4-Fluorophenyl)sulfonyl]-1H-indol-4-yl}methyl)dimethylamine,
1-[(4-Fluorophenyl)sulfonyl]-4-(piperazin-1-ylmethyl)-1H-indole,
1-[(2-Methylphenyl)sulfonyl]-4-(piperazin-1-ylmethyl)-1H-indole,
1-[(2-Methylphenyl)sulfonyl]-4-[(4-methylpiperazin-1-yl)methyl]-1H-indole,
1-({1-[(2-Methylphenyl)sulfonyl]-1H-indol-4-yl}methyl)pyrrolidin-3-ol,
1-[(2-Methylphenyl)sulfonyl]-4-(pyrrolidin-1-ylmethyl)-1H-indole,
2-[Methyl({1-[(2-methylphenyl)sulfonyl]-1H-indol-4-yl}methyl)amino]ethanol,
N,N-Dimethyl-1-{1-[(2-methylphenyl)sulfonyl]-1H-indol-4-yl}methanamine,
4-(piperazin-1-ylmethyl)-1-{[3-(trifluoromethyl)phenyl]sulfonyl}-1H-indole,
{(2R)-1-[(1-{[3-(Trifluoromethyl)phenyl]sulfonyl}-1H-indol-4-yl)methyl]pyrrolidin-2-yl}methanol,
4-(Pyrrolidin-1-ylmethyl)-1-{[3-(trifluoromethyl)phenyl]sulfonyl}-1H-indole,
2-{Methyl[(1-{[3-(trifluoromethyl)phenyl]sulfonyl}-1H-indol-4-yl)methyl]amino}ethanol,
N,N-Dimethyl-1-(1-{[3-(trifluoromethyl)phenyl]sulfonyl}-1H-indol-4-yl)methanamine,
4-(piperazin-1-ylmethyl)-1-(2-thienylsulfonyl)-1H-indole,
N-Ethyl-N-{[1-(2-thienylsulfonyl)-1H-indol-4-yl]methyl}ethanamine,
4-(Pyrrolidin-1-ylmethyl)-1-(2-thienylsulfonyl)-1H-indole,
4-[(4-Propylpiperazin-1-yl)methyl]-1-(2-thienylsulfonyl)-1H-indole,
N,N-Dimethyl-1-[1-(2-thienylsulfonyl)-1H-indol-4-yl]methanamine,
4-(piperazin-1-ylmethyl)-1-(pyridin-3-ylsulfonyl)-1H-indole,
N,N-Dimethyl-1-[1-(pyridin-3-ylsulfonyl)-1H-indol-4-yl]methanamine,
1-(Pyridin-3-ylsulfonyl)-4-(pyrrolidin-1-ylmethyl)-1H-indole,
1-(Phenylsulfonyl)-4-(pyrrolidin-1-ylmethyl)-1H-indole,
N,N-Dimethyl-1-[1-(phenylsulfonyl)-1H-indol-4-yl]methanamine,
3-Methyl-1-(phenylsulfonyl)-4-(piperazin-1-ylmethyl)-1H-indole,
3-Methyl-4-[(4-methylpiperazin-1-yl)methyl]-1-(phenylsulfonyl)-1H-indole, 3-Methyl-1-(phenylsulfonyl)-4-(pyrrolidin-1-ylmethyl)-1H-indole,
N,N-Dimethyl-1-[3-methyl-1-(phenylsulfonyl)-1H-indol-4-yl]methanamine,
6-Methoxy-1-(phenylsulfonyl)-4-(piperazin-1-ylmethyl)-1H-indole,
{6-Methoxy-1-(phenylsulfonyl)-1H-indol-4-yl]methyl}dimethylamine,
6-Methoxy-4-{[(3R)-3-methylpiperazin-1-yl]methyl}-1-(phenylsulfonyl)-1H-indole,
6-Methoxy-4-{[(3S)-3-methylpiperazin-1-yl]methyl}-1-(phenylsulfonyl)-1H-indole,
6-Methoxy-4-[(4-methylpiperazin-1-yl)methyl]-1-(phenylsulfonyl)-1H-indole,
4-(1,4-Diazepan-1-ylmethyl)-6-methoxy-1-(phenylsulfonyl)-1H-indole,
6-Methoxy-1-(phenylsulfonyl)-4-(pyrrolidin-1-ylmethyl)-1H-indole,
2-[{[6-Methoxy-1-(phenylsulfonyl)-1H-indol-4-yl]methyl}(methyl)amino]ethanol,
6-Fluoro-1-(phenylsulfonyl)-4-(piperazin-1-ylmethyl)-1H-indole,
4-(1,4-Diazepan-1-ylmethyl)-6-fluoro-1-(phenylsulfonyl)-1H-indole,
6-Fluoro-4-{[(3S)-3-methylpiperazin-1-yl]methyl}-1-(phenylsulfonyl)-1H-indole,
6-Fluoro-4-{[(3R)-3-methylpiperazin-1-yl]methyl}-1-(phenylsulfonyl)-1H-indole,
6-Fluoro-1-(phenylsulfonyl)-4-(pyrrolidin-1-ylmethyl)-1H-indole,
2-[{[6-Fluoro-1-(phenylsulfonyl)-1H-indol-4-yl]methyl}(methyl)amino]ethanol,
{[6-Fluoro-1-(phenylsulfonyl)-1H-indol-4-yl]methyl}dimethylamine,
6-Fluoro-4-[(4-methylpiperazin-1-yl)methyl]-1-(phenylsulfonyl)-1H-indole,
1-(Phenylsulfonyl)-4-(pyrrolidin-1-ylmethyl)-1H-indol-6-yl dimethylcarbamate,
4-(1,4-Diazepan-1-ylmethyl)-1-(phenylsulfonyl)-1H-indol-6-ol,
1-[(4-Fluorophenyl)sulfonyl]-6-methoxy-4-(piperazin-1-ylmethyl)-1H-indole,
6-Methoxy-4-(piperazin-1-ylmethyl)-1-{[3-(trifluoromethyl)phenyl]sulfonyl}-1H-indole,
1-[(2-Chlorophenyl)sulfonyl]-6-methoxy-4-(piperazin-1-ylmethyl)-1H-indole,
1-[(3-Chloro-2-methylphenyl)sulfonyl]-6-methoxy-4-(piperazin-1-ylmethyl)-1H-indole,
1-[(2,5-Dimethoxyphenyl)sulfonyl]-6-methoxy-4-(piperazin-1-ylmethyl)-1H-indole,
2-{[6-Methoxy-4-(piperazin-1-ylmethyl)-1H-indol-1-yl]sulfonyl}benzonitrile,
({1-[(4-Fluorophenyl)sulfonyl]-1H-indol-4-yl}methyl)amine,
N-({1-[(4-Fluorophenyl)sulfonyl]-1H-indol-4-yl}methyl)ethanamine,
7-Methoxy-1-(phenylsulfonyl)-4-(piperazin-1-ylmethyl)-1H-indole,
2-Methyl-1-(phenylsulfonyl)-4-(piperazin-1-ylmethyl)-1H-indole,
Methyl 4-{[1-(phenylsulfonyl)-1H-indol-4-yl]methyl}piperazine-2-carboxylate,
(4-{[1-(Phenylsulfonyl)-1H-indol-4-yl]methyl}piperazin-2-yl)methanol,
(2-Methoxyethyl){[1-(phenylsulfonyl)-1H-indol-4-yl]methyl}amine,
N-{[1-(Phenylsulfonyl)-1H-indol-4-yl]methyl}propan-2-amine,
4-{[4-(2-Methoxyethyl)piperazin-1-yl]methyl)}-1-(phenylsulfonyl)-1H-indole,
((2R)-1-{[1-(Phenylsulfonyl)-1H-indol-4-yl]methyl}pyrrolidin-2-yl)methanol,
4-(Azetidin-1-ylmethyl)-1-(phenylsulfonyl)-1H-indole,
Ethyl 5-methoxy-1-(phenylsulfonyl)-4-(piperazin-1-ylmethyl)-1H-indole-2-carboxylate,
5-Methoxy-N-methyl-1-(phenylsulfonyl)-4-(piperazin-1-ylmethyl)-1H-indole-2-carboxamide,
N-Ethyl-5-methoxy-1-(phenylsulfonyl)-4-(piperazin-1-ylmethyl)-1H-indole-2-carboxamide,
5-Ethoxy-1-(phenylsulfonyl)-4-(piperazin-1-ylmethyl)-N-(2-thienylmethyl)-1H-indole-2-carboxamide,
4-(Azetidin-1-ylmethyl)-6-methoxy-1-(phenylsulfonyl)-1H-indole,
1-(Phenylsulfonyl)-4-(piperazin-1-ylmethyl)-1H-indol-5-ol,
1-(Phenylsulfonyl)-4-piperazin-2-yl-1H-indole,
4-(1,4-Dimethylpiperazin-2-yl)-1-(phenylsulfonyl)-1H-indole,
[7-Methoxy-1-(phenylsulfonyl)-1H-indol-4-yl](piperazin-1-yl)acetonitrile,
4-(Azetidin-1-ylmethyl)-7-methoxy-1-(phenylsulfonyl)-1H-indole,
{[1-(Phenylsulfonyl)-4-(piperazin-1-ylmethyl)-1H-indol-5-yl]oxy}acetonitrile,
5-Isopropoxy-1-(phenylsulfonyl)-4-(piperazin-1-ylmethyl)-1H-indole,
5-(Benzyloxy)-1-(phenylsulfonyl)-4-(piperazin-1-ylmethyl)-1H-indole,
4-{[(2-Hydroxyethyl)(methyl)amino]methyl}-1-(phenylsulfonyl)-1H-indol-5-ol,
4-[(3-Hydroxypyrrolidin-1-yl)methyl]-1-(phenylsulfonyl)-1H-indol-5-ol,
[1-(Phenylsulfonyl)-4-(piperazin-1-ylmethyl)-6-(trifluoromethyl)-1H-indol-2-yl]methanol,
5-Methoxy-1-(phenylsulfonyl)-4-(piperazin-1-ylmethyl)-1H-indole,
5-Ethoxy-1-(phenylsulfonyl)-4-(piperazin-1-ylmethyl)-1H-indole,
1-Phenyl-N-{[1-(phenylsulfonyl)-1H-indol-4-yl]methyl}methanamine,
N-{[5-Methoxy-1-(phenylsulfonyl)-1H-indol-4-yl]methyl}cyclopropanamine,
{[5-Methoxy-1-(phenylsulfonyl)-1H-indol-4-yl]methyl}dimethylamine,
N-{[5-Methoxy-1-(phenylsulfonyl)-1H-indol-4-yl]methyl}cyclobutanamine,
N-{[5-Methoxy-1-(phenylsulfonyl)-1H-indol-4-yl]methyl}-N-methylcyclobutanamine,
1-{[1-(Phenylsulfonyl)-1H-indol-4-yl]methyl}azetidin-3-ol,
4-(Azetidin-1-ylmethyl)-5-methoxy-1-(phenylsulfonyl)-1H-indole,
4-{[4-(Azetidin-1-ylmethyl)-1H-indol-1-yl]sulfonyl}benzonitrile,
2-((2S)-1-{([1-(Phenylsulfonyl)-1H-indol-4-yl]methyl}azetidin-2-yl)propan-2-ol,
4-(Azetidin-1-ylmethyl)-2-methyl-1-(phenylsulfonyl)-1H-indole,
4-(Azetidin-1-ylmethyl)-1-[(2-chlorophenyl)sulfonyl]-1H-indole,
4-(Azetidin-1-ylmethyl)-1-[(5-chloro-2-thienyl)sulfonyl]-1H-indole,
4-(Azetidin-1-ylmethyl)-1-(2-naphthylsulfonyl)-1H-indole,
4-(Azetidin-1-ylmethyl)-1-[(2-methoxy-5-methylphenyl)sulfonyl]-1H-indole, 4-(Azetidin-1-ylmethyl)-1-[(6-chloroimidazo[2,1-b][1,3]
thiazol-5-yl)sulfonyl]-1H-indole,
4-(Azetidin-1-ylmethyl)-1-[(4-tert-butylphenyl)sulfonyl]-
1H-indole,
4-(Azetidin-1-ylmethyl)-1-[(2,6-difluorophenyl)sulfonyl]-
1H-indole,
4-(Azetidin-1-ylmethyl)-1-{[2-(trifluoromethyl)phenyl]sulfonyl}-1H-indole,
3-{[4-(Azetidin-1-ylmethyl)-1H-indol-1-yl]
sulfonyl}benzonitrile,
4-(Azetidin-1-ylmethyl)-1-{[4-bromo-2-(trifluoromethyl)
phenyl]sulfonyl}-1H-indole,
4-(Azetidin-1-ylmethyl)-1-(2-thienylsulfonyl)-1H-indole,
4-(Azetidin-1-ylmethyl)-1-[(2,5-difluorophenyl)sulfonyl]-
1H-indole,
[(5-Methoxy-1-{[3-(trifluoromethyl)phenyl]sulfonyl}-1H-
indol-4-yl)methyl]dimethylamine,
4-(Azetidin-1-ylmethyl)-7-(benzyloxy)-1-(methylsulfonyl)-
1H-indole,
({1-[(6-Chloroimidazo[2,1-b][1,3]thiazol-5-yl)sulfonyl]-5-
methoxy-1H-indol-4-yl}methyl)dimethylamine,
4-[(Dimethylamino)methyl]-1-(phenylsulfonyl)-1H-indol-
5-ol,
{[5-Ethoxy-1-(phenylsulfonyl)-1H-indol-4-yl]
methyl}dimethylamine,
({5-Ethoxy-1-[(2-methoxy-5-methylphenyl)sulfonyl]-1H-
indol-4-yl}methyl)dimethylamine,
{[5-Ethoxy-1-(1-naphthylsulfonyl)-1H-indol-4-yl]
methyl}dimethylamine,
{[5-Ethoxy-1-(2-naphthylsulfonyl)-1H-indol-4-yl]
methyl}dimethylamine,
({1-[(2-Chlorophenyl)sulfonyl]-5-ethoxy-1H-indol-4-
yl}methyl)dimethylamine,
({1-[(3-Chloro-2-methylphenyl)sulfonyl]-5-ethoxy-1H-indol-4-yl}methyl)dimethylamine,
({5-Methoxy-1-[(2-methoxy-5-methylphenyl)sulfonyl]-1H-
indol-4-yl}methyl)dimethylamine,
({1-[(2,3-Dichlorophenyl)sulfonyl]-5-methoxy-1H-indol-4-
yl}methyl)dimethylamine,
{[5-Ethoxy-1-(quinolin-8-ylsulfonyl)-1H-indol-4-yl]
methyl}dimethylamine,
{[5-Ethoxy-1-({5-[1-methyl-3-(trifluoromethyl)-1H-pyrazol-5-yl]-2-thienyl}sulfonyl)-1H-indol-4-yl]
methyl}dimethylamine,
({1-[(2,5-Dichlorophenyl)sulfonyl]-5-ethoxy-1H-indol-4-
yl}methyl)dimethylamine,
({5-Ethoxy-1-[(2,4,6-trichlorophenyl)sulfonyl]-1H-indol-4-
yl}methyl)dimethylamine,
1-[5-Methoxy-1-(phenylsulfonyl)-1H-indol-4-yl]-N-methylmethanamine,
({1-[(2-Methoxy-5-methylphenyl)sulfonyl]-1H-indol-4-
yl}methyl)methylamine,
4-[(Dimethylamino)methyl]-6-fluoro-1-(phenylsulfonyl)-
1H-indol-5-ol,
1-[6-Fluoro-5-methoxy-1-(phenylsulfonyl)-1H-indol-4-yl]-
N,N-dimethylmethanamine,
6-Fluoro-1-(phenylsulfonyl)-4-(pyrrolidin-1-ylmethyl)-1H-
indol-5-ol,
6-Fluoro-5-methoxy-1-(phenylsulfonyl)-4-(pyrrolidin-1-ylmethyl)-1H-indole,
4-(Azetidin-1-ylmethyl)-6-fluoro-1-(phenylsulfonyl)-1H-
indol-5-ol,
4-(Azetidin-1-ylmethyl)-6-fluoro-5-methoxy-1-(phenylsulfonyl)-1H-indole, 4-{[Ethyl(methyl)amino]methyl}-6-
fluoro-1-(phenylsulfonyl)-1H-indol-5-ol,
N-{[6-Fluoro-5-methoxy-1-(phenylsulfonyl)-1H-indol-4-
yl]methyl}-N-methylethanamine,
6-Fluoro-4-[(methylamino)methyl]-1-(phenylsulfonyl)-1H-
indol-5-ol,
{[6-Fluoro-5-methoxy-1-(phenylsulfonyl)-1H-indol-4-yl]
methyl}methylamine,
1-{5-Methoxy-1-[(4-methoxyphenyl)sulfonyl]-1H-indol-4-
yl}-N,N-dimethylmethanamine,
1-{1-[(3-Chlorophenyl)sulfonyl]-5-methoxy-1H-indol-4-
yl}-N,N-dimethylmethanamine,
1-{1-[(2,5-Difluorophenyl)sulfonyl]-5-methoxy-1H-indol-
4-yl}-N,N-dimethylmethanamine,
1-(1-{[4-Fluoro-3-(trifluoromethyl)phenyl]sulfonyl}-5-
methoxy-1H-indol-4-yl)-N,N-dimethylmethanamine,
1-[5-Methoxy-1-(quinolin-8-ylsulfonyl)-1H-indol-4-yl]-N,
N-dimethylmethanamine,
1-{1-[(2-Chlorophenyl)sulfonyl]-5-methoxy-1H-indol-4-
yl}-N,N-dimethylmethanamine,
1-{1-[(2-Chloro-6-methylphenyl)sulfonyl]-5-methoxy-1H-
indol-4-yl}-N,N-dimethylmethanamine,
1-{1-[(3-Chloro-4-fluorophenyl)sulfonyl]-5-methoxy-1H-
indol-4-yl}-N,N-dimethylmethanamine,
1-{5-Methoxy-1-[(2-methylphenyl)sulfonyl]-1H-indol-4-
yl}-N,N-dimethylmethanamine,
2-({4-[(Dimethylamino)methyl]-5-methoxy-1H-indol-1-
yl}sulfonyl)benzonitrile,
1-{1-[(2,6-Difluorophenyl)sulfonyl]-5-methoxy-1H-indol-
4-yl}-N,N-dimethylmethanamine,
1-{1-[(1,2-Dimethyl-1H-imidazol-4-yl)sulfonyl]-5-methoxy-1H-indol-4-yl}-N,N-dimethylmethanamine,
1-{5-Methoxy-1-[(5-methyl-1-benzothien-2-yl)sulfonyl]-
1H-indol-4-yl}-N,N-dimethylmethanamine,
1-{5-Methoxy-1-[(2-methoxy-4-methylphenyl)sulfonyl]-
1H-indol-4-yl}-N,N-dimethylmethanamine,
1-{1-[(2,4-Dichlorophenyl)sulfonyl]-5-methoxy-1H-indol-
4-yl}-N,N-dimethylmethanamine,
1-{1-[(5-Bromo-2-methoxyphenyl)sulfonyl]-5-methoxy-
1H-indol-4-yl}-N,N-dimethylmethanamine,
1-[1-(2,1,3-Benzothiadiazol-4-ylsulfonyl)-5-methoxy-1H-
indol-4-yl]-N,N-dimethylmethanamine,
1-[1-(3,4-Dihydro-2H-1,5-benzodioxepin-7-ylsulfonyl)-5-
methoxy-1H-indol-4-yl]-N,N-dimethylmethanamine,
1-{1-[(2,5-Dimethoxyphenyl)sulfonyl]-5-methoxy-1H-indol-4-yl}-N,N-dimethylmethanamine,
1-(5-Methoxy-1-{[2-(trifluoromethyl)phenyl]sulfonyl}-1H-
indol-4-yl)-N,N-dimethylmethanamine,
1-(5-Methoxy-1-{[4-(trifluoromethoxy)phenyl]sulfonyl}-
1H-indol-4-yl)-N,N-dimethylmethanamine,
3-({4-[(Dimethylamino)methyl]-5-methoxy-1H-indol-1-
yl}sulfonyl)benzonitrile,
1-[5-Methoxy-1-(pyridin-3-ylsulfonyl)-1H-indol-4-yl]-N,
N-dimethylmethanamine,
Methyl {1-[1-(phenylsulfonyl)-1H-indol-4-yl]ethyl}amine,
{1-[1-(Phenylsulfonyl)-1H-indol-4-yl]ethyl}amine,
Dimethyl {1-[1-(phenylsulfonyl)-1H-indol-4-yl]
ethyl}amine,
4-(Azetidin-1-ylmethyl)-2,3-dichloro-5-methoxy-1-(phenylsulfonyl)-1H-indole,
{[1-(Phenylsulfonyl)-1H-indol-4-yl]methyl}amine,
4-[(dimethylamino)methyl]-6-methoxy-1-(phenylsulfonyl)-
1H-indol-5-ol,
1-[5,6-dimethoxy-1-(phenylsulfonyl)-1H-indol-4-yl]-N,N-
dimethylmethanamine,
{[3-chloro-5-methoxy-1-(phenylsulfonyl)-1H-indol-4-yl]
methyl}dimethylamine,
{[3-chloro-5-methoxy-1-(phenylsulfonyl)-1H-indol-4-yl]
methyl}methylamine,
{[5-methoxy-1-(phenylsulfonyl)-1H-indol-4-yl]
methyl}amine, 6-fluoro-4-[1-(methylamino)ethyl]-1-(phenylsulfonyl)-1H-indol-5-ol,
4-[1-(dimethylamino)ethyl]-6-fluoro-1-(phenylsulfonyl)-1H-indol-5-ol,
{1-[6-fluoro-5-methoxy-1-(phenylsulfonyl)-1H-indol-4-yl]ethyl}methylamine, and
{1-[6-fluoro-5-methoxy-1-(phenylsulfonyl)-1H-indol-4-yl]ethyl}dimethylamine and the pharmaceutically acceptable salts thereof.

In another aspect, this invention relates to a process for the preparation of a compound according to formula (I) of the invention which includes:

a) reaction of 4-methyl-1-$R^1$-substituted sulfonyl-1H-indole with N-bromosuccinimide;

b) reaction of the product from step a) with groups selected from:

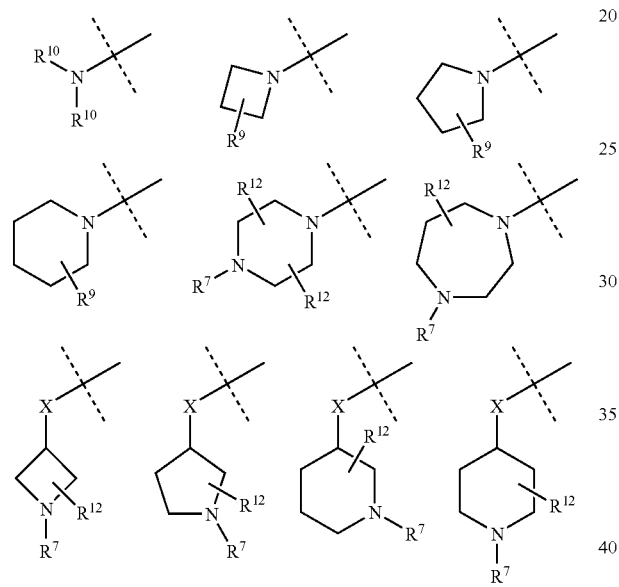

wherein the groups $R^1$, $R^7$, $R^9$, $R^{10}$, $R^{12}$ and X are as defined for formula (I), or a salt or a protected derivative thereof;

and optionally thereafter forming a pharmaceutically acceptable salt of the compound of formula (I).

In a further aspect, this invention relates to a process for the preparation of a compound according to formula (I), wherein ══ represents a double bond, which includes:

aa) reacting a 4-bromoindole derivative of formula (III)

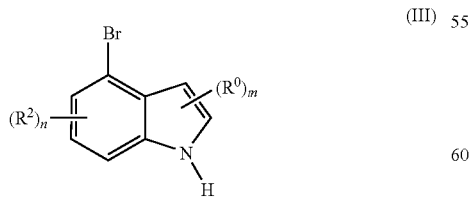

wherein m, n, $R^0$ and $R^2$ are as defined above,
with a sulfonyl chloride of the formula $R^1SO_2Cl$, wherein $R^1$ is as defined above, to give a compound of formula (IV)

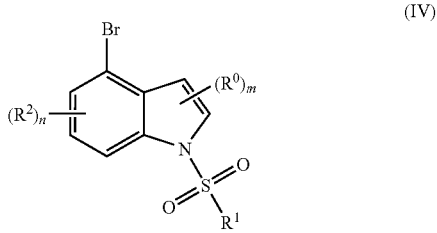

wherein $R^0$, $R^1$ and $R^2$ are as defined above;

bb) reacting the compound of formula (IV) with tributyl (vinyl)stannane in the presence of a palladium complex such as bis(triphenylphosphine)palladium(II) diacetate $[Pd(PPh_3)_2OAc_2]$ as a catalyst, to give a compound of formula (V)

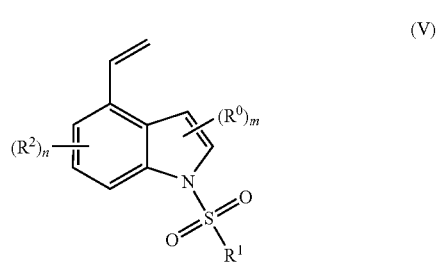

wherein m, n, $R^0$, $R^1$ and $R^2$ are as defined above;

cc) reacting the compound of formula (V) with osmium tetroxide ($OsO_4$) and sodium periodate, to produce the aldehyde derivative of formula (VI)

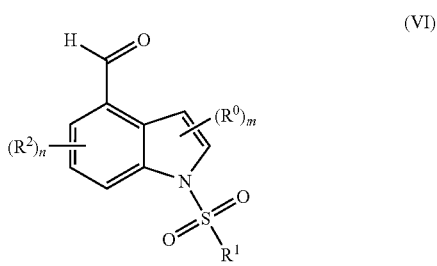

wherein m, n, $R^0$, $R^1$ and $R^2$ are as defined above;

dd) reacting the compound of formula (VI) with an appropriate amine selected from:

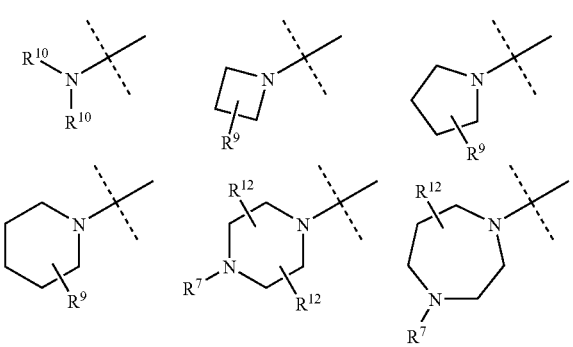

-continued

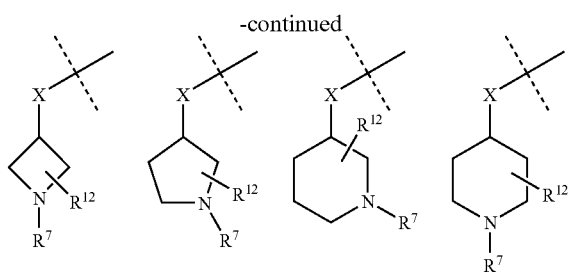

wherein X is NR$^6$, and R$^6$, R$^7$, R$^9$, R$^{10}$, and R$^{12}$ are as defined above, or a salt or a protected derivative thereof, in the presence of a suitable reducing agent such as NaBH$_4$, NaBH$_3$CN or sodium triacetoxyborohydride [NaB(OAc)$_3$)H], to produce a compound of formula (I) wherein ═ represents a double bond; and optionally thereafter forming a pharmaceutically acceptable salt of the compound of formula (I).

In one aspect, this invention relates to a process for the preparation of a compound according to formula (I), wherein ═ represents a single bond, which includes:

aaa) reacting a compound of formula (IV) with a reducing agent such as NaBH$_3$CN in trifluoroacetic acid (TFA) to give a compound of formula (VII)

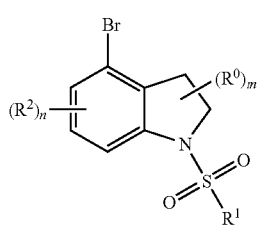
(VII)

wherein R$^0$, R$^1$ and R$^2$ are as defined above;

bbb) reacting a compound of formula (VII) according to steps bb)-dd) described above to produce a compound of formula (I) wherein ═ represents a single bond; and optionally thereafter forming a pharmaceutically acceptable salt of the compound of formula (I).

The reactions used in the processes described above can be carried out using conventional methods and reagents that are known to those skilled in the art and/or are illustrated herein. The necessary starting materials for preparing the compounds described herein are either known in the art, may be prepared in analogy with the preparation of known compounds, and/or may be prepared as described herein.

In reaction step aa) the reaction may be carried out in the presence of a base such as an alkali metal hydroxide such as, for example, an aqueous solution of sodium hydroxide, and a phase transfer catalyst such as tetrabutylammonium hydrogensulfate in a solvent such as dichloromethane. See, for example: *Liebigs Ann. Chem.* 1986, 2065-2080.

In reaction step bb) the palladium-catalyzed cross-coupling reaction (Stille coupling) may be conducted in a solvent such as toluene or acetonitrile. The reaction may optionally be conducted under the influence of microwaves.

In reaction step cc) the oxidative cleavage of the alkene into an aldehyde function may be performed by conditions described in *Org. Lett.* 2004, 6, 3217-3219. The alkene is treated with osmium tetroxide/sodium periodate in a mixture of polar solvents such as dioxane and water in the presence of a base such as 2,6-lutidine.

In reaction step dd) the reaction may be performed using standard methods for reductive amination. See, for example: *J. Med. Chem.* 2005, 48, 1745-1758 (preparation of compound 68 therein) and *J. Org. Chem.* 1996, 61, 3849-3862. Additionally, the reaction may optionally be conducted under the influence of microwaves.

Reaction step aaa) may be performed as described, for example, in *Tetrahedron Lett.* 1989, 30, 6833-6836.

In case the reacting amine corresponding to a group selected from

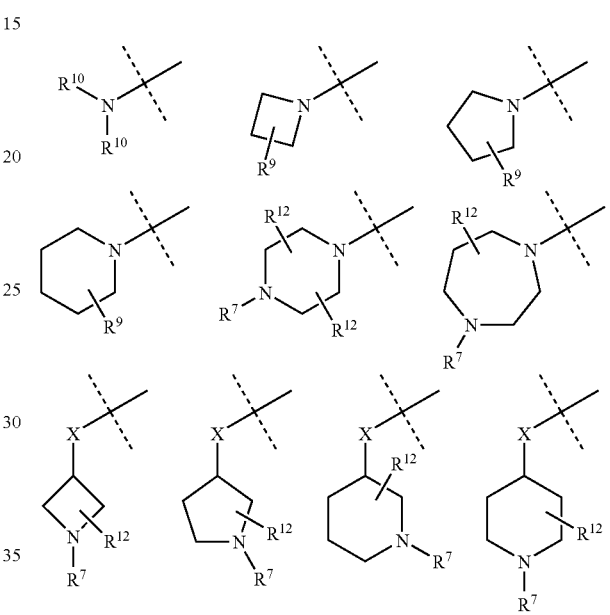

in step b) or dd) does possess additional primary or secondary amino nitrogens, a suitable protecting group such as tert-butoxycarbonyl (t-BOC) may be introduced prior to reaction in order to prevent undesired reactions at such primary or secondary amino nitrogens. Exemplary N-protected amines having more than one reactive nitrogen atom are N-tert-butoxycarbonylpiperazine and tert-butyl 4-aminopiperidine-1-carboxylate. The said protecting group may be cleaved off when it is no longer needed to provide the compound of formula (I). The reaction conditions of removing the said protecting group depend upon the choice and the characteristics of this group. Thus e.g. tert-butoxycarbonyl may be removed by treatment with a suitable acid. Protecting group methodologies (protection and deprotection) are known in the art and are described in, for example, T. W. Greene and P. G. M. Wuts, *Protective Groups in Organic Synthesis*, 3$^{rd}$ Ed., John Wiley & Sons (1999).

An obtained compound of formula (I) may be converted to another compound of formula (I) by methods well known in the art. For example, a compound of formula (I) wherein R$^2$ is selected from C$_{1-4}$-alkoxy may be transformed into another compound of formula (I) wherein R$^2$ is hydroxy by standard literature methods for cleavage of ethers. The reaction conditions may be those described in Example 70.

Another example comprises the transformation of a compound of formula (I) wherein R$^2$ is selected from hydroxy into another compound of formula (I) wherein R$^2$ is selected from —OCONR$^5$R$^5$, wherein R$^5$ is as defined above, by reaction with an appropriate carbamoyl chloride derivative of the formula ClCONR$^5$R$^5$. The reaction conditions may be those described in Example 69.

Moreover, a compound of formula (I) wherein R$^1$ is optionally substituted aryl may be converted to another compound of formula (I) wherein R$^1$ is a different optionally substituted aryl. The reaction conditions may be those described in Intermediate 40 and Example 73.

Compounds of formula (III) are commercially available, may be prepared using procedures described herein or by analogous methods thereto or according to known methods.

In another aspect, this invention relates to the use of the compounds corresponding to Formula (I) and Formula (Ib) described herein in therapy, e.g., for use in the treatment or prophylaxis of a 5-HT$_6$ receptor-related disorder or to achieve reduction of body weight and/or of body weight gain.

In a further aspect, this invention relates to a pharmaceutical formulation that includes a compound as mentioned above as active ingredient, in combination with a pharmaceutically acceptable diluent or carrier, e.g., for use in the treatment or prophylaxis of a 5-HT$_6$ receptor-related disorder or to achieve reduction of body weight and/or of body weight gain.

In one aspect, this invention relates to a method for treating a human or animal subject suffering from a 5-HT$_6$ receptor-related disorder or for achieving reduction of body weight and/or of body weight gain in a human or animal subject. The method can include administering to a subject (e.g., a human or an animal, dog, cat, horse, cow) in need thereof an effective amount of one or more compounds of any of Formula (I) or Formula (Ib) herein, their salts, or compositions containing the compounds or salts.

In another aspect, this invention relates to a method for treating a human or animal subject suffering from a 5-HT$_6$ receptor-related disorder, which includes administering to a subject (e.g., a human or an animal, dog, cat, horse, cow) in need thereof an effective amount of one or more compounds of any of Formula (I) or Formula (Ib) herein, their salts, or compositions containing the compounds or salts.

In a further aspect, this invention relates to a method for reducing body weight and/or reducing body weight gain in a human or animal subject, which includes administering to a subject (e.g., a human or an animal, dog, cat, horse, cow) in need thereof an effective amount of one or more compounds of any of Formula (I) or Formula (Ib) herein, their salts, or compositions containing the compounds or salts. The subject can be an overweight or obese subject. In some embodiments, the subject can have a body mass index (BMI) of from about 18.5 kg/m$^2$ to about 39.9 kg/m$^2$ (e.g., from about 18.5 kg/m$^2$ to about 24.9 kg/m$^2$; from about 25.0 kg/m$^2$ to about 29.9 kg/m$^2$; from about 30.0 kg/m$^2$ to about 34.9 kg/m$^2$; from about 35.0 kg/m$^2$ to about 39.9 kg/m$^2$). In some embodiments, the subject can have a BMI that is equal to or greater than about 40 kg/m$^2$. In some embodiments, the subject can have a waist circumference that is equal to or greater than about 35 inches (e.g., a waist circumference that is equal to or greater than about 40 inches). In certain embodiments, the subject can be a female subject having a waist circumference that is equal to or greater than about 35 inches. In certain embodiments, the subject can be a male subject having a waist circumference that is equal to or greater than about 40 inches. In some embodiments the subject can have any combination of BMI and waist circumference described herein (e.g. and without limitation, the subject can have a BMI of from about 18.5 kg/m$^2$ to about 24.9 kg/m$^2$ and a waist circumference that is equal to or greater than about 35 inches (e.g., a waist circumference that is equal to or greater than about 40 inches)). The measurement of BMI and waist circumference, can be carried out according to the methods described in, e.g., Aronne, L. J. *Obesity Research* 2002, 10, 105S (Arrone). The identification of overweight or obese subjects can also be made using other markers such as those described in Arrone.

In one aspect, this invention relates to a method for treating type II diabetes in a human or animal subject in need thereof, which includes administering to the subject (e.g., a human or an animal, dog, cat, horse, cow) in need thereof an effective amount of one or more compounds of any of Formula (I) or Formula (Ib) herein, their salts, or compositions containing the compounds or salts.

In another aspect, this invention relates to a method for treating a central nervous system disorder in a human or animal subject in need thereof, which includes administering to the subject (e.g., a human or an animal, dog, cat, horse, cow) in need thereof an effective amount of one or more compounds of any of Formula (I) or Formula (Ib) herein, their salts, or compositions containing the compounds or salts. The central nervous system disorder can be, e.g., anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder, or withdrawal from drug abuse.

In a further aspect, this invention relates to a method for treating pain in a human or animal subject in need thereof, which includes administering to the subject (e.g., a human or an animal, dog, cat, horse, cow) in need thereof an effective amount of one or more compounds of any of Formula (I) or Formula (Ib) herein, their salts, or compositions containing the compounds or salts.

In one aspect, this invention relates to a method for treating a neurodegenerative disorder in a human or animal subject in need thereof, which includes administering to the subject (e.g., a human or an animal, dog, cat, horse, cow) in need thereof an effective amount of one or more compounds of any of Formula (I) or Formula (Ib) herein, their salts, or compositions containing the compounds or salts. The neurodegenerative disorder can be, e.g., Alzheimer's disease, Parkinson's disease, or Huntington's chorea.

In another aspect, this invention relates to a method of improving the bodily appearance of a mammal (in need thereof) which includes orally administering to said mammal a one or more compounds of any of Formula (I) or Formula (Ib) herein, their salts, or compositions containing the compounds or salts in a dosage effective to reduce appetite. The method can include repeating administration of the dosage until a cosmetically beneficial loss of body weight has occurred.

The methods delineated herein can also include the step of identifying that the subject is in need of treatment of the 5-HT$_6$ receptor-related disorder, or to achieve reduction of body weight and/or of body weight gain. Identifying a subject in need of such treatment can be in the judgment of a subject or a health care professional and can be subjective (e.g., opinion) or objective (e.g., measurable by a test or diagnostic method).

Another object of the present invention is a method for the prophylaxis of a 5-HT$_6$ receptor-related disorder, or to achieve reduction of body weight and/or of body weight gain, which comprises administering to a subject in need of such treatment an effective amount of a compound as mentioned above.

In one aspect, this invention relates to a method for modulating 5-HT$_6$ receptor activity. The methods can include contacting a 5-HT$_6$ receptor with one or more compounds of any of Formula (I) or Formula (Ib) herein, their salts, or compositions containing the compounds or salts (e.g., administering to a subject in need of such treatment an effective amount of a compound as mentioned above).

In a further aspect, this invention relates to the use of a compound of any of Formula (I) or Formula (Ib) as described herein for the manufacture of a medicament for use in the prophylaxis or treatment of a 5-HT$_6$ receptor-related disorder or to achieve reduction of body weight and/or of body weight gain.

The compounds as mentioned above can be agonists, partial agonists or antagonists for the 5-HT$_6$ receptor. Preferably, the compounds act as partial agonists or antagonists for the 5-HT$_6$ receptor. More preferably, the compounds act as antagonists for the 5-HT$_6$ receptor.

Examples of 5-HT$_6$ receptor-related disorders include obesity; type II diabetes; disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse (e.g. abuse of cocaine, amphetamine and/or nicotine), neurodegenerative diseases characterized by impaired neuronal growth, and pain.

The compounds and compositions are useful for treating diseases or to achieve reduction of body weight and/or of body weight gain. The diseases include obesity; type II diabetes; disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse (e.g. abuse of cocaine, amphetamine and/or nicotine), neurodegenerative diseases characterized by impaired neuronal growth, and pain.

In one aspect, this invention relates to the cosmetic use of compounds of Formula (I), as described herein, e.g., for causing loss of weight, as well as cosmetic compositions containing said compounds as active ingredient, in combination with a cosmetically acceptable diluent or carrier. The invention further provides a non-therapeutic method of improving the bodily appearance of a healthy non-obese mammal, including a human, which comprises orally administering to said mammal a compound of formula I, as described herein, or a pharmaceutically effective salt thereof, in a dosage effective to reduce appetite, (and repeating said dosage until a cosmetically beneficial reduction of body weight or of body weight gain has occurred).

DEFINITIONS

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Likewise, "aryl-$C_{1-6}$-alkyl" means a $C_{1-4}$-alkyl group substituted by one or more aryl groups.

Unless otherwise stated, "fluoro-$C_{1-6}$-alkyl" means a $C_{1-6}$-alkyl group substituted by one or more fluorine atoms. Examples of said fluoro-$C_{1-6}$-alkyl include 2-fluoroethyl, fluoromethyl, trifluoromethyl and 2,2,2-trifluoroethyl.

Unless otherwise stated or indicated, the term "hydroxy-$C_{1-4}$-alkyl" denotes a straight or branched alkyl group that has a hydrogen atom thereof replaced with OH. Examples of said hydroxy-$C_{1-4}$-alkyl include hydroxymethyl, 2-hydroxyethyl, 2-hydroxypropyl and 2-hydroxy-2-methylpropyl.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

Unless otherwise stated or indicated, "fluoro-$C_{1-6}$-alkoxy" means a $C_{1-6}$-alkoxy group substituted by one or more fluorine atoms. Examples of said fluoro-$C_{1-6}$-alkoxy include trifluoromethoxy, difluoromethoxy, monofluoromethoxy, 2-fluoroethoxy, 2,2,2-trifluoroethoxy, and 1,1,2,2-tetrafluoroethoxy.

Unless otherwise stated or indicated, the term "$C_{1-4}$-alkoxy-$C_{2-4}$-alkyl" denotes a straight or branched alkoxy group having from 1 to 4 carbon atoms connected to an alkyl group having from 1 to 4 carbon atoms. Examples of said $C_{1-4}$-alkoxy-$C_{2-4}$-alkyl include methoxymethyl, ethoxymethyl, iso-propoxymethyl, n-butoxymethyl, and t-butoxymethyl. For parts of the range "$C_{1-4}$-alkoxy-$C_{2-4}$-alkyl" all subgroups thereof are contemplated such as $C_{1-3}$-alkoxy-$C_{2-4}$-alkyl, $C_{1-4}$-alkoxy-$C_{2-3}$-alkyl, $C_{1-2}$-alkoxy-$C_{2-3}$-alkyl, $C_{2-4}$-alkoxy-$C_{2-4}$-alkyl, $C_{2-3}$-alkoxy-$C_{2-4}$-alkyl, $C_{2-4}$-alkoxy-$C_{2-3}$-alkyl, etc.

Unless otherwise stated or indicated, the term "$C_{2-6}$-alkenyl" denotes a straight or branched alkenyl group having from 2 to 6 carbon atoms. Examples of said $C_{2-6}$-alkenyl include vinyl, allyl, 2,3-dimethylallyl, 1-butenyl, 1-pentenyl, and 1-hexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc. Likewise, "aryl-$C_{2-6}$-alkenyl" means a $C_{2-6}$-alkenyl group substituted by one or more aryl groups. Examples of said aryl-$C_{2-4}$-alkenyl include styryl and cinnamyl.

Unless otherwise stated or indicated, the term "fluoro-$C_{2-6}$-alkenyl" denotes a straight or branched alkenyl group having from 2 to 6 carbon atoms substituted by one or more fluorine atoms. Examples of said fluoro-$C_{2-6}$-alkenyl include 1-fluorovinyl, 1,2-difluorovinyl, trifluorovinyl, and 2-fluoropropenyl.

Unless otherwise stated or indicated, the term "$C_{3-4}$-alkynyl" denotes a straight or branched alkynyl group having from 3 to 4 carbon atoms. Examples of said $C_{3-4}$-alkynyl include 1-propynyl, 2-propynyl, 1-butynyl, and 2-butynyl.

Unless otherwise stated or indicated, the term "$C_{3-7}$-cycloalkyl" denotes a cyclic alkyl group having a ring size from 3 to 7 carbon atoms. Examples of said cycloalkyl include cyclopropyl, cyclobutyl, cyclopentyl, cyclohexyl, methylcyclohexyl, and cycloheptyl. For parts of the range "$C_{3-7}$-cycloalkyl" all subgroups thereof are contemplated such as $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{6-7}$-cycloalkyl, etc.

Unless otherwise stated or indicated, the term "aryl" refers to a hydrocarbon ring system of one, two or three rings, having at least one aromatic ring and having from 6-14 carbon atoms. Examples of aryls are phenyl, pentalenyl, indenyl, indanyl, 1,2,3,4-tetrahydronaphthyl, 1-naphthyl, 2-naphthyl, fluorenyl and anthryl. The aryl rings may be optionally substituted. Likewise, phenoxy refers to a phenyl group bonded to an oxygen atom.

An aryl group can be linked to the remainder of the molecule through any available ring carbon whether the ring carbon is in an aromatic ring or a partially saturated ring.

The term "heteroaryl" refers to a mono- or bicyclic aromatic ring system, only one ring need be aromatic, and the said heteroaryl moiety can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings include furyl, pyrrolyl, thienyl, oxazolyl, isoxazolyl, imidazolyl, thiazolyl, isothiazolyl, pyridinyl, pyrimidinyl, pyrazinyl, imidazothiazolyl, chromanyl, quinazolinyl, indolyl, isoindolyl, indolinyl, isoindolinyl, indazolyl, pyrazolyl, pyridazinyl, quinolinyl, isoquinolinyl, benzofuranyl, dihydrobenzofuranyl, benzodioxolyl, benzodioxinyl, benzothienyl, benzimidazolyl, benzothiazolyl, benzothiadiazolyl, benzotriazolyl groups, imidazo[2,1-b][1,3]thiazolyl, and 3,4-dihydro-2H-1,5-benzodioxepinyl. If a bicyclic heteroaryl ring is substituted, it may be substituted in any ring.

Unless otherwise stated or indicated, the term "heterocyclic" refers to a non-aromatic (i.e., partially or fully saturated) mono- or bicyclic ring system having 4 to 10 ring atoms with at least one heteroatom such as O, N, or S, and the remaining ring atoms are carbon. Examples of heterocyclic groups include piperidyl, tetrahydropyranyl, tetrahydrofuranyl, azepinyl, azetidinyl, pyrrolidinyl, morpholinyl, imidazolinyl, thiomorpholinyl, pyranyl, dioxanyl, and piperazinyl groups. When present in heterocyclic groups, the sulfur atom may optionally be in an oxidized form (i.e., S=O or O=S=O).

Unless otherwise stated or indicated, the term "halogen" shall mean fluorine, chlorine, bromine or iodine.

The term $-S(O)_e R^8$, wherein e is 0, 1, 2 or 3, has the meaning as illustrated by formula (VIII)-(XI):

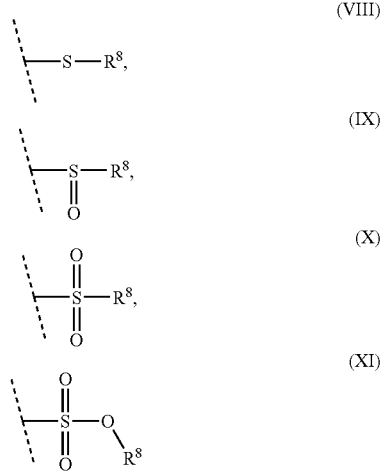

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, $8^{th}$ ed., Mc-Graw-Hill, Int. Ed. 1992, "Biotransformation of Drugs", p. 13-15; and "The Organic Chemistry of Drug Design and Drug Action" by Richard B. Silverman. Chapter 8, p 352. (Academic Press, Inc. 1992. ISBN 0-12-643730-0).

The following abbreviations have been used:
CV means Coefficient of Variation,
DCM means dichloromethane,
DMSO means dimethyl sulphoxide,
EDTA means ethylenediamine tetraacetic acid,
EGTA means ethylenebis(oxyethylenenitrilo)tetraacetic acid,
ESI means electrospray ionisation,
HEPES means 4-(2-hydroxyethyl)-1-piperazineethanesulfonic acid,
HPLC means high performance liquid chromatography,
LAH means lithium aluminum hydride,
LSD means lysergic acid, diethylamide,
MeCN means acetonitrile,
SPA means Scintillation Proximity Assay,
TFA means trifluoroacetic acid,
THF means tetrahydrofuran,
UV means ultraviolet
aq. means aqueous
sat. means saturated
rt. or r.t. means room temperature
deg means degrees Celcius
MeOH means methanol
TLC means thin liquid chromatography
eq. means equivalents All isomeric forms possible (pure enantiomers, diastereomers, tautomers, racemic mixtures and unequal mixtures of two enantiomers) for the compounds delineated are within the scope of the invention. Such compounds can also occur as cis- or trans-, E- or Z-double bond isomer forms. All isomeric forms are contemplated.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention can be formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parentral use and more preferably between 1-50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. Useful compounds are expected to have a beneficial effect when administered in the range of from about 0.001 mg/kg/d to about 200 mg/kg/d (e.g., from about 0.01 mg/kg/d to about 200 mg/kg/d, from about 0.1 mg/kg/d to about 200 mg/kg/d; from about 1 mg/kg/d to about 200 mg/kg/d; or from about 5 mg/kg/d to about 200 mg/kg/d; from about 0.001 mg/kg/d to about 100 mg/kg/d; from about 0.01 mg/kg/d to about 100 mg/kg/d, from about 0.1 mg/kg/d to about 100 mg/kg/d; from about 1 mg/kg/d to about 100 mg/kg/d; or from about 5 mg/kg/d to about 100 mg/kg/d; from about 0.001 mg/kg/d to about 50 mg/kg/d; from about 0.01 mg/kg/d to about 50 mg/kg/d, from about 0.1 mg/kg/d to about 50 mg/kg/d; from about 1 mg/kg/d to about 50 mg/kg/d; or from about 5 mg/kg/d to about 50 mg/kg/d). In some embodiments, the daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

In a further aspect the invention relates to methods of making compounds of any of the formulae herein comprising reacting any one or more of the compounds of the formulae delineated herein, including any processes delineated herein.

The compounds of the formula (I) above may be prepared by, or in analogy with, conventional methods.

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds.

In addition, various synthetic steps may be performed in an alternate sequence or order to give the desired compounds. Synthetic chemistry transformations useful in synthesizing applicable compounds are known in the art and include, for example, those described in R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The necessary starting materials for preparing the compounds of formula (I) are either known or may be prepared in analogy with the preparation of known compounds.

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Methods $^1$H nuclear magnetic resonance (NMR) and $^{13}$C NMR were recorded on a Bruker Advance DPX 400 spectrometer at 400.1 and 100.6 MHz, respectively, or alternatively, on a Varian Inova 400 spectrometer at 400 and 100.5 MHz respectively, or alternatively, on a Bruker NMR 500 spectrometer at 500.1 MHz and 125.1 MHz, respectively or alternatively, on a JEOL eclipse 270 spectrometer at 270.0 MHz and 67.5 MHz, respectively. All spectra were recorded using residual solvent as internal standard.

Preparative HPLC/MS was performed on a Waters/Micromass Platform ZQ system equipped with System A: ACE 5 C8 column (19×50 mm), eluents: MilliQ water, MeCN and MilliQ/MeCN/0.1% TFA and System B: Xterra MS C18, 5 µm column (19×50 mm), eluents: MilliQ water, MeCN and $NH_4HCO_3$ (50 mM) and System C: Gilson/YMC AQ C18; 150×30 mm. Electrospray mass spectrometry (MS) was performed using an Agilent 1100 Series Liquid Chromatograph/Mass Selective Detector (MSD) or alternatively on a Perkin- Elmer API 150EX mass spectrometer, to obtain the pseudo molecular [M+H]$^+$ ion of the target molecules. Preparative HPLC/UV was performed on a Gilson system equipped with System A: YMC ODS-AQ (150×30 mm) gradient time 8.5 min, or System B: ACE 5 C8 (5 μm, 30×100 mm) column, or System C: YMC ODS-AQ (50×20 mm) gradient time 5 min using the eluent system: water/0.1% TFA and CH$_3$CN. Analytical HPLC were performed on Agilent 1100 system equipped with System A: ACE 3 (C8, 50×3.0 mm) or System B: YMC ODS-AQ, (33×3.0 mm) using the eluent system: water/0.1% TFA and CH$_3$CN, 1 mL/min, with a gradient time of 3 min. GC-MS analysis were performed on a Hewlett Packard 5890 gas chromatograph with a HP-5MS 15 m*0.25 mm*0.25 μm column connected to a 5971 MS detector. Preparative flash chromatography was performed on Merck silica gel 60 (230-400 mesh). The compounds were named using ACD Name 6.0. Microwave reactions were performed with a Personal Chemistry Smith Creator using 0.5-2 mL or 2-5 mL Smith Process Vials fitted with aluminum caps and septa.

TABLE 1

| Example | Chemical Name | Structure |
| --- | --- | --- |
| 1 | 1-(Phenylsulfonyl)-4-(piperazin-1-ylmethyl)-1H-indole, hydrochloride | 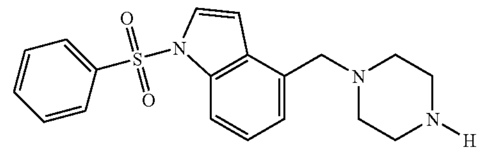 |
| 2 | 4-(1,4-Diazepan-1-ylmethyl)-1-(phenylsulfonyl)-1H-indole, hydrochloride | 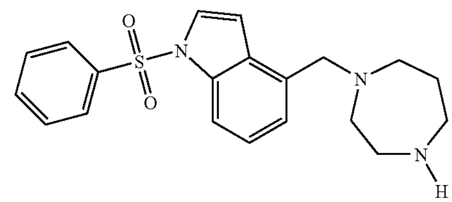 |
| 3 | 1-({[1-(Phenylsulfonyl)-1H-indol-4-yl]methyl}pyrrolidin-3-amine | 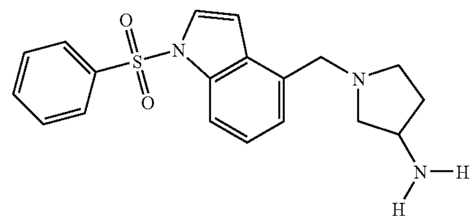 |
| 4 | 1-{[1-(Phenylsulfonyl)-1H-indol-4-yl]methyl}pyrrolidin-3-amine, trifluoroacetate | 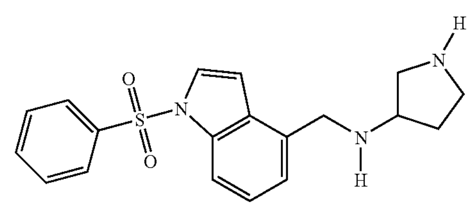 |
| 5 | 1-[(4-Methylphenyl)sulfonyl]-4-(piperazin-1-ylmethyl)-1H-indole, bis(trifluoroacetate) | 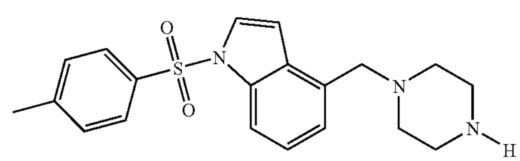 |
| 6 | 1-[(4-Methylphenyl)sulfonyl]-4-[(3-methylpiperazin-1-yl)methyl]-1H-indole, bis(trifluoroacetate) | 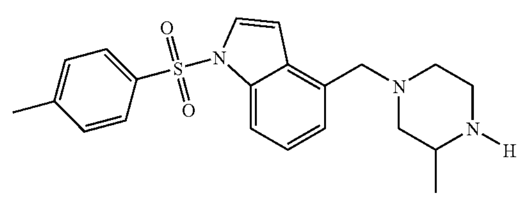 |
| 7 | 4-(1,4-Diazepan-1-ylmethyl)-1-[(4-methylphenyl)sulfonyl]-1H-indole, bis(trifluoroacetate) | 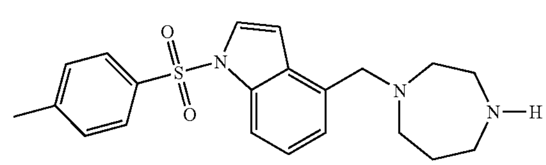 |

TABLE 1-continued

| Example | Chemical Name |
|---|---|
| 8 | 4-[(4-Methyl-1,4-diazepan-1-yl)methyl]-1-[(4-methylphenyl)sulfonyl]-1H-indole, bis(trifluoroacetate) |
| 9 | 1-[(4-Methylphenyl)sulfonyl]-4-[(4-methylpiperazin-1-yl)methyl]-1H-indole, bis(trifluoroacetate) |
| 10 | 4-[(4-Isopropylpiperazin-1-yl)methyl]-1-[(4-methylphenyl)sulfonyl]-1H-indole, bis(trifluoroacetate) |
| 11 | 1-[(4-Methylphenyl)sulfonyl]-4-[(4-propylpiperazin-1-yl)methyl]-1H-indole, bis(trifluoroacetate) |
| 12 | 1-[(4-Methylphenyl)sulfonyl]-4-(pyrrolidin-1-ylmethyl)-1H-indole, trifluoroacetate |
| 13 | 1-[(2-Methoxy-5-methylphenyl)sulfonyl]-4-(piperazin-1-ylmethyl)-1H-indole bis(trifluoroacetate) |
| 14 | 1-[(2-Methoxy-5-methylphenyl)sulfonyl]-4-[(3-methylpiperazin-1-yl)methyl]-1H-indole, bis(trifluoroacetate) |
| 15 | N-({1-[(2-Methoxy-5-methylphenyl)sulfonyl]-1H-indol-4-yl}methyl)piperidin-4-amine, bis(trifluoroacetate) |

TABLE 1-continued

| Example | Chemical Name | Structure |
|---|---|---|
| 16 | 1-Isopropyl-N-({1-[(2-methoxy-5-methylphenyl)sulfonyl]-1H-indol-4-yl}methyl)piperidin-4-amine, bis(trifluoroacetate) | 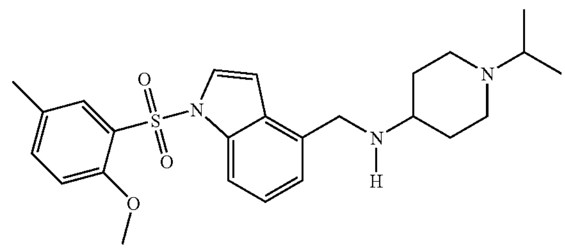 |
| 17 | 1-[(2-Methoxy-5-methylphenyl)sulfonyl]-4-[(2-methylpyrrolidin-1-yl)methyl]-1H-indole, trifluoroacetate | 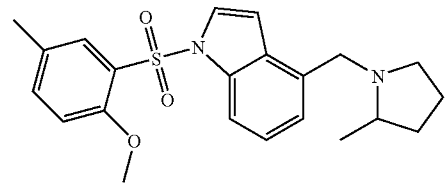 |
| 18 | 1-[(2-Methoxy-5-methylphenyl)sulfonyl]-4-[(3-methylpiperazin-1-yl)methyl]indoline, bis(trifluoroacetate) | 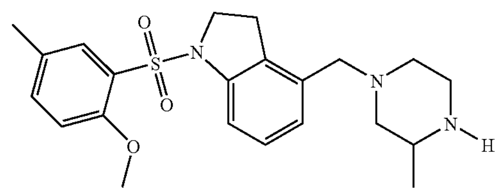 |
| 19 | 1-[(2-Methoxy-5-methylphenyl)sulfonyl]-4-[(4-methylpiperazin-1-yl)methyl]indoline, bis(trifluoroacetate) | 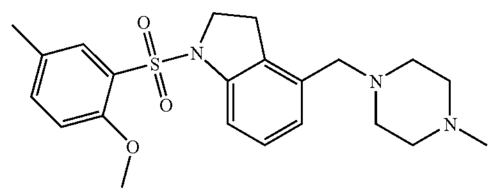 |
| 20 | 1-[(2-Methoxy-5-methylphenyl)sulfonyl]-4-(pyrrolidin-1-ylmethyl)indoline, trifluoroacetate | 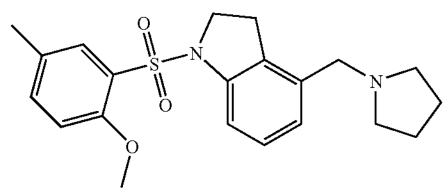 |
| 21 | ({1-[(2-Methoxy-5-methylphenyl)sulfonyl]-2,3-dihydro-1H-indol-4-yl}methyl)dimethylamine, trifluoroacetate | 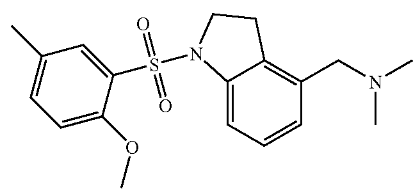 |
| 22 | 1-[(4-Fluorophenyl)sulfonyl]-4-[(3-methylpiperazin-1-yl)methyl]-1H-indole, bis(trifluoroacetate) | 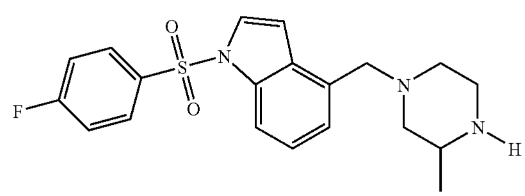 |

TABLE 1-continued

| Example | Chemical Name | Structure |
|---|---|---|
| 23 | 4-(1,4-Diazepan-1-ylmethyl)-1-[(4-fluorophenyl)sulfonyl]-1H-indole, bis(trifluoroacetate) | 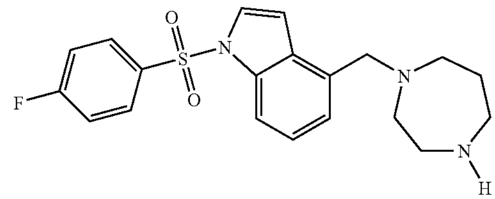 |
| 24 | ({1-[(4-Fluorophenyl)sulfonyl]-4-(pyrrolidin-1-ylmethyl)-1H-indole trifluoroacetate | 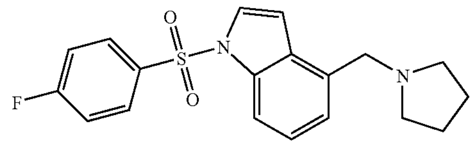 |
| 25 | ({1-[(4-Fluorophenyl)sulfonyl]-1H-indol-4-yl}methyl)dimethylamine, trifluoroacetate | 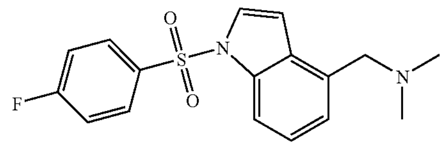 |
| 26 | 1-[(4-Fluorophenyl)sulfonyl]-4-(piperazin-1-ylmethyl)-1H-indole, bis(trifluoroacetate) | 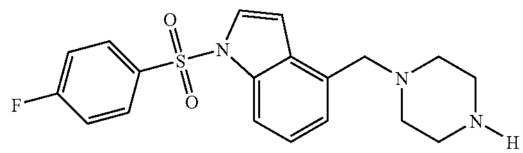 |
| 27 | 1-[(2-Methylphenyl)sulfonyl]-4-(piperazin-1-ylmethyl)-1H-indole bis(trifluoroacetate) | 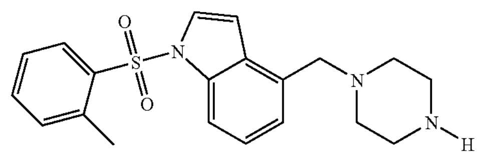 |
| 28 | 1-[(2-Methylphenyl)sulfonyl]-4-[(4-methylpiperazin-1-yl)methyl]-1H-indole, bis(trifluoroacetate) | 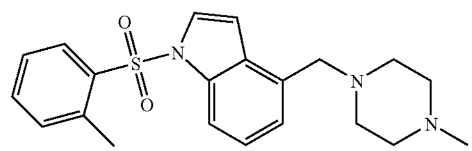 |
| 29 | 1-({1-[(2-Methylphenyl)sulfonyl]-1H-indol-4-yl}methyl)pyrrolidin-3-ol, trifluoroacetate | 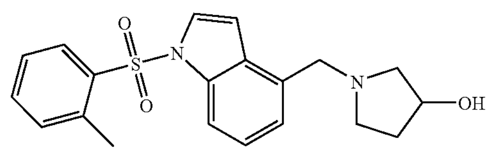 |
| 30 | 1-[(2-Methylphenyl)sulfonyl]-4-(pyrrolidin-1-ylmethyl)-1H-indole, trifluoroacetate | 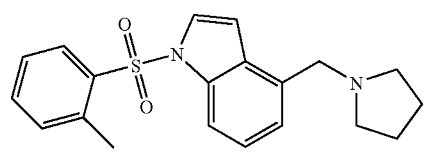 |
| 31 | 2-[Methyl({1-[(2-methylphenyl)sulfonyl]-1H-indol-4-yl}methyl)amino]ethanol, trifluoroacetate | 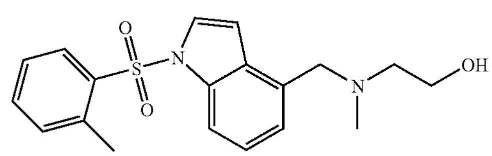 |

TABLE 1-continued

| Example | Chemical Name |
|---|---|
| 32 | N,N-Dimethyl-1-{1-[(2-methylphenyl)sulfonyl]-1H-indol-4-yl)methanamine, trifluoroacetate |
| 33 | 4-(Piperazin-1-ylmethyl)-1-{[3-(trifluoromethyl)phenyl]sulfonyl}-1H-indole, bis(trifluoroacetate) |
| 34 | {(2R)-1-[(1-{[3-(Trifluoromethyl)phenyl]sulfonyl}-1H-indol-4-yl)methyl]pyrrolidin-2-yl}methanol, trifluoroacetate |
| 35 | 4-(Pyrrolidin-1-ylmethyl)-1-{[3-(trifluoromethyl)phenyl]sulfonyl}-1H-indole, trifluoroacetate |
| 36 | 2-{Methyl[(1-{[3-(trifluoromethyl)phenyl]sulfonyl}-1H-indol-4-yl)methyl]amino}ethanol, trifluoroacetate |
| 37 | N,N-Dimethyl-1-(1-{[3-(trifluoromethyl)phenyl]sulfonyl}-1H-indol-4-yl)methanamine, trifluoroacetate |
| 38 | 4-(Piperazin-1-ylmethyl)-1-(2-thienylsulfonyl)-1H-indole, bis(trifluoroacetate) |
| 39 | N-Ethyl-N-{[1-(2-thienylsulfonyl)-1H-indol-4-yl]methyl}ethanamine, trifluoroacetate |
| 40 | 4-(Pyrrolidin-1-ylmethyl)-1-(2-thienylsulfonyl)-1H-indole, trifluoroacetate |

TABLE 1-continued

| Example | Chemical Name | Structure |
|---|---|---|
| 41 | 4-[(4-Propylpiperazin-1-yl)methyl]-1-(2-thienylsulfonyl)-1H-indole, bis(trifluoroacetate) | 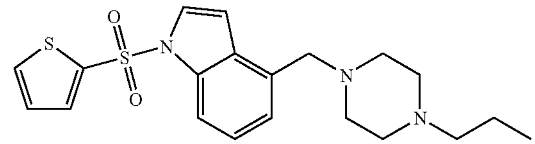 |
| 42 | N,N-Dimethyl-1-[1-(2-thienylsulfonyl)-1H-indol-4-yl]methanamine, trifluoroacetate | 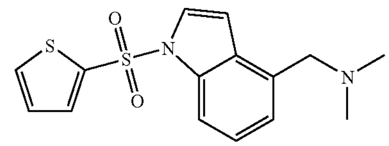 |
| 43 | 4-(Piperazin-1-ylmethyl)-1-(pyridin-3-ylsulfonyl)-1H-indole, tris(trifluoroacetate) | 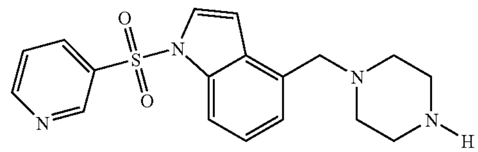 |
| 44 | N,N-Dimethyl-1-[1-(pyridin-3-ylsulfonyl)-1H-indol-4-yl]methanamine, bis(trifluoroacetate) | 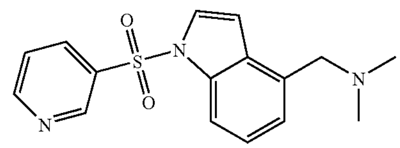 |
| 45 | 1-(Pyridin-3-ylsulfonyl)-4-(pyrrolidin-1-ylmethyl)-1H-indole, bis(trifluoroacetate) | 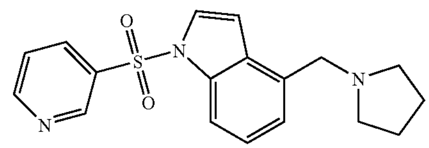 |
| 46 | 1-(Phenylsulfonyl)-4-(pyrrolidm-1-ylmethyl)-1H-indole, trifluoroacetate | 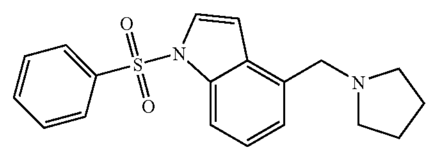 |
| 47 | N,N-Dimethyl-1-[1-(phenylsulfonyl)-1H-indol-4-yl]methanamine, trifluoroacetate | 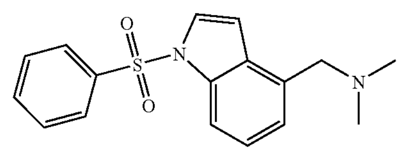 |
| 48 | Comparative example: 4-{[(1-methylpyrrolidin-3-yl)oxy]methyl}-1-(phenylsulfonyl)-1H-indole, trifluoroacetate | 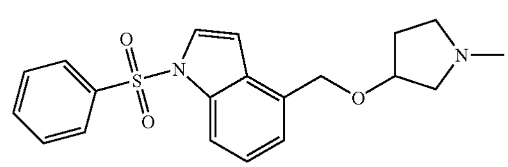 |
| 49 | 3-Methyl-1-(phenylsulfonyl)-4-(piperazin-1-ylmethyl)-1H-indole, bis(trifluoroacetate) | 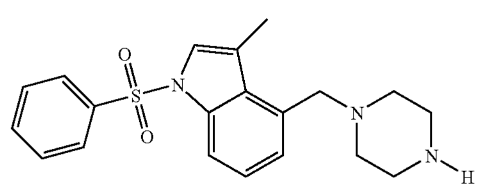 |

TABLE 1-continued

| Example | Chemical Name |
|---|---|
| 50 | 3-Methyl-4-[(4-methylpiperazin-1-yl)methyl]-1-(phenylsulfonyl)-1H-indole, bis(trifluoroacetate) |
| 51 | 3-Methyl-1-(phenylsulfonyl)-4-(pyrrolidin-1-ylmethyl)-1H-indole, trifluoroacetate |
| 52 | N,N-Dimethyl-1-[3-methyl-1-(phenylsulfonyl)-1H-indol-4-yl]methanamine, trifluoroacetate |
| 53 | 6-Methoxy-1-(phenylsulfonyl)-4-(piperazin-1-ylmethyl)-1H-indole, bis(trifluoroacetate) |
| 54 | {[6-Methoxy-1-(phenylsulfonyl)-1H-indol-4-yl]methyl}dimethylamine, trifluoroacetate |
| 55 | 6-Methoxy-4-{[(3S)-3-methylpiperazin-1-yl]methyl}-1-(phenylsulfonyl)-1H-indole, bis(trifluoroacetate) |
| 56 | 6-Methoxy-4-{[(3S)-3-methylpiperazin-1-yl]methyl}-1-(phenylsulfonyl)-1H-indole, bis(trifluoroacetate) |

TABLE 1-continued

| Example | Chemical Name |
|---|---|
| 57 | 6-Methoxy-4-[(4-methylpiperazin-1-yl)methyl]-1-(phenylsulfonyl)-1H-indole, bis(trifluoroacetate) |
| 58 | 4-(1,4-Diazepan-1-ylmethyl)-6-methoxy-1-(phenylsulfonyl)-1H-indole, bis(trifluoroacetate) |
| 59 | 6-Methoxy-1-(phenylsulfonyl)-4-(pyrrolidin-1-ylmethyl)-1H-indole, trifluoroacetate |
| 60 | 2-[{[6-Methoxy-1-(phenylsulfonyl)-1H-indol-4-yl]methyl}(methyl)amino]ethanol, trifluoroacetate |
| 61 | 6-Fluoro-1-(phenylsulfonyl)-4-(piperazin-1-ylmethyl)-1H-indole, bis(trifluoroacetate) |
| 62 | 4-(1,4-Diazepan-1-ylmethyl)-6-fluoro-1-(phenylsulfonyl)-1H-indole, bis(trifluoroacetate) |
| 63 | 6-Fluoro-4-{[(3S)-3-methylpiperazin-1-yl]methyl}-1-(phenylsulfonyl)-1H-indole, bis(trifluoroacetate) |

TABLE 1-continued

| Example | Chemical Name | Structure |
|---|---|---|
| 64 | 6-Fluoro-4-{[(3R)-3-methylpiperazin-1-yl]methyl}-1-(phenylsulfonyl)-1H-indole, bis(trifluoroacetate) | 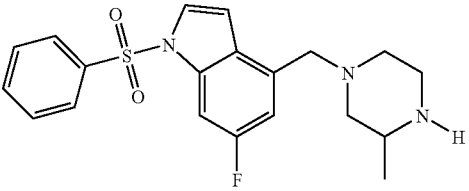 |
| 65 | 6-Fluoro-1-(phenylsulfonyl)-4-(pyrrolidin-1-ylmethyl)-1H-indole, trifluoroacetate | 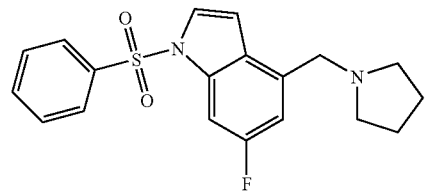 |
| 66 | 2-[{[6-Fluoro-1-(phenylsulfonyl)-1H-indol-4-yl]methyl}(methyl)amino]ethanol, trifluoroacetate | 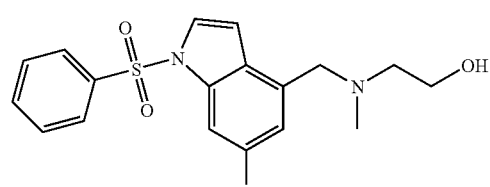 |
| 67 | {[6-Fluoro-1-(phenylsulfonyl)-1H-indol-4-yl]methyl}dimethylamine, trifluoroacetate | 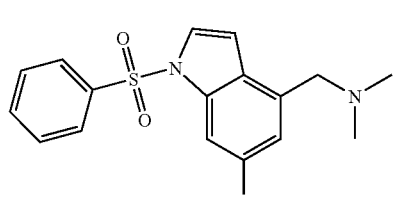 |
| 68 | 6-Fluoro-4-[(4-methylpiperazin-1-yl)methyl]-1-(phenylsulfonyl)-1H-indole, bis(trifluoroacetate) | 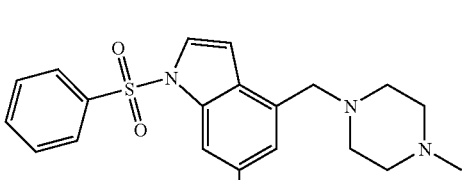 |
| 69 | 1-(Phenylsulfonyl)-4-(pyrrolidin-1-ylmethyl)-1H-indol-6-yl dimethylcarbamate, trifluoroacetate | 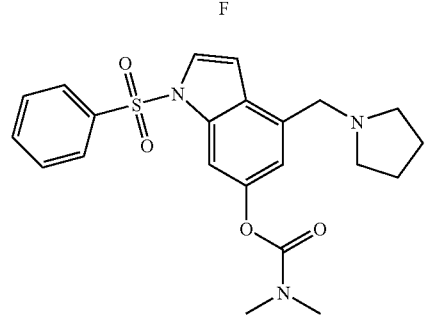 |
| 70 | 4-(1,4-Diazepan-1-ylmethyl)-1-(phenylsulfonyl)-1H-indol-6-ol | 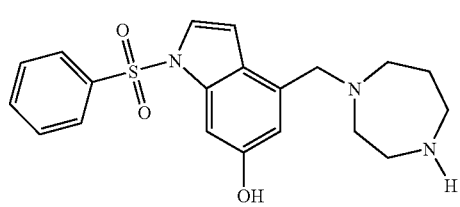 |

TABLE 1-continued

| Example | Chemical Name | Structure |
|---|---|---|
| 71 | 1-[(4-Fluorophenyl)sulfonyl]-6-methoxy-4-(piperazin-1-ylmethyl)-1H-indole, acetate | 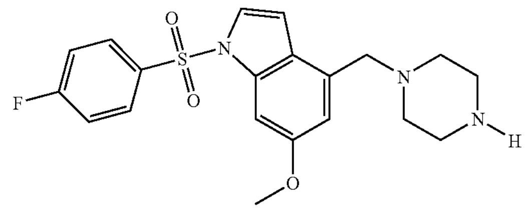 |
| 72 | 6-Methoxy-4-(piperazin-1-ylmethyl)-1-{[3-(trifluoromethyl)phenyl]sulfonyl}-1H-indole, bis(trifluoroacetate) | 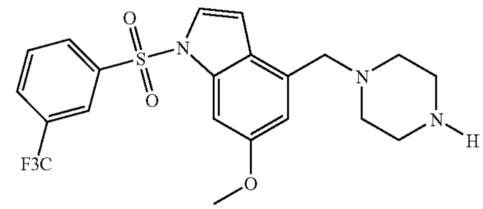 |
| 73 | 1-[(2-Chlorophenyl)sulfonyl]-6-methoxy-4-(piperazin-1-ylmethyl)-1H-indole, bis(trifluoroacetate) | 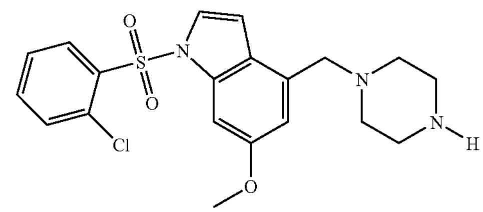 |
| 74 | 1-[(3-Chloro-2-methylphenyl)sulfonyl]-6-methoxy-4-(piperazin-1-ylmethyl)-1H-indole, bis(trifluoroacetate) | 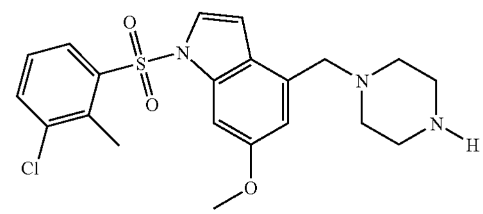 |
| 75 | 1-[(2,5-Dimethoxyphenyl)sulfonyl]-6-methoxy-4-(piperazin-1-ylmethyl)-1H-indole, bis(trifluoroacetate) | 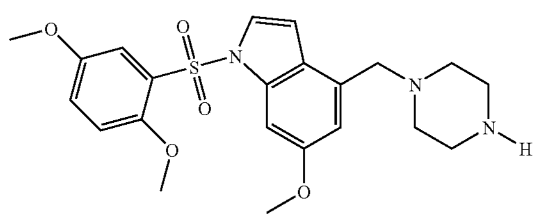 |
| 76 | 2-{[6-Methoxy-4-(piperazin-1-ylmethyl)-1H-indol-1-yl]sulfonyl}benzonitrile, bis(trifluoroacetate) | 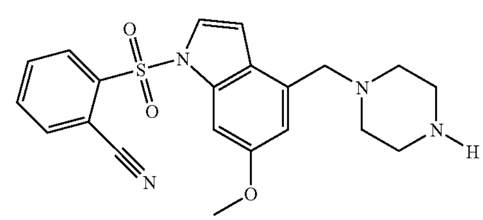 |
| 77 | ({1-[(4-Fluorophenyl)sulfonyl]-1H-indol-4-yl}methyl)amine, trifluoroacetate | 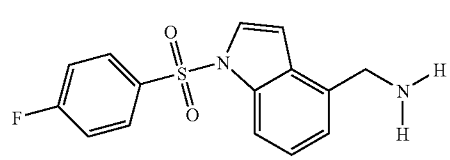 |

TABLE 1-continued

| Example | Chemical Name | Structure |
|---|---|---|
| 78 | N-({1-[(4-Fluorophenyl)sulfonyl]-1H-indol-4-yl}methyl)ethanamine, trifluoroacetate | 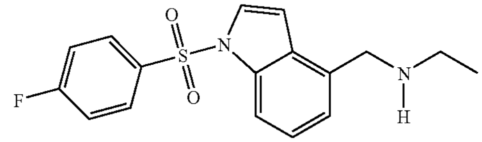 |
| 79 | 7-Methoxy-1-(phenylsulfonyl)-4-(piperazin-1-ylmethyl)-1H-indole bis(trifluoroacetate) | 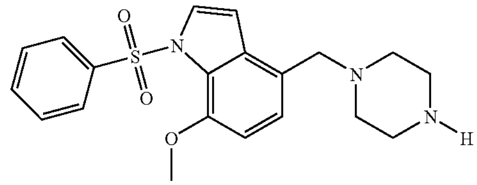 |
| 80 | 2-Methyl-1-(phenylsulfonyl)-4-(piperazin-1-ylmethyl)-1H-indole hydrochloride | 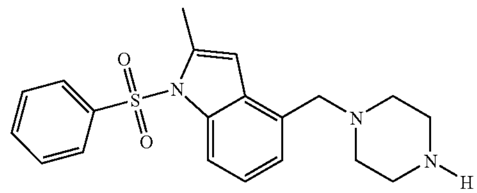 |
| 81 | Methyl 4-{[1-(phenylsulfonyl)-1H-indol-4-yl]methyl}piperazine-2-carboxylate bis(trifluoroacetate) | 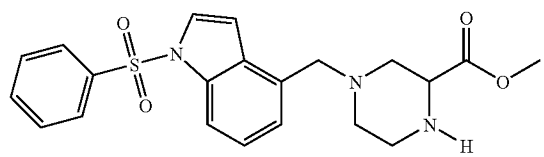 |
| 82 | (4-{[1-(Phenylsulfonyl)-1H-indol-4-yl]methyl}piperazin-2-yl)methanol bis(trifluoroacetate) | 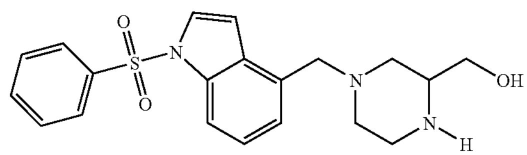 |
| 83 | (2-Methoxyethyl){[1-(phenylsulfonyl)-1H-indol-4-yl]methyl} amine trifluoroacetate | 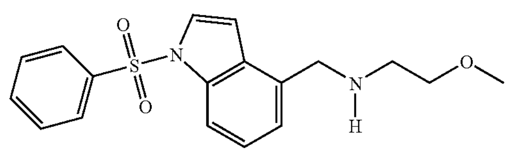 |
| 84 | N-{[1-(Phenylsulfonyl)-1H-indol-4-yl]methyl}propan-2-amine trifluoroacetate | 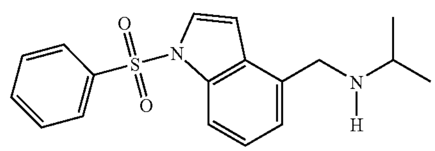 |
| 85 | 4-{[4-(2-Methoxyethyl)piperazin-1-yl]methyl}-1-(phenylsulfonyl)-1H-indole bis(trifluoroacetate) | 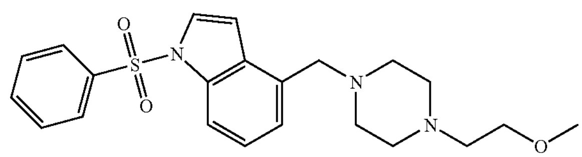 |
| 86 | ((2R)-1-{[1-(Phenylsulfonyl)-1H-indol-4-yl]methyl}pyrrolidin-2-yl)methanol trifluoroacetate | 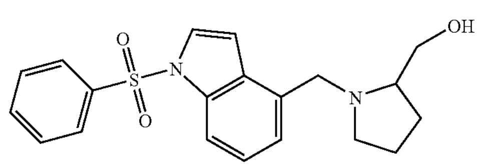 |

TABLE 1-continued

| Example | Chemical Name |
|---|---|
| 87 | 4-(Azetidin-1-ylmethyl)-1-(phenylsulfonyl)-1H-indole trifluoroacetate |
| 88 | Ethyl 5-methoxy-1-(phenylsulfonyl)-4-(piperazin-1-ylmethyl)-1H-indole-2-carboxylate |
| 89 | 5-Methoxy-N-methyl-1-(phenylsulfonyl)-4-(piperazin-1-ylmethyl)-1H-indole-2-carboxamide trifluoroacetate |
| 90 | N-Ethyl-5-methoxy-1-(phenylsulfonyl)-4-(piperazin-1-ylmethyl)-1H-indole-2-carboxamide trifluoroacetate |
| 91 | 5-Ethoxy-1-(phenylsulfonyl)-4-(piperazin-1-ylmethyl)-N-(2-thienylmethyl)-1H-indole-2-carboxamide trifluoroacetate |
| 92 | 4-(Azetidin-1-ylmethyl)-6-methoxy-1-(phenylsulfonyl)-1H-indole trifluoroacetate |

TABLE 1-continued

| Example | Chemical Name | Structure |
| --- | --- | --- |
| 93 | 1-(Phenylsulfonyl)-4-(piperazin-1-ylmethyl)-1H-indol-5-ol trifluoroacetate | 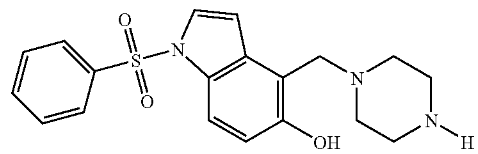 |
| 94 | 1-(Phenylsulfonyl)-4-piperazin-2-yl-1H-indole bis(trifluoroacetate) | 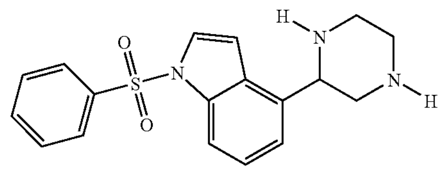 |
| 95 | 4-(1,4-Dimethylpiperazin-2-yl)-1-(phenylsulfonyl)-1H-indole bis(trifluoroacetate) | 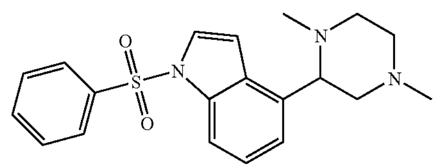 |
| 96 | [7-Methoxy-1-(phenylsulfonyl)-1H-indol-4-yl](piperazin-1-yl)acetonitrile trifluoroacetate | 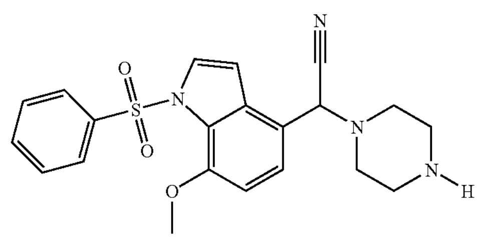 |
| 97 | 4-(Azetidin-1-ylmethyl)-7-methoxy-1-(phenylsulfonyl)-1H-indole trifluoroacetate | 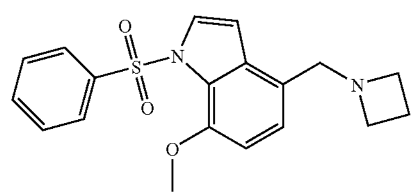 |
| 98 | {[1-(Phenylsulfonyl)-4-(piperazin-1-ylmethyl)-1H-indol-5-yl]oxy}acetonitrile | 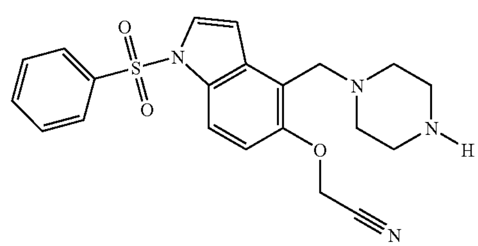 |
| 99 | 5-Isopropoxy-1-(phenylsulfonyl)-4-(piperazin-1-ylmethyl)-1H-indole | 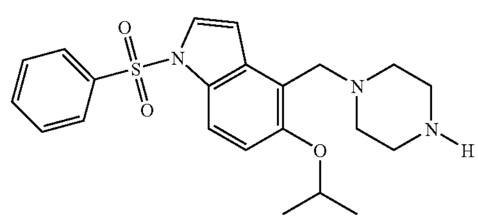 |

TABLE 1-continued

| Example | Chemical Name | Structure |
|---|---|---|
| 100 | 5-(Benzyloxy)-1-(phenylsulfonyl)-4-(piperazin-1-ylmethyl)-1H-indole | 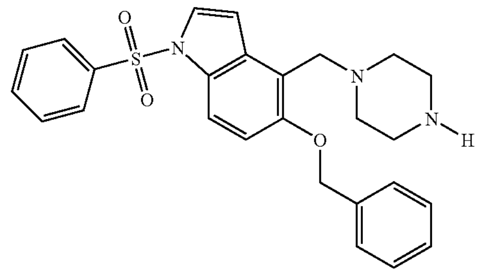 |
| 101 | 4-{[(2-Hydroxyethyl)(methyl)amino]methyl}-1-(phenylsulfonyl)-1H-indol-5-ol | 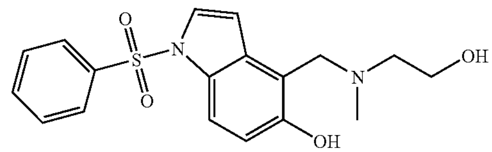 |
| 102 | 4-[(3-Hydroxypyrrolidin-1-yl)methyl]-1-(phenylsulfonyl)-1H-indol-5-ol | 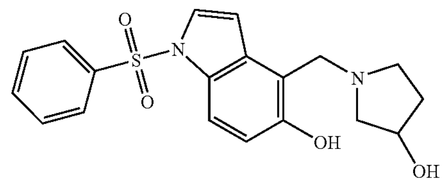 |
| 103 | [1-(Phenylsulfonyl)-4-(piperazin-1-ylmethyl)-6-(trifluoromethyl)-1H-indol-2-yl]methanol bis(trifluoroacetate) | 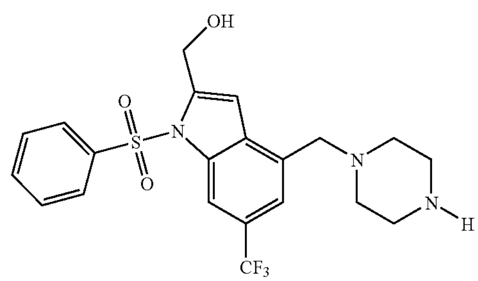 |
| 104 | 5-Methoxy-1-(phenylsulfonyl)-4-(piperazin-1-ylmethyl)-1H-indole bis(trifluoroacetate) | 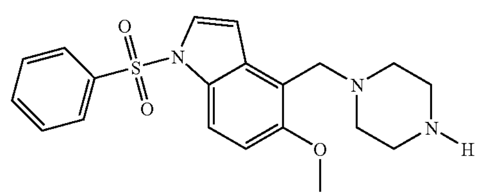 |
| 105 | 5-Ethoxy-1-(phenylsulfonyl)-4-(piperazin-1-ylmethyl)-1H-indole trifluoroacetate | 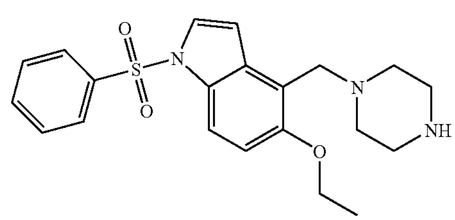 |
| 106 | 1-Phenyl-N-{[1-(phenylsulfonyl)-1H-indol-4-yl]methyl}methanamine trifluoroacetate | 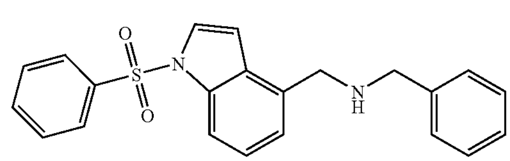 |

TABLE 1-continued

| Example | Chemical Name |
|---|---|
| 107 | N-{[5-Methoxy-1-(phenylsulfonyl)-1H-indol-4-yl]methyl}cyclopropanamine trifluoroacetate |
| 108 | {[5-Methoxy-1-(phenylsulfonyl)-1H-indol-4-yl]methyl}dimethylamine hydrochloride |
| 109 | N-{[5-Methoxy-1-(phenylsulfonyl)-1H-indol-4-yl]methyl}cyclobutanamine trifluoroacetate |
| 110 | N-{[5-Methoxy-1-(phenylsulfonyl)-1H-indol-4-yl]methyl}-N-methylcyclobutanamine trifluoroacetate |
| 111 | 1-{[1-(Phenylsulfonyl)-1H-indol-4-yl]methyl}azetidin-3-ol trifluoroacetate |
| 112 | 4-(Azetidin-1-ylmethyl)-5-methoxy-1-(phenylsulfonyl)-1H-indole trifluoroacetate |
| 113 | 4-{[4-(Azetidin-1-ylmethyl)-1H-indol-1-yl]sulfonyl}benzonitrile trifluoroacetate |
| 114 | 2-((2S)-1-{[1-(Phenylsulfonyl)-1H-indol-4-yl]methyl}azetidin-2-yl)propan-2-ol trifluoroacetate |

TABLE 1-continued

| Example | Chemical Name |
|---|---|
| 115 | 4-(Azetidin-1-ylmethyl)-2-methyl-1-(phenylsulfonyl)-1H-indole trifluoroacetate |
| 116 | 4-(Azetidin-1-ylmethyl)-1-[(2-chlorophenyl)sulfonyl]-1H-indole trifluoroacetate |
| 117 | 4-(Azetidin-1-ylmethyl)-1-[(5-chloro-2-thienyl)sulfonyl]-1H-indole trifluoroacetate |
| 118 | 4-(Azetidin-1-ylmethyl)-1-(2-naphthylsulfonyl)-1H-indole trifluoroacetate |
| 119 | 4-(Azetidin-1-ylmethyl)-1-[(2-methoxy-5-methylphenyl)sulfonyl]-1H-indole trifluoroacetate |
| 120 | 4-(Azetidin-1-ylmethyl)-1-[(6-chloroimidazo[2,1-b][1,3]thiazol-5-yl)sulfonyl]-1H-indole trifluoroacetate |
| 121 | 4-(Azetidin-1-ylmethyl)-1-[(4-tert-butylphenyl)sulfonyl]-1H-indole trifluoroacetate |
| 122 | 4-(Azetidin-1-ylmethyl)-1-[(2,6-difluorophenyl)sulfonyl]-1H-indole trifluoroacetate |

TABLE 1-continued

| Example | Chemical Name |
|---------|---------------|
| 123 | 4-(Azetidin-1-ylmethyl)-1-{[2-(trifluoromethyl)phenyl]sulfonyl}-1H-indole trifluoroacetate |
| 124 | 3-{[4-(Azetidin-1-ylmethyl)-1H-indol-1-yl]sulfonyl}benzonitrile trifluoroacetate |
| 125 | 4-(Azetidin-1-ylmethyl)-1-{[4-bromo-2-(trifluoromethyl)phenyl]sulfonyl}-1H-indole trifluoroacetate |
| 126 | 4-(Azetidin-1-ylmethyl)-1-(2-thienylsulfonyl)-1H-indole trifluoroacetate |
| 127 | 4-(Azetidin-1-ylmethyl)-1-[(2,5-difluorophenyl)sulfonyl]-1H-indole trifluoroacetate |
| 128 | [(5-Methoxy-1-{[3-(trifluoromethyl)phenyl]sulfonyl}-1H-indol-4-yl)methyl]dimethylamine trifluoroacetate |
| 129 | 4-(Azetidin-1-ylmethyl)-7-(benzyloxy)-1-(methylsulfonyl)-1H-indole trifluoroacetate |

TABLE 1-continued

| Example | Chemical Name | Structure |
|---|---|---|
| 130 | ({1-[(6-Chloroimidazo[2,1-b][1,3]thiazol-5-yl)sulfonyl]-5-methoxy-1H-indol-4-yl}methyl)dimethylamine trifluoroacetate | 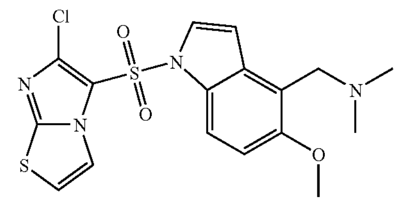 |
| 131 | 4-[(Dimethylamino)methyl]-1-(phenylsulfonyl)-1H-indol-5-ol trifluoroacetate | 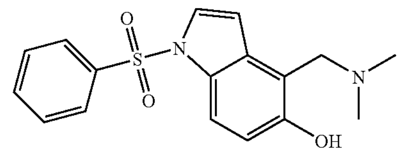 |
| 132 | {[5-Ethoxy-1-(phenylsulfonyl)-1H-indol-4-yl]methyl}dimethylamine trifluoroacetate | 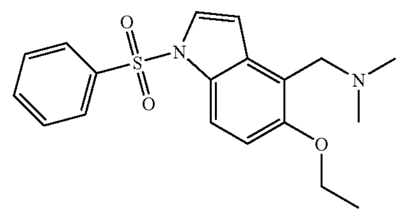 |
| 133 | ({5-Ethoxy-1-[(2-methoxy-5-methylphenyl)sulfonyl]-1H-indol-4-yl}methyl)dimethylamine trifluoroacetate | 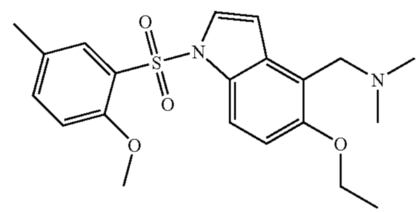 |
| 134 | {[5-Ethoxy-1-(1-naphthylsulfonyl)-1H-indol-4-yl]methyl}dimethylamine trifluoroacetate | 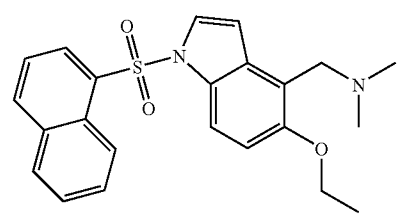 |
| 135 | {[5-Ethoxy-1-(2-naphthylsulfonyl)-1H-indol-4-yl]methyl}dimethylamine trifluoroacetate | 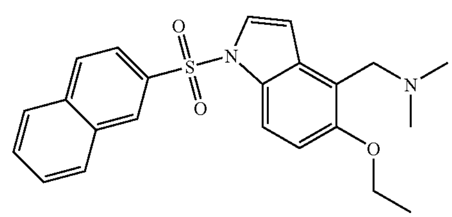 |
| 136 | ({1-[(2-Chlorophenyl)sulfonyl]-5-ethoxy-1H-indol-4-yl}methyl)dimethylamine trifluoroacetate | 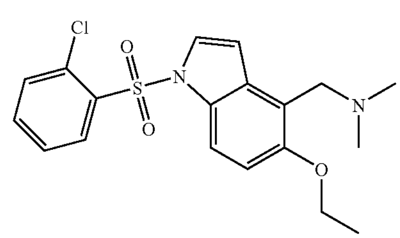 |

TABLE 1-continued

| Example | Chemical Name |
|---|---|
| 137 | ({1-[(3-Chloro-2-methylphenyl)sulfonyl]-5-ethoxy-1H-indol-4-yl}methyl)dimethylamine trifluoroacetate |
| 138 | ({5-Methoxy-1-[(2-methoxy-5-methylphenyl)sulfonyl]-1H-indol-4-yl}methyl)dimethylamine trifluoroacetate |
| 139 | ({1-[(2,3-Dichlorophenyl)sulfonyl]-5-methoxy-1H-indol-4-yl}methyl)dimethylamine trifluoroacetate |
| 140 | {[5-Ethoxy-1-(quinolin-8-ylsulfonyl)-1H-indol-4-yl]methyl}dimethylamine bis(trifluoroacetate) |
| 141 | {[5-Ethoxy-1-({5-[1-methyl-3-(trifluoromethyl)-1H-pyrazol-5-yl]-2-thienyl}sulfonyl)-1H-indol-4-yl]methyl}dimethylamine trifluoroacetate |
| 142 | ({1-[(2,5-Dichlorophenyl)sulfonyl]-5-ethoxy-1H-indol-4-yl}methyl)dimethylamine trifluoroacetate |

TABLE 1-continued

| Example | Chemical Name | Structure |
|---------|---------------|-----------|
| 143 | ({5-Ethoxy-1-[(2,4,6-trichlorophenyl)sulfonyl]-1H-indol-4-yl}methyl)dimethylamine trifluoroacetate | 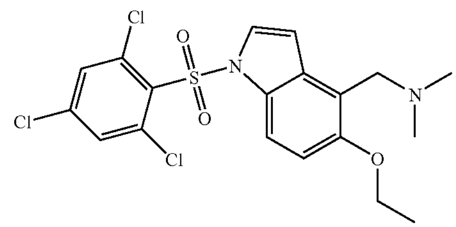 |
| 144 | 1-[5-Methoxy-1-(phenylsulfonyl)-1H-indol-4-yl]-N-methylmethanamine trifluoroacetate | 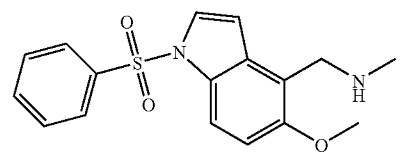 |
| 145 | ({1-[(2-Methoxy-5-methylphenyl)sulfonyl]-1H-indol-4-yl}methyl)methylamine trifluoroacetate | 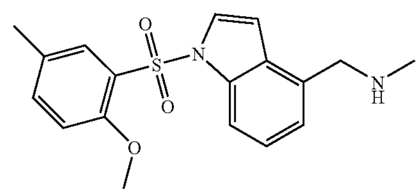 |
| 146 | 4-[(Dimethylamino)methyl]-6-fluoro-1-(phenylsulfonyl)-1H-indol-5-ol trifluoroacetate | 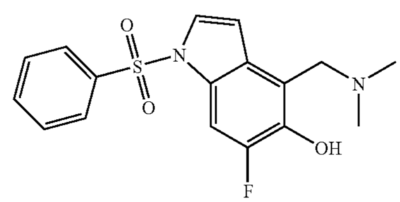 |
| 147 | 1-[6-Fluoro-5-methoxy-1-(phenylsulfonyl)-1H-indol-4-yl]-N,N-dimethylmethanamine | 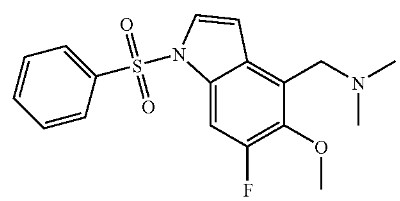 |
| 148 | 6-Fluoro-1-(phenylsulfonyl)-4-(pyrrolidin-1-ylmethyl)-1H-indol-5-ol | 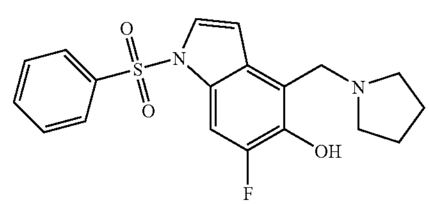 |
| 149 | 6-Fluoro-5-methoxy-1-(phenylsulfonyl)-4-(pyrrolidin-1-ylmethyl)-1H-indole trifluoroacetate | 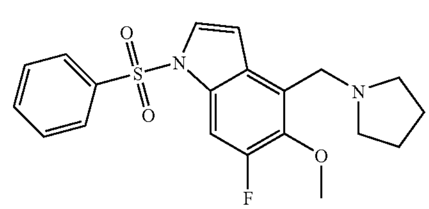 |

TABLE 1-continued

| Example | Chemical Name | Structure |
|---|---|---|
| 150 | 4-(Azetidin-1-ylmethyl)-6-fluoro-1-(phenylsulfonyl)-1H-indol-5-ol trifluoroacetate | 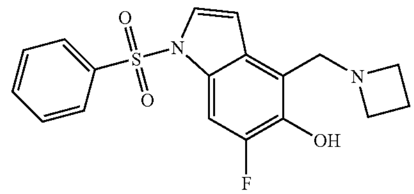 |
| 151 | 4-(Azetidin-1-ylmethyl)-6-fluoro-5-methoxy-1-(phenylsulfonyl)-1H-indole trifluoroacetate | 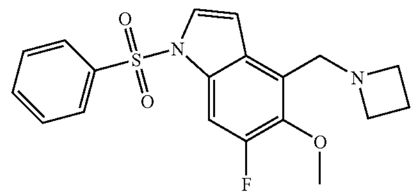 |
| 152 | 4-{[Ethyl(methyl)amino]methyl}-6-fluoro-1-(phenylsulfonyl)-1H-indol-5-ol | 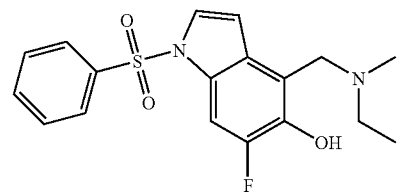 |
| 153 | N-{[6-Fluoro-5-methoxy-1-(phenylsulfonyl)-1H-indol-4-yl]methyl}-N-methylethanamine trifluoroacetate | 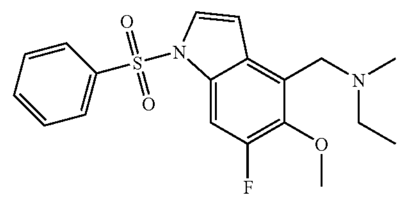 |
| 154 | 6-Fluoro-4-[(methylamino)methyl]-1-(phenylsulfonyl)-1H-indol-5-ol trifluoroacetate | 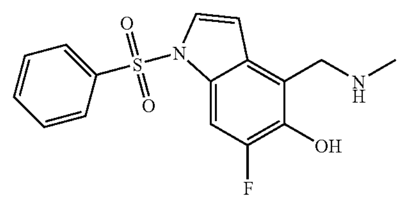 |
| 155 | {[6-Fluoro-5-methoxy-1-(phenylsulfonyl)-1H-indol-4-yl]methyl}methylamine trifluoroacetate | 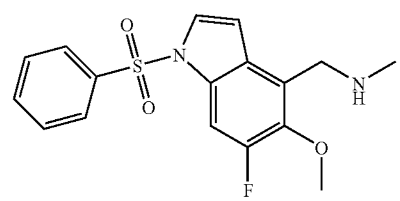 |
| 156 | 1-{5-Methoxy-1-[(4-methoxyphenyl)sulfonyl]-1H-indol-4-yl}-N,N-dimethylmethanamine | 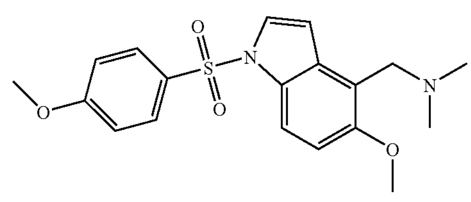 |

TABLE 1-continued

| Example | Chemical Name |
|---|---|
| 157 | 1-{1-[(3-Chlorophenyl)sulfonyl]-5-methoxy-1H-indol-4-yl}-N,N-dimethylmethanamine |
| 158 | 1-{1-[(2,5-Difluorophenyl)sulfonyl]-5-methoxy-1H-indol-4-yl}-N,N-dimethylmethanamine |
| 159 | 1-(1-{[4-Fluoro-3-(trifluoromethyl)phenyl]sulfonyl}-5-methoxy-1H-indol-4-yl)-N,N-dimethylmethanamine |
| 160 | 1-[5-Methoxy-1-(quinolin-8-ylsulfonyl)-1H-indol-4-yl]-N,N-dimethylmethanamine |
| 161 | 1-{1-[(2-Chlorophenyl)sulfonyl]-5-methoxy-1H-indol-4-yl}-N,N-dimethylmethanamine |
| 162 | 1-{1-[(2-Chloro-6-methylphenyl)sulfonyl]-5-methoxy-1H-indol-4-yl}-N,N-dimethylmethanamine |
| 163 | 1-{1-[(3-Chloro-4-fluorophenyl)sulfonyl]-5-methoxy-1H-indol-4-yl}-N,N-dimethylmethanamine |

TABLE 1-continued

| Example | Chemical Name |
|---|---|
| 164 | 1-{5-Methoxy-1-[(2-methylphenyl)sulfonyl]-1H-indol-4-yl}-N,N-dimethylmethanamine |
| 165 | 2-({4-[(Dimethylamino)methyl]-5-methoxy-1H-indol-1-yl}sulfonyl)benzonitrile |
| 166 | 1-{1-[(2,6-Difluorophenyl)sulfonyl]-5-methoxy-1H-indol-4-yl}-N,N-dimethylmethanamine |
| 167 | 1-{1-[(1,2-Dimethyl-1H-imidazol-4-yl)sulfonyl]-5-methoxy-1H-indol-4-yl}-N,N-dimethylmethanamine |
| 168 | 1-{5-Methoxy-1-[(5-methyl-1-benzothien-2-yl)sulfonyl]-1H-indol-4-yl}-N,N-dimethylmethanamine |
| 169 | 1-{5-Methoxy-1-[(2-methoxy-4-methylphenyl)sulfonyl]-1H-indol-4-yl}-N,N-dimethylmethanamine |
| 170 | 1-{1-[(2,4-Dichlorophenyl)sulfonyl]-5-methoxy-1H-indol-4-yl}-N,N-dimethylmethanamine |

TABLE 1-continued

| Example | Chemical Name |
|---|---|
| 171 | 1-{1-[(5-Bromo-2-methoxyphenyl)sulfonyl]-5-methoxy-1H-indol-4-yl}-N,N-dimethylmethanamine |
| 172 | 1-[1-(2,1,3-Benzothiadiazol-4-ylsulfonyl)-5-methoxy-1H-indol-4-yl]-N,N-dimethylmethanamine |
| 173 | 1-[1-(3,4-Dihydro-2H-1,5-benzodioxepin-7-ylsulfonyl)-5-methoxy-1H-indol-4-yl]-N,N-dimethylmethanamine |
| 174 | 1-{1-[(2,5-Dimethoxyphenyl)sulfonyl]-5-methoxy-1H-indol-4-yl}-N,N-dimethylmethanamine |
| 175 | 1-(5-Methoxy-1-{[2-(trifluoromethyl)phenyl]sulfonyl}-1H-indol-4-yl)-N,N-dimethylmethanamine |
| 176 | 1-(5-Methoxy-1-{[4-(trifluoromethoxy)phenyl]sulfonyl}-1H-indol-4-yl)-N,N-dimethylmethanamine |
| 177 | 3-({4-[(Dimethylamino)methyl]-5-methoxy-1H-indol-1-yl}sulfonyl)benzonitrile |

TABLE 1-continued

| Example | Chemical Name | Structure |
|---|---|---|
| 178 | 1-[5-Methoxy-1-(pyridin-3-ylsulfonyl)-1H-indol-4-yl]-N,N-dimethylmethanamine | 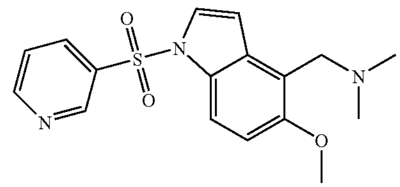 |
| 179 | Methyl{1-[1-(phenylsulfonyl)-1H-indol-4-yl]ethyl}amine | 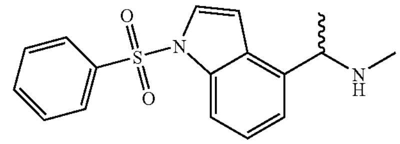 |
| 180 | {1-[1-(Phenylsulfonyl)-1H-indol-4-yl]ethyl}amine | 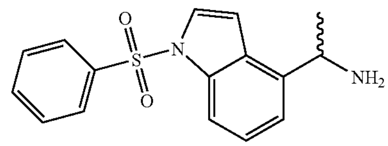 |
| 181 | Dimethyl{1-[1-(phenylsulfonyl)-1H-indol-4-yl]ethyl}amine | 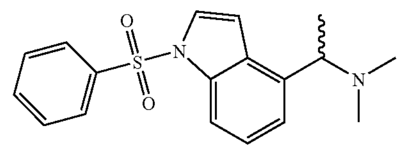 |
| 182 | 4-(Azetidin-1-ylmethyl)-2,3-dichloro-5-methoxy-1-(phenylsulfonyl)-1H-indole | 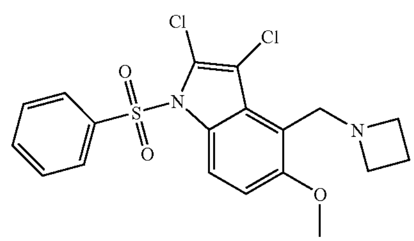 |
| 183 | {[1-(Phenylsulfonyl)-1H-indol-4-yl]methyl}amine | 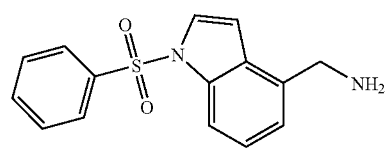 |
| 184 | 4-[(Dimethylamino)methyl]-6-methoxy-1-(phenylsulfonyl)-1H-indol-5-ol | 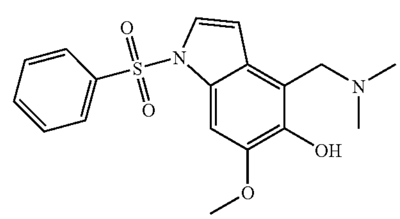 |
| 185 | 1-[5,6-Dimethoxy-1-(phenylsulfonyl)-1H-indol-4-yl]-N,N-dimethylmethanamine | 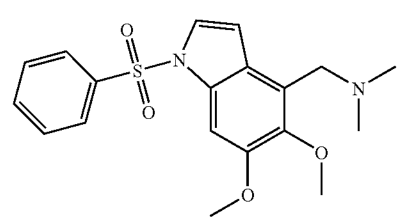 |

TABLE 1-continued

| Example | Chemical Name | Structure |
|---|---|---|
| 186 | {[3-Chloro-5-methoxy-1-(phenylsulfonyl)-1H-indol-4-yl]methyl}dimethylamine trifluoroacetate | 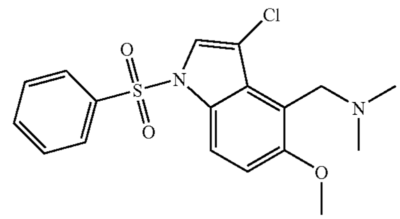 |
| 187 | {[3-Chloro-5-methoxy-1-(phenylsulfonyl)-1H-indol-4-yl]methyl}methylamine trifluoroacetate | 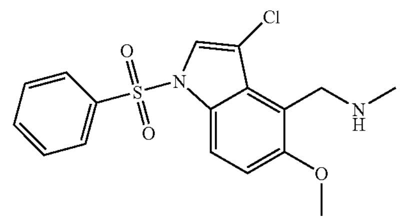 |
| 188 | {[5-Methoxy-1-(phenylsulfonyl)-1H-indol-4-yl]methyl}amine trifluoroacetate | 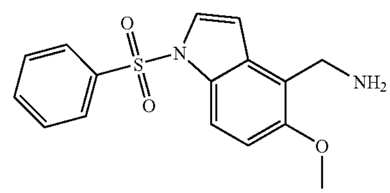 |
| 189 | 6-Fluoro-4-[1-(methylamino)ethyl]-1-(phenylsulfonyl)-1H-indol-5-ol trifluoroacetate | 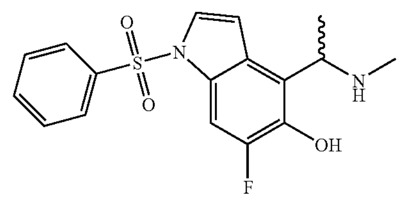 |
| 190 | 4-[1-(Dimethylamino)ethyl]-6-fluoro-1-(phenylsulfonyl)-1H-indol-5-ol | 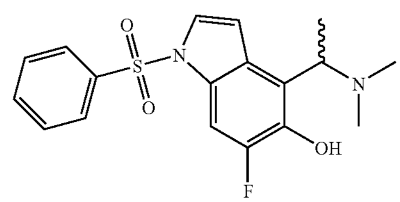 |
| 191 | {1-[6-Fluoro-5-methoxy-1-(phenylsulfonyl)-1H-indol-4-yl]ethyl}methylamine trifluoroacetate | 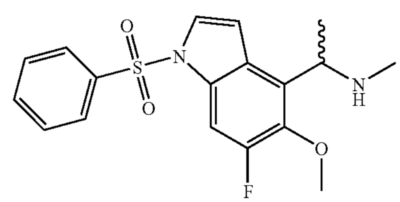 |
| 192 | {1-[6-Fluoro-5-methoxy-1-(phenylsulfonyl)-1H-indol-4-yl]ethyl}dimethylamine trifluoroacetate | 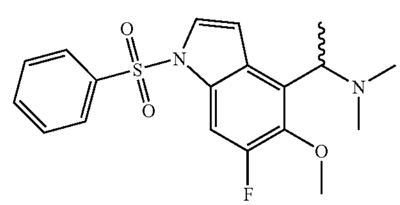 |

Intermediate 1

4-Methyl-1-(phenylsulfonyl)-1H-indole

The material was prepared according to the literature method (Chemical & Pharmaceutical Bulletin (1994), 42(10), 2150-3, Tetrahedron Letters (1993), 34(3), 489-92). MS (ESI+) for $C_{15}H_{13}NO_2S$ m/z 272 (M+H)$^+$.

Intermediate 2

4-(Bromomethyl)-1-(phenylsulfonyl)-1H-indole

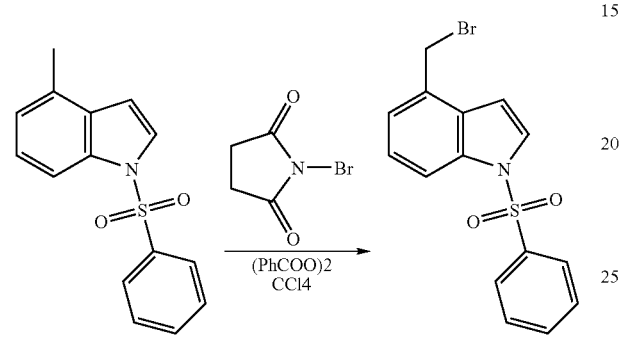

The compound was obtained using N-bromosuccinimide (1.2 eq), as bromination agent, and benzoyl peroxide (0.25 eq), as initiator, in $CCl_4$. The final product was purified by flash-chromatography (eluent-system chloroform-hexane 1:1) Yield 61.6%, 3.5 g). MS (ESI+) for $C_{15}H_{12}BrNO_2S$ m/z 351 (M+H)$^+$ (The title compound has been described previously in WO 9602502 A1 19960201)

EXAMPLE 1

1-(Phenylsulfonyl)-4-(piperazin-1-ylmethyl)-1H-indole hydrochloride 4-(Bromomethyl)-1-(phenylsulfonyl)-1H-indole Intermediate 2 (1.025 g), $NaHCO_3$ (1.5 eq) and N—BOC-piperazine (1.5 eq) were refluxed in ethanol for 40 min. The reaction was monitored by TLC (eluent-system $CHCl_3$-EtOH 20:1). The work up of the crude-extraction and further purification by column chromatography (eluent —$CHCl_3$)—yielded the final product as an oil. This material was treated with HCl 5M in i-PrOH to yield the salt of the final product (300 mg, 24%). The synthetic route followed for preparing Example 1 is depicted in the following scheme:

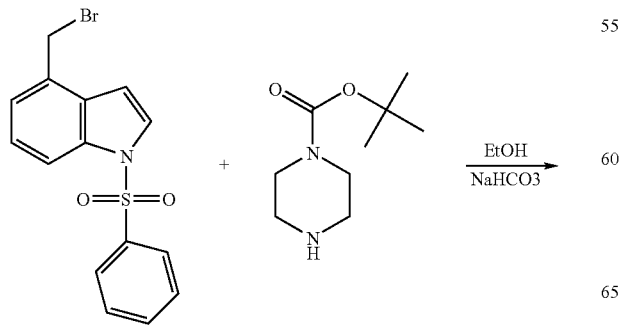

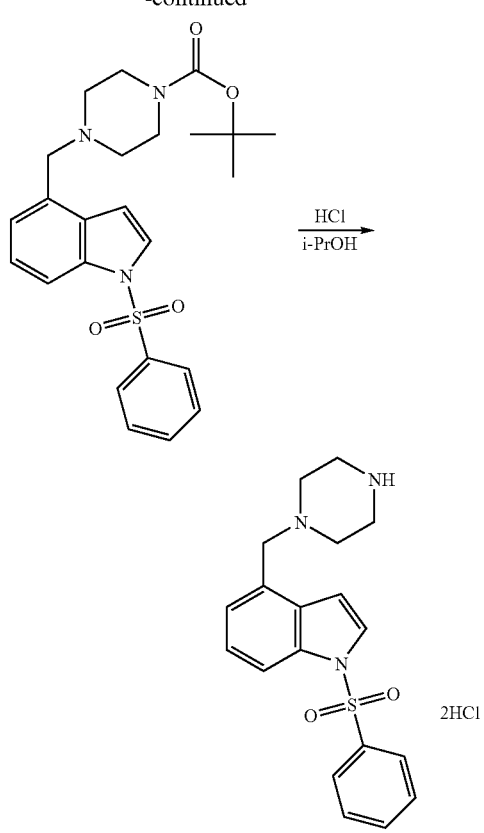

Yield (HCl-salt) 300 mg (24%); MS (ESI+) for $C_{19}H_{21}N_3O_2S$*HCl m/z 356 (M+H)$^+$.

EXAMPLE 2

4-(1,4-Diazepan-1-ylmethyl)-1-(phenylsulfonyl)-1H-indole hydrochloride 4-(Bromomethyl)-1-(phenylsulfonyl)-1H-indole Intermediate 2, $NaHCO_3$ and 1-BOC-homopiperazine were dissolved in ethanol and refluxed at 85° C. overnight. The solvent was evaporated and the residue was purified using preparative HPLC/MS, (System A), 20-50%, yielding 25.3 mg (19%) of the protected product. The protected product was dissolved in dry DCM and 2M HCl in diethylether was added. After 6 h of stirring was the solvent evaporated yielding 16.5 mg (83%) of the product as a HCl salt. $^1$H NMR (400 MHz, MeOD) δ ppm 2.18 (s, 2 H) 3.30-3.51 (m, 4 H) 3.64 (app. d, 4 H) 4.61 (s, 2 H) 7.07 (s, 1 H) 7.34-7.50 (m, 4 H) 7.51-7.58 (m, 1 H) 7.79 (d, J=3.51 Hz, 1 H) 7.90 (d, J=7.53 Hz, 2 H) 8.07 (d, J=8.28 Hz, 1 H).

EXAMPLE 3

1-{[1-(Phenylsulfonyl)-1H-indol-4-yl]methyl}pyrrolidin-3-amine

The experimental for Example 2 was followed using tert-butyl pyrrolidin-3-ylcarbamate.

Yield: 821 mg (84%). (ESI+) for $C_{19}H_{21}N_3O_2S$ m/z 356 (M+H)$^+$.

EXAMPLE 4

1-{[1-(Phenylsulfonyl)-1H-indol-4-yl]methyl}pyrrolidin-3-amine trifluoroacetate

The experimental for Example 2 was followed using tert-butyl 3-aminopyrrolidine-1-carboxylate. Yield: 163 mg (99%). (ESI+) for $C_{19}H_{21}N_3O_2S$ m/z 356 (M+H)$^+$.

Intermediate 3

4-Bromo-1-[(4-methylphenyl)sulfonyl]-1H-indole

4-Bromoindole (1.24 g, 6.3 mmol), p-toluenesulfonyl chloride (1.32 g, 6.9 mmol) and tetrabutyl-ammonium hydrogen sulfate (42 mg, 0.1 mmol) was dissolved in DCM (50 mL). NaOH 2.5 M aq (6 mL, 15 mmol) was added and the mixture was stirred vigorously for 1 h. Diluted with water and DCM, collected the DCM phase and washed it twice with water, dried and concentrated to give the product as white crystalline material (2.07 g, 5.9 mmol). Yield 94%. MS (ESI+) for $C_{15}H_{12}BrNO_2S$ m/z 352 (M+H)$^+$.

Intermediate 4

1-[(4-Methylphenyl)sulfonyl]-4-vinyl-1H-indole 4-bromo-1-[(4-methylphenyl)sulfonyl]-1H-indole (600 mg, 1.71 mmol; Intermediate 3), tributyl(vinyl)stannane (0.550 mL, 1.88 mmol) and Pd(PPh$_3$)$_2$OAc$_2$ (32 mg, 0.043 mmol) were mixed in dry toluene (8 mL) and stirred 24 h at 110° C. using a STEM block, then rt. for 40 h. The reaction mixture was filtered and concentrated under reduced pressure. The crude product was purified by flash chromatography (20% DCM in hexane-50% DCM in hexane). This afforded the title compound 390 mg, 77% as a colorless sticky oil. MS (ESI+) for $C_{17}H_{15}NO_2S$ m/z 298 (M+H)$^+$.

Intermediate 5; Batch 1

1-[(4-Methylphenyl)sulfonyl]-1H-indole-4-carbaldehyde

OsO$_4$ (6 mg, 0.023 mmol) was added to a stirred mixture of 1-[(4-methylphenyl)sulfonyl]-4-vinyl-1H-indole (68 mg, 0.23 mmol; Intermediate 4) and 2,6-lutidine (54 µL, 0.46 mmol) in dioxane (6 mL). The mixture turned from colorless to black in 1 minute. Sodium periodate (0.197 g, 0.92 mmol) in water (1.5 mL, warmed to dissolve) was added. A grey precipitation was immediately formed. The mixture was stirred for 20 min. and partitioned between 2M aqueous HCl (25 mL) and DCM (25 mL). The organic layer was dried, filtered and combined with Intermediate 5 batch 2.

Intermediate 5; Batch 2

1-[(4-Methylphenyl)sulfonyl]-1H-indole-4-carbaldehyde

The experimental for Intermediate 5 Batch 1 was followed using OsO$_4$ (27 mg, 0.11 mmol), 1-[(4-methylphenyl)sulfonyl]-4-vinyl-1H-indole (0.321 g, 1.08 mmol; Intermediate 4), 2,6-lutidine (0.251 mL, 0.23 mmol), dioxane (12 mL), sodium periodate (0.924 g, 4.32 mmol) and water (4 mL). The mixture was stirred for 20 min. and partitioned between 2M aqueous HCl (25 mL) and DCM (25 mL). The organic layer was dried, filtered, combined with Intermediate 5 Batch 1, and concentrated to give a total yield of 390 mg, 99% of a black solid. MS (ESI+) for $C_{16}H_{13}NO_3S$ m/z 300 (M+H)$^+$.

EXAMPLE 5

1-[(4-Methylphenyl)sulfonyl]-4-(piperazin-1-ylmethyl)-1H-indole bis(trifluoroacetate)

1-[(4-methylphenyl)sulfonyl]-1H-indole-4-carbaldehyde (40 mg, 0.13 mmol; Intermediate 5), 1-BOC-piperazine (27 mg, 0.15 mmol), acetic acid (76 µL, 1.33 mmol) and NaB(OAc)$_3$H (57 mg, 0.27 mmol) were, in that order, added to dry THF (4 mL). The mixture was irradiated using microwaves for 600 s at 130° C. Additional 1-BOC-piperazine (27 mg, 0.15 mmol) and NaB(OAc)$_3$H (57 mg, 0.27 mmol) were added and the mixture was irradiated at 130° C. for 300 s. This gave 100% conversion to product. The reaction mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 25-47% MeCN, 0.1% TFA). The title compound (29 mg, 36%) was obtained as a light brown solid. MS (ESI+) for $C_{20}H_{23}N_3O_2S$ m/z 370 (M+H)$^+$.

EXAMPLE 6

1-[(4-Methylphenyl)sulfonyl]-4-[(3-methylpiperazin-1-yl)methyl]-1H-indole bis(trifluoroacetate)

The experimental for Example 5 was followed using 2-methylpiperazine (15 mg, 0.15 mmol), except the deprotection step. Purification was performed using preparative HPLC/UV (System A, 22-44% MeCN, 0.1% TFA). The title compound (32 mg, 39%) was obtained as a brown solid. MS (ESI+) for $C_{21}H_{25}N_3O_2S$ m/z 384 (M+H)$^+$.

EXAMPLE 7

4-(1,4-Diazepan-1-ylmethyl)-1-[(4-methylphenyl)sulfonyl]-1H-indole bis(trifluoroacetate)

1-[(4-methylphenyl)sulfonyl]-1H-indole-4-carbaldehyde (30 mg, 0.10 mmol; Intermediate 5), 1-BOC-homopiperazine (30 mg, 0.15 mmol), acetic acid (57 µL, 1.00 mmol) and NaB(OAc)$_3$H (51 mg, 0.24 mmol) were, in that order, added to dry THF (4 mL). The mixture was irradiated using microwaves for 420 s at 130° C. The reaction mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 21-43% MeCN, 0.1% TFA). The title compound (24 mg, 39%) was obtained as a brown solid. MS (ESI+) for $C_{21}H_{25}N_3O_2S$ m/z 384 (M+H)$^+$.

EXAMPLE 8

4-[(4-Methyl-1,4-diazepan-1-yl)methyl]-1-[(4-methylphenyl)sulfonyl]-1H-indole bis(trifluoroacetate)

The procedure for Example 7 was followed, except the deprotection step, using N-methylhomopiperazine (17 mg, 0.15 mmol). Preparative HPLC/UV (System A, 23-44% MeCN, 0.1% TFA). The title compound (35 mg, 56%) was obtained as a brown solid. MS (ESI+) for $C_{22}H_{27}N_3O_2S$ m/z 398 (M+H)$^+$.

EXAMPLE 9

1-[(4-Methylphenyl)sulfonyl]-4-[(4-methylpiperazin-1-yl)methyl]-1H-indole bis(trifluoroacetate)

The procedure for Example 7 was followed, except the deprotection step, using N-methylpiperazine (15 mg, 0.15 mmol). Preparative HPLC/UV (System A, 25-48% MeCN, 0.1% TFA). The title compound (24 mg, 40%) was obtained as a gray solid. MS (ESI+) for $C_{21}H_{25}N_3O_2S$ m/z 384 (M+H)$^+$.

EXAMPLE 10

4-[(4-Isopropylpiperazin-1-yl)methyl]-1-[(4-methylphenyl)sulfonyl]-1H-indole bis(trifluoroacetate)

The procedure for Example 7 was followed, except the deprotection step, using 1-isopropylpiperazine (19 mg, 0.15 mmol). Preparative HPLC/UV (System A, 28-50% MeCN, 0.1% TFA). The title compound (21 mg, 32%) was obtained as a brown solid. MS (ESI+) for $C_{23}H_{29}N_3O_2S$ m/z 412 (M+H)$^+$.

EXAMPLE 11

1-[(4-Methylphenyl)sulfonyl]-4-[(4-propylpiperazin-1-yl)methyl]-1H-indole bis(trifluoroacetate)

The procedure for Example 7 was followed, except the deprotection step, using N-propylpiperazine dihydrobromide (44 mg, 0.15 mmol). Additional N-propylpiperazine dihydrobromide (15 mg, 0.05 mmol) and NaB(OAc)$_3$H (20 mg, 0.09 mmol) and irradiation at 130° C. for 300 s afforded full conversion. Preparative HPLC/UV (System A, 28-51% MeCN, 0.1% TFA). The title compound (19 mg, 29%) was obtained as a gray solid. MS (ESI+) for $C_{23}H_{29}N_3O_2S$ m/z 412 (M+H)$^+$.

EXAMPLE 12

1-[(4-Methylphenyl)sulfonyl]-4-(pyrrolidin-1-ylmethyl)-1H-indole trifluoroacetate The procedure for Example 7 was followed, except the deprotection step, using pyrrolidine (13 μL, 0.115 mmol). Preparative HPLC/UV (System A, 30-53% MeCN, 0.1% TFA). The title compound (20 mg, 44%) was obtained as a brown solid. MS (ESI+) for $C_{20}H_{22}N_2O_2S$ m/z 355 (M+H)$^+$.

Intermediate 6

4-Bromo-1-[(2-methoxy-5-methylphenyl)sulfonyl]-1H-indole

The procedure for Intermediate 3 was followed using (2-methoxy-5-methylphenyl)sulfonyl chloride. Yield 1.4 g (72%). MS (ESI+) for $C_{16}H_{14}BrNO_3S$ m/z 382 (M+H)$^+$.

Intermediate 7

1-[(2-Methoxy-5-methylphenyl)sulfonyl]-4-vinyl-1H-indole 4-bromo-1-[(2-methoxy-5-methylphenyl)sulfonyl]-1H-indole (518 mg, 1.36 mmol; Intermediate 6), tributyl(vinyl) stannane (0.438 mL, 1.50 mmol) and Pd(PPh$_3$)$_2$OAc$_2$ (51 mg, 0.068 mmol) were mixed in dry toluene (8 mL) and stirred 17 h at 110° C. using a STEM block. The mixture was filtered and additional tributyl(vinyl)stannane (0.200 mL, 0.68 mmol) and Pd(PPh$_3$)$_2$OAc$_2$ (30 mg, 0.040 mmol) were added with continuous stirring for 23 h. Same procedure was repeated once more (additional reagents) with continuous stirring 24 h gave full conversion. The mixture was filtered and concentrated under reduced pressure. The crude product was purified by flash chromatography (DCM/hexane 2:3). This gave the desired product (2.62 g, 59%) as an off white solid. MS (ESI+) for $C_{18}H_{17}NO_3S$ m/z 328 (M+H)$^+$.

Intermediate 8

1-[(2-Methoxy-5-methylphenyl)sulfonyl]-1H-indole-4-carbaldehyde

OsO$_4$ (10 mg, 0.05 mmol) was added to a stirred mixture of 1-[(2-methoxy-5-methylphenyl)sulfonyl]-4-vinyl-1H-indole (262 mg, 0.80 mmol; Intermediate 7) and 2,6-2,6-lutidine (186 μL, 0.46 mmol) in dioxane (9 mL). The mixture turned from colorless to black in 1 minute. Sodium periodate (0.684 g, 3.2 mmol) in water (3 mL, warmed to dissolve) was added. A grey precipitation was immediately formed. The mixture was stirred for 30 min. and partitioned between 2M aqueous HCl (25 mL) and DCM (25 mL). The organic layer was dried, filtered and concentrated to give the title compound (290 mg, 110%, still some dioxane according to HNMR) as a black solid. MS (ESI+) for $C_{17}H_{15}NO_4S$ m/z 330 (M+H)$^+$.

EXAMPLE 13

1-[(2-Methoxy-5-methylphenyl)sulfonyl]-4-(piperazin-1-ylmethyl)-1H-indole bis(trifluoroacetate)

1-[(2-methoxy-5-methylphenyl)sulfonyl]-1H-indole-4-carbaldehyde (27 mg, 0.082 mmol; Intermediate 8), 1-BOC-piperazine (23 mg, 0.12 mmol), acetic acid (47 μL, 0.82 mmol) and NaB(OAc)$_3$H (42 mg, 0.20 mmol) were, in that order, added to dry THF (4 mL). The mixture was irradiated using microwaves for 420 s at 130° C. Additional 1-BOC-piperazine (23 mg, 0.12 mmol), acetic acid (23 μL, 0.41 mmol) and NaB(OAc)$_3$H (42 mg, 0.20 mmol) were added and the reaction mixture was irradiated once more at 130° C. for 600 s. The mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 23-44% MeCN, 0.1% TFA). The title compound (22 mg, 45%) was obtained as a light brown solid. MS (ESI+) for $C_{21}H_{25}N_3O_3S$ m/z 400 (M+H)$^+$.

EXAMPLE 14

1-[(2-Methoxy-5-methylphenyl)sulfonyl]-4-[(3-methylpiperazin-1-yl)methyl]-1H-indole bis(trifluoroacetate)

1-[(2-methoxy-5-methylphenyl)sulfonyl]-1H-indole-4-carbaldehyde (27 mg, 0.082 mmol; Intermediate 8), 2-methylpiperazine (12 mg, 0.12 mmol), acetic acid (47 μL, 0.82 mmol) and NaB(OAc)$_3$H (42 mg, 0.20 mmol) were, in that order, added to dry THF (4 mL). The mixture was irradiated using microwaves for 420 s at 130° C. The reaction mixture was filtered and concentrated. Purification was performed by preparative HPLC/UV (System A, 25-47% MeCN, 0.1% TFA). The title compound (18 mg, 34%) was obtained as a light brown solid. MS (ESI+) for $C_{22}H_{27}N_3O_3S$ m/z 414 (M+H)$^+$.

EXAMPLE 15

N-({1-[(2-Methoxy-5-methylphenyl)sulfonyl]-1H-indol-4-yl}methyl)piperidin-4-amine bis(trifluoroacetate)

1-[(2-methoxy-5-methylphenyl)sulfonyl]-1H-indole-4-carbaldehyde (27 mg, 0.082 mmol; Intermediate 8), tert-butyl 4-aminopiperidine-1-carboxylate (25 mg, 0.12 mmol), acetic acid (47 µL, 0.82 mmol) and NaB(OAc)$_3$H (42 mg, 0.20 mmol) were, in that order, added to dry THF (4 mL). The mixture was irradiated using microwaves for 420 s at 130° C. Additional tert-butyl 4-aminopiperidine-1-carboxylate (25 mg, 0.12 mmol), acetic acid (23 µL, 0.41 mmol) and NaB(OAc)$_3$H (42 mg, 0.20 mmol) were added and the reaction mixture was irradiated once more at 130° C. for 600 s. About 30% starting material was still present. The mixture was filtered and partitioned between DCM (15 mL) and aq. saturated NaHCO$_3$ (15 mL). The organic layer was concentrated. Purification by flash tube (FlashTube™ från Trikonex; eluting with 10% MeOH in DCM) gave 50 mg. Part of this material (25 mg) was dissolved in MeOH (1.5 mL) and conc. HCl (0.5 mL) and irradiated using microwaves at 100° C. for 300 s. Purification by preparative HPLC/UV (System A, 23-44% MeCN, 0.1% TFA). The title compound (7 mg, 27%) was obtained as a light brown solid. MS (ESI+) for $C_{22}H_{27}N_3O_3S$ m/z 414 (M+H)$^+$.

EXAMPLE 16

1-Isopropyl-N-({1-[(2-methoxy-5-methylphenyl)sulfonyl]-1H-indol-4-yl}methyl)piperidin-4-amine bis(trifluoroacetate)

1-[(2-methoxy-5-methylphenyl)sulfonyl]-1H-indole-4-carbaldehyde (27 mg, 0.082 mmol; Intermediate 8), 1-isopropylpiperidine-4-amine (17 mg, 0.12 mmol), acetic acid (47 µL, 0.82 mmol) and NaB(OAc)$_3$H (42 mg, 0.20 mmol) were, in that order, added to dry THF (4 mL). The mixture was irradiated using microwaves for 420 s at 130° C. Additional 1-isopropylpiperidine-4-amine (17 mg, 0.12 mmol), acetic acid (23 µL, 0.41 mmol) and NaB(OAc)$_3$H (42 mg, 0.20 mmol) were added and the reaction mixture was irradiated once more at 130° C. for 60 min. About 45% starting material was still present. The mixture was filtered and concentrated. Purification was performed by preparative HPLC/UV (System A, 24-46% MeCN, 0.1% TFA). The title compound (16 mg, 29%) was obtained as a light brown solid. MS (ESI+) for $C_{25}H_{33}N_3O_3S$ m/z 456 (M+H)$^+$.

EXAMPLE 17

1-[(2-Methoxy-5-methylphenyl)sulfonyl]-4-[(2-methylpyrrolidin-1-yl)methyl]-1H-indole trifluoroacetate The procedure for Example 16 was followed using 2-methylpyrrolidine (13 µL, 0.12 mmol). Preparative HPLC/UV (System A, 32-55% MeCN, 0.1% TFA). The title compound (16 mg, 36%) was obtained as a light brown solid. MS (ESI+) for $C_{22}H_{26}N_2O_3S$ m/z 399 (M+H)$^+$.

Intermediate 9

4-Bromo-1-[(2-methoxy-5-methylphenyl)sulfonyl]indoline

NaBH$_3$CN (480 mg, 7.63 mmol) was added portionwise, under N$_2$, to ice cold TFA (15 mL). The mixture was stirred for 15 min. and 4-bromo-1-[(2-methoxy-5-methylphenyl) sulfonyl]-1H-indole (645 mg, 1.70 mmol; Intermediate 6) was added in portions. The mixture was allowed to attain rt. and stirred 1.5 h. Additional NaBH$_3$CN (480 mg, 7.63 mmol) was added with continuous stirring 1 h. The reaction mixture was quenched with water (30 mL) and extracted twice with DCM. The DCM layers were combined and extracted with aq. Na$_2$CO$_3$ (~pH 10). The organic layer was dried, filtered and concentrated to give the title compound (525 mg, 80%) as a yellow viscous oil. MS (ESI+) for $C_{16}H_{16}BrNO_3S$ m/z 382 (M+H)$^+$.

Intermediate 10

1-[(2-Methoxy-5-methylphenyl)sulfonyl]-4-vinylindoline 4-bromo-1-[(2-methoxy-5-methylphenyl)sulfonyl]indoline (tot 721 mg, 1.89 mmol; Intermediate 9), tributyl(vinyl)stannane (tot 1.10 mL, 3.78 mmol) and Pd(PPh$_3$)$_2$OAc$_2$ (tot 142 mg, 0.19 mmol) in dry toluene (tot 12 mL) was distributed into 3 tubes and stirred at 110° C. using a STEM block over weekend (68 h). Still about 30% starting material. The reactions were combined, filtered and concentrated. Redissolved in dry MeCN (8 mL), distributed into 2 Micro wave tubes followed by addition of tributyl(vinyl)stannane (300 µL, 1.03 mmol) and Pd(PPh$_3$)$_2$OAc$_2$ (30 mg, 0.04 mmol) to each tube. The mixtures were irradiated by micro waves 180° C. for 600 s. Filtration and concentration followed by purification by flash (30% hexane in DCM) gave the title compound (300 mg, 48%) as a colorless viscous oil. MS (ESI+) for $C_{18}H_{19}NO_3S$ m/z 330 (M+H)$^+$.

Intermediate 11

1-[(2-Methoxy-5-methylphenyl)sulfonyl]indoline-4-carbaldehyde

OsO$_4$ (9 mg, 0.05 mmol) was added to a stirred mixture of 1-[(2-methoxy-5-methylphenyl)sulfonyl]-4-vinylindoline (240 mg, 0.73 mmol; Intermediate 10) and 2,6-lutidine (170 µL, 1.46 mmol) in dioxane (12 mL). The mixture turned from colorless to black in 1 minute. Sodium periodate (0.625 g, 2.92 mmol) in water (4 mL, warmed to dissolve) was added. A grey precipitation was immediately formed. The mixture was stirred for 25 min, combined with an earlier batch of this intermediate (followed this experimental and starting from Intermediate 10; 60 mg, 18 mmol), and partitioned between 2M aqueous HCl (25 mL) and DCM (25 mL). The organic layer was dried, filtered and concentrated to give the title compound (360 mg, still some dioxane according to HNMR) as a black sticky oil. MS (ESI+) for $C_{17}H_{17}NO_4S$ m/z 332 (M+H)$^+$.

EXAMPLE 18

1-[(2-Methoxy-5-methylphenyl)sulfonyl]-4-[(3-methylpiperazin-1-yl)methyl]indoline bis(trifluoroacetate)

1-[(2-methoxy-5-methylphenyl)sulfonyl]indoline-4-carbaldehyde (30 mg, 0.091 mmol; Intermediate 11), 2-methylpiperazine (18 mg, 0.18 mmol), acetic acid (52 µL, 0.91 mmol) and NaB(OAc)$_3$H (58 mg, 0.27 mmol) were, in that order, added to dry THF (4 mL). The mixture was irradiated with microwaves for 660 s at 130° C., filtered, concentrated and purified using preparative HPLC (System A, MeCN/H$_2$O, 0.1% TFA). The title compound (13 mg, 22%) was obtained as a light brown solid. MS (ESI+) for $C_{22}H_{29}N_3O_3S$ m/z 416 (M+H)$^+$.

EXAMPLE 19

1-[(2-Methoxy-5-methylphenyl)sulfonyl]-4-[(4-methylpiperazin-1-yl)methyl]indoline bis(trifluoroacetate)

The experimental for Example 18 was followed using 1-methylpiperazine (18 mg, 0.18 mmol). The title compound (21 mg, 36%) was obtained as a colorless solid. MS (ESI+) for $C_{22}H_{29}N_3O_3S$ m/z 416 (M+H)+.

EXAMPLE 20

1-[(2-Methoxy-5-methylphenyl)sulfonyl]-4-(pyrrolidin-1-ylmethyl)indoline trifluoroacetate The experimental for Example 18 was followed using pyrrolidine (15 µL, 0.18 mmol). The title compound (15 mg, 33%) was obtained as a light brown solid. MS (ESI+) for $C_{21}H_{26}N_2O_3S$ m/z 387 (M+H)+.

EXAMPLE 21

({1-[(2-Methoxy-5-methylphenyl)sulfonyl]-2,3-dihydro-1H-indol-4-yl}methyl)dimethylamine trifluoroacetate The experimental for Example 18 was followed using dimethylamine hydrochloride (15 mg, 0.18 mmol). The title compound (13 mg, 30%) was obtained as a light brown solid. MS (ESI+) for $C_{19}H_{24}N_2O_3S$ m/z 361 (M+H)+.

Intermediate 12

1-[(4-Fluorophenyl)sulfonyl]-4-vinyl-1H-indole

The experimental for Intermediate 7 was followed. Flash chromatography (30% DCM in hexane) afforded 347 mg, 75% of a white solid. MS (ESI+) for $C_{16}H_{12}FNO_2S$ m/z 302 (M+H)+.

Intermediate 13

1-[(4-Fluorophenyl)sulfonyl]-1H-indole-4-carbaldehyde

The procedure for Intermediate 8 was followed using $OsO_4$ (15 mg, 0.058 mmol), 1-[(4-fluorophenyl)sulfonyl]-4-vinyl-1H-indole (347 mg, 1.15 mmol; Intermediate 12), 2,6-lutidine (268 µL, 2.3 mmol), dioxane (15 mL), sodium periodate (0.984 g, 4.6 mmol) and water (5 mL). The title compound (360 mg, 103%, still some dioxane according to HNMR) was obtained as a black sticky oil. MS (ESI+) for $C_{15}H_{10}FNO_3S$ m/z 304 (M+H)+.

EXAMPLE 22

1-[(4-Fluorophenyl)sulfonyl]-4-[(3-methylpiperazin-1-yl)methyl]-1H-indole bis(trifluoroacetate)

1-[(4-fluorophenyl)sulfonyl]-1H-indole-4-carbaldehyde (30 mg, 0.099 mmol; Intermediate 13), 2-methylpiperazine (20 mg, 0.20 mmol), acetic acid (57 µL, 0.99 mmol) and $NaB(OAc)_3H$ (63 mg, 0.30 mmol) were, in that order, added to dry THF (4 mL). The mixture was irradiated using microwaves for 900 s at 130° C. The mixture was filtered and concentrated. Purification was performed by preparative HPLC/UV (System A, MeCN, 0.1% TFA). The title compound (26 mg, 43%) was obtained as a light brown solid. MS (ESI+) for $C_{20}H_{22}FN_3O_2S$ m/z 388 (M+H)+.

EXAMPLE 23

4-(1,4-Diazepan-1-ylmethyl)-1-[(4-fluorophenyl)sulfonyl]-1H-indole bis(trifluoroacetate)

1-[(4-fluorophenyl)sulfonyl]-1H-indole-4-carbaldehyde (30 mg, 0.099 mmol; Intermediate 13), 1-BOC-homopiperazine (39 µL, 0.20 mmol), acetic acid (57 µL, 0.99 mmol) and $NaB(OAc)_3H$ (63 mg, 0.30 mmol) were, in that order, added to dry THF (4 mL). The mixture was irradiated using microwaves for 900 s at 130° C. The mixture was filtered and concentrated. The residue was dissolved in MeOH (1.5 mL) and conc. HCl (0.5 mL) and irradiated using microwaves at 100° C. for 300 s. The mixture was filtered and purified by preparative HPLC/UV (System A, MeCN, 0.1% TFA). The title compound (24 mg, 39%) was obtained as a colorless solid. MS (ESI+) for $C_{20}H_{22}FN_3O_2S$ m/z 388 (M+H)+.

EXAMPLE 24

1-[(4-Fluorophenyl)sulfonyl]-4-(pyrrolidin-1-ylmethyl)-1H-indole trifluoroacetate The experimental for Example 22 was followed using pyrrolidine (16 µL, 0.20 mmol). The title compound (21 mg, 45%) was obtained as a light brown solid. MS (ESI+) for $C_{19}H_{19}FN_2O_2S$ m/z 359 (M+H)+.

EXAMPLE 25

({1-[(4-Fluorophenyl)sulfonyl]-1H-indol-4-yl}methyl)dimethylamine trifluoroacetate The experimental for Example 22 was followed using dimethylamine hydrochloride (16 mg, 0.20 mmol). The title compound (13 mg, 29%) was obtained as a light brown solid. MS (ESI+) for $C_{17}H_{17}FN_2O_2S$ m/z 333 (M+H)+.

EXAMPLE 26

1-[(4-Fluorophenyl)sulfonyl]-4-(piperazin-1-ylmethyl)-1H-indole bis(trifluoroacetate)

1-[(4-Fluorophenyl)sulfonyl]-1H-indole-4-carbaldehyde (75 mg, 0.25 mmol; Intermediate 13), 1-BOC-piperazine (92 mg, 0.50 mmol), acetic acid (0.141 mL, 2.47 mmol) and $NaB(OAc)_3H$ (157 mg, 0.74 mmol) were, in that order, added to dry THF (5 mL). The mixture was irradiated using microwaves for 900 s at 130° C. The mixture was filtered and concentrated. The residue was dissolved in MeOH (3 mL) and conc. HCl (1.5 mL) and irradiated using microwaves at 100° C. for 300 s. MeOH was evaporated and the resulting slurry was partitioned between DCM and saturated aq. $Na_2CO_3$. The organic layer was dried, filtered and concentrated. Half the amount of crude product was purified by preparative HPLC/UV (System A, MeCN, 0.1% TFA). The title compound (26 mg, 17%) was obtained as a light brown solid. MS (ESI+) for $C_{19}H_{20}FN_3O_2S$ m/z 374 (M+H)+.

Intermediate 14

4-Bromo-1-[(2-methylphenyl)sulfonyl]-1H-indole

Aq. 2.5 M NaOH (5 mL) was added to a stirring mixture of 4-bromo-1H-indole (1000 mg, 5.3 mmol), 2-methylbenzenesulfonyl chloride (1100 mg, 5.6 mmol) and tetrabutylammonium hydrogen sulfate (173 mg, 0.5 mmol) in DCM (10 mL). The reaction mixture was stirred at ambient temperature overnight. The mixture was diluted with DCM and water and the layers were separated. DCM was washed with water 2 times, dried (MgSO$_2$) and concentrated to give 1.6 g of crude material that was purified using flash chromatography (SiO$_2$, eluent EtOAc:hexane 9:1) giving the title product (1 g, 54%). MS (ESI+) for C$_{15}$H$_{12}$BrNO$_2$S m/z 350 (M+H)$^+$.

Intermediate 15

1-[(2-Methylphenyl)sulfonyl]-4-vinyl-1H-indole

4-Bromo-1-[(2-methylphenyl)sulfonyl]-1H-indole (500 mg, 1.43 mmol; Intermediate 14) was dissolved in dry MeCN (8 mL) and distributed into two microwave vials. Tributyl (vinyl)stannane (0.417 mL, 1.43 mmol) and Pd(PPh$_3$)$_2$OAc$_2$ (27 mg, 0.036 mmol) was added to each vial. The reaction mixtures were irradiated with microwaves at 180° C. for 720 s. The mixtures were combined, filtered and concentrated. Purification was performed by flash chromatography (30% hexane in DCM). This afforded the product (300 mg, 71%) as a yellow sticky oil. MS (ESI+) for C$_{17}$H$_{15}$NO$_2$S m/z 298 (M+H)$^+$.

Intermediate 16

1-[(2-Methylphenyl)sulfonyl]-1H-indole-4-carbaldehyde

OsO$_4$ (15 mg, 0.06 mmol) was added to a stirred mixture of 1-[(2-methylphenyl)sulfonyl]-4-vinyl-1H-indole (300 mg, 1.01 mmol; Intermediate 15) and 2,6-lutidine (235 μl, 2.02 mmol) in dioxane (24 mL). The mixture turned from colorless to black in 3 minutes. Sodium periodate (0.865 g, 4.04 mmol) in water (8 mL, warmed to dissolve) was added. A grey precipitation was immediately formed. The mixture was stirred for 1.40 h and extracted with 2M aqueous HCl (25 mL) and DCM (2×25 mL). The organic layers were combined, dried, filtered and concentrated to give the title compound (358 mg, 118%, still some dioxane according to HNMR) as a black gum. MS (ESI+) for C$_{16}$H$_{13}$NO$_3$S m/z 300 (M+H)$^+$.

EXAMPLE 27

1-[(2-Methylphenyl)sulfonyl]-4-(piperazin-1-ylmethyl)-1H-indole bis(trifluoroacetate)

1-[(2-methylphenyl)sulfonyl]-1H-indole-4-carbaldehyde (50 mg, 0.17 mmol; Intermediate 16), 1-BOC-piperazine (62 mg, 0.33 mmol), acetic acid (95 μL, 1.67 mmol) and NaB(OAc)$_3$H (106 mg, 0.50 mmol) were, in that order, added to dry THF (4 mL). The mixture was irradiated with microwaves for 720 s at 130° C. The mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 19-42% MeCN, 0.1% TFA). The title compound (7 mg, 7%) was obtained as a light brown solid. MS (ESI+) for C$_{20}$H$_{23}$N$_3$O$_2$S m/z 370 (M+H)$^+$.

EXAMPLE 28

1-[(2-Methylphenyl)sulfonyl]-4-[(4-methylpiperazin-1-yl)methyl]-1H-indole bis(trifluoroacetate)

1-[(2-Methylphenyl)sulfonyl]-1H-indole-4-carbaldehyde (50 mg, 0.17 mmol; Intermediate 16), 1-methylpiperazine (34 μL, 0.33 mmol), acetic acid (95 μL, 1.67 mmol) and NaB(OAc)$_3$H (106 mg, 0.50 mmol) were, in that order, added to dry THF (4 mL). The mixture was irradiated with microwaves for 720 s at 130° C., filtered, concentrated and purified using preparative HPLC/UV (System A, 23-50% MeCN, 0.1% TFA). The title compound (17 mg, 16%) was obtained as an off white solid. MS (ESI+) for C$_{21}$H$_{25}$N$_3$O$_2$S m/z 384 (M+H)$^+$.

EXAMPLE 29

1-({1-[(2-Methylphenyl)sulfonyl]-1H-indol-4-yl}methyl)pyrrolidin-3-ol trifluoroacetate The experimental for Example 28 was followed using pyrrolidin-3-ol (28 μL, 0.33 mmol). HPLC/UV (System A, 22-49% MeCN, 0.1% TFA). The title compound (17 mg, 20%) was obtained as a light brown solid. MS (ESI+) for C$_{20}$H$_{22}$N$_2$O$_3$S m/z 371 (M+H)$^+$.

EXAMPLE 30

1-[(2-Methylphenyl)sulfonyl]-4-(pyrrolidin-1-ylmethyl)-1H-indole trifluoroacetate The experimental for Example 28 was followed using pyrrolidine (28 μL, 0.33 mmol). HPLC/UV (System A, 28-53% MeCN, 0.1% TFA). The title compound (12 mg, 17%) was obtained as a light brown solid. MS (ESI+) for C$_{20}$H$_{22}$N$_2$O$_2$S m/z 355 (M+H)$^+$.

EXAMPLE 31

2-[Methyl({1-[(2-methylphenyl)sulfonyl]-1H-indol-4-yl}methyl)amino]ethanol trifluoroacetate The experimental for Example 28 was followed using 2-(methylamino)ethanol (27 μL, 0.33 mmol). HPLC/UV (System A, 22-49% MeCN, 0.1% TFA). The title compound (16 mg, 21%) was obtained as a light brown solid. MS (ESI+) for C$_{19}$H$_{22}$N$_2$O$_3$S m/z 359 (M+H)$^+$.

EXAMPLE 32

N,N-Dimethyl-1-{1-[(2-methylphenyl)sulfonyl]-1H-indol-4-yl}methanamine trifluoroacetate The experimental for Example 28 was followed using dimethylamine hydrochloride (27 mg, 0.33 mmol). HPLC/UV (System A, 23-50% MeCN, 0.1% TFA). The title compound (11 mg, 15%) was obtained as a light brown solid. MS (ESI+) for C$_{18}$H$_{20}$N$_2$O$_2$S m/z 329 (M+H)$^+$.

Intermediate 17

4-Bromo-1-{[3-(trifluoromethyl)phenyl]sulfonyl}-1H-indole

Aq. 2.5M NaOH (5 mL) was added to a stirring mixture of 4-bromo-1H-indole (1000 mg, 5.3 mmol), 3-(trifluoromethyl)benzenesulfonyl chloride (1300 mg, 5.6 mmol) and tetrabutylammonium hydrogen sulfate (173 mg, 0.5 mmol) in DCM (10 mL). The reaction mixture was stirred at ambient temperature overnight. The mixture was diluted with DCM and water and the layers were separated. DCM was washed with water 2 times, dried (MgSO$_2$) and concentrated to give 1.6 g of crude material that was purified using flash chromatography (SiO$_2$, eluent EtOAc:hexane 9:1) giving the title product (0.91 g, 44%).

MS (ESI+) for C$_{15}$H$_9$BrF$_3$NO$_2$S m/z 404.2 (M+H)$^+$.

Intermediate 18

1-{[3-(Trifluoromethyl)phenyl]sulfonyl}-4-vinyl-1H-indole

The experimental for Intermediate 15 was followed using 4-bromo-1-{[3-(trifluoromethyl)phenyl]sulfonyl}-1H-indole (500 mg, 1.24 mmol; Intermediate 17), tributyl(vinyl)stannane (tot 0.723 mL, 2.86 mmol) and Pd(PPh$_3$)$_2$OAc$_2$ (tot 46 mg, 0.062 mmol). The title compound (348 mg, 80%) was obtained as a yellow sticky oil. MS (ESI+) for $C_{17}H_{12}F_3NO_2S$ m/z 352 (M+H)$^+$.

Intermediate 19

1-{[3-(Trifluoromethyl)phenyl]sulfonyl}-1H-indole-4-carbaldehyde

The experimental for Intermediate 16 was followed using 1-{[3-(trifluoromethyl)phenyl]sulfonyl}-4-vinyl-1H-indole (348 mg, 0.99 mmol; Intermediate 18), OsO$_4$ (13 mg, 0.05 mmol), 2,6-lutidine (230 μL, 2.0 mmol) and sodium periodate (0.848 g, 3.96 mmol). The title compound was obtained (368 mg, 105%, still some dioxane according to HNMR) as a black gum. MS (ESI+) for $C_{16}H_{10}F_3NO_3S$ m/z 354 (M+H)$^+$.

EXAMPLE 33

4-(piperazin-1-ylmethyl)-1-{[3-(trifluoromethyl)phenyl]sulfonyl}-1H-indole bis(trifluoroacetate)

1-{[3-(Trifluoromethyl)phenyl]sulfonyl}-1H-indole-4-carbaldehyde (58 mg, 0.16 mmol; Intermediate 19), 1-BOC-piperazine (61 mg, 0.33 mmol), acetic acid (94 μL, 1.64 mmol) and NaB(OAc)$_3$H (104 mg, 0.49 mmol) were, in that order, added to dry THF (4 mL). The mixture was irradiated with microwaves for 720 s at 130° C. The mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-45% MeCN, 0.1% TFA). The title compound (57 mg, 53%) was obtained as a light brown solid. MS (ESI+) for $C_{20}H_{20}F_3N_3O_2S$ m/z 424 (M+H)$^+$.

EXAMPLE 34

{(2R)-1-[(1-{[3-(Trifluoromethyl)phenyl]sulfonyl}-1H-indol-4-yl)methyl]pyrrolidin-2-yl}methanol trifluoroacetate 1-{[3-(Trifluoromethyl)phenyl]sulfonyl}-1H-indole-4-carbaldehyde (58 mg, 0.16 mmol; Intermediate 19), (2R)-pyrrolidin-2-ylmethanol (32 μL, 0.33 mmol), acetic acid (94 μL, 1.64 mmol) and NaB(OAc)$_3$H (104 mg, 0.49 mmol) were, in that order, added to dry THF (4 mL). The mixture was irradiated with microwaves for 720 s at 130° C., filtered, concentrated and purified using preparative HPLC/UV (System A, 27-49% MeCN, 0.1% TFA). The title compound (40 mg, 44%) was obtained as a light brown solid. MS (ESI+) for $C_{21}H_{21}F_3N_2O_3S$ m/z 439 (M+H)$^+$.

EXAMPLE 35

4-(Pyrrolidin-1-ylmethyl)-1-{[3-(trifluoromethyl)phenyl]sulfonyl}-1H-indole trifluoroacetate The experimental for Example 34 was followed using pyrrolidine (27 μL, 0.33 mmol). Preparative HPLC/UV (System A, 29-51% MeCN, 0.1% TFA). The title compound (32 mg, 38%) was obtained as a light brown solid. MS (ESI+) for $C_{20}H_{19}F_3N_2O_2S$ m/z 409 (M+H)$^+$.

EXAMPLE 36

2-{Methyl[(1-{[3-(trifluoromethyl)phenyl]sulfonyl}-1H-indol-4-yl)methyl]amino}ethanol trifluoroacetate The experimental for Example 34 was followed using 2-(methylamino)ethanol (26 μL, 0.33 mmol). Preparative HPLC/UV (System A, 27-49% MeCN, 0.1% TFA). The title compound (33 mg, 38%) was obtained as a light brown solid. MS (ESI+) for $C_{19}H_{19}F_3N_2O_3S$ m/z 413 (M+H)$^+$.

EXAMPLE 37

N,N-Dimethyl-1-(1-{[3-(trifluoromethyl)phenyl]sulfonyl}-1H-indol-4-yl)methanamine trifluoroacetate The experimental for Example 34 was followed using dimethylamine hydrochloride (27 mg, 0.33 mmol). Preparative HPLC/UV (System A, 27-49% MeCN, 0.1% TFA). The title compound (33 mg, 38%) was obtained as a light brown solid. MS (ESI+) for $C_{18}H_{17}F_3N_2O_2S$ m/z 383 (M+H)$^+$.

Intermediate 20

4-Bromo-1-(2-thienylsulfonyl)-1H-indole

Aq. 2.5M NaOH (3 mL) was added to a stirring mixture of 2-thiophenesulfonyl chloride (1.03 g, 5.61 mmol), 4-bromoindole (1.00 g, 5.10 mmol) and tetrabutylammonium hydrogen sulfate (87 mg, 0.05 mmol). The reaction was stirred over night (22 h). Additional 2-thiophenesulfonyl chloride (50 mg, 0.27 mmol) was added with continuous stirring for 3 h. The layers were allowed to separate. The organic layer was washed twice with water, dried and concentrated to get the title compound (1.67 g, 96%) as a gray solid.

MS (ESI+) for $C_{12}H_8BrNO_2S_2$ m/z 342 (M+H)$^+$.

Intermediate 21

1-(2-Thienylsulfonyl)-4-vinyl-1H-indole

The experimental for Intermediate 15 was followed using 4-bromo-1-(2-thienylsulfonyl)-1H-indole (500 mg, 1.46 mmol; Intermediate 20), tributyl(vinyl)stannane (tot 0.864 mL, 2.92 mmol) and Pd(PPh$_3$)$_2$OAc$_2$ (tot 55 mg, 0.073 mmol). The title compound (333 mg, 79%) was obtained as a colorless solid. MS (ESI+) for $C_{14}H_{11}NO_2S_2$ m/z 290 (M+H)$^+$.

Intermediate 22

1-(2-Thienylsulfonyl)-1H-indole-4-carbaldehyde

The experimental for Intermediate 16 was followed using 1-(2-thienylsulfonyl)-4-vinyl-1H-indole (333 mg, 1.15 mmol; Intermediate 21), OsO$_4$ (15 mg, 0.06 mmol), 2,6-lutidine (268 μL, 2.30 mmol) and sodium periodate (0.984 g, 4.60 mmol). The title compound was obtained (306 mg, 91%, still some dioxane according to HNMR) as a black gum. MS (ESI+) for $C_{13}H_9NO_3S_2$ m/z 292 (M+H)$^+$.

EXAMPLE 38

4-(piperazin-1-ylmethyl)-1-(2-thienylsulfonyl)-1H-indole bis(trifluoroacetate)

1-(2-thienylsulfonyl)-1H-indole-4-carbaldehyde (51 mg, 0.18 mmol; Intermediate 22), 1-BOC-piperazine (65 mg, 0.35 mmol), acetic acid (100 μL, 1.75 mmol) and NaB(OAc)$_3$H (111 mg, 0.53 mmol) were, in that order, added to dry THF (4 mL). The mixture was irradiated with microwaves for 720 s at 130° C. The mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 18-44% MeCN, 0.1% TFA). The title compound (32 mg, 31%) was obtained as a brown solid. MS (ESI+) for $C_{17}H_{19}N_3O_2S_2$ m/z 362 (M+H)$^+$.

EXAMPLE 39

N-Ethyl-N-{[1-(2-thienylsulfonyl)-1H-indol-4-yl]methyl}ethanamine trifluoroacetate 1-(2-thienylsulfonyl)-1H-indole-4-carbaldehyde (51 mg, 0.18 mmol; Intermediate 22), N-ethylethaneamine (36 µL, 0.35 mmol), acetic acid (100 µL, 1.75 mmol) and NaB(OAc)$_3$H (111 mg, 0.53 mmol) were, in that order, added to dry THF (4 mL). The mixture was irradiated with microwaves for 720 s at 130° C., filtered, concentrated and purified using preparative HPLC/UV (System A, 23-50% MeCN, 0.1% TFA). The title compound (7 mg, 9%) was obtained as a brown solid. MS (ESI+) for $C_{17}H_{20}N_2O_2S_2$ m/z 349 (M+H)$^+$.

EXAMPLE 40

4-(Pyrrolidin-1-ylmethyl)-1-(2-thienylsulfonyl)-1H-indole trifluoroacetate

The experimental for Example 39 was followed using pyrrolidine (29 µL, 0.35 mmol). Preparative HPLC/UV (System A, 21-48% MeCN, 0.1% TFA). The title compound (34 mg, 43%) was obtained as a brown solid. MS (ESI+) for $C_{17}H_{18}N_2O_2S_2$ m/z 347 (M+H)$^+$.

EXAMPLE 41

4-[(4-Propylpiperazin-1-yl)methyl]-1-(2-thienylsulfonyl)-1H-indole bis(trifluoroacetate)

The experimental for Example 39 was followed using 1-propylpiperazine dihydrobromide (102 mg, 0.35 mmol). Preparative HPLC/UV (System A, 19-45% MeCN, 0.1% TFA). The title compound (24 mg, 45%) was obtained as a gray solid. MS (ESI+) for $C_{20}H_{25}N_3O_2S_2$ m/z 404 (M+H)$^+$.

EXAMPLE 42

N,N-Dimethyl-1-[1-(2-thienylsulfonyl)-1H-indol-4-yl]methanamine trifluoroacetate The experimental for Example 39 was followed using dimethylamine hydrochloride (29 mg, 0.35 mmol). Preparative HPLC/UV (System A, 20-45% MeCN, 0.1% TFA). The title compound (20 mg, 26%) was obtained as a brown solid. MS (ESI+) for $C_{15}H_{16}N_2O_2S_2$ m/z 321 (M+H)$^+$.

Intermediate 23

Pyridine-3-sulfonyl chloride hydrochloride

Pyridine-3-sulfonic acid (3.00 g, 18.8 mmol) and PCl$_5$ (4.79 g, 23.0 mmol) were mixed in POCl$_3$ (6 mL). The reaction was stirred and refluxed at 120° C. over night (15 h). Cooled to rt., diluted with CHCl$_3$ (20 mL) and saturated with HCl (g). This gave a white precipitation, which was filtered off, washed with CHCl$_3$ and dried under reduced pressure to give the title compound (3.36 µg, 83%) as a white powder.

Intermediate 24

4-Bromo-1-(pyridine-3-ylsulfonyl)-1H-indole

Aq. 2M NaOH (1 mL) was added to a stirred mixture of pyridine-3-sulfonyl chloride hydrochloride (240 mg, 1.12 mmol; Intermediate 23), 4-bromoindole (200 mg, 1.02 mmol) and tetrabutylammonium hydrogen sulfate (35 mg, 0.10 mmol). The reaction was stirred 45 min. and the layers were allowed to separate. The organic layer was washed twice with diluted aq. NaOH, dried and concentrated to get the title compound (325 mg, 95%) as an off white solid. MS (ESI+) for $C_{13}H_9BrN_2O_2S$ m/z 337 (M+H)$^+$.

Intermediate 25

1-(Pyridine-3-ylsulfonyl)-4-vinyl-1H-indole

The experimental for Intermediate 15 was followed using 4-bromo-1-(pyridin-3-ylsulfonyl)-1H-indole (285 mg, 0.85 mmol; Intermediate 24) in dry MeCN (5 mL, one vial), tributyl(vinyl)stannane (0.494 mL, 1.69 mmol) and Pd(PPh$_3$)$_2$OAc$_2$ (32 mg, 0.042 mmol). Flash chromatography (1% MeOH in DCM) afforded the title compound (208 mg, 80%) as a yellow sticky oil. MS (ESI+) for $C_{15}H_{12}N_2O_2S$ m/z 285 (M+H)$^+$.

Intermediate 26

1-(Pyridine-3-ylsulfonyl)-1H-indole-4-carbaldehyde

The experimental for Intermediate 16 was followed using 1-(pyridine-3-ylsulfonyl)-4-vinyl-1H-indole (208 mg, 0.73 mmol; Intermediate 25), OsO$_4$ (9 mg, 0.04 mmol), 2,6-lutidine (170 µL, 1.46 mmol) and sodium periodate (0.625 g, 2.92 mmol). After flash purification by flash chromatography, some material was insoluble in DCM/MeOH and filtered off. The title compound (123 mg, 59%, still some dioxane according to HNMR) was obtained as a black gum. MS (ESI+) for $C_{14}H_{10}N_2O_3S$ m/z 287 (M+H)$^+$.

EXAMPLE 43

4-(piperazin-1-ylmethyl)-1-(pyridin-3-ylsulfonyl)-1H-indole tris(trifluoroacetate)

1-(Pyridine-3-ylsulfonyl)-1H-indole-4-carbaldehyde (41 mg, 0.14 mmol; Intermediate 26), 1-BOC-piperazine (53 mg, 0.29 mmol), acetic acid (82 µL, 1.43 mmol) and NaB(OAc)$_3$H (91 mg, 0.43 mmol) were, in that order, added to dry THF (4 mL). Additional 1-BOC-piperazine (27 mg, 0.14 mmol), acetic acid (41 µL, 0.72 mmol) and NaB(OAc)$_3$H (45 mg, 0.21 mmol) The mixture was irradiated with microwaves for 900 s at 130° C. The mixture was filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 13-33% MeCN, 0.1% TFA). The title compound (9 mg, 9%) was obtained as a brown solid. MS (ESI+) for $C_{18}H_{20}N_4O_2S$ m/z 357 (M+H)$^+$.

EXAMPLE 44

N,N-Dimethyl-1-[1-(pyridin-3-ylsulfonyl)-1H-indol-4-yl]methanamine bis(trifluoroacetate)

1-(Pyridine-3-ylsulfonyl)-1H-indole-4-carbaldehyde (41 mg, 0.14 mmol; Intermediate 26), dimethylamine hydrochloride (23 mg, 0.29 mmol), acetic acid (82 µL, 1.43 mmol) and NaB(OAc)₃H (91 mg, 0.43 mmol) were, in that order, added to dry THF (4 mL). Additional dimethylamine hydrochloride (12 mg, 0.14 mmol), acetic acid (41 µL, 0.72 mmol) and NaB(OAc)₃H (45 mg, 0.21 mmol) The mixture was irradiated with microwaves for 900 s at 130° C., filtered, concentrated and purified by preparative HPLC/UV (System A, 18-45% MeCN, 0.1% TFA). The title compound (5 mg, 7%) was obtained as a brown solid. MS (ESI+) for $C_{16}H_{17}N_3O_2S$ m/z 316 (M+H)⁺.

EXAMPLE 45

1-(Pyridin-3-ylsulfonyl)-4-(pyrrolidin-1-ylmethyl)-1H-indole bis(trifluoroacetate)

The experimental for Example 44 was followed using pyrrolidine (24 µL, 0.29 mmol). Preparative HPLC/UV (System A, 22-48% MeCN, 0.1% TFA). The title compound (12 mg, 15%) was obtained as a brown solid. MS (ESI+) for $C_{18}H_{19}N_3O_2S$ m/z 342 (M+H)⁺.

EXAMPLE 46

1-(Phenylsulfonyl)-4-(pyrrolidin-1-ylmethyl)-1H-indole trifluoroacetate

K₂CO₃ (59 mg, 0.43 mmol) and pyrrolidine (35 µL, 0.43 mmol) were added to 4-(bromomethyl)-1-(phenylsulfonyl)-1H-indole (30 mg, 0.086 mmol; Intermediate 2) in dry MeCN (4 mL). The mixture was irradiated with micro waves at 150° C. for 600 s. The reaction mixture was filtered, concentrated and purified by preparative HPLC/UV (System A, 25-52% MeCN, 0.1% TFA). The title compound (23 mg, 60%) was obtained as a colorless solid. MS (ESI+) for $C_{19}H_{20}N_2O_2S$ m/z 341 (M+H)⁺.

EXAMPLE 47

N,N-Dimethyl-1-[1-(phenylsulfonyl)-1H-indol-4-yl]methanamine trifluoroacetate The experimental for Example 46 was followed using dimethylamine hydrochloride (35 mg, 0.43 mmol) and K₂CO₃ (118 mg, 0.86 mmol). Preparative HPLC/UV (System A, 20-46% MeCN, 0.1% TFA). The title compound (20 mg, 55%) was obtained as a colorless solid. MS (ESI+) for $C_{17}H_{18}N_2O_2S$ m/z 315 (M+H)⁺.

COMPARATIVE EXAMPLE 48

4-{[(1-Methylpyrrolidin-3-yl)oxy]methyl}-1-(phenylsulfonyl)-1H-indole trifluoroacetate 1-methylpyrrolidin-3-ol (3.2 mg, 0.030 mmol) was dissolved in dry THF (1 mL) and potassium carbonate (7.9 mg, 0.060 mmol) was added and the mixture was heated in STEM-block at 75° C. After 20 min 4-(bromomethyl)-1-(phenylsulfonyl)-1H-indole (0.01 g, 0.03 mmol; Intermediate 2) was added and the mixture was heated for additional 1 h. Water (2 mL) and ethyl acetate (2 mL) was added and separated. The organic layer was extracted with brine (2 mL) and the solvent was evaporated. The residue was purified by preparative HPLC/UV (System A 10-40% MeCN 0.1% TFA) yielding 2.9 mg (14%) of the title compound as a light yellow gum. MS (ESI+) for $C_{20}H_{22}N_2O_3S$ m/z 371 (M+H)⁺.

Intermediate 27

4-Bromo-1H-indole-3-carbaldehyde

POCl₃ (1.02 g, 6.63 mmol) was added dropwise to ice cold DMF (3 mL) and stirred for 15 min. 4-Bromoindole (1.00 g, 5.10 mmol) in DMF (1 mL) was added slowly. The mixture was heated to 35° C. with continuous stirring for 1.20 h (yellow precipitation was formed). The reaction mixture was cold on ice and treated with ice and 20% W/w aq. NaOH to pH 14 (pink color). Heating at reflux for 15 min. afforded a yellow clear solution, which formed a white precipitation when allowed to attain rt. The precipitation was filtered off, rinsed with ice cold water and dried under reduced pressure over weekend to give the title compound (1.14 g, 65%) as an off white solid. MS (ESI+) for $C_9H_6BrNO$ m/z 224 (M+H)⁺.

Intermediate 28

4-Bromo-3-methyl-1H-indole

LAH (1.0M in THF, 5.75 mL, 5.75 mmol) was added dropwise to refluxing 4-bromo-1H-indole-3-carbaldehyde (644 mg, 2.87 mmol; Intermediate 27) in dry THF (20 mL). The mixture was refluxed 1 h, allowed to attain rt. and quenched with water (220 µL), W/w 15% aq. NaOH (220 µL) and water (650 µL). The resulting precipitation was filtered off, the filtrate concentrated and the residue was extracted with aq. NaOH (10 mL) and DCM (2×10 mL). The organic layers were combined with combined with an earlier batch of this intermediate (followed this experimental and starting from 4-bromo-1H-indole-3-carbaldehyde, 100 mg, 0.45 mmol; Intermediate 27), dried and concentrated to give the title compound (556 mg, 80%) as a light brown oil. MS (ESI+) for $C_9H_8BrN$ m/z 210 (M+H)⁺.

Intermediate 29

4-Bromo-3-methyl-1-(phenylsulfonyl)-1H-indole

Aq. 4M NaOH (3 mL) was added to a stirring mixture of 4-bromo-3-methyl-1H-indole (456 mg, 2.17 mmol; Intermediate 28), benzenesulfonyl chloride (306 µg, 2.39 mmol) and tetrabutylammonium hydrogen sulfate (74 mg, 0.22 mmol) in DCM (30 mL). The reaction mixture was stirred 1 h, combined with an earlier batch of this intermediate (followed this experimental and starting with 4-bromo-3-methyl-1H-indole, 100 mg, 0.48 mmol; Intermediate 28), washed twice with water, dried and concentrated. The crude product was purified by flash column chromatography (DCM/hexane 1:3). The product (650 mg, 70%) was obtained as a white solid. MS (ESI+) for $C_{15}H_{12}BrNO_2S$ m/z 350 (Monoisotop+H)⁺.

Intermediate 30

3-Methyl-1-(phenylsulfonyl)-4-vinyl-1H-indole

Tributyl(vinyl)stannane (0.400 mL, 1.37 mmol) and Pd(PPh₃)₂OAc₂ (51 mg, 0.069 mmol) were added to 4-bromo-3-methyl-1-(phenylsulfonyl)-1H-indole (240 mg, 0.69 mmol; Intermediate 29) in dry MeCN (4 mL). The reaction mixture was irradiated with micro-waves at 180° C. for 720 s. The mixture was combined with earlier batches of this intermediate (followed this experimental and starting with 4-bromo-3-methyl-1-(phenylsulfonyl)-1H-indole, 50 and 310 mg; Intermediate 29), filtered and concentrated. Purification was performed by flash chromatography (30% hexane in DCM). This afforded the product (420 mg, 82%) as a white solid. MS (ESI+) for $C_{17}H_{15}NO_2S$ m/z 298 (M+H)$^+$.

Intermediate 31

3-Methyl-1-(phenylsulfonyl)-1H-indole-4-carbaldehyde

OsO$_4$ (29 mg, 0.12 mmol) was added to a stirred mixture of 3-methyl-1-(phenylsulfonyl)-4-vinyl-1H-indole (342 mg, 1.15 mmol; Intermediate 30) and 2,6-lutidine (268 µL, 2.3 mmol) in dioxane (15 mL). The mixture turned from colorless to black in 1 minute. Sodium periodate (0.984 g, 4.6 mmol) in water (5 mL, warmed to dissolve) was added. A grey precipitation was immediately formed. The mixture was stirred for 50 min, combined with an earlier batch of this intermediate (followed this experimental and starting with 3-methyl-1-(phenylsulfonyl)-4-vinyl-1H-indole, 70 mg; Intermediate 30), extracted with water (30 mL) and DCM (2×30 mL). The organic layers were combined, dried, filtered and concentrated to give the title compound (463 mg, 89%) as a black solid. MS (ESI+) for $C_{16}H_{13}NO_3S$ m/z 300 (M+H)$^+$.

EXAMPLE 49

3-Methyl-1-(phenylsulfonyl)-4-(piperazin-1-ylmethyl)-1H-indole bis(trifluoroacetate)

3-methyl-1-(phenylsulfonyl)-1H-indole-4-carbaldehyde (40 mg, 0.13 mmol; Intermediate 31), 1-BOC-piperazine (50 mg, 0.27 mmol), acetic acid (76 µL, 1.34 mmol) and NaB(OAc)$_3$H (85 mg, 0.40 mmol) were, in that order, added to dry THF (4 mL). The mixture was irradiated with microwaves for 720 s at 130° C., filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-45% MeCN, 0.1% TFA). The title compound (32 mg, 40%) was obtained as a light brown solid. MS (ESI+) for $C_{20}H_{23}N_3O_2S$ m/z 370 (M+H)$^+$.

EXAMPLE 50

3-Methyl-4-[(4-methylpiperazin-1-yl)methyl]-1-(phenylsulfonyl)-1H-indole bis(trifluoroacetate)

3-methyl-1-(phenylsulfonyl)-1H-indole-4-carbaldehyde (40 mg, 0.13 mmol; Intermediate 31), 1-methylpiperazine (27 mg, 0.27 mmol), acetic acid (76 µL, 1.34 mmol) and NaB(OAc)$_3$H (85 mg, 0.40 mmol) were, in that order, added to dry THF (4 mL). The mixture was irradiated with microwaves for 720 s at 130° C., filtered, concentrated and purified using preparative HPLC/UV (System A, 23-50% MeCN, 0.1% TFA). The title compound (31 mg, 38%) was obtained as a light brown solid. MS (ESI+) for $C_{21}H_{25}N_3O_2S$ m/z 384 (M+H)$^+$.

EXAMPLE 51

3-Methyl-1-(phenylsulfonyl)-4-(pyrrolidin-1-ylmethyl)-1H-indole trifluoroacetate The experimental for Example 50 was followed using pyrrolidine (22 µL, 0.27 mmol). Preparative HPLC/UV (System A, 28-53% MeCN, 0.1% TFA). The title compound (20 mg, 32%) was obtained as a light brown solid. MS (ESI+) for $C_{20}H_{22}N_2O_2S$ m/z 355 (M+H)$^+$

EXAMPLE 52

N,N-Dimethyl-1-[3-methyl-1-(phenylsulfonyl)-1H-indol-4-yl]methanamine trifluoroacetate The experimental for Example 50 was followed using dimethylamine hydrochloride (22 mg, 0.27 mmol). Preparative HPLC/UV (System A, 23-50% MeCN, 0.1% TFA). The title compound (12 mg, 20%) was obtained as a colorless solid. MS (ESI+) for $C_{18}H_{20}N_2O_2S$ m/z 329 (M+H)$^+$.

Intermediate 32

4-Bromo-6-methoxy-1-(phenylsulfonyl)-1H-indole

4-Bromo-6-methoxy indole (0.07 g, 0.3 mmol) was dissolved in dry dichloromethane (4 mL) and benzenesulphonyl chloride (0.06 g, 0.3 mmol), tetrabutylammonium hydrogen sulphate (0.01 g, 0.01 mmol) and 4N NaOH (0.5 mL) were added and the mixture was stirred at rt for 50 min. The mixture was extracted with water (2×4 mL), dried (Na$_2$SO$_4$) and evaporated. The crude product was combined with an earlier batch of this intermediate (followed this experimental and starting with 4-bromo-6-methoxy indole (0.35 g, 1.5 mmol). MS (ESI+) for $C_{15}H_{12}BrNO_3S$ m/z 366 (M+H)$^+$.

Intermediate 33

6-Methoxy-1-(phenylsulfonyl)-4-vinyl-1H-indole

4-Bromo-6-methoxy-1-(phenylsulfonyl)-1H-indole (0.33 g, 0.9 mmol; Intermediate 32) was dissolved in dry toluene (4 mL) and tributyl(vinyl)stannane (0.53 mL, 1.8 mmol) and bis(triphenylphosphine)palladium(II)acetate (0.03 g, 0.05 mmol) were added. The mixture was stirred in STEM-block at 110° C. for 16 h. The crude product was combined with an earlier batch of this intermediate, filtrated and the solvent was evaporated. The residue was purified by flash chromatography using isohexane:dichloromethane 1:1 as eluent yielding 0.30 g (89%) of the title compound. MS (ESI+) for $C_{17}H_{15}NO_3S$ m/z 314 (M+H)$^+$.

Intermediate 34

6-Methoxy-1-(phenylsulfonyl)-1H-indole-4-carbaldehyde

6-Methoxy-1-(phenylsulfonyl)-4-vinyl-1H-indole (0.27 g, 0.9 mmol; Intermediate 33) was dissolved in dioxane (24 mL) and 2,6-lutidine (0.2 mL, 1.7 mmol) was added. Osmium tetraoxide (0.011 g, 0.04 mmol) was added and after 15 min of stirring did the mixture change colour to black. Sodium periodate (0.74 g, 3.4 mmol) dissolved in water (8 mL, warmed to dissolve) was added and a precipitation started to form. After 1 h of stirring at rt was the mixture portioned between 2N HCl and dichloromethane. The organic layer was dried (Na$_2$SO$_4$) and concentrated to give 0.41 g of the crude product. MS (ESI+) for $C_{16}H_{13}NO_4S$ m/z 316 (M+H)$^+$.

EXAMPLE 53

6-Methoxy-1-(phenylsulfonyl)-4-(piperazin-1-ylmethyl)-1H-indole bis(trifluoroacetate)

6-Methoxy-1-(phenylsulfonyl)-1H-indole-4-carbaldehyde (0.03 g, 0.1 mmol; Intermediate 34) was dissolved in dry THF (2 mL) and tert-butyl piperazine-1-carboxylate (0.035 g, 0.2 mmol), acetic acid (0.05 mL, 1.0 mmol) and sodium triacetoxyborohydride (0.061 g, 0.3 mmol) were added. The mixture was irradiated in microwave at 130° C. for 600 s. The mixture was filtrated and the solvent was evaporated. The residue was dissolved in 1.5 mL methanol and a few drops conc. HCl was added and the mixture was BOC-deprotected in STEM-block at 50° C. for 1 h. The mixture was purified by preparative HPLC/UV, (System A 20-50% MeCN 0.1% TFA) yielding 15 mg (25%) of the product as a brown gum. MS (ESI+) for $C_{20}H_{23}N_3O_3S$ m/z 386 (M+H)$^+$.

EXAMPLE 54

{[6-Methoxy-1-(phenylsulfonyl)-1H-indol-4-yl]methyl}dimethylamine trifluoroacetate Prepared by the procedure described for Example 53 using dimethylamine hydrochloride (0.021 g, 0.3 mmol). Yield: 16 mg (38%) of a brown gum after purification by preparative HPLC/UV (System A 20-50% MeCN 0.1% TFA). MS (ESI+) for $C_{18}H_{20}N_2O_3S$ m/z 345 (M+H)$^+$.

EXAMPLE 55

6-Methoxy-4-{[(3R)-3-methylpiperazin-1-yl]methyl}-1-(phenylsulfonyl)-1H-indole bis(trifluoroacetate)

Prepared by the procedure described for Example 53 using (2R)-2-methylpiperazine (0.025 g, 0.30 mmol). Yield: 22 mg (37%) of a brown gum after purification by preparative HPLC/UV (System A 20-50% MeCN 0.1% TFA). MS (ESI+) for $C_{21}H_{25}N_3O_3S$ m/z 400 (M+H)$^+$.

EXAMPLE 56

6-Methoxy-4-{[(3S)-3-methylpiperazin-1-yl]methyl}-1-(phenylsulfonyl)-1H-indole bis(trifluoroacetate)

Prepared by the procedure described for Example 53 using (2S)-2-methylpiperazine (0.025 g, 0.3 mmol). Yield: 26 mg (44%) of a brown gum after purification by preparative HPLC/UV (System A 20-50% MeCN 0.1% TFA). MS (ESI+) for $C_{21}1H_{25}N_3O_3S$ m/z 400 (M+H)$^+$.

EXAMPLE 57

6-Methoxy-4-[(4-methylpiperazin-1-yl)methyl]-1-(phenylsulfonyl)-1H-indole bis(trifluoroacetate)

Prepared by the procedure described for Example 53 using 1-methylpiperazine (0.03 mL, 0.3 mmol). Yield: 40 mg (67%) of a gray gum after purification by preparative HPLC/UV (System A 20-50% MeCN 0.1% TFA). MS (ESI+) for $C_{21}H_{25}N_3O_3S$ m/z 400 (M+H)$^+$.

EXAMPLE 58

4-(1,4-Diazepan-1-ylmethyl)-6-methoxy-1-(phenylsulfonyl)-1H-indole bis(trifluoroacetate)

Prepared by the procedure described for Example 53 using BOC-homopiperazine (0.051 g, 0.3 mmol). Yield: 41 mg (69%) of a light brown gum after purification by preparative HPLC/UV (System A 20-50% MeCN 0.1% TFA). MS (ESI+) for $C_{21}H_{25}N_3O_3S$ m/z 400 (M+H)$^+$.

EXAMPLE 59

6-Methoxy-1-(phenylsulfonyl)-4-(pyrrolidin-1-ylmethyl)-1H-indole trifluoroacetate Prepared by the procedure described for Example 53 using pyrrolidine (0.02 mL, 0.2 mmol). Yield: 27 mg (59%) of a brown gum after purification by preparative HPLC/UV (System A 20-50% MeCN 0.1% TFA). MS (ESI+) for $C_{20}H_{22}N_2O_3S$ m/z 371 (M+H)$^+$.

EXAMPLE 60

2-[{[6-Methoxy-1-(phenylsulfonyl)-1H-indol-4-yl]methyl}(methyl)amino]ethanol trifluoroacetate Prepared by the procedure described for Example 53 using 2-(methylamino)ethanol (0.02 mL, 0.1 mmol). Yield: 11 mg (30%) of a brown gum after purification by preparative HPLC/UV (System A 20-50% MeCN 0.1% TFA). MS (ESI+) for $C_{19}H_{22}N_2O_4S$ m/z 375 (M+H)$^+$.

Intermediate 35

4-Bromo-6-fluoro-1H-indole

1-Bromo-5-fluoro-2-methyl-3-nitrobenzene (2.00 g, 8.55 mmol) and (dimethoxymethyl)dimethylamine (5.66 mL, 42.7 mmol) in dry DMF (20 mL) was refluxed under $N_2$ for 8 h, then rt. over night. The mixture was diluted with DCM and extracted 5 times with water. The organic layer was dried, filtered and concentrated under reduced pressure. The residue was dissolved in AcOH (10 mL) and added drop wise to a boiling mixture of Fe(s, fine powder) in AcOH (10 mL). The mixture was refluxed for 40 min., partitioned between DCM and saturated aq. $Na_2CO_3$/brine (the mixture was filtered through celite before phase separation). The water layer was extracted once more with DCM. The organic layers were combined, dried and concentrated. Purification was performed by flash column chromatography (DCM/hexane 1:3) and afforded the title compound (660 mg, 39%) as a yellow oil. MS (ESI+) for $C_8H_5BrFN$ m/z 214 (M+H)$^+$.

Intermediate 36

4-Bromo-6-fluoro-1-(phenylsulfonyl)-1H-indole

Aq. 4 M NaOH (5 mL) was added to a stirring mixture of 4-bromo-6-fluoro-1H-indole (500 mg, 2.34 mmol; Intermediate 35), benzenesulfonyl chloride (329 μL g, 2.57 mmol) and tetrabutylammonium hydrogen sulfate (78 mg, 0.23 mmol) in DCM (30 mL). The reaction mixture was stirred 1 h, combined with an earlier batch of this intermediate (followed this experimental and starting with 4-bromo-6-fluoro-1H-indole, 152 mg, 0.71 mmol; Intermediate 35), washed twice with water, dried and concentrated. The product (1.08 g, 100%) was obtained as a beige solid. MS (ESI+) for $C_{14}H_9BrFNO_2S$ m/z 354 (M+H)$^+$.

Intermediate 37

6-Fluoro-1-(phenylsulfonyl)-4-vinyl-1H-indole

Tributyl(vinyl)stannane (0.413 mL, 1.41 mmol) and $Pd(PPh_3)_2OAc_2$ (53 mg, 0.071 mmol) were added to 2 micro wave vials containing 4-bromo-6-fluoro-1-(phenylsulfonyl)-1H-indole (250 mg, 0.71 mmol; Intermediate 36) in dry MeCN (4 mL) each. The reaction mixture was irradiated with microwaves at 180° C. for 720 s. The mixture was combined with an earlier batch of this intermediate (followed this experimental and starting with 4-bromo-6-fluoro-1-(phenylsulfonyl)-1H-indole, 50 mg; Intermediate 36), filtered and concentrated. Purification was performed by flash chromatography (hexane/DCM 2:1). This afforded the product (316 mg, 68%) as a white solid. MS (ESI+) for $C_{16}H_{12}FNO_2S$ m/z 302 (M+H)$^+$.

Intermediate 38

6-Fluoro-1-(phenylsulfonyl)-1H-indole-4-carbaldehyde $OsO_4$ (26 mg, 0.1 mmol) was added to a stirred mixture of 6-fluoro-1-(phenylsulfonyl)-4-vinyl-1H-indole (309 mg, 1.03 mmol; Intermediate 37) and 2,6-lutidine (239 µL, 2.05 mmol) in dioxane (18 mL). The mixture turned from colorless to black in 1 minute. Sodium periodate (0.877 g, 4.1 mmol) in water (6 mL, warmed to dissolve) was added. A grey precipitation was immediately formed. The mixture was stirred for 15 min, extracted with water (30 mL) and DCM (2×30 mL). The organic layers were combined, dried, filtered and concentrated to give the title compound (326 mg, 105%) as a black solid. MS (ESI+) for $C_{15}H_{10}FNO_3S$ m/z 304 (M+H)$^+$.

EXAMPLE 61

6-Fluoro-1-(phenylsulfonyl)-4-(piperazin-1-ylmethyl)-1H-indole bis(trifluoroacetate)

6-fluoro-1-(phenylsulfonyl)-1H-indole-4-carbaldehyde (38 mg, 0.13 mmol; Intermediate 38), 1-BOC-piperazine (47 mg, 0.25 mmol), acetic acid (72 µL, 1.25 mmol) and NaB(OAc)$_3$H (80 mg, 0.38 mmol) were, in that order, added to dry THF (4 mL). The mixture was irradiated with microwaves for 720 s at 130° C., filtered and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-50% MeCN, 0.1% TFA). The title compound (35 mg, 47%) was obtained as an off white solid. MS (ESI+) for $C_{19}H_{20}FN_3O_2S$ m/z 374 (M+H)$^+$.

EXAMPLE 62

4-(1,4-Diazepan-1-ylmethyl)-6-fluoro-1-(phenylsulfonyl)-1H-indole bis(trifluoroacetate)

The experimental for Example 61 was followed using 1-BOC-homopiperazine (50 mg, 0.25 mmol). Preparative HPLC/UV (System A, 20-50% MeCN, 0.1% TFA). The title compound (35 mg, 45%) was obtained as a light brown solid. MS (ESI+) for $C_{20}H_{22}FN_3O_2S$ m/z 388 (M+H)$^+$.

EXAMPLE 63

6-Fluoro-4-{[(3S)-3-methylpiperazin-1-yl]methyl}-1-(phenylsulfonyl)-1H-indole bis(trifluoroacetate)

6-fluoro-1-(phenylsulfonyl)-1H-indole-4-carbaldehyde (38 mg, 0.13 mmol; Intermediate 38), (2S)-2-methylpiperazine (25 mg, 0.25 mmol), acetic acid (72 µL, 1.25 mmol) and NaB(OAc)$_3$H (80 mg, 0.38 mmol) were, in that order, added to dry THF (4 mL). The mixture was irradiated with microwaves for 720 s at 130° C., filtered, concentrated and purified using preparative HPLC/UV (System A, 25-55% MeCN, 0.1% TFA). The title compound (13 mg, 17%) was obtained as a light brown solid. MS (ESI+) for $C_{20}H_{22}FN_3O_2S$ m/z 388 (M+H)$^+$.

EXAMPLE 64

6-Fluoro-4-{[(3R)-3-methylpiperazin-1-yl]methyl}-1-(phenylsulfonyl)-1H-indole bis(trifluoroacetate)

The experimental for Example 63 was followed using (2R)-2-methylpiperazine (25 mg, 0.25 mmol). Preparative HPLC/UV (System A, 23-50% MeCN, 0.1% TFA). The title compound (16 mg, 20%) was obtained as a light brown solid. MS (ESI+) for $C_{20}H_{22}FN_3O_2S$ m/z 388 (M+H)$^+$.

EXAMPLE 65

6-Fluoro-1-(phenylsulfonyl)-4-(pyrrolidin-1-ylmethyl)-1H-indole trifluoroacetate The experimental for Example 63 was followed using pyrrolidine (21 µL, 0.25 mmol). Preparative HPLC/UV (System A, 25-55% MeCN, 0.1% TFA). The title compound (22 mg, 37%) was obtained as a colorless solid. MS (ESI+) for $C_{19}H_{19}FN_2O_2S$ m/z 359 (M+H)$^+$.

EXAMPLE 66

2-[{[6-Fluoro-1-(phenylsulfonyl)-1H-indol-4-yl]methyl}(methyl)amino]ethanol trifluoroacetate The experimental for Example 63 was followed using 2-(methylamino)ethanol (20 µL, 0.25 mmol). Preparative HPLC/UV (System A, 20-50% MeCN, 0.1% TFA). The title compound (25 mg, 42%) was obtained as a colorless solid. MS (ESI+) for $C_{18}H_{19}FN_2O_3S$ m/z 363 (M+H)$^+$.

EXAMPLE 67

{[6-Fluoro-1-(phenylsulfonyl)-1H-indol-4-yl]methyl}dimethylamine trifluoroacetate The experimental for Example 63 was followed using dimethylamine hydrochloride (20 mg, 0.25 mmol). Preparative HPLC/UV (System A, 22-52% MeCN, 0.1% TFA). The title compound (15 mg, 27%) was obtained as a colorless solid. MS (ESI+) for $C_{17}H_{17}FN_2O_2S$ m/z 333 (M+H)$^+$.

EXAMPLE 68

6-Fluoro-4-[(4-methylpiperazin-1-yl)methyl]-1-(phenylsulfonyl)-1H-indole bis(trifluoroacetate)

The experimental for Example 63 was followed using 1-methylpiperazine (28 µL, 0.25 mmol). Preparative HPLC/UV (System A, 22-52% MeCN, 0.1% TFA). The title compound (15 mg, 27%) was obtained as a brown solid. MS (ESI+) for $C_{20}H_{22}FN_3O_2S$ m/z 388 (M+H)$^+$.

Intermediate 39

1-(Phenylsulfonyl)-4-(pyrrolidin-1-ylmethyl)-1H-indol-6-ol

Prepared by the procedure described for Example 70 using 6-methoxy-1-(phenylsulfonyl)-4-(pyrrolidin-1-ylmethyl)-1H-indole (0.018 g, 0.05 mmol; Example 59). Yield: 12 mg (71%) of a brownish-red solid. MS (ESI+) for $C_{19}H_{20}N_2O_3S$ m/z 357 (M+H)$^+$.

EXAMPLE 69

1-(Phenylsulfonyl)-4-(pyrrolidin-1-ylmethyl)-1H-indol-6-yl dimethylcarbamate trifluoroacetate 1-(Phenylsulfonyl)-4-(pyrrolidin-1-ylmethyl)-1H-indol-6-ol (12.2 mg; 0.034 mmol; Intermediate 39) was dissolved in 1 mL pyridine and dimethylcarbamoyl chloride (18.0 mg; 0.171 mmol) was added. The reaction was allowed to stir at r.t for 1 hour. The reaction was stripped of solvent and the crude material purified by preparative HPLC.

Yield: 4.9 mg (25%). MS (ESI+) for $C_{22}H_{25}N_3O_4S$ m/z 428 (M+H)$^+$.

EXAMPLE 70

4-(1,4-Diazepan-1-ylmethyl)-1-(phenylsulfonyl)-1H-indol-6-ol

To 4-(1,4-Diazepan-1-ylmethyl)-6-methoxy-1-(phenylsulfonyl)-1H-indole (0.12 g, 0.03 mmol; Example 58) was 33% HBr in acetic acid (2 mL) added and the mixture was refluxed in STEM-block at 125° C. for 20 h which gave 70% conversion to product. Additional HBr in acetic acid (1 mL) was added and the mixture was refluxed for additional 20 h which gave 90% conversion product. Additional HBr in acetic acid (1 mL) was added and the mixture was refluxed for additional 21 h. The mixture was cooled to rt and sat. NaHCO$_3$-solution was added (foaming) until neutral pH. The mixture was extracted with 3*EtOAc/ethanol (10:1). The organic layers were dried (Na$_2$SO$_4$), filtrated and the solvent was evaporated yielding 9.5 mg (82%) of a brownish-red solid. MS (ESI+) for $C_{20}H_{23}N_3O_3S$ m/z 386 (M+H)$^+$.

Intermediate 40 tert-Butyl 4-[(6-methoxy-1H-indol-4-yl)methyl]piperazine-1-carboxylate

40% W/w aq. NaOH (1 mL) was added to tert-butyl 4-({1-[(4-fluorophenyl)sulfonyl]-6-methoxy-1H-indol-4-yl}methyl)piperazine-1-carboxylate (626 mg, 1.12 mmol) in EtOH (10 mL). The reaction was refluxed for 1.5 h, allowed to attain rt. and extracted with DCM (2×50 mL) and water (40 mL). The organic layers were combined, dried and concentrated to give 450 mg crude product. Purification was performed by preparative HPLC/UV (System A, 30-65% MeCN, 0.1% NH$_4$OAc). The residue was extracted with DCM and water and the organic layer was dried, filtered and concentrated to give the title compound (130 mg, 32%, from 1-[(4-fluorophenyl)sulfonyl]-6-methoxy-4-vinyl-1H-indole; prepared according to the method of Intermediate 33) as a light brown solid. MS (ESI+) for $C_{19}H_{27}N_3O_3$ m/z 346 (M+H)$^+$.

EXAMPLE 71

1-[(4-Fluorophenyl)sulfonyl]-6-methoxy-4-(piperazin-1-ylmethyl)-1H-indole acetate NaH (6 mg, 0.14 mmol, 60% in mineral oil) was added to tert-butyl 4-[(6-methoxy-1H-indol-4-yl)methyl]piperazine-1-carboxylate (10 mg, 0.029 mmol; Intermediate 40) in dry THF (1 mL). The reaction mixture was stirred for 5 min, 4-fluorobenzenesulfonyl chloride (8 mg, 0.044 mmol) in dry THF (0.5 mL) was added and the mixture was stirred over night. The reaction mixture was cooled on ice and quenched with ice and THF was evaporated. The residue was dissolved in MeOH (3 mL) and conc. HCl (0.5 mL) was added. The mixture was irradiated by microwaves at 100° C. for 300 s, the volume concentrated to ~1.5 mL, followed of filtering and purification by preparative HPLC/UV (System A, 25-55% MeCN, 0.1% NH$_4$OAc). The title compound (5 mg, 39%) was obtained as a white solid. MS (ESI+) for $C_{20}H_{22}FN_3O_3S$ m/z 404 (M+H)$^+$.

EXAMPLE 72

6-Methoxy-4-(piperazin-1-ylmethyl)-1-{[3-(trifluoromethyl)phenyl]sulfonyl}-1H-indole bis(trifluoroacetate)

NaH (8 mg, 0.20 mmol, 60% in mineral oil) was added to tert-butyl 4-[(6-methoxy-1H-indol-4-yl)methyl]piperazine-1-carboxylate (23 mg, 0.067 mmol; Intermediate 40) in dry THF (1.5 mL). The reaction mixture was stirred for 45 min, 3-(trifluoromethyl)benzenesulfonyl chloride (16 µL, 0.099 mmol) in dry THF (2 mL) was added and the mixture was stirred over night. Additional NaH (1 eq.) and 3-(trifluoromethyl)benzenesulfonyl chloride (1.5 eq) were added with continuous stirring 1 h 30 min. Additional NaH (3 eq) was added with continuous stirring 1 h. The mixture was cooled on ice, quenched with a few drops of water and acidified with conc. HCl (0.5 mL). The THF was evaporated and MeOH (1.5 mL) was added. The mixture was irradiated by microwaves at 100° C. for 300 s, followed of filtering and purification by preparative HPLC/UV (System A, 33-63% MeCN, 0.1% TFA). The title compound (10 mg, 21%) was obtained as a colorless solid. MS (ESI+) for $C_{21}H_{22}F_3N_3O_3S$ m/z 454 (M+H)$^+$.

EXAMPLE 73

1-[(2-Chlorophenyl)sulfonyl]-6-methoxy-4-(piperazin-1-ylmethyl)-1H-indole bis(trifluoroacetate)

NaH (18 mg, 0.47 mmol, 60% in mineral oil) was added to tert-butyl 4-[(6-methoxy-1H-indol-4-yl)methyl]piperazine-1-carboxylate (23 mg, 0.067 mmol; Intermediate 40) in dry THF (1.5 mL). The reaction mixture was stirred for 30 min and the color turned from orange to green. 2-Chlorobenzenesulfonyl chloride (36 µL, 0.27 mmol) in dry THF (0.5 mL) was added and the mixture was stirred over night. Additional NaH (3 eq) was added with continuous stirring 1.40 h. Additional NaH (3 eq) was added, stirred 15 min, followed by addition of 2-chlorobenzenesulfonyl chloride (1 eq) with continuous stirring 2 h. This afforded ~90% conversion to product. The mixture was cooled on ice, quenched with a few drops of water and extracted with DCM (×2) and brine. The organic layers were combined, dried and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-50% MeCN, 0.1% TFA). The title compound (10 mg, 24%) was obtained as a blue solid. MS (ESI+) for $C_{20}H_{22}ClN_3O_3S$ m/z 420 (M+H)$^+$.

EXAMPLE 74

1-[(3-Chloro-2-methylphenyl)sulfonyl]-6-methoxy-4-(piperazin-1-ylmethyl)-1H-indole bis(trifluoroacetate)

NaH (18 mg, 0.47 mmol, 60% in mineral oil) was added to tert-butyl 4-[(6-methoxy-1H-indol-4-yl)methyl]piperazine- 1-carboxylate (23 mg, 0.067 mmol; Intermediate 40) in dry THF (1.5 mL). The reaction mixture was stirred for 30 min and the color turned from orange to green. 3-Chloro-2-methylbenzenesulfonyl chloride (60 mg, 0.27 mmol) in dry THF (0.5 mL) was added and the mixture was stirred over night. Additional NaH (3 eq) was added with continuous stirring 1.40 h. Additional NaH (3 eq) was added, stirred 15 min, followed by addition of 3-chloro-2-methylbenzenesulfonyl chloride (2 eq) with continuous stirring 2 h. Additional NaH (3 eq) and 3-chloro-2-methylbenzenesulfonyl chloride (1 eq) were added with continuous stirring over night. This afforded ~80% conversion to product. The mixture was cooled on ice, quenched with a few drops of water and extracted with DCM (×2) and brine. The organic layers were combined, dried and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-50% MeCN, 0.1% TFA). The title compound (14 mg, 32%) was obtained as a blue solid. MS (ESI+) for $C_{21}H_{24}ClN_3O_3S$ m/z 434 (M+H)$^+$.

EXAMPLE 75

1-[(2,5-Dimethoxyphenyl)sulfonyl]-6-methoxy-4-(piperazin-1-ylmethyl)-1H-indole bis(trifluoroacetate)

NaH (18 mg, 0.47 mmol, 60% in mineral oil) was added to tert-butyl 4-[(6-methoxy-1H-indol-4-yl)methyl]piperazine-1-carboxylate (23 mg, 0.067 mmol; Intermediate 40) in dry THF (1.5 mL). The reaction mixture was stirred for 30 min and the color turned from orange to green. 2,5-dimethoxybenzenesulfonyl chloride (63 mg, 0.27 mmol) in dry THF (0.5 mL) was added and the mixture was stirred over night. Additional NaH (3 eq) was added with continuous stirring 1.40 h. Additional NaH (3 eq) was added, stirred 15 min, followed by addition of 2,5-dimethoxybenzenesulfonyl chloride (2 eq) with continuous stirring 2 h. The mixture was cooled on ice, quenched with a few drops of water and extracted with DCM (×2) and brine. The organic layers were combined, dried and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 20-50% MeCN, 0.1% TFA). The title compound (14 mg, 31%) was obtained as a blue solid. MS (ESI+) for $C_{22}H_{27}N_3O_5S$ m/z 446 (M+H)$^+$.

EXAMPLE 76

2-{[6-Methoxy-4-(piperazin-1-ylmethyl)-1H-indol-1-yl]sulfonyl}benzonitrile bis(trifluoroacetate)

NaH (18 mg, 0.47 mmol, 60% in mineral oil) was added to tert-butyl 4-[(6-methoxy-1H-indol-4-yl)methyl]piperazine-1-carboxylate (23 mg, 0.067 mmol; Intermediate 40) in dry THF (1.5 mL). The reaction mixture was stirred for 30 min and the color turned from orange to green. 2-Cyanobenzenesulfonyl chloride (54 mg, 0.27 mmol) in dry THF (0.5 mL) was added and the mixture was stirred over night. Additional NaH (2 eq) and 2-cyanobenzenesulfonyl chloride (1 eq) were added with continuous stirring 1.40 h. Additional NaH (3 eq) was added, stirred 15 min, followed by addition of 2-cyanobenzenesulfonyl chloride (1 eq) with continuous stirring 2 h. This afforded ~70% conversion to product. The mixture was cooled on ice, quenched with a few drops of water and extracted with DCM (×2) and brine. The organic layers were combined, dried and concentrated. The residue was dissolved in MeOH (1.5 mL) and conc. HCl (0.5 mL) and irradiated using microwaves at 100° C. for 300 s. The mixture was filtered and purified using preparative HPLC/UV (System A, 16-47% MeCN, 0.1% TFA). The title compound (13 mg, 31%) was obtained as a blue solid. MS (ESI+) for $C_{21}H_{22}N_4O_3S$ m/z 411 (M+H)$^+$.

EXAMPLE 77

({1-[(4-Fluorophenyl)sulfonyl]-1H-indol-4-yl}methyl)amine, trifluoroacetate

To 1-[(4-Fluorophenyl)sulfonyl]-1H-indole-4-carbaldehyde (30 mg, 0.10 mmol; Intermediate 13) in dry MeOH (2 mL) were added ammonium acetate (76 mg, 1.0 mmol) and NaBH$_3$CN (19 mg, 0.30 mmol). The mixture was irradiated with microwaves for 10 minutes at 130° C. followed by filtration and purification by preparative HPLC/UV (System A, 20-50% MeCN, 0.1% TFA). This afforded the title compound (5 mg, 12%) as a colorless solid. MS (ESI+) for $C_{15}H_{13}FN_2O_2S$ m/z 288 [M-NH$_2$]$^+$.

EXAMPLE 78

N-({1-[(4-Fluorophenyl)sulfonyl]-1H-indol-4-yl}methyl)ethanamine, trifluoroacetate Ethylamine (2M in THF, 0.20 mL, 0.40 mmol) was added to 1-[(4-fluorophenyl)sulfonyl]-1H-indole-4-carbaldehyde (30 mg, 0.10 mmol; Intermediate 13) in dry THF (3 mL). The mixture was stirred for 20 min. followed by addition of acetic acid (57 µL, 0.99 mmol) and NaBH$_3$(OAc)$_3$ (105 mg, 0.50 mmol). The reaction mixture was irradiated with microwaves for 30 min. at 130° C., filtered and concentrated. Purification was performed by preparative HPLC/UV (System A, 20-50% MeCN, 0.1% TFA). This afforded the title compound (4 mg, 10%) as a colorless solid. MS (ESI+) for $C_{17}H_{17}FN_2O_2S$ m/z 333 (M+H)$^+$.

Intermediate 41

4-Bromo-3-methyl-2-nitrophenol

2-Nitro-3-methylphenol (10 g, 65 mmol) was dissolved in CHCl$_3$ (10 mL) and cooled on ice. Br$_2$ (3.2 mL, 62 mmol) was dissolved in concentrated acetic acid (7.5 mL) and added dropwise to the solution. The reaction mixture was stirred at 0 deg for 2 hrs. Ice was added and the layers were separated. The aqueous layer was extracted with CHCl$_3$, the combined organic layers were washed with H$_2$O and brine, dried over Na$_2$SO$_4$, filtered and concentrated to give 4-bromo-3-methyl-2-nitrophenol, 15 g (99%).

Intermediate 42

4-Bromo-3-methyl-2-nitrophenyl methyl ether

4-Bromo-3-methyl-2-nitrophenol (7.17 g, 31 mmol, Intermediate 41) was dissolved in acetone (50 mL). K$_2$CO$_3$ (8.65 g, 62 mmol) was added, followed by MeI (3.9 mL, 62 mmol) and the reaction mixture was stirred at ambient temperature for 18 hrs. The crude mixture was concentrated, H$_2$O was added and the mixture was extracted with CH$_2$Cl$_2$, dried over Na$_2$SO$_4$, filtered and evaporated to give 4-bromo-3-methyl-2-nitrophenyl methyl ether, 7 g (92%).

Intermediate 43

4-Bromo-7-methoxy-1-(phenylsulfonyl)-1H-indole

4-Bromo-3-methyl-2-nitrophenyl methyl ether (6.8 g, 27.6 mmol, Intermediate 42) was dissolved in DMF (20 mL). Dimethylformamide dimethylacetal (6 mL) and pyrrolidine (2.3 mL, 28 mmol) were added and the reaction mixture was heated at 90 deg for 18 hrs. The reaction mixture was allowed to cool to ambient temperature, $CH_2Cl_2$ was added and the mixture was extracted with $H_2O$, the organic layer was dried over $Na_2SO_4$, filtered and concentrated.

The crude material was dissolved in acetic acid, and added dropwise to a solution of Fe (4.5 g, 82 mmol) in boiling acetic acid (40 mL). The reaction mixture was heated at reflux for 30 min and then allowed to cool to ambient temperature. $H_2O$ was added and the mixture was neutralised with $Na_2CO_3$, extracted with $CH_2Cl_2$, dried over $Na_2SO_4$, filtered and concentrated. The crude material was purified by column chromatography on silica (ethyl acetate/heptane 1:1) to give 4-bromo-7-methoxy indole as a dark oil. The material was immediately used in the next step.

4-Bromo-7-methoxy indole (2 g, 8.8 mmol) was dissolved in $CH_2Cl_2$ (300 mL). $PhSO_2Cl$ (2.4 g, 9.4 mmol was added, followed by tetrabutylammonium hydrogen sulfate (0.34 g, 0.88 mmol) and 4M aqueous NaOH (17 mL), in that order. The reaction mixture was stirred at ambient temperature for 3 hrs. The layers were separated and the aqueous layer was extracted with $CH_2Cl_2$, washed with $H_2O$, dried over $Na_2SO_4$, filtered and concentrated. The crude material was recrystallised from ethanol to give 4-bromo-7-methoxy-1-(phenylsulfonyl)-1H-indole, 0.9 g.

EXAMPLE 79

7-Methoxy-1-(phenylsulfonyl)-4-(piperazin-1-ylmethyl)-1H-indole bis(trifluoroacetate)

4-Bromo-7-methoxy-1-(phenylsulfonyl)-1H-indole (200 mg, 0.55 mmol, Intermediate 43), tributylvinyltin (348 mg, 1.1 mmol) and bis(acetate)bis(triphenylphosphine)-palladium(II) (46 mg, 0.06 mmol) were mixed in dry acetonitrile (2 mL) and heated in microwave at 180 deg for 10 min. The reaction mixture was filtered through celite and concentrated. The crude product was purified by column chromatography on silica ($CHCl_3$/hexane 7:3) to give 4-vinyl-7-methoxy-1-(phenylsulfonyl)-1H-indole, 0.19 g, which was used immediately in the next step.

This material (0.19 g, 0.61 mmol) was dissolved in dioxane (7 mL), 2,6-lutidine (0.13 g, 1.22 mmol) and $OsO_4$ (23 mg, 0.09 mmol) were added and the mixture was stirred at ambient temperature for a minute and $NaIO_4$ (0.51 g, 2.4 mmol) in $H_2O$ (ca 1 mL) was added. The mixture was stirred at ambient temperature for 30 min. $CHCl_3$ was added and the mixture was extracted with 2M aqueous HCl, dried over $Na_2SO_4$, filtered and concentrated to yield 4-Carbaldehyde-7-methoxy-1-(phenylsulfonyl)-1H-indole. The crude aldehyde was used in the next step without further purification.

4-Carbaldehyde-7-methoxy-1-(phenylsulfonyl)-1H-indole (0.25 g, 0.8 mmol) was dissolved in methanol (10 mL), boc-piperazine (0.3 g, 1.6 mmol) and $NaCNBH_3$ (64 mg, 0.96 mmol) were added, followed by acetic acid (until pH=5). The reaction mixture was stirred at ambient temperature for 18 hrs.

The reaction mixture was concentrated and the crude material was purified by column chromatography on silica (ethyl acetate/heptane 2:1) to give tert-butyl 4-{[7-methoxy-1-(phenylsulfonyl)-1H-indol-4-yl]methyl}piperazine-1-carboxylate, 0.38 g, which was immediately used in the next step.

tert-Butyl 4-{[7-methoxy-1-(phenylsulfonyl)-1H-indol-4-yl]methyl}piperazine-1-carboxylate (0.38 g, 0.78 mmol) was dissolved in methanol (1 ml), methanol/conc. HCl 4:1 (1 ml) was added and the reaction mixture was heated in microwave at 100 deg for 3 min. $H_2O$ was added and the mixture was extracted with $CHCl_3$, the aqueous phase was basified with $Na_2CO_3$ and extracted with ethyl acetate, dried over $Na_2SO_4$, filtered and concentrated to give the crude product which was purified by reversed phase preparative HPLC using ACE Prep UV C8 150×30 mm, flow 38 ml/min, gradient time 8.5 min using the eluent system: water/0.1% TFA and $CH_3CN$ (15-45% MeCN), fractions collected based on UV-signal (254 nm). The purest fractions were pooled and the acetonitrile was evaporated. Yield: 12 mg (2.5%). Light brown gum. MS (electronspray; [M+H]+) m/z 386.

Intermediate 44

4-Bromo-1-(phenylsulfonyl)-1H-indole

Sodium hydride (2.8 g, 60%, 70.4 mmol) was washed with heptane to remove the mineral oil prior reaction. The sodium hydride was mixed with THF (250 mL) and cooled on an ice bath before 4-bromoindole (4.6 g, 23.5 mmol) was added. The reaction mixture was stirred for 15 minutes before benzenesulfonyl chloride (6.22 g, 35.2 mmol) was added. The reaction mixture was stirred at RT ON. Ice and water was added followed by EtOAc. The phases were separated and the aqueous phase was extracted with EtOAc twice. The combined organic phases were dried (MgSO4) before the solvent was evaporated. The obtained crude product was pure enough to be used in the next step. Got 8.52 g of an oil which solidified on standing, yield 100%. MS (ESI+) for $C_{14}H_{10}BrNO_2S$ m/z 336 (M+H)+.

Intermediate 45

1-(Phenylsulfonyl)-4-vinyl-1H-indole

4-Bromo-1-(phenylsulfonyl)-1H-indole (8.52 g, 25.3 mmol, Intermediate 44) was dissolved in dry toluene (20 mL) under an $N_2(g)$ atmosphere before vinylstannane (16.07 g, 50.7 mmol) and bis[triphenylphosphine)palladium(II) acetate (0.95 g, 1.3 mmol) was added. The reaction was heated to 110° C. for 16 h cooled the reaction mixture to RT and filtered the reaction mixture through a celite pad, and evaporated the solvent. Dissolved the obtained oil in acetonitrile and hexanes, separated the phases. Evaporated the acetonitrile phase and purified the obtained crude product by flash chromatography using 30% DCM in hexanes. Isolated 4.4 g of the desired product as a white solid, yield 62%. MS (ESI+) for $C_{16}H_{13}NO_2S$ m/z 284 (M+H)+.

Intermediate 46

2-Methyl-1-(phenylsulfonyl)-4-vinyl-1H-indole 1-(Phenylsulfonyl)-4-vinyl-1H-indole (190 mg, 0.7 mmol, Intermediate 45) was weight in to a pre dried reaction flask and purged with nitrogen gas for 1 h. Dry THF (50 mL) was added and the reaction flask was cooled to −78° C. before LDA (0.35 mL, 0.7 mmol, 2M) was added. The reaction was stirred for 15 minutes before iodomethane (95.2 mg, 0.7 mmol) was added. Allowed the reaction mixture to slowly reach RT ON. Added 1 mL MeOH and evaporated the reaction mixture on silica. Purified by flash chromatography using 20% DCM in hexanes. Got 61 mg of a white solid, 30% yield. MS (ESI+) for $C_{17}H_{15}NO_2S$ m/z 298 (M+H)+.

Intermediate 47

2-Methyl-1-(phenylsulfonyl)-1H-indole-4-carbaldehyde

2-Methyl-1-(phenylsulfonyl)-4-vinyl-1H-indole-4 (61 mg, 0.2 mmol, Intermediate 46) was dissolved in dioxane (50 mL) before 2,6-lutidine (44 mg, 0.4 mmol) was added. Osmium tetraoxide (2.61 mg, 0.01 mmol) was added as a solid. Sodium periodate (175 mg, 0.8 mmol) dissolved in the water (6 mL) (warmed to dissolve) was added to the dioxane solution. The reaction mixture was stirred for 2 h at RT. Water and DCM was added, separated the phases. Extracted the aqueous phase with DCM 5 times. The combined organic phases were dried ($MgSO_4$) and the solvent was evaporated. The crude product was purified by flash chromatography using 15% DCM in hexanes as eluent. Got 50 mg, of the product as a violet oil, yield 83%. MS (ESI+) for $C_{16}H_{13}NO_3S$ m/z 300 (M+H)+.

Intermediate 48 tert-Butyl 4-{[2-methyl-1-(phenylsulfonyl)-1H-indol-4-yl]methyl}piperazine-1-carboxylate 2-Methyl-1-(phenylsulfonyl)-1H-indole-4-carbaldehyde (94 mg, 0.3 mmol, Intermediate 47) was dissolved in THF (dry) (4 mL) before boc-piperazine (87.7 mg, 0.5 mmol) was added followed by acetic acid (188 mg, 3.1 mmol) and sodium triacetoxyborohydride (199 mg, 0.9 mmol) was added. The reaction mixture was heated in microwave for 720 s at 130° C. The solvent was evaporated, added water and DCM. Separated the phases and extracted the aqueous phase with DCM twice. The combined organic phases were dried (MgSO4) and the solvent was evaporated. The crude product was purified by preparative HPLC (30-60). Isolated 110 mg, as an oil, yield 80%. MS (ESI+) for $C_{25}H_{31}N_3O_4S$ m/z 470 (M+H)+.

EXAMPLE 80

2-Methyl-1-(phenylsulfonyl)-4-(piperazin-1-ylmethyl)-1H-indole hydrochloride tert-Butyl 4-{[2-methyl-1-(phenylsulfonyl)-1H-indol-4-yl]methyl})piperazine-1-carboxylate (110 mg, 0.23 mmol, Intermediate 48) was dissolved in MeOH (4 mL) and 1 mL conc HCl and heated to 100° C. for 3 minutes in microwave. Evaporated the solvent, got 86 mg of a white solid, yield 100%. MS (ESI+) for $C_{20}H_{23}N_3O_2S$ m/z 370 (M+H)+.

Intermediate 49

1-(Phenylsulfonyl)-1H-indole-4-carbaldehyde

1H-Indole-4-carbaldehyde (0.300 g, 2.01 mmol), benzensulfonyl chloride (0.47 g, 2.67 mmol) and tetrabutylammonium hydrogen sulfate (0.070 g, 0.21 mmol) were dissolved in dichloromethane (10 mL) and NaOH (413 mg, 10.33 mmol) in water (3 mL) was added. The mixture was stirred overnight and diluted with water and extracted with dichloromethane (1×). The combined organics were dried ($MgSO_4$) and the crude product was purified with a plug of silica using 1% MeOH in dichloromethane as the eluent.

Yield: 541 mg (95%). White solid. MS (electronspray; [M+H]+) m/z 286.3.

Intermediate 50

1-tert-Butyl 2-methyl 4-{[1-(phenylsulfonyl)-1H-indol-4-yl]methyl}piperazine-1,2-dicarboxylate 1-tert-butyl 2-methyl piperazine-1,2-dicarboxylate (0.205 g, 0.64 mmol), 1-(phenylsulfonyl)-1H-indole-4-carbaldehyde (0.160 g, 0.56 mmol, Intermediate 49) and acetic acid (0.100 g, 1.68 mmol) were dissolved in MeOH (5 mL) and stirred for 3 minutes before sodium cyanoborohydride (0.060 g, 0.95 mmol) was added. The mixture was stirred at room temperature for 15 minutes and the mixture was evaporated and partitioned between water and dichloromethane. The organic phase was dried ($MgSO_4$) and evaporated. The crude product was purified by flash chromatography using 1% MeOH to 2.5% MeOH in dichloromethane. Colorless oil. This intermediate was used directly in the next step to yield Intermediate 51. MS (electronspray; [M+H]+) m/z 514.6.

Intermediate 51

1-(tert-Butoxycarbonyl)-4-{[1-(phenylsulfonyl)-1H-indol-4-yl]methyl}piperazine-2-carboxylic acid 1-tert-Butyl 2-methyl 4-{[1-(phenylsulfonyl)-1H-indol-4-yl]methyl}piperazine-1,2-dicarboxylate (all of Intermediate 50) was dissolved in 1M KOH (3 mL) in MeOH (3 mL) and THF (3 mL) and stirred overnight. The mixture was evaporated and diluted with dichloromethane and water. pH was adjusted to 4 with 1N HCl (2.5 mL) and saturated solution of dihydrogenphosphate. The organic phase was evaporated and purified by flash chromatography using 2.5% MeOH to 5% MeOH in dichloromethane. Yield: 85 mg (30%, calculated from 1-(phenylsulfonyl)-1H-indole-4-carbaldehyde). White solid. MS (electronspray; [M+H]+) m/z 500.4.

EXAMPLE 81

Methyl 4-{[1-(phenylsulfonyl)-1H-indol-4-yl]methyl}piperazine-2-carboxylate bis(trifluoroacetate)

1-tert-Butyl 2-methyl 4-{[1-(phenylsulfonyl)-1H-indol-4-yl]methyl}piperazine-1,2-dicarboxylate (0.013 g, 0.025 mmol, Intermediate 50) was dissolved in dichloromethane (1 mL) and TFA (0.5 mL) was added. The mixture was stirred for 1 h and evaporated. Yield: 16 mg (100%). Colorless oil. MS (electronspray; [M+H]+) m/z 414.6.

EXAMPLE 82

(4-{[1-(Phenylsulfonyl)-1H-indol-4-yl]methyl}piperazin-2-yl)methanol bis(trifluoroacetate)

1M $BH_3$ in THF (0.2 mL, 0.2 mmol) was added dropwise to a solution of 1-(tert-butoxycarbonyl)-4-{[1-(phenylsulfonyl)-1H-indol-4-yl]methyl}piperazine-2-carboxylic acid (0.010 g, 0.020 mmol, Intermediate 51) in THF (0.5 mL) and the mixture was stirred for 2 days at room temperature. TFA (1 mL) and water (0.5 mL) were added and the mixture was stirred overnight. The mixture was evaporated and dissolved in MeOH, filtered and purified by reversed phase preparative HPLC using ACE Prep UV C8 150×30 mm, flow 38 mL/min, gradient time 8.5 min using the eluent system: water/0.1% TFA and $CH_3CN$ (31-62% MeCN), fractions collected based on UV-signal (254 nm). The purest fractions were pooled and the acetonitrile was evaporated. Yield: 2.7 mg (22%). Colorless oil. MS (electronspray; [M+H]+) m/z 386.4.

General Procedure for Reductive Amination Used in Examples 83-87:

1-(Phenylsulfonyl)-1H-indole-4-carbaldehyde (0.015 g, 0.053 mmol, Intermediate 49), requisite amine (0.16 mmol) and acetic acid (0.031 g, 0.53 mmol) were dissolved in THF (1 mL) and sodium triacetoxyborohydride (0.033 g, 0.16 mmol) was added. The mixtures were stirred at 40° C. for 3 hours, evaporated and purified as described below:

EXAMPLE 83

(2-Methoxyethyl){[1-(phenylsulfonyl)-1H-indol-4-yl]methyl}amine trifluoroacetate Amine: 2-Methoxyethylamine (0.012 g, 0.16 mmol)

Purified by reversed phase preparative HPLC using ACE Prep UV C8 21×50 mm, flow 25 mL/min, gradient time 11 min using the eluent system: water/0.1% TFA and $CH_3CN$ (11-41% MeCN), fractions collected based on UV-signal (254 nm). The purest fractions were pooled and the acetonitrile was evaporated. Yield: 22.3 mg. Colorless gum. MS (electronspray; [M+H]+) m/z 345.4.

EXAMPLE 84

N-{[1-(Phenylsulfonyl)-1H-indol-4-yl]methyl}propan-2-amine trifluoroacetate

Amine: iso-Propylamine (0.0093 g, 0.16 mmol)

Purified by reversed phase preparative HPLC using ACE Prep UV C8 21×50 mm, flow 25 mL/min, gradient time 11 min using the eluent system: water/0.1% TFA and $CH_3CN$ (12-42% MeCN), fractions collected based on UV-signal (254 nm). The purest fractions were pooled and the acetonitrile was evaporated. Yield: 6.2 mg. White solid. MS (electronspray; [M+H]+) m/z 329.4.

EXAMPLE 85

4-{[4-(2-Methoxyethyl)piperazin-1-yl]methyl}-1-(phenylsulfonyl)-1H-indole bis(trifluoroacetate)

Amine: 1-(2-Methoxyethyl)piperazine (0.015 g, 0.11 mmol)

Purified by reversed phase preparative HPLC using ACE Prep UV C8 21×50 mm, flow 25 mL/min, gradient time 11 min using the eluent system: water/0.1% TFA and $CH_3CN$ (9-39% MeCN), fractions collected based on UV-signal (254 nm). The purest fractions were pooled and the acetonitrile was evaporated. Yield: 24.1 mg (86%). Colorless gum. MS (electronspray; [M+H]+) m/z 414.5.

EXAMPLE 86

((2R)-1-{[1-(Phenylsulfonyl)-1H-indol-4-yl]methyl}pyrrolidin-2-yl)methanol trifluoroacetate Amine: D-Prolinol (0.011 g, 0.11 mmol)

Purified by reversed phase preparative HPLC using ACE Prep UV C8 21×50 mm, flow 25 mL/min, gradient time 11 min using the eluent system: water/O. 1% TFA and $CH_3CN$ (11-41% MeCN), fractions collected based on UV-signal (254 nm). The purest fractions were pooled and the acetonitrile was evaporated.

Yield: 23.0 mg (86%). Colorless gum. MS (electronspray; [M+H]+) m/z 371.4.

EXAMPLE 87

4-Azetidin-1-ylmethyl)-1-(phenylsulfonyl)-1H-indole trifluoroacetate

Amine: Azetidine hydrochloride (0.010 g, 0.11 mmol)

Purified by reversed phase preparative HPLC using ACE Prep UV C8 21×50 mm, flow 25 mL/min, gradient time 11 min using the eluent system: water/0.1% TFA and $CH_3CN$ (11-41% MeCN), fractions collected based on UV-signal (254 nm). The purest fractions were pooled and the acetonitrile was evaporated.

Yield: 14.9 mg (64%). Colorless gum. MS (electronspray; [M+H]+) m/z 327.4.

Intermediate 52

Ethyl 4-bromo-5-methoxy-1H-indole-2-carboxylate

The target molecule was made according to literature (Kruse, L. I., Meyer, M. D. Ergoline synthons. 2. Synthesis of 1,5-DiHydrobenz[cd]indol-4(3H)-ones and 1,3,4,5-Tetrahydrobenz[cd]indol-4-amines. *J. Org. Chem.* 1984, 49, 4761-4768). MS (ESI+) for $C_{12}H_{12}BrNO_3$ m/z 298/300 (M+H)+.

Intermediate 53

Ethyl 4-bromo-5-methoxy-1-(phenylsulfonyl)-1H-indole-2-carboxylate

Procedure; as for Intermediate 44.

Ethyl 4-bromo-5-methoxy-1H-indole-2-carboxylate (1.5 g, 5.0 mmol, Intermediate 52) gave 0.96 g of a white powder, yield 44%. MS (ESI+) for $C_{18}H_{16}BrNO_5S$ m/z 438 (M+H)+.

Intermediate 54

Ethyl 5-methoxy-1-(phenylsulfonyl)-4-vinyl-1H-indole-2-carboxylate

Procedure; as for Intermediate 45.

Ethyl 4-bromo-5-methoxy-1-(phenylsulfonyl)-1H-indole-2-carboxylate (0.96 g, 2.2 mmol, Intermediate 53) gave quantitative yield of the product as a off white solid. MS (ESI+) for $C_{20}H_{19}NO_5S$ m/z 386 (M+H)+.

Intermediate 55

Ethyl 4-formyl-5-methoxy-1-(phenylsulfonyl)-1H-indole-2-carboxylate

Procedure, as for Intermediate 47.

Ethyl 5-methoxy-1-(phenylsulfonyl)-4-vinyl-1H-indole-2-carboxylate (860 mg, 2.2 mmol, Intermediate 54) gave 440 mg of the product as an off-white solid, yield 51%. MS (ESI+) for $C_{19}H_{17}NO_6S$ m/z 388 (M+H)+.

Intermediate 56

Ethyl 4-{[4-(tert-butoxycarbonyl)piperazin-1-yl]methyl}-5-methoxy-1-(phenylsulfonyl)-1H-indole-2-carboxylate Procedure, as for Intermediate 48.

Ethyl 4-formyl-5-methoxy-1-(phenylsulfonyl)-1H-indole-2-carboxylate (440 mg, 1.2 mmol, Intermediate 55)

gave 330 mg of the desired product as a colourless solid, yield 52%. MS (ESI+) for $C_{28}H_{35}N_3O_7S$ m/z 558 (M+H)$^+$.

EXAMPLE 88

Ethyl 5-methoxy-1-(phenylsulfonyl)-4-(piperazin-1-ylmethyl)-1H-indole-2-carboxylate Procedure, as for Example 80.

Ethyl 4-{[4-(tert-butoxycarbonyl)piperazin-1-yl]methyl}-5-methoxy-1-(phenylsulfonyl)-1H-indole-2-carboxylate (32 mg, 0.057 mmol, Intermediate 56) gave 15.9 mg, yield 61% after neutral conditions preparative MS (ESI+) for $C_{23}H_{27}N_3O_5S$ m/z 458 (M+H)$^+$.

Intermediate 57

Lithium 4-{[4-(tert-butoxycarbonyl)piperazin-1-yl]methyl}-5-methoxy-1-(phenylsulfonyl)-1H-indole-2-carboxylate Ethyl 4-{[4-(tert-butoxycarbonyl)piperazin-1-yl]methyl}-5-methoxy-1-(phenylsulfonyl)-1H-indole-2-carboxylate (330 mg, 0.6 mmol, Intermediate 56) was dissolved in THF (10 mL) before lithium hydroxide (17 mg, 0.7 mmol) was added followed by 4 mL water. The reaction mixture was heated to 70° C. for 24 h before the reaction was completed. The reaction mixture was evaporated. This gave 3 g of a white solid which was washed with several portions of hot DCM and then hot THF. The combined wash phases were evaporated. This gave 270 mg of a slightly brown solid. Yield 83%. MS (ESI+) for $C_{26}H_{30}N_3O_7SLi$ m/z 530 (M+H)$^+$.

Intermediate 58 tert-Butyl 4-{[5-methoxy-2-[(methylamino)carbonyl]-1-(phenylsulfonyl)-1H-indol-4-yl]methyl}piperazine-1-carboxylate 4-{[4-(tert-Butoxycarbonyl)piperazin-1-yl]methyl}-5-methoxy-1H-indole-2-carboxylic acid (14 mg, 0.0274 mmol, Intermediate 57) was dissolved in DCM (5 mL) before triethylamine (11 mg, 109 mmol) followed by methylamine hydrochloride (4 mg, 0.055 mmole) was added. To the reaction mixture were dimethylaminopropyl)carbodiimide hydrochloride (11 mg, 0.055 mmole) and 1-hydroxybenzotriazole (10 mg, 0.055 mmole) added. The reaction mixture was stirred at 40° C. for 24 h. Water was added and the phases were separated. The organic phase was evaporated and the obtained crude product was purified by preparative HPLC. This gave 3.4 mg of the product as a white solid, yield 23%.

MS (ESI+) for $C_{27}H_{34}N_4O_6S$ m/z 543 (M+H)$^+$.

Intermediate 59 tert-Butyl 4-{[2-[(ethylamino)carbonyl]-5-methoxy-1-(phenylsulfonyl)-1H-indol-4-yl]methyl}piperazine-1-carboxylate Procedure, as for Intermediate 58.

Using 4-{[4-(tert-Butoxycarbonyl)piperazin-1-yl]methyl}-5-methoxy-1H-indole-2-carboxylic acid (14 mg, 0.0274 mmol, Intermediate 57) and methanamine hydrochloride (3.709 mg, 0.0549 mmol as the starting material gave 6.3 mg of the product as a white solid, yield 42%. MS (ESI+) for $C_{28}H_{36}N_4O_6S$ m/z 557 (M+H)$^+$.

Intermediate 60 tert-Butyl 4-[(5-methoxy-1-(phenylsulfonyl)-2-{[(2-thienylmethyl)amino]carbonyl}-1H-indol-4-yl)methyl]piperazine-1-carboxylate Procedure, as for Intermediate 58.

Using 4-{[4-(tert-Butoxycarbonyl)piperazin-1-yl]methyl}-5-methoxy-1H-indole-2-carboxylic acid (14 mg, 0.0274 mmol, Intermediate 57) and 1-(2-thienyl)methanamine (6.21 mg, 0.0549 mmol) as the starting material gave 2.8 mg of the product as a white solid, yield 16%. MS (ESI+) for $C_{31}H_{36}N_4O_6S_2$ m/z 625 (M+H)$^+$.

EXAMPLE 89

5-Methoxy-N-methyl-1-(phenylsulfonyl)-4-(piperazin-1-ylmethyl)-1H-indole-2-carboxamide trifluoroacetate tert-Butyl 4-{[5-methoxy-2-[(methylamino)carbonyl]-1-(phenylsulfonyl)-1H-indol-4-yl]methyl}piperazine-1-carboxylate (3.4 mg, 0.063 mmol, Intermediate 58) was dissolved in DCM (2 mL) before TFA (1 mL) was added. The reaction mixture was stirred for 2 h at RT before completed. The solvent was evaporated and the obtained oil was dissolved in methanol and the solvent was evaporated. The obtained brown solid was stored under vacuum for 24 h. Quantitative yield was obtained. MS (ESI+) for $C_{22}H_{26}N_4O_4S$ m/z 443 (M+H)$^+$.

EXAMPLE 90

N-Ethyl-5-methoxy-1-(phenylsulfonyl)-4-(piperazin-1-ylmethyl)-1H-indole-2-carboxamide trifluoroacetate Procedure; as for Example 89.

tert-Butyl 4-{[2-[(ethylamino)carbonyl]-5-methoxy-1-(phenylsulfonyl)-1H-indol-4-yl]methyl}piperazine-1-carboxylate (6.3 mg, 0.113 mmol, Intermediate 59), gave quantitative yield of the product which was obtained as a brown solid. MS (ESI+) for $C_{23}H_{28}N_4O_4S \cdot C_2HF_3O_2$ m/z 457 (M+H)$^+$.

EXAMPLE 91

5-Methoxy-1-(phenylsulfonyl)-4-(piperazin-1-ylmethyl)-N-(2-thienylmethyl)-1H-indole-2-carboxamide trifluoroacetate Procedure; as for Example 89.

tert-Butyl 4-[(5-methoxy-1-(phenylsulfonyl)-2-{[(2-thienylmethyl)amino]carbonyl}-1H-indol-4-yl)methyl]piperazine-1-carboxylate (2.8 mg, 0.0045 mmol, Intermediate 60), gave quantitative yield of the product which was obtained as a brown solid. MS (ESI+) for $C_{26}H_{28}N_4O_4S_2 \cdot C_2HF_3O_2$ m/z 525 (M+H)$^+$.

EXAMPLE 92

4-(Azetidin-1-ylmethyl)-6-methoxy-1-(phenylsulfonyl)-1H-indole trifluoroacetate

6-Methoxy-1-(phenylsulfonyl)-1H-indole-4-carbaldehyde (Intermediate 34, 0.020 g, 0.063 mmol), azetidine hydrochloride (0.071 g, 0.76 mmol) and acetic acid (0.019 g, 0.32 mmol) were dissolved in MeOH (2 mL) and sodium triacetoxy borohydride (0.67 g, 0.32 mmol) were added. The mixture was stirred for 1 hour before 5 drops of 1N HCl was added and the mixture was filtered and purified by reversed phase preparative HPLC using ACE Prep UV C8 150×30 mm, flow 38 mL/min, gradient time 8.5 min using the eluent system: water/0.1% TFA and CH$_3$CN (25-51% MeCN), fractions collected based on UV-signal (254 nm). The purest fractions were pooled and the acetonitrile was evaporated. Yield: 15 mg (51%). White solid. MS (electrospray; [M+H]+) m/z 357.4.

Intermediate 61

4-Bromo-5-(benzyloxy)-1-(phenylsulfonyl)-1H-indole

Using the same procedure as for Intermediate 44 starting from 5-(benzyloxy)-4-bromo-1H-indole, 3.85 g (12.7 mmol) yielded 5.71 g (101%) a dark green crystallizing oil. MS (ESI+) for C$_{21}$H$_{16}$BrNO$_3$S m/z 442/444 (M+H)$^+$.

Intermediate 62

5-(Benzyloxy)-1-(phenylsulfonyl)-1H-indole-4-carbaldehyde

The reaction was performed using the same procedure as for Intermediate 75 with Intermediate 61, 4.74 g (10.7 mmol) as starting material. The crude was chromatographed on a column of silica with initially with petroleum ether/EtOAc 90/10 followed by 80/20 as eluent to give 5-(Benzyloxy)-1-(phenylsulfonyl)-1H-indole-4-carbaldehyde, 2.44 g (58%) as a yellow solid. MS (ESI+) for C$_{22}$H$_{17}$NO$_4$S m/z 392 (M+H)$^+$.

Intermediate 63 tert-Butyl 4-{[5-(benzyloxy)-1-(phenylsulfonyl)-1H-indol-4-yl]methyl}piperazine-1-carboxylate To 5-(Benzyloxy)-1-(phenylsulfonyl)-1H-indole-4-carbaldehyde, Intermediate 62 205 mg (0.52 mmol) in dichloroethane[DCE] (10 mL) were added BOC-piperazine, 137 mg (0.74 mmol), NaBH(OAc)$_3$, 333 mg (1.6 mmol) and HOAc, 45 mg (0.8 mmol) and the mixture was stirred at room temperature in sealed test tube over night. Water was added, the phases were separated and the dried (MgSO$_4$) organic phase was evaporated at reduced pressure and the black residue was chromatographed on a column of silica with CHCl$_3$ 100% as eluent to yield 260 mg (88%) of a blackish oil. MS (ESI+) for C$_{31}$H$_{35}$N$_3$O$_5$S m/z 562 (M+H)$^+$.

Intermediate 64 tert-Butyl 4-{[5-hydroxy-1-(phenylsulfonyl)-1H-indol-4-yl]methyl}piperazine-1-carboxylate To a solution of 5-(benzyloxy)-1-(phenylsulfonyl)-4-(piperazin-1-ylmethyl)-1H-indole, Intermediate 63, 1.20 g (2.1 mmol) in MeOH was added 10% Pd/C, 200 mg and the suspension was flushed several times with N$_2$. The stirring was stopped and the Pd/C was allowed to settle, ammonium formate was added, the N$_2$-atmosphere was applied again and the reaction mixture was stirred at room temperature over night. The reaction mixture was filtered through a pad of Celite, the solvent was removed at reduced pressure and the light yellow oil was chromatographed on a column of silica with CHCl$_3$ (100%) to yield the target molecule as a colorless foam, 0.59 g (59%). MS (ESI+) for C$_{24}$H$_{29}$N$_3$O$_5$S m/z 472 (M+H)$^+$.

EXAMPLE 93

1-(Phenylsulfonyl)-4-(piperazin-1-ylmethyl)-1H-indol-5-ol trifluoroacetate tert-Butyl 4-{[5-hydroxy-1-(phenylsulfonyl)-1H-indol-4-yl]methyl}piperazine-1-carboxylate, (10 mg, 0.018 mmol, Intermediate 64) was dissolved in DCM/TFA 50/50 (1 mL) and left in RT for 4 hours after which time the solvent was removed at reduced pressure and the residue was purified on a preparative HPLC, Method A, to yield 5.5 mg (53%) of the target compound as a colourless oil. MS (ESI+) for C$_{19}$H$_{21}$N$_3$O$_3$S m/z 372 (M+H)$^+$.

Intermediate 65

4-Pyrazin-2-yl-1H-indole

4-Bromoindole (0.1 g, 0.51 mmol), bis(pinacolato)diboron (0.172 g, 0.77 mmol), potassium acetate (0.075 g, 0.765 mmol) and PdCl$_2$ (0.022 g, 0.031 mmol) were dissolved in DME (3 mL) and heated in the microwave for 900 seconds at 125° C. The reaction was cooled and NaHCO$_3$ (0.129 g, 1.53 mmol), 2-chloropyrazine (0.087 g, 0.77 mmol) tetrakis(triphenylphosphine)palladium (0.0295 g, 0.026 mmol), H$_2$O (1 mL) and DME (1 mL) were added and the mixture was stirred in the microwave for 900 seconds at 120° C. The mixture was diluted with dichloromethane and filtered. The filtrate was washed with water (2×), dried (MgSO$_4$) and evaporated. The crude product was purified by flash chromatography using 2.5% to 5% CH$_3$OH in dichloromethane. Not pure, purified by flash chromatography using hexane/EtOAc 7:3 to 1:1 as the eluent. Yield: 93 mg (47%). White solid. MS (electronspray; [M+H]+) m/z 196.3.

Intermediate 66

1-(Phenylsulfonyl)-4-pyrazin-2-yl-1H-indole

4-Pyrazin-2-yl-1H-indole (0.060 g, 0.307 mmol, Intermediate 65), benzensulfonyl chloride (0.071 g, 0.40 mmol) and tetrabutylammonium hydrogen sulfate (0.010 g, 0.031 mmol) were dissolved in dichloromethane (3 mL) and NaOH (0.061 g, 1.5 mmol) in water (1 mL) was added. The mixture was stirred at rt overnight and the mixture was diluted with dichloromethane and water and extracted with dichloromethane (2×). The organic phase was dried (MgSO$_4$) and evaporated. The crude product was purified by flash chromatography using CH$_2$Cl$_2$ to 1% MeOH in CH$_2$Cl$_2$ as the eluent. Yield: 81 mg (79%). White solid. MS (electronspray; [M+H]+) m/z 336.4.

EXAMPLE 94

1-(Phenylsulfonyl)-4-piperazin-2-yl-1H-indole bis (trifluoroacetate)

1-(phenylsulfonyl)-4-pyrazin-2-yl-1H-indole (0.081 g, 0.242 mmol, Intermediate 66) and Pd(OAc)$_2$ (0.020 g, 0.089 mmol) were dissolved in acetic acid (20 mL) and shaked under an atmosphere of H2 (55 psi). After 2.5 hour the reaction was evaporated and partitioned between dichloromethane and 1N Na$_2$CO$_3$. The organic phase was dried (MgSO$_4$) and evaporated. The crude product was purified by reversed phase preparative HPLC using ACE Prep UV C8 150×30 mm, flow 38 mL/min, gradient time 8.5 min using the eluent system: water/0.1% TFA and $CH_3CN$ (10-35% MeCN), fractions collected based on UV-signal (254 nm). The purest fractions were pooled and the acetonitrile was evaporated. Isolated as the TFA salt. Yield: 30 mg (22%). White solid. MS (electronspray; [M+H]+) m/z 342.4.

EXAMPLE 95

4-(1,4-Dimethylpiperazin-2-yl)-1-(phenylsulfonyl)-1H-indole bis(trifluoroacetate)

1-(phenylsulfonyl)-4-piperazin-2-yl-1H-indole bis(trifluoroacetate) (0.015 g, 0.044 mmol, Example 94) and formaldehyde 30% in water (0.044 g, 0.44 mmol) were dissolved in MeOH (2 mL) and sodium triacetoxyborohydride (0.046 g, 0.22 mmol) were added. The mixture was stirred for 2 hours at room temperature and 3 drops of 1N HCl was added. The reaction was filtered and purified by reversed phase preparative HPLC using ACE Prep UV C8 150×30 mm, flow 38 mL/min, gradient time 8.5 min using the eluent system: water/0.1% TFA and $CH_3CN$ (19-46% MeCN), fractions collected based on UV-signal (254 nm). Yield: 4.0 mg (15%). White solid. MS (electronspray; [M+H]+) m/z 370.4.

EXAMPLE 96

[7-Methoxy-1-(phenylsulfonyl)-1H-indol-4-yl](piperazin-1-yl)acetonitrile trifluoroacetate 1-Benzenesulfonyl-7-methoxy-1H-indole-4-carbaldehyde (50 mg, 0.2 mmol, prepared as in Example 79), piperazine (28 mg, 0.3 mmol) and methanol (0.5 mL) was charged into a tube suitable for microwave irradiation. The mixture was heated at 100° for 1 min in the microwave oven. Trimethylsilyl cyanide (21 µl, 0.2 mmol) was added and the heat treatment, 100° 1 min, was repeated. LCMS indicated the formation of expected product. The crude product was purified using prep LC on a YMC column (24-52% MeCN over 16 min). Obtained 26.2 mg (40%). MS ESI+ for $C_{16}H_{13}NO_4S$, m/z 325 (M-piperazine)+, m/z 384 (M-nitrile)+, m/z 411 (M+H)+.

EXAMPLE 97

4-(Azetidin-1-ylmethyl)-7-methoxy-1-(phenylsulfonyl)-1H-indole trifluoroacetate

1-Benzenesulfonyl-7-methoxy-1H-indole-4-carbaldehyde (20 mg, 0.06 mmol prepared as in Example 79) azetidine hydrochloride (30 mg, 0.32 mmol) and sodium acetate (26 mg, 0.32 mmol) were mixed in 1,2-dichloroethane (1 mL), and stirred at 40° for 1 h, cooled to room temp followed by addition of sodium triacetoxyborohydride (22 mg, 0.1 mmol). The mixture was stirred over night. No remaining starting material according to LCMS. The mixture was evaporated, dissolved in DMF, filtered an purified on prep HPLC YMC 40 mL/min 22-50 mL MeCN over 16 min. Obtained 9.8 mg (43%). MS ESI+ for $C_{19}H_{20}N_2O_3S$ m/z 357 (M+H)+.

EXAMPLE 98

{[1-(Phenylsulfonyl)-4-(piperazin-1-ylmethyl)-1H-indol-5-yl]oxy}acetonitrile

To a solution of tert-Butyl 4-{[5-hydroxy-1-(phenylsulfonyl)-1H-indol-4-yl]methyl}piperazine-1-carboxylate (45 mg, 0.10 mmol; Intermediate 64) in dry DCM (2 mL) was added bromoacetonitrile, 57 mg (0.48 mmol), tetrabutylammonium hydrogensulphate, 8 mg (0.02 mmol), 2M NaOH (1 mL) and the two phase system was vigorously stirred at room temperature over night. The organic phase was separated and the aqueous phase was washed once with water. The solvent from the combined organic phases was removed at reduced pressure and the residue was purified on a on a preparative HPLC, method B, to yield 2.9 mg (7%) of the target compound as a light brown oil. MS (ESI+) for $C_{21}H_{22}N_4O_3S$ m/z 411 (M+H)+.

EXAMPLE 99

5-Isopropoxy-1-(phenylsulfonyl)-4-(piperazin-1-ylmethyl)-1H-indole

With the same procedure as for Example 105 using isopropanol as the alcohol, 4.6 mg (31%) of the target compound was achieved. MS (ESI+) for $C_{22}H_{27}N_3O_3S$ m/z 414 (M+H)+.

EXAMPLE 100

5-(Benzyloxy)-1-(phenylsulfonyl)-4-(piperazin-1-ylmethyl)-1H-indole tert-Butyl 4-{[5-(benzyloxy)-1-(phenylsulfonyl)-1H-indol-4-yl]methyl}piperazine-1-carboxylate (30 mg, 0.05 mmol, Intermediate 63) was stirred with a 50/50 mixture of TFA/dichlorometane (3 mL) in room temperature for four hours. The solvent was removed at reduced pressure and the crude was purified on a preparative HPLC, method B, to give 9.5 mg (40%) of a colorless oil. MS (ESI+) for $C_{26}H_{27}N_3O_3S$ m/z 462 (M+H)+.

EXAMPLE 101

4-{[(2-Hydroxyethyl)(methyl)amino]methyl}-1-(phenylsulfonyl)-1H-indol-5-ol

To a solution of 5-(Benzyloxy)-1-(phenylsulfonyl)-1H-indole-4-carbaldehyde (50 mg, 0.12 mmol, Intermediate 62) in DCE (3 mL) was added N-methyl ethanolamine, 22 mg (0.26 mmol) and sodium triacetoxyborohydride, 80 mg (0.38 mmol) and the mixture was heated in a sealed test tube at 40° C. over night. The solvent was removed at reduced pressure and the residue was dissolved in MeOH (2 mL), 10% Pd/C, 20 mg was added and the mixture was flushed with $N_2$, $NH_4^+$ $HCOO^-$ (50 mg, 0.8 mmol) was added, the reaction mixture was again flushed with $N_2$ and the reaction mixture was stirred at 40° C. over night. The solvent was removed at reduced pressure, the semisolid was taken up between $CHCl_3/H_2O$, washed with $H_2O$ (×1), brine (×1), dried ($MgSO_4$) and the solvent was removed at reduced pressure. A sample was withdrawn and purified with on a preparative HPLC, method B, to yield 6.3 mg of a colorless oil. MS (ESI+) for $C_{18}H_{20}N_2O_4S$ m/z 361 (M+H)+.

EXAMPLE 102

4-[(3-Hydroxypyrrolidin-1-yl)methyl]-1-(phenylsulfonyl)-1H-indol-5-ol

Using the same procedure as for Example 101, using 3-hydroxypyrrolidine 6.7 mg of the target compound was synthesized. MS (ESI+) for $C_{19}H_{20}N_2O_4S$ m/z 373 (M+H)+.

Intermediate 66

[3-Bromo-4-(trifluoromethyl)phenyl]hydrazine hydrochloride

A solution of NaNO$_2$ (949 mg, 13.75 mmol) in water (4 mL) was added drop wise to an ice cold mixture of [3-bromo-5-(trifluoromethyl)phenyl]amine (3.00 g, 12.5 mmol) in conc. HCl/water (8 mL, 1:1). The reaction mixture was stirred at 0° C. for 1 h. Additional two solutions of NaNO$_2$ (431 mg, 6.25 mmol) in water (2 mL) were added, with continuous stirring 1 h after each addition. SnCl$_2$ (8.46 g, 37.5 mmol) in conc. HCl (8 mL) (milky suspension) was added slowly; a brown precipitation was immediately formed. The mixture was diluted with water, basified with W/w 50% aq NaOH and extracted with DCM (×2) together with brine. The water layer was extracted once more with ether and allowed to phase separate over weekend. The organic layers were combined, dried, filtered and concentrated. The crude product was purified by flash column chromatography (DCM->2% MeOH in DCM). 2M HCl in ether was added to get the title compound (1.13 g, 31%) as an off white solid. MS (ESI+) for C$_7$H$_6$BrF$_3$N$_2$ m/z 255 (M+H)$^+$.

Intermediate 67

Ethyl 4-bromo-6-(trifluoromethyl)-1H-indole-2-carboxylate and ethyl 6-bromo-4-(trifluoromethyl)-1H-indole-2-carboxylate

[3-bromo-4-(trifluoromethyl)phenyl]hydrazine hydrochloride Intermediate 66 (554 mg, 1.90 mmol), ethyl pyruvate (211 μL, 1.90 mmol) and p-toluenesulfonic acid monohydrate (11 mg, 0.06 mmol) in dry toluene (15 mL) was refluxed for 2 h using a Dean-Stark trap. This mixture was added to a refluxed mixture (2 h, Dean-Stark trap) of p-toluenesulfonic acid monohydrate in dry toluene (15 mL). Reflux was continued over night. The reaction was allowed to cool and extracted with DCM and aq. saturated NaHCO$_3$. The organic layer was dried, filtered and concentrated. The crude products was purified by flash column chromatography (DCM/hexane) to give the title compounds (285 mg, 45%), not separated, as an off white solid. GCMS for C$_{12}$H$_9$BrF$_3$NO$_2$ m/z 335 (Monoisotop)$^+$, shows two peaks with same mass.

Intermediate 68

Ethyl 4-bromo-1-(phenylsulfonyl)-6-(trifluoromethyl)-1H-indole-2-carboxylate and ethyl 6-bromo-1-(phenylsulfonyl)-4-(trifluoromethyl)-1H-indole-2-carboxylate Aq. 4M NaOH (1.5 mL) was added to a stirring mixture of ethyl 4-bromo-6-(trifluoromethyl)-1H-indole-2-carboxylate and ethyl 6-bromo-4-(trifluoromethyl)-1H-indole-2-carboxylate Intermediate 67 (283 mg, 0.84 mmol), benzenesulfonyl chloride (164 mg, 0.93 mmol) and tetrabutylammonium hydrogen sulfate (17 mg, 0.084 mmol) in DCM (10 mL). The reaction mixture was stirred 5 h and additional benzenesulfonyl chloride (11 μL, 0.084 mmol.) was added with continuous stirring for 2 h. The reactions mixture was put in fridge over night. The mixture was diluted with DCM and washed twice with water. The organic layer was dried, filtered and concentrated to give the title compounds (369 mg, 92%) as a red sticky oil. GCMS for C$_{18}$H$_{13}$BrF$_3$NO$_4$S m/z 477 (Monoisotop)$^+$, shows two peaks with same mass.

Intermediate 69

[4-Bromo-1-(phenylsulfonyl)-6-(trifluoromethyl)-1H-indol-2-yl]methanol and [6-bromo-1-(phenylsulfonyl)-4-(trifluoromethyl)-1H-indol-2-yl]methanol LAH (32 mg, 0.85 mmol) was added in portions over 10 min. to an ice cold solution ethyl 4-bromo-1-(phenylsulfonyl)-6-(trifluoromethyl)-1H-indole-2-carboxylate and ethyl 6-bromo-1-(phenylsulfonyl)-4-(trifluoromethyl)-1H-indole-2-carboxylate Intermediate 68 (290 mg, 0.61 mmol) in dry THF:ether (2:1, 6 mL). The mixture was stirred 10 min. at 0° C. and ice cold water was added. The resulting precipitation was filtered off, rinsed with THF and the eluate was concentrated. The residue was extracted with DCM (×2) and water, the organic layer was dried, filtered, concentrated and combined with a previous batch of [4-bromo-1-(phenylsulfonyl)-6-(trifluoromethyl)-1H-indol-2-yl]methanol and [6-bromo-1-(phenylsulfonyl)-4-(trifluoromethyl)-1H-indol-2-yl]methanol (followed the same procedure as above using 78 mg starting material). Purification by flash column chromatography (DCM/hexane 3:1) afforded the products (100 mg, 30%) as a white solid. GCMS for C$_{16}$H$_{11}$BrF$_3$NO$_3$S m/z 433 (Monoisotop)$^+$, shows two peaks with same mass.

Intermediate 70

[1-(Phenylsulfonyl)-6-(trifluoromethyl)-4-vinyl-1H-indol-2-yl]methanol and [1-(phenylsulfonyl)-4-(trifluoromethyl)-6-vinyl-1H-indol-2-yl]methanol Tributyl(vinyl)stannane (0.114 mL, 0.39 mmol) and Pd(PPh$_3$)$_2$OAc$_2$ (15 mg, 0.020 mmol) were added to [4-bromo-1-(phenylsulfonyl)-6-(trifluoromethyl)-1H-indol-2-yl]methanol and [6-bromo-1-(phenylsulfonyl)-4-(trifluoromethyl)-1H-indol-2-yl]methanol Intermediate 69 (85 mg, 0.20 mmol) in dry MeCN (2 mL) each. The reaction mixture was irradiated with microwaves at 180° C. for 720 s. The mixture was combined with a previous batch of the title compounds (followed the same experimental procedure as above, starting with 13 mg), filtered and concentrated. Purification was performed by flash chromatography (hexane/DCM 1:3). This afforded the products (85 mg, 99%) as a colorless viscous oil.

Intermediate 71

2-(Hydroxymethyl)-1-(phenylsulfonyl)-6-(trifluoromethyl)-1H-indole-4-carbaldehyde and 2-(Hydroxymethyl)-1-(phenylsulfonyl)-4-(trifluoromethyl)-1H-indole-6-carbaldehyde OsO$_4$ (5 mg, 0.02 mmol) was added to a stirred mixture of [1-(phenylsulfonyl)-6-(trifluoromethyl)-4-vinyl-1H-indol-2-yl]methanol and [1-(phenylsulfonyl)-4-(trifluoromethyl)-6-vinyl-1H-indol-2-yl]methanol Intermediate 70 (82 mg, 0.22 mmol) and 2,6-lutidine (50 μL, 0.43 mmol) in dioxane (6 mL). The mixture turned from colorless to black in 1 minute. Sodium periodate (0.184 g, 0.86 mmol) in water (2 mL, warmed to dissolve) was added. A grey precipitation was immediately formed. The mixture was stirred for 30 min, extracted with water (20 mL) and DCM (2×20 mL). The organic layers were combined, dried, filtered and concentrated to give the title compounds (94 mg, 114%) as a black gum. MS (ESI+) for $C_{17}H_{12}F_3NO_4S$ m/z 384 (M+H)$^+$.

EXAMPLE 103

[1-(Phenylsulfonyl)-4-(piperazin-1-ylmethyl)-6-(trifluoromethyl)-1H-indol-2-yl]methanol bis(trifluoroacetate)

2-(Hydroxymethyl)-1-(phenylsulfonyl)-6-(trifluoromethyl)-1H-indole-4-carbaldehyde and 2-(Hydroxymethyl)-1-(phenylsulfonyl)-4-(trifluoromethyl)-1H-indole-6-carbaldehyde (Intermediates 71) in dry THF (8 mL), was distributed into two micro wave vials (47 mg, 0.12 mmol, in each), where after 1-BOC-piperazine (46 mg, 0.25 mmol), acetic acid (70 µL, 1.23 mmol) and NaB(OAc)$_3$H (78 mg, 0.37 mmol) were added to each vial. The mixtures were irradiated with microwaves for 720 s at 130° C., filtered and concentrated. The residues were dissolved in MeOH (1.5 mL) and conc. HCl (0.5 mL) and irradiated using microwaves at 100° C. for 300 s, filtered and purified using preparative HPLC/UV (System A, 20-50% MeCN, 0.1% TFA). Concentration of fractions from the compound with shortest retention time gave 38 mg of [1-(phenylsulfonyl)-4-(piperazin-1-ylmethyl)-6-(trifluoromethyl)-1H-indol-2-yl]methanol. Purification was performed by preparative HPLC/UV (System A, 20-50% MeCN, 0.1% NH$_4$OAc). Concentration was followed by extraction using DCM (×2) and aq. Na$_2$CO$_3$/brine. The organic layers were combined, dried, filtered and concentrated to give 7 mg, 6% of a light yellow solid. HPLC purity 98% R$_T$=1.59 min (System A, 10-97% MeCN over 3 minutes), 98% R$_T$=1.35 min (System B, 10-97% MeCN over 3 minutes). $^1$H NMR (500 MHz, CHLOROFORM-D) δ ppm 2.37 (s, 4 H) 2.88 (t, J=4.71 Hz, 4 H) 3.60 (s, 2 H) 4.95 (s, 2 H) 6.82 (s, 1 H) 7.45 (t, J=7.85 Hz, 2 H) 7.49 (s, 1 H) 7.56 (t, J=7.54 Hz, 1 H) 7.85 (d, J=8.48 Hz, 2 H) 8.19 (s, 1H). $^{13}$C NMR (126 MHz, CHLOROFORM-D) δ ppm 45.97 (s, 2 C) 54.23 (s, 2 C) 58.43 (s, 1 C) 63.31 (s, 1 C) 109.04 (s, 1 C) 117.93 (s, 1 C) 121.88-127.09 (m, 1 C) 122.09 (s, 1 C) 124.91 (s, 2 C) 126.55 (s, 2 C) 129.49 (s, 2 C) 134.32 (s, 1 C) 135.61 (s, 1 C) 137.53 (s, 1 C) 138.15 (s, 1 C) 141.98 (s, 1 C). COSY, HSQC and HMBC were also run to confirm the structure. MS (ESI+) for $C_{21}H_{22}F_3N_3O_3S$ m/z 454 (M+H)$^+$ Intermediate 72

2-Bromo-3-methyl-4-nitro-phenol

The bromination of 3-methyl-4-nitrophenol was made as described in the literature (Muntwyler, R., Widmer, J., Keller-Schierlein, W. Synthese des 5-Chlor-6-methyl-salicylsäure-methylathers, eines Abbauproduktes des Chlorothricins. *Helv Chim Acta* 1970, 53, 1544-1547). This gave a 2:1 mixture of 2-bromo-3-methyl-4-nitrophenol and 2-bromo-5-methyl-4-nitrophenol. 2-Bromo-5-methyl-4-nitro-phenol, $^1$H NMR (400 MHz, CHLOROFORM-D) δ ppm 2.58 (s, 3 H) 5.98 (s, 1 H) 6.94 (s, 1 H) 8.29 (s, 1 H). 2-Bromo-3-methyl-4-nitro-phenol, $^1$H NMR (400 MHz, CHLOROFORM-D) δ ppm 2.67 (s, 3 H) 6.16 (s, 1 H) 6.98 (d, J=9.03 Hz, 1 H) 7.88 (d, J=9.03 Hz, 1 H). MS (ESI+) for $C_7H_6BrNO_3$ m/z 232/234 (M+H)$^+$.

Intermediate 73

4-Bromo-5-methoxy-1H-indole

2-Bromo-3-methyl-4-nitro-phenol, (100 g, 0.43 mol, Intermediate 72) was dissolved in acetone (500 mL), grinded K$_2$CO$_3$, 119 g (0.86 mol) and methyl iodide, 83 g (0.59 mol) were added and the reaction mixture was heated at reflux for one hour. The suspension was filtered and the solvent was removed at reduced pressure to give a brown spontaneously crystallizing oil that was used directly in the next synthetic step. Quantitative yield. The crude methoxy ether, 106 g (0.43 mol) was dissolved in dry DMF (350 mL), dimethylformamid dimethylacetal[DMFDMA], 103 g (0.87 mol) was added and the reaction was heated and stirred at 90° C. for two days. During the next three days were each day a portion of DMFDMA, 20 g (0.17 mol) added while the mixture was continued to be heated. The solvent was removed at reduced pressure and the black/red oily residue was dissolved in HOAc (300 mL). The viscous solution was carefully added to a well stirred suspension of iron powder, 72 g (1.3 mol) in warm HOAc (700 mL) at such rate the exothermic reaction allowed. The thick reaction mixture was heated at reflux for one hour, the solids were filtered of and the solvent was removed at reduced pressure. The black residue was dissolved in warm CHCl$_3$ (700 mL), heptane (600 mL) and 50 g of silica gel was added, the mixture was filtered through a pad of silica, washed with 50/50 CHCl3/heptane and the solvent was again removed at reduced pressure. The black residue was chromatographed on a column of silica with petroleum ether/EtOAc 90/10 as eluent to give 14.9 g (15%) of the target compound as a olive green solid. MS (ESI+) for $C_9H_8BrNO$ m/z 226/228 (M+H)$^+$.

Intermediate 74

4-Bromo-5-methoxy-1-(phenylsulfonyl)-1H-indole

To a solution of 4-Bromo-5-methoxy-1H-indole, 2.59 g (11.5 mmol, Intermediate 73) in DCM (20 mL) was added benzene sulphonyl chloride, 2.12 g (12.0 mmol), tetrabutylammonium hydrogensulphate, 0.23 g (0.7 mmol) and 2M NaOH (20 mL) and the two phase mixture was vigorously stirred at room temperature for 30 minutes. The organic phase was washed once with water and once with brine, dried (MgSO$_4$) and the solvent was removed at reduced pressure to yield the sulphon amide as a spontaneously crystallizing oil 4.20 g (98%).

Intermediate 75

5-Methoxy-1-(phenylsulfonyl)-1H-indole-4-carbaldehyde

To a warm solution of 4-Bromo-5-methoxy-1-(phenylsulfonyl)-1H-indole (3.91 g, 10.7 mmol, Intermediate 74) in toluene (7 mL) was added tributylvinyltin, 5.08 g (16.0 mmol) and Pd(PPh3)$_2$Cl$_2$, 0.37 g (0.5 mmol). The solution was heated at reflux over night, a teaspoon of silica was added and the mixture was filtered through a pad of silica. The solvent was removed at reduced pressure and the resulting oil was triturated with petroleum ether to give a semicrystalline mass that was used directly in the next step.

The crude above was dissolved in dioxane (110 mL), 2,6-lutidine, 2.29 g (21.3 mmol) and OsO$_4$, 0.27 g (1.1 mmol) was added and the mixture was stirred at room temperature for five minutes. To the dark solution was added a warm solution of sodium periodate, 6.85 g (32.0 mmol) in water (35 mL) and the resulting suspension was stirred over night. More dioxane was added (40 mL) the solids were filtered off and the solvent from the filtrate was evaporated at reduced pressure to give a dark red oil that was recrystallized from EtOH to yield 1.55 g (46%) over two steps of a light brown solid. MS (ESI+) for $C_{16}H_{13}NO_4S$ m/z 316 (M+H)$^+$.

Intermediate 76 tert-Butyl 4-{[5-methoxy-1-(phenylsulfonyl)-1H-indol-4-yl]methyl}piperazine-1-carboxylate 5-Methoxy-1-(phenylsulfonyl)-1H-indole-4-carbaldehyde (0.10 g, 0.317 mmol, Intermediate 75), boc-piperazine (0.118 g, 0.634 mmol) and acetic acid (0.095 g, 1.58 mmol) were dissolved in THF (5 mL) and sodium triacetoxyborohydride (0.134 g, 0.63 mmol) were added. The mixture was stirred for 2 hours and diluted with dichloromethane and 1N $Na_2CO_3$. The mixture was extracted with dichloromethane (2×) and the combined organics were dried ($MgSO_4$) and evaporated. The crude product was ran through a plug of silica gel eluating with 5% MeOH in dichloromethane. Yield 100 mg (65%). White solid.
MS (ESI+) for $C_{25}H_{31}N_3O_5S$ m/z 486.4 $(M+H)^+$.

EXAMPLE 104

5-Methoxy-1-(phenylsulfonyl)-4-(piperazin-1-ylmethyl)-1H-indole bis(trifluoroacetate)

tert-Butyl 4-{[5-methoxy-1-(phenylsulfonyl)-1H-indol-4-yl]methyl}piperazine-1-carboxylate (0.050 g, 0.102 mmol, Intermediate 76) was dissolved in dichloromethane (4 mL) and TFA (1 mL) was added. The mixture was stirred and rt for 2 h and evaporated. The crude product was purified by reversed phase preparative HPLC using ACE Prep UV C8 150×30 mm, flow 38 mL/min, gradient time 8.5 min using the eluent system: water/0.1% TFA and $CH_3CN$ (20-40% MeCN), fractions collected based on UV-signal (254 nm). The purest fractions were pooled and the acetonitrile was evaporated. Yield: 29 mg (46%). Brown liquid, off white solid after 1 h. Isolated as the TFA salt. MS (ESI+) for $C_{20}H_{23}N_3O_3S$ m/z 386.4 $(M+H)^+$.

EXAMPLE 105

5-Ethoxy-1-(phenylsulfonyl)-4-(piperazin-1-ylmethyl)-1H-indole trifluoroacetate

To a solution of tert-Butyl 4-{[5-hydroxy-1-(phenylsulfonyl)-1H-indol-4-yl]methyl}piperazine-1-carboxylate, 60 mg (0.13 mmol) Intermediate 64 in dry DCM (4 mL) was added triphenylphosphine, 43 mg (0.16 mmol), TMAD, 33 mg (0.19 mmol) and EtOH, 9 mg (0.19 mmol) and the reaction mixture was stirred at room temperature over night. The solvent was removed at reduced pressure and the oily residue was dissolved in a 50/50 mixture of TFA/dichloromethane and stirred for 4 hours. The solvent from the deBOC:ed crude was removed at reduced pressure and the residue was purified on a preparative HPLC, method B, to yield 8.3 mg (12%) of the target compound as a colorless oil. MS (ESI+) for $C_{21}H_{25}N_3O_3S$ m/z 400 $(M+H)^+$.

EXAMPLE 106

1-Phenyl-N-{[1-(phenylsulfonyl)-1H-indol-4-yl]methyl}methanamine trifluoroacetate To a solution of Intermediate 49, 300 mg (1.1 mmol) in DCE (15 mL) was added benzylamine (135 mg, 1.3 mmol) and $NaBH(OAc)_3$, (443 mg, 2.1 mmol) and the mixture was stirred at 40° C. for five hours. Water was added and the reaction was stirred for 15 minutes, the phases were separated and the organic phase was washed once with water. A small analytical sample was withdrawn and purified on a preparative HPLC, ACE C8 column with 0.1% TFA/ACN as eluent to give 6.2 mg of the target compound. MS (ESI+) for $C_{22}H_{20}N_2O_2S$ m/z 377 $(M+H)^+$.

EXAMPLE 107

N-{[5-Methoxy-1-(phenylsulfonyl)-1H-indol-4-yl]methyl}cyclopropanamine trifluoroacetate 5-Methoxy-1-(phenylsulfonyl)-1H-indole-4-carbaldehyde (50 mg, 0.16 mmol; Intermediate 75), was dissolved in dry THF (4 mL) before cyclopropanamine (57 mg, 0.24 mmol) was added followed by acetic acid (95 mg, 1.59 mmol) and sodium triacetoxyborohydride (101 mg, 0.48 mmol). The reaction mixture was heated in microwave for 720 s at 130° C. The solvent was removed and the crude product was purified using preparative HPLC/UV (System A, 30-60% MeCN, 0.1% TFA). The title compound (39.4 mg, 69%) was obtained as a white solid. MS (ESI+) for $C_{19}H_{20}N_2O_3S$ $C_2HF_3O_2$ m/z 357 $(M+H)^+$.

EXAMPLE 108

{[5-Methoxy-1-(phenylsulfonyl)-1H-indol-4-yl]methyl}dimethylamine hydrochloride

5-Methoxy-1-(phenylsulfonyl)-1H-indole-4-carbaldehyde (0.5 g, 1.6 mmol; Intermediate 75), 5.5 M dimethylamine in EtOH (5 ml, 27.5 mmol) and acetic acid (2 ml, 31.7 mmol) were dissolved in MeOH (50 ml) and heated to 50° C. for 20 minutes before sodiumcyanoborohydride (0.5 g, 7.9 mmol) was added all in one portion. The mixture was stirred for 30 min and evaporated to half its volume. The mixture was added dropwise to a cold 0.1 N NaOH solution and extracted with dichloromethane (2×). The combined organics were washed with brine, dried ($MgSO_4$) and evaporated. The crude product was purified by flash chromatography using 2.5% MeOH in dichloromethane to 5% MeOH in dichloromethane with 1% $NEt_3$ to give 440 mg (63%) of the final product as a colorless oil. The oil was dissolved in diethylether and 1N HCl in diethylether (1.5 ml, 1.5 mmol) was added dropwise while stirring. The mixture was evaporated and the white crystals were dried in vacuo. MS (ESI+) for $C_{18}H_{20}N_2O_3S$ m/z 345 $(M+H)^+$.

EXAMPLE 109

N-{[5-Methoxy-1-(phenylsulfonyl)-1H-indol-4-yl]methyl}cyclobutanamine trifluoroacetate 5-Methoxy-1-(phenylsulfonyl)-1H-indole-4-carbaldehyde (50 mg, 0.16 mmol; Intermediate 75), was dissolved in dry THF (4 mL) before cyclobutanamine (71 mg, 0.24 mmol) was added followed by acetic acid (95 mg, 1.59 mmol) and sodium triacetoxyborohydride (101 mg, 0.48 mmol). The reaction mixture was heated in microwave for 720 s at 130° C. The solvent was removed and the crude product was purified using preparative HPLC/UV (System A, 30-60% MeCN, 0.1% TFA). The title compound (10 mg, 17%) was obtained as a white solid. MS (ESI+) for $C_{20}H_{22}N_2O_3S$ $C_2HF_3O_2$ m/z 371 $(M+H)^+$.

EXAMPLE 110

N-{[5-Methoxy-1-(phenylsulfonyl)-1H-indol-4-yl]methyl}-N-methylcyclobutanamine trifluoroacetate 5-Methoxy-1-(phenylsulfonyl)-1H-indole-4-carbaldehyde (50 mg, 0.16 mmol, Intermediate 75), was dissolved in dry THF (4 mL) before cyclobutanamine (71 mg, 0.24 mmol) was added followed by acetic acid (95 mg, 1.59 mmol) and sodium triacetoxyborohydride (101 mg, 0.48 mmol). The reaction mixture was heated in microwave for 720 s at 130° C. Acetic acid (95 mg, 1.59 mmol) and sodium triacetoxyborohydride (101 mg, 0.48 mmol) and formalin (1 mL) was added and the reaction mixture was once more heated in microwave for 720 s at 130° C. The solvent was removed and the crude product was purified using preparative HPLC/UV (System A, 30-60% MeCN, 0.1% TFA). The title compound (24.5 mg, 40%) was obtained as a white solid. MS (ESI+) for $C_{21}H_{24}N_2O_3S$ $C_2HF_3O_2$ m/z 385 (M+H)$^+$.

EXAMPLE 111

1-{[1-(Phenylsulfonyl)-1H-indol-4-yl]methyl}azetidin-3-ol trifluoroacetate

Azetidine-3-ol hydrochloride salt (27 mg, 0.27 mmol) and NaOAc (30 mg, 0.36 mmol) was suspended in DMSO (2 mL) and sonicated for about 2 minutes. Intermediate 49 (35 mg, 0.12 mmol) and NaBH(OAc)$_3$, (62 mg, 0.29 mmol) was added and the reaction mixture was stirred at 40° for 30 min. Water (10 mL) was added and the reaction mixture was extracted 3 times with DCM, pooled organic phases were washed once with water and the organic phase was evaporated. Resulting oil was purified on preparative LC, System B, to give 19.9 mg, (35%) of the target compound as a colorless oil. MS (ESI+) for $C_{18}H_{18}N_2O_3S$ m/z 343 (M+H)$^+$.

EXAMPLE 112

4-(Azetidin-1-ylmethyl)-5-methoxy-1-(phenylsulfonyl)-1H-indole trifluoroacetate

5-Methoxy-1-(phenylsulfonyl)-1H-indole-4-carbaldehyde (50 mg, 0.16 mmol; Intermediate 75), was dissolved in dry THF (4 mL) before azetidine (13 mg, 0.24 mmol) was added followed by acetic acid (95 mg, 1.59 mmol) and sodium triacetoxyborohydride (101 mg, 0.48 mmol). The reaction mixture was heated in microwave for 720 s at 130° C. The solvent was removed and the crude product was purified using preparative HPLC/UV (System A, 30-60% MeCN, 0.1% TFA). The title compound (22.3 mg, 40%) was obtained as a white solid. MS (ESI+) for $C_{19}H_{20}N_2O_3S$ $C_2HF_3O_2$ m/z 357 (M+H)$^+$.

Intermediate 77

4-(Azetidin-1-ylmethyl)-1H-indole

Sodium triacetoxy borohydride (1.46 g, 6.9 mmol) was added to a solution of 1H-indole-4-carbaldehyde (0.5 g, 3.4 mmol) and azetidine (0.39 g, 6.87 mmol) in THF (15 ml). The mixture was stirred for 1 h and diluted with dichloromethane and NaHCO$_3$ (aq). The organic phase was washed with brine (1×), dried (MgSO$_4$) and evaporated. The crude product was dissolved in dichloromethane and hexane was added (1:1). The off white powder was filtered and washed with a mixture of dichloromethane hexane (1:1). Yield: 400 mg (52%). Off white solid. MS (ESI+) for $C_{12}H_{14}N_2$ m/z 187 (M+H)$^+$.

EXAMPLE 113

4-{[4-(Azetidin-1-ylmethyl)-1H-indol-1-yl]sulfonyl}benzonitrile trifluoroacetate DMF (1 ml) was added to a vial containing 4-(Azetidin-1-ylmethyl)-1H-indole (10 mg, 0.054 mmol; Intermediate 77) and 60% NaH (4.3 mg, 0.1 mmol) at rt. The mixture was stirred for 20 minutes before the 4-cyanobenzenesulphonyl chloride (21.7 mg, 0.11 μmol) was added. The mixture was allowed to stir for 30 minutes and 2 drops of 1N HCl was added. The mixture was filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 6.0 mg (24%). Light brown oil. MS (ESI+) for $C_{19}H_{17}N_3O_2S$ m/z 352 (M+H)$^+$.

Intermediate 78

Methyl (2S)-1-{[1-(phenylsulfonyl)-1H-indol-4-yl]methyl}azetidine-2-carboxylate trifluoroacetate The target compound was made with the same procedure as for Example 111 using intermediate 49, 124 mg (0.43 mmol) and methyl (2S)-azetidine-2-carboxylate hydrochloride salt, 100 mg (0.66 mmol). The crude was and purified on a preparative HPLC with an ACE C8-column with 0.1% TFA/ACN as eluent to give 72 mg (33%) of the target compound as a colorless oil. MS (ESI+) for $C_{20}H_{20}N_2O_4S$ m/z 385 (M+H)$^+$. Though perfectly clean in the LC methods there are some aromatic impurities with about 10 mol % intensity noticed in the 1-NMR spectra.

EXAMPLE 114

2-((2S)-1-{[1-(Phenylsulfonyl)-1H-indol-4-yl]methyl}azetidin-2-yl)propan-2-ol trifluoroacetate Intermediate 78 (25 mg, 0.065 mmol), was partioned between ice cold 0.1M NaOH/CHCl$_3$, the aq phase was extracted once with CHCl$_3$, the combined organic phases were dried (Na$_2$SO$_4$) and the solvent was removed at reduced pressure. The resulting colorless oil was dissolved in dry THF (5 mL), under a N$_2$ atmosphere was added the 1.2M MeLi in THF, 0.5 mL (0.6 mmol) solution and the brownish solution was left in RT for 20 minutes. MeOH was added, the solvent was evaporated at reduced pressure and the residue was purified with preparative HPLC, System B, to give 4.8 mg (15%) of a colorless oil. MS (ESI+) for $C_{21}H_{24}N_2O_3S$ m/z 385 (M+H)$^+$.

EXAMPLE 115

4-(Azetidin-1-ylmethyl)-2-methyl-1-(phenylsulfonyl)-1H-indole trifluoroacetate

2-Methyl-1-(phenylsulfonyl)-1H-indole-4-carbaldehyde (32 mg, 0.11 mmol; Intermediate 47), was dissolved in dry THF (4 mL) before azetidine (9.2 mg, 0.16 mmol) was added followed by acetic acid (64 mg, 1.07 mmol) and sodium triacetoxyborohydride (68 mg, 0.32 mmol). The reaction mixture was heated in microwave for 720 s at 130° C. The solvent was removed and the crude product was purified using preparative HPLC/UV (System A, 30-60% MeCN, 0.1% TFA). The title compound (2.3 mg, 6%) was obtained as a clear oil. MS (ESI+) for $C_{19}H_{20}N_2O_2S$ $C_2HF_3O_2$ m/z 341 (M+H)$^+$.

EXAMPLE 116

4-(Azetidin-1-ylmethyl)-1-[(2-chlorophenyl)sulfonyl]-1H-indole trifluoroacetate

DMF (1 ml) was added to a vial containing 4-(Azetidin-1-ylmethyl)-1H-indole (10 mg, 0.054 mmol; Intermediate 77)

and 60% NaH (5.4 mg, 0.13 mmol) at rt. The mixture was stirred for 20 minutes before the 2-chlorobenzenesulphonyl chloride (22.7 mg, 0.11 mmol) was added. The mixture were allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 12.0 mg (47%). White solid. MS (ESI+) for $C_{18}H_{17}ClN_2O_2S$ m/z 361 (M+H)$^+$.

EXAMPLE 117

4-(Azetidin-1-ylmethyl)-1-[(5-chloro-2-thienyl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before the 5-chlorothiophene-2-sulphonyl chloride (23.3 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 12.0 mg (46%). White solid. MS (ESI+) for $C_{16}H_{15}ClN_2O_2S_2$ m/z 367 (M+H)$^+$.

EXAMPLE 118

4-(Azetidin-1-ylmethyl)-1-(2-naphthylsulfonyl)-1H-indole trifluoroacetate

DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 2-naphtylsulfonyl chloride (24.3 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 7.5 mg (28%). Light red solid. MS (ESI+) for $C_{22}H_{20}N_2O_2S$ m/z 377 (M+H)$^+$.

EXAMPLE 119

4-(Azetidin-1-ylmethyl)-1-[(2-methoxy-5-methylphenyl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 6-methoxy-m-toluenesulfonyl chloride (22.7 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 13.3 mg (50%). White solid. MS (ESI+) for $C_{20}H_{22}N_2O_3S$ m/z 371 (M+H)$^+$.

EXAMPLE 120

4-(Azetidin-1-ylmethyl)-1-[(6-chloroimidazo[2,1-b][1,3]thiazol-5-yl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 6-Chloroimidazo[2,1-b]thiazole-5-sulphonyl chloride (23.7 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 8.9 mg (32%). White solid. MS (ESI+) for $C_{17}H_{15}ClN_4O_2S_2$ m/z 407 (M+H)$^+$.

EXAMPLE 121

4-(Azetidin-1-ylmethyl)-1-[(4-tert-butylphenyl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 4-tert-butylbenzenesulfonyl chloride (27.6 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 4.3 mg (16%). Colorless liquid. MS (ESI+) for $C_{22}H_{26}N_2O_2S$ m/z 383 (M+H)$^+$.

EXAMPLE 122

4-(Azetidin-1-ylmethyl)-1-[(2,6-difluorophenyl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 2,6-difluorobenzenesulfonyl chloride (20.5 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 8.0 mg (31%). Light brown solid. MS (ESI+) for $C_{18}H_{16}F_2N_2O_2S$ m/z 363 (M+H)$^+$.

EXAMPLE 123

4-(Azetidin-1-ylmethyl)-1-{[2-(trifluoromethyl)phenyl]sulfonyl}-1H-indole trifluoroacetate DMF (1 ml) was added to a vial containing 4-(azetidin-1-ylmethyl)-1H-indole (10 mg, 0.054 mmol; Intermediate 77) and 60% NaH (5.4 mg, 0.13 mmol) at rt. The mixture was stirred for 20 minutes before 2-trifluoromethylsulphonyl chloride (22.8 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 13.7 mg (50%). Light brown liquid. MS (ESI+) for $C_{19}H_{17}F_3N_2O_2S$ m/z 395 (M+H)$^+$.

EXAMPLE 124

3-{[4-(Azetidin-1-ylmethyl)-1H-indol-1-yl]sulfonyl}benzonitrile trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 3-cyanaobenzenesulphonyl chloride (26.3 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 2.4 mg (10%). Colorless liquid. MS (ESI+) for $C_{19}H_{17}N_3O_2S$ m/z 352 (M+H)$^+$.

EXAMPLE 125

4-(Azetidin-1-ylmethyl)-1-{[4-bromo-2-(trifluoromethyl)phenyl]sulfonyl}-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 4-bromo-2-(trifluoromethyl)benzenesulphonyl chloride (24.2 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 11 mg (35%). Light brown liquid. MS (ESI+) for $C_{19}H_{16}BrF_3N_2O_2S$ m/z 475 (M+H)$^+$.

EXAMPLE 126

4-(Azetidin-1-ylmethyl)-1-(2-thienylsulfonyl)-1H-indole trifluoroacetate

DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 2-thiophenesulphonyl chloride (26.4 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 12 mg (50%). Colorless liquid. MS (ESI+) for $C_{16}H_{16}N_2O_2S_2$ m/z 333 (M+H)$^+$.

EXAMPLE 127

4-(Azetidin-1-ylmethyl)-1-[(2,5-difluorophenyl)sulfonyl]-1H-indole trifluoroacetate DMF (1 ml) was added to a vial containing 4-(Azetidin-1-ylmethyl)-1H-indole (10 mg, 0.054 mmol; Intermediate 77) and 60% NaH (5.4 mg, 0.13 mmol) at rt. The mixture was stirred for 20 minutes before 2,5-difluorobenzenesulfonyl chloride (19.6 mg, 0.11 mmol) was added. The mixture was allowed to stir for 1 hour and 2 drops of 1N HCl was added. The mixture was diluted with MeOH, filtered and purified using preparative HPLC with ACE C8 5 μm (21.2×100 mm) column. Water containing 0.1% TFA and acetonitrile were used as mobile phases at a flow rate of 20 ml/min with gradient times of 11.5 min. Yield: 4.5 mg (18%). Colorless liquid. MS (ESI+) for $C_{18}H_{16}F_2N_2O_2S$ m/z 363 (M+H)$^+$.

Intermediate 79

(5-Methoxy-1H-indol-4-ylmethyl)-dimethyl-amine

5-Methoxy-1-(phenylsulfonyl)-1H-indole-4-carbaldehyde (366 mg, 1.16 mmol; Intermediate 75) was dissolved in DCE, dimethylamine (3.48 mmol as 2M in MeOH) and sodium triacetoxyborohydride (738 mg, 3.48 mmol) was added in sequence. The reaction mixture was left stirring at r.t. for 23 h, diluted with DCM, NaOH (2M aq) was added until sustained pH at 10. The organic phase was separated, and the water-phase extracted once DCM. The combined organic phases were dried over $Na_2SO_4$ and purified by preparative HPLC. Yield: 57 mg residue mauve color

EXAMPLE 128

[(5-Methoxy-1-{[3-(trifluoromethyl)phenyl]sulfonyl}-1H-indol-4-yl)methyl]dimethylamine trifluoroacetate (5-Methoxy-1H-indol-4-ylmethyl)-dimethyl-amine (23.5 mg, 0.115 mmol; Intermediate 79) was distributed in two portions in DMF, NaH (60%) added and the mixture was stirred for 30 min before adding 3-trifluoromethylbenzenesulfonyl chloride (56.3 mg, 0.230 mmol). The reaction mixture was diluted with water and extracted with DCM, dried and concentrated. This residue was purified by preparative HPLC. Yield: 7 mg. MS (ESI+) for $C_{19}H_{19}F_3N_2O_3S$ m/z 413 (M+H)$^+$.

Intermediate 80

4-Bromo-3-methyl-2-nitrophenol

3-Methyl-2-nitrophenol (11.4 g, 74.4 mmol) was dissolved in chloroform (11 ml) and cooled on an ice-water bath. Bromine (3.8 ml, 74.4 mmol) in HOAc (9 ml) was added drop wise to the stirred, cooled solution. The solution was stirred at 0° for 2 h. Ice was added to the reaction mixture. The organic phase was separated and the water phase was extracted with chloroform. The combined organic phase was washed with brine and water. Evaporation gave 17.2 g. MS (ESI+) for $C_7H_6BrNO_3$ m/z 232, 234 (M+H)$^+$.

Intermediate 81

Benzyl 4-bromo-3-methyl-2-nitrophenyl ether

Intermediate 80 (17.2 g, 74.1 mmol) was dissolved in acetone (150 ml). $K_2CO_3$ (15.4 g, 111.2 mmol, 1.5 eq) was added. The solution was stirred for 5 min and then benzyl bromide (10 ml, 81.2 mmol, 1.1 eq) was added. The solution was refluxed for 90 min. The potassium carbonate was filtered off and the solution was evaporated. The residue was re-crystallised from ethanol. Obtained 20.2 g.

Intermediate 82

1-{(E)-2-[3-(Benzyloxy)-6-bromo-2-nitrophenyl]vinyl}pyrrolidine

1-Benzyloxy-4-bromo-3-methyl-2-nitro-benzene (20 g, 62.1 mmol; Intermediate 81) was dissolved in DMF. DMFDMA (9.93 ml, 74.5 mmol) and pyrrolidine (6.22 ml, 74.5 mmol) was added. The solution was heated at 110° under nitrogen. TLC (EtOAc/Hexane 1/3) indicated that the starting material was consumed after 2 h. The heating was turned off. The reaction mixture was allowed to adopt room temperature, and was left over night. The solution was evaporated and the residue solidified on standing in the refrigerator. 50 mL of methanol was added and the mixture was heated. The solid was partly dissolved. The mixture was allowed to adopt room temperature, and was then filtered. The solid was washed with methanol and dried. Obtained 17 g.

Intermediate 83

7-(Benzyloxy)-4-bromo-1H-indole

1-[-2-(3-Benzyloxy-6-bromo-2-nitro-phenyl)-vinyl]-pyrrolidine (10 g, 24.8 mmol; Intermediate 82) suspended in HOAc (25 mL) was added to a boiling mixture of iron (4.15 g, 74.4 mmol) in HOAc. After 2 h boiling TLC indicated that no starting material is left. The reaction mixture was filtered while still warm. The residue was evaporated and dissolved in toluene. The toluene slurry was applied to a silica column and eluted with toluene/hexane 1/1. Obtained 3.1 g. MS (ESI+) for $C_{15}H_{12}BrNO$ m/z 302, 304 (M+H)$^+$.

Intermediate 84

7-(Benzyloxy)-4-bromo-1-(methylsulfonyl)-1H-indole

Sodium hydride (60% oil suspension) (0.48 g, 19.9 mmol) was washed with hexane and dried in vaccuo. The indole derivative (2.0 g, 5.6 mmol; Intermediate 83) was added dissolved in DMF (12 ml). The suspension was stirred for 10 minutes and then the methanesulfonyl chloride (1.54 ml, 19.9 mmol) was added. The mixture was stirred for 2 h at room temperature. Water was added and the reaction mixture was extracted with DCM. Evaporation gave a solid that was washed with methanol. Obtained 1.6 g. MS (ESI+) for $C_{16}H_{14}BrNO_3S$ m/z 380, 382 (M+H)$^+$.

Intermediate 85

7-(Benzyloxy)-1-(methylsulfonyl)-1H-indole-4-carbaldehyde

To a solution of 7-benzyloxy-1-methanesulfonyl-4-vinyl-1H-indole (1.3 g, 3.9 mmol; Intermediate 84) in dioxane (25 ml), lutidine (900 µl, 7.9 mmol), sodium metaperiodate (3.37 g, 15.8 mmol) (in water (10 ml)) and osmium tetroxide (100 mg, 0.1 mmol) was added (in that order). A precipitate was almost immediately formed, and the mixture was stirred for 1 h at room temperature. Water was added. The precipitate was filtered off, and washed with water. The solid material was extracted with acetonitrile. The acetonitrile-solution was evaporated. The product was purified by strait phase chromatography using Biotage flash-chromatograph 5-40% EtOAc in petroleum ether 40-60° C. Obtained 0.40 mg. MS (ESI+) for $C_{17}H_{15}NO_4S$ m/z 330 (M+H)$^+$.

EXAMPLE 129

4-(Azetidin-1-ylmethyl)-7-(benzyloxy)-1-(methylsulfonyl)-1H-indole trifluoroacetate Azetidine hydrochloride (17 mg, 0.18 mmol) and 7-Benzyloxy-1-methanesulfonyl-1H-indole-4-carbaldehyde (30 mg, 0.09 mmol) were dissolved in 2 mL 1,2-dichloroethane. Sodium acetoxyborohydride (58 mg, 0.27 mmol) was added, and the mixture was stirred over night at RT. The product was purified by reverse phase preparative HPLC (YMC C8, 0.1% TFA/CH$_3$CN) to give the trifluoroacetate salt of title compound 7.8 mg. MS ESI+m/z 371 (M+H)$^+$.

EXAMPLE 130

({1-[(6-Chloroimidazo[2,1-b][1,3]thiazol-5-yl)sulfonyl]-5-methoxy-1H-indol-4-yl}methyl)dimethylamine trifluoroacetate 5-Methoxy-1-(phenylsulfonyl)-1H-indole-4-carbaldehyde (296 mg, 0.939 mmol; Intermediate 75) was dissolved in DCE, dimethylamine (2.82 mmol as 2M in MeOH) and sodium triacetoxyborohydride (597 mg, 2.82 mmol) was added in sequence. The reaction mixture was left stirring at r.t. for 4 h. NaOH aq. was added until alkaline and the mixture was extracted with DCM, dried and concentrated.

Thereafter, 10 mL of EtOH and 2 mL of NaOH (6M aq) was added and the reaction mixture was heated to reflux for 2 h. and left at r.t. over night. The intermediate desulfonylated product was purified by preparative HPLC.

This product (46 mg, 0.23 mmol) was dissolved in 1 mL DMF, NaH (60%) (10.8 mg, 0.45 mmol) was added and the mixture stirred for 30 min before adding 6-chloro-imidazo[2,1-b]thiazole-5-sulfonyl chloride (115 mg, 0.45 mmol). TFA was added to neutralize excess base and the crude product was purified by preparative HPLC. Yield: 6 mg. MS (ESI+) for $C_{17}H_{17}ClN_4O_3S_2$ m/z 425 (M+H)$^+$.

Intermediate 86

5-(Benzyloxy)-1-(phenylsulfonyl)-1H-indole

DCM (200 mL) was added to 5-benzyloxyindole (15 g, 67 mmol), benzylsulfonic acid (17.8 g, 101 mmol) and tetrabutyl ammoniumsulfat (6.84 g, 20 mmol) followed by 5 M NaOH (40 mL). The reaction mixture was stirred at rt for 3 h. The aqueous layer was washed with DCM (2×30 mL) and the organic layers were combined and washed with brine (30 mL). Drying (MgSO$_4$) and concentration in vacco was followed by crystallization from MeOH to give the product in 83% yield (20.3 g).

Intermediate 87

1-(Phenylsulfonyl)-1H-indol-5-ol

To a solution of 5-(benzyloxy)-1-(phenylsulfonyl)-1H-indole (0.50 g, 1.37 mmol; Intermediate 86) in EtOH (3 mL), Pd/C (30 wt %, 0.15 g), cyclohexene (1 mL), and HCl (1 mL) and was added. The reaction mixture was warmed to 150° C. for 1 h using microwave heating. The Pd/C was filtered off and the solvent was removed under reduced pressure. The product (about 95% pure) was used without further purification.

EXAMPLE 131

4-[(Dimethylamino)methyl]-1-(phenylsulfonyl)-1H-indol-5-ol trifluoroacetate

Paraformaldehyde (65 mg, 2.20 mmol) and 2 M dimethylamine in EtOH (1.1 ml, 2.20 mmol) was heated until a clear solution was obtain. The solution was added to 1-(phenylsulfonyl)-1H-indol-5-ol (500 mg, 1.82 mmol; Intermediate 87) in EtOH (10 ml) and the mixture was stirred at ambient temperature for 3 d. Solvent was evaporated. Yield: 528 mg (87%); white solid. LC-MS: 88% pure. A small portion (28 mg) was purified on Gilson HPLC using 15-50% MeCN in 0.1% TFA. Yield: 18 mg; brown gum. MS (ESI+) for $C_{17}H_{18}N_2O_3S$ m/z 331 (M+H)$^+$.

EXAMPLE 132

{[5-Ethoxy-1-(phenylsulfonyl)-1H-indol-4-yl]methyl}dimethylamine trifluoroacetate NaH (95%) (101 mg, 4.23 mmol), was added to a solution of 4-[(dimethylamino)methyl]-1-(phenylsulfonyl)-1H-indol-5-ol (700 mg, 2.11 mmol; Example 131) in DMF (20 ml) at ambient temperature. The mixture was stirred for 15 min before iodoethane (0.203 ml, 2.54 mmol) was added. After 1 h water was added and the mixture extracted with Et2O. A small portion was purified on Gilson HPLC using 20-50% MeCN in 0.1% TFA. Yield: 65 mg; colorless oil. MS (ESI+) for $C_{19}H_{22}N_2O_3S$ m/z 359 (M+H)$^+$.

Intermediate 88

1-(5-Ethoxy-1H-indol-4-yl)-N,N-dimethylmethanamine

{[5-Ethoxy-1-(phenylsulfonyl)-1H-indol-4-yl]methyl}dimethylamine (655 mg, 1.831 mmol; Example 133) was added EtOH (5 ml) and 2 M NaOH (5 ml) and heated at 70 oC for 5 h. Water was added and white material precipitated. The mixture was extracted with DCM. The organic phase was extracted with 1 M HCl (3×20 ml). The aqueous phase was made alkaline (pH 9) using 2 M NaOH and extracted with DCM (3×50 ml). The combined organic layers were dried (MgSO$_4$) and evaporated. Yield: 293 mg (74%); brown oil. MS (ESI+) for $C_{13}H_{18}N_2O$ m/z 219 (M+H)$^+$.

EXAMPLE 133

({5-Ethoxy-1-[(2-methoxy-5-methylphenyl)sulfonyl]-1H-indol-4-yl}methyl)-dimethylamine trifluoroacetate NaH (7 mg, 0.29 mmol) was added to a solution of 1-(5-ethoxy-1H-indol-4-yl)-N,N-dimethylmethanamine (28 mg, 0.128 mmol; Intermediate 88) in DMF (1 ml) and the mixture was stirred at rt for 10 min before 6-methoxy-3-methylsulfonyl chloride (42 mg, 0.192 mmol) The mixture was stirred at rt for 1 h before the mixture was divided between water (2 ml) and DCM (10 ml). The aqueous phase was extracted with dcm (5 ml) and the combined organic layers concentrated. The residue was purified on Gilson HPLC using 30-60% MeCN in 0.1% TFA as eluent. Yield: 15.8 mg (24%); brown oil. MS (ESI+) for $C_{21}H_{26}N_2O_4S$ m/z 403 (M+H)$^+$.

EXAMPLE 134

{[5-Ethoxy-1-(1-naphthylsulfonyl)-1H-indol-4-yl]methyl}dimethylamine trifluoroacetate NaH (7 mg, 0.29 mmol) was added to a solution of 1-(5-ethoxy-1H-indol-4-yl)-N,N-dimethylmethanamine (28 mg, 0.128 mmol; Intermediate 88) in DMF (1 ml) and the mixture was stirred at rt for 10 min before 1-naphtalenesulfonyl chloride (44 mg, 0.192 mmol) was added. The mixture was stirred at rt for 1 h before the mixture was divided between water (2 ml) and DCM (10 ml). The aqueous phase was extracted with DCM (5 ml) and the combined organic layers concentrated. The residue was purified on Gilson HPLC using 30-60% MeCN in 0.1% TFA as eluent. Yield: 25.3 mg (38%); brown oil. MS (ESI+) for $C_{23}H_{24}N_2O_3S$ m/z 409 (M+H)$^+$.

EXAMPLE 135

{[5-Ethoxy-1-(2-naphthylsulfonyl)-1H-indol-4-yl]methyl}dimethylamine trifluoroacetate NaH (7 mg, 0.29 mmol) was added to a solution of 1-(5-ethoxy-1H-indol-4-yl)-N,N-dimethylmethanamine (28 mg, 0.128 mmol; Intermediate 88) in DMF (1 ml) and the mixture was stirred at rt for 10 min before 2-naphtalenesulfonyl chloride (44 mg, 0.192 mmol) was added. The mixture was stirred at rt for 1 h before the mixture was divided between water (2 ml) and DCM (10 ml). The aqueous phase was extracted with dcm (5 ml) and the combined organic layers concentrated. The residue was purified on Gilson HPLC using 30-60% MeCN in 0.1% TFA as eluent. Yield: 13.8 mg (21%); brown oil. MS (ESI+) for $C_{23}H_{24}N_2O_3S$ m/z 409 (M+H)$^+$.

EXAMPLE 136

({1-[(2-Chlorophenyl)sulfonyl]-5-ethoxy-1H-indol-4-yl}methyl)dimethylamine trifluoroacetate NaH (7 mg, 0.29 mmol) was added to a solution of 1-(5-ethoxy-1H-indol-4-yl)-N,N-dimethylmethanamine (28 mg, 0.128 mmol; Intermediate 88) in DMF (1 ml) and the mixture was stirred at rt for 10 min before 2-chlorobenzene-1-sulfonyl chloride (41 mg, 0.192 mmol) was added. The mixture was stirred at rt for 1 h before the mixture was divided between water (2 ml) and DCM (10 ml). The aqueous phase was extracted with dcm (5 ml) and the combined organic layers concentrated. The residue was purified on Gilson HPLC using 30-60% MeCN in 0.1% TFA as eluent. Yield: 28.5 mg (44%); brown oil. MS (ESI+) for $C_{19}H_{21}ClN_2O_3S$ m/z 393 (M+H)$^+$.

EXAMPLE 137

({1-[(3-Chloro-2-methylphenyl)sulfonyl]-5-ethoxy-1H-indol-4-yl}methyl)dimethylamine trifluoroacetate NaH (7 mg, 0.29 mmol) was added to a solution of 1-(5-ethoxy-1H-indol-4-yl)-N,N-dimethylmethanamine (28 mg, 0.128 mmol; Intermediate 88) in DMF (1 ml) and the mixture was stirred at rt for 10 min before 3-chloro-2-methylbenzenesulfonyl chloride (43 mg, 0.192 mmol) was added. The mixture was stirred at rt for 1 h before the mixture was divided between water (2 ml) and DCM (10 ml). The aqueous phase was extracted with dcm (5 ml) and the combined organic layers concentrated. The residue was purified on Gilson HPLC using 30-60% MeCN in 0.1% TFA as eluent. Yield: 17.8 mg (27%); brown oil. MS (ESI+) for $C_{20}H_{23}ClN_2O_3S$ m/z 407 (M+H)$^+$.

Intermediate 89

[(5-Methoxy-1H-indol-4-yl)methyl]dimethylamine trifluoroacetate

{[5-Methoxy-1-(phenylsulfonyl)-1H-indol-4-yl]methyl}dimethylamine trifluoroacetate (127 mg, 0.278 mmol) was refluxed in EtOH (2 ml) and 1 M NaOH (2 ml) for 3 h. The mixture was extracted with DCM The product was purified on Gilson HPLC using 20-40% MeCN in 0.1% TFA. Yield: 54.6 mg (62%); colourless oil.

EXAMPLE 138

({5-Methoxy-1-[(2-methoxy-5-methylphenyl)sulfonyl]-1H-indol-4-yl}methyl)-dimethylamine trifluoroacetate NaH (4 mg, 0.160 mmol, 95%) was added to a solution of 1-(5-methoxy-1H-indol-4-yl)-N,N-dimethylmethanamine (17 mg, 0.053 mmol, TFA-salt; Intermediate 89) in DMF (1 ml) and the mixture was stirred for 10 min before 2-methoxy-5-methylbenzenesulfonyl chloride (18 mg, 0.080 mmol) was added. After 1 h the reaction was quenched with a few drops of TFA and diluted with MeOH and filtered. The mixture was purified on Waters HPLC using 15-60% MeCN in 0.1% TFA. Yield: 2.4 mg (9%); brown oil. MS (ESI+) for $C_{20}H_{24}N_2O_4S$ m/z 389 (M+H)$^+$.

EXAMPLE 139

({1-[(2,3-Dichlorophenyl)sulfonyl]-5-methoxy-1H-indol-4-yl}methyl)dimethylamine trifluoroacetate NaH (4 mg, 0.160 mmol, 95%) was added to a solution of 1-(5-methoxy-1H-indol-4-yl)-N,N-dimethylmethanamine (17 mg, 0.053 mmol, TFA-salt; Intermediate 77) in DMF (1 ml) and the mixture was stirred for 10 min before 2,3-dichlorobenzenesulfonyl chloride (20 mg, 0.080 mmol) was added. After 1 h the reaction was quenched with a few drops of TFA and diluted with MeOH and filtered. The mixture was purified on Waters HPLC using 15-60% MeCN in 0.1% TFA. Yield: 7.7 mg (28%); brown oil. MS (ESI+) for $C_{18}1H_8Cl_2N_2O_3S$ m/z 413 (M+H)$^+$.

EXAMPLE 140

{[5-Ethoxy-1-(quinolin-8-ylsulfonyl)-1H-indol-4-yl]methyl}dimethylamine bis(trifluoroacetate)

NaH (5 mg, 0.21 mmol) was added to a solution of 1-(5-ethoxy-1H-indol-4-yl)-N,N-dimethylmethanamine (14 mg, 0.064 mmol; Intermediate 88) in DMF (0.5 ml) and the mixture was stirred at rt for 10 min before 8-quinolinesulfonyl chloride (22 mg, 0.096 mmol) was added. The mixture was stirred at rt for 1 h before the mixture was divided between water (2 ml) and DCM (10 ml). The aqueous phase was extracted with dcm (5 ml) and the combined organic layers concentrated. The residue was purified on Gilson HPLC using 30-60% MeCN in 0.1% TFA as eluent. Yield: 5.7 mg (17%); brown oil. MS (ESI+) for $C_{22}H_{23}N_3O_3S$ m/z 410 (M+H)$^+$.

EXAMPLE 141

{[5-Ethoxy-1-({5-[1-methyl-3-(trifluoromethyl)-1H-pyrazol-5-yl]-2-thienyl}sulfonyl)-1H-indol-4-yl]methyl}dimethylamine trifluoroacetate NaH (5 mg, 0.21 mmol) was added to a solution of 1-(5-ethoxy-1H-indol-4-yl)-N,N-dimethylmethanamine (14 mg, 0.064 mmol; Intermediate 88) in DMF (0.5 ml) and the mixture was stirred at rt for 10 min 5-(1-methyl-3-fluoromethyl)-1H-pyrazol-5-yl)thiophene-2-sulfonyl chloride (32 mg, 0.096 mmol) was added. The mixture was stirred at rt for 1 h before the mixture was divided between water (2 ml) and DCM (10 ml). The aqueous phase was extracted with dcm (5 ml) and the combined organic layers concentrated. The residue was purified on Waters HPLC using 15-60% MeCN in 0.1% TFA as eluent. Yield: 4.4 mg (11%); brown oil. MS (ESI+) for $C_{22}H_{23}F_3N_4O_3S_2$ m/z 513 (M+H)$^+$.

EXAMPLE 142

({1-[(2,5-Dichlorophenyl)sulfonyl]-5-ethoxy-1H-indol-4-yl}methyl)dimethylamine trifluoroacetate NaH (5 mg, 0.21 mmol) was added to a solution of 1-(5-ethoxy-1H-indol-4-yl)-N,N-dimethylmethanamine (14 mg, 0.064 mmol; Intermediate 88) in DMF (0.5 ml) and the mixture was stirred at rt for 10 min before 2,5-dichlorobenzenesulfonyl chloride (23.5 mg, 0.096 mmol) was added. The mixture was stirred at rt for 20 min before the mixture was quenched with a few drops of TFA and diluted with MeOH and filtered. The mixture was purified on Waters HPLC using 15-60% MeCN in 0.1% TFA in water. Yield: 11.3 mg (33%); brown oil. MS (ESI+) for $C_{19}H_{20}Cl_2N_2O_3S$ m/z 427 (M+H)$^+$.

EXAMPLE 143

({5-Ethoxy-1-[(2,4,6-trichlorophenyl)sulfonyl]-1H-indol-4-yl}methyl)dimethylamine trifluoroacetate NaH (5 mg, 0.21 mmol) was added to a solution of 1-(5-ethoxy-1H-indol-4-yl)-N,N-dimethylmethanamine (14 mg, 0.064 mmol; Intermediate 88) in DMF (0.5 ml) and the mixture was stirred at rt for 10 min before 2,4,6-Trichlorobenzenesulfonyl chloride (26.9 mg, 0.096 mmol) was added. The mixture was stirred at rt for 20 min before the mixture was quenched with a few drops of TFA and diluted with MeOH and filtered. The mixture was purified on Waters HPLC using 15-60% MeCN in 0.1% TFA in water. Yield: 8.4 mg (23%); brown oil. MS (ESI+) for $C_{19}H_{19}Cl_3N_2O_3S$ m/z 461 (M+H)$^+$.

EXAMPLE 144

1-[5-Methoxy-1-(phenylsulfonyl)-1H-indol-4-yl]-N-methylmethanamine trifluoroacetate 2M methylamine in MeOH (0.1 ml, 0.2 mmol) was added to a solution of 5-methoxy-1-(phenylsulfonyl)-1H-indole-4-carbaldehyde (10 mg, 0.032 mmol; Intermediate 75) in THF (1 ml) and stirred for 10 minutes at rt before sodium triacetoxyborohydride (10 mg, 0.048 mmol) was added. The mixture was stirred overnight and NaBH$_4$ (2 mg, 0.053 mmol) was added. The mixture was stirred for 40 minutes and 1 drop of water was added and the mixture was purified preparative HPLC using ACE C8 5 μm (21.2×100 mm) column. Water containing 0.1% TFA and acetonitrile were used as mobile phases at a flow rate of 20 ml/min with gradient times of 11.5 min. Yield: 5.1 mg (36%). Colorless oil. MS (ESI+) for $C_{17}H_{18}N_2O_3S$ m/z 331 (M+H)$^+$.

Intermediate 90

1-[(2-Methoxy-5-methylphenyl)sulfonyl]-1H-indole-4-carbaldehyde

To a slurry of sodium hydride (165 mg, 6.9 mmol) in DMF (5 ml) indole-4-carboxaldehyde (500 mg, 3.4 mmol) was added. The mixture was stirred for 15 min and then the 2-methoxy-5-methyl-benzenesulfonyl chloride (1140 mg, 5.2 mmol) was added and the mixture was stirred for 1 h at room temperature. Water was added and the reaction mixture was extracted with EtOAc. Evaporation gave 1.2 g. MS (ESI+) for $C_{17}H_{15}NO_4S$ m/z 330 (M+H)$^+$.

EXAMPLE 145

({1-[(2-Methoxy-5-methylphenyl)sulfonyl]-1H-indol-4-yl}methyl)methylamine trifluoroacetate Intermediate 90 (50 mg, 0.2 mmol) was dissolved in DCE (2 ml) and methylamine 2M in THF (152 µl, 0.3 mmol) was added. The solution was stirred for 10 min and then triacetoxyborohydride (64 mg, 0.3 mmol) was added. After 3 h the starting material was gone, the wanted product was formed as well as the dimer m/z 659.

The reaction mixture was evaporated. Water was added and the reaction mixture extracted with EtOAc. The EtOAc phase contained the dimer and only a small amount of the monomer. The Water phase was made alkaline with 1M NaOH and extracted with EtOAc. The EtOAc phase was evaporated and purified on reversed phase prep HPLC. Obtained 11.6 mg. MS (ESI+) m/z 345 (M+H)+

Intermediate 91

5-Hydroxy-4-fluoro-2-nitrotoluene 25 g (198.2 mmol, 1 eq.) of 2-fluoro-5-methylphenole was dissolved in mixture of 53.5 mL of acetic acid and 7.9 mL of concentrated sulphuric acid and stirred at 0° C. To this mixture a solution of 13.7 g (198.2 mmol, 1 eq.) of NaNO$_2$ in 40 mL of water was added over period of 2 hours. The brown suspension was stirred for 1 hour and poured into large amount of ice water. The nitroso compound was filtered off and partially dried. It was then added in portions to a stirred solution of 17.8 mL of 70% nitric acid and 53.5 mL of water and kept at 40-50° C. until the evolution of gas stopped and the suspension changed colour to light-yellow. The suspension was poured into large amount of ice water, the yellowish precipitate was filtered off and dried in vacuum. The compound was purified on silica gel column using 1% MeOH/CH$_2$Cl$_2$ as eluent to give 24.0 g (140.2 mmol) of 5-hydroxy-4-fluoro-2-nitrotoluene as yellowish solid (yield 71%). The compound can be additionally purified by recrystallization from CH$_2$Cl$_2$/iso-hexane or toluene. MS (ESI-) for C$_7$H$_6$FNO$_3$ m/z 170 (M-H)$^-$.

Intermediate 92

5-Benzyloxy-4-fluoro-2-nitrotoluene 22.0 g (128.6 mmol, 1 eq.) of Intermediate was dissolved in 250 mL of dry acetonitrile and 35.5 g (257.2 mmol, 2 eq.) of K$_2$CO$_3$ was added to the solution. To this suspension 16.8 mL (141.4 mmol, 1.1 eq.) of benzyl bromide was added drop wise and the reaction mixture was heated at 60° C. overnight. The solvent was evaporated and the residue was dissolved in CH$_2$Cl$_2$/water. The phases were separated, the organic phase was dried over MgSO$_4$, filtered and evaporated to give the crude product as brownish-yellow solid. The material was recrystallised from hot diethyl ether to produce 29.5 g (112.9 mmol) of light-yellow crystals (yield 88%).

Intermediate 93

5-Benzyloxy-6-fluoroindole

A suspension of 10.55 g (40.4 mmol, 1 eq.) of Intermediate 92 in 13.5 mL (64.6 mmol, 1.6 eq.) of bis-dimethylamino-1-butoxymethane was stirred at 90° C. overnight. The resulting red-orange solid was dried in vacuum and redissolved in 250 mL of 1/10 mixture of ethanol/dioxane and ~1 g of Raney nickel was added. The compound was hydrogenated using hydrogen gas at room temperature for 5 hours. The catalyst was filtered off over celite and the solvents were evaporated to give the crude indole as dark brown oil. The crude product was chromatographed on silica gel using CH$_2$Cl$_2$ as eluent to yield 2.2 g (9.1 mmol) as yellow solid (yield 23%). The compound can be additionally purified by recrystallization from CH$_2$Cl$_2$/iso-hexane. MS (ESI+) for C$_{15}$H$_{12}$FNO m/z 242 (M+H)$^+$.

Intermediate 94

N-Benzenesulphonyl-5-benzyloxy-6-fluoroindole

To the stirred solution of 2.0 g (8.29 mmol, 1 eq.) of Intermediate 93 in 30 mL dry DMF 0.35 g (8.70 mmol, 1.05 eq.) of NaH (60% in mineral oil) was added at 0° C. and the solution was stirred for 30 min at room temperature. After that the reaction mixture was again cooled to 0° C. and 1.17 mL (9.12 mmol, 1.1 eq) of benzenesulphonyl chloride was added drop wise. The reaction mixture was kept at 4° C. overnight, then a drop of methanol was added and the solvent was removed in vacuum. The crude indole was dissolved in CH$_2$Cl$_2$ and poured into saturated NaHCO$_3$. The phases were separated, the organic layer was dried over MgSO$_4$, filtered and evaporated to give Intermediate 94 as yellow oil. The compound was cromatographed on silica gel using CH$_2$Cl$_2$ as eluent to give 2.88 g (7.54 mmol) as light-yellow oil, which solidified upon standing (yield 91%). MS (ESI+) for C$_{21}$H$_{16}$FNO$_3$S m/z 382 (M+H)$^+$.

Intermediate 95

6-Fluoro-1-(phenylsulfonyl)-1H-indol-5-ol

To a solution of 2.5 g (6.55 mmol) of Intermediate 94 in 100 mL of ethanol 0.25 g of 10% Pd/C was added. The suspension was hydrogenated at room temperature for 2 hours. The catalyst was filtered off over celite and solvents were removed. The crude product was purified on silica gel column using 0.5% MeOH/CH$_2$Cl$_2$ as eluent to give 1.79 g (6.16 mmol) of final product as white solid (yield 94%). MS (ESI+) for C$_{14}$H$_{10}$FNO$_3$S m/z 292 (M+H)$^+$.

EXAMPLE 146

4-[(Dimethylamino)methyl]-6-fluoro-1-(phenylsulfonyl)-1H-indol-5-ol trifluoroacetate Paraformaldehyde (48.7 mg, 1.620 mmol) and 2 M dimethylamine in MeOH (0.85 ml, 1.70 mmol) was heated until a clear solution was obtained. This was added to a suspension of 6-fluoro-1-(phenylsulfonyl)-1H-indol-5-ol (236 mg, 0.810 mmol; Intermediate 95) in EtOH (4 ml) and the mixture was heated in microwave oven at 90 oC for 10 min. Solvent was evaporated. Yield: 277 mg; white solid. 25 mg of the material was purified on Waters HPLC using 20-60% MeCN in 0.1% TFA. Yield: 28.4 mg (73%, two step); colourless oil. MS (ESI+) for C$_{17}$H$_{17}$FN$_2$O$_3$S m/z 349 (M+H)$^+$.

EXAMPLE 147

1-[6-Fluoro-5-methoxy-1-(phenylsulfonyl)-1H-indol-4-yl]-N,N-dimethylmethanamine

N,N-dimethylformamide dimethyl acetal (0.964 ml, 7.233 mmol) was added to a solution of 4-[(dimethylamino)methyl]-6-fluoro-1-(phenylsulfonyl)-1H-indol-5-ol (252 mg, 0.723 mmol; Example 146) in DMF (8 ml) and the mixture was divided into two tubes and heated in microwave oven at 180 0 C for 180 s. Solvent was evaporated and residue purified on Gilson HPLC using 30-70% MeCN in 50 nM ammonium bicarbonate buffer as eluent (Xterra). Yield: 101.7 mg (39%); white solid. MS (ESI+) for $C_{18}H_{19}FN_2O_3S$ m/z 363 (M+H)$^+$.

EXAMPLE 148

6-Fluoro-1-(phenylsulfonyl)-4-(pyrrolidin-1-ylmethyl)-1H-indol-5-ol

Paraformaldehyde (20.6 mg, 0.686 mmol) and pyrrolidine (0.057 ml, 0.686 mmol) in EtOH (1 ml) was heated until a clear solution was obtained. The solution was added to 6-fluoro-1-(phenylsulfonyl)-1H-indol-5-ol (100 mg, 0.343 mmol; Intermediate 95) in EtOH (1 ml) and the mixture was heated at 90 oC for 10 min. Solvent was evaporated. Yield: 137 mg and ca. 20% of material was purified on Gilson HPLC using 15-45% MeCN in 50 nM ammonium hydrogencarbonate buffer. Yield: 21 mg (82%); white solid. MS (ESI+) for $C_{19}H_{19}FN_2O_3S$ m/z 375 (M+H)$^+$.

EXAMPLE 149

6-Fluoro-5-methoxy-1-(phenylsulfonyl)-4-(pyrrolidin-1-ylmethyl)-1H-indole trifluoroacetate Paraformaldehyde (20.6 mg, 0.686 mmol) and pyrrolidine (0.057 ml, 0.686 mmol) in EtOH (1 ml) was heated until a clear solution was obtained. The solution was added to 6-fluoro-1-(phenylsulfonyl)-1H-indol-5-ol (100 mg, 0.343 mmol; Intermediate 95) in EtOH (1 ml) and the mixture was heated at 90° C. for 10 min. Solvent was evaporated. Yield: 137 mg and ca. 20% of material was purified on Gilson HPLC using 15-45% MeCN in 50 nM ammonium hydrogencarbonate buffer. Yield: 21 mg (82%); white solid. DMF (2.5 ml) and DMF-DMA (500 µl) was added 80% of the crude material from above and the mixture was heated at 180° C. in microwave oven for 180 s. LC-MS: sm: prod 1:2. Solvent evaporated and residue purified on Waters HPLC using 15-60% MeCN in 0.1% TFA Yield: 28 mg (26%); brown oil. MS (ESI+) for $C_{20}H_{21}FN_2O_3S$ m/z 389 (M+H)$^+$.

EXAMPLE 150

4-(Azetidin-1-ylmethyl)-6-fluoro-1-(phenylsulfonyl)-1H-indol-5-ol trifluoroacetate Paraformaldehyde (20.6 mg, 0.686 mmol) and azetidine (0.041 ml, 0.686 mmol) in EtOH (1 ml) was heated until a clear solution was obtained. The solution was added to 6-fluoro-1-(phenylsulfonyl)-1H-indol-5-ol (100 mg, 0.343 mmol; Intermediate 95) in EtOH (1 ml) and the mixture was heated in microwave oven at 90° C. for 10 min. Solvent was evaporated and 20% of material was purified on Waters HPLC using 20-60% MeCN in 0.1%). Yield: 16.5 mg (51%); brown oil. MS (ESI+) for $C_{18}H_{17}FN_2O_3S$ m/z 361 (M+H)$^+$.

EXAMPLE 151

4-(Azetidin-1-ylmethyl)-6-fluoro-5-methoxy-1-(phenylsulfonyl)-1H-indole trifluoroacetate Paraformaldehyde (20.6 mg, 0.686 mmol) and azetidine (0.041 ml, 0.686 mmol) in EtOH (1 ml) was heated until a clear solution was obtained. The solution was added to 6-fluoro-1-(phenylsulfonyl)-1H-indol-5-ol (100 mg, 0.343 mmol, Intermediate 95) in EtOH (1 ml) and the mixture was heated in microwave oven at 90° C. for 10 min. Solvent was evaporated and 20% of material was purified on Waters HPLC using 20-60% MeCN in 0.1% TFA. Yield: 16.5 mg (51%); brown oil. 80% of the crude material from above was dissolved in DMF (2.5 ml) and DMF-DMA (500 µl) was added. The mixture was heated at 180° C. for 180 s. Solvent was evaporated and residue purified on Waters HPLC using 20-60% MeCN in 0.1% TFA. Yield: 21.1 mg; brown oil. MS (ESI+) for $C_{19}H_{19}FN_2O_3S$ m/z 375 (M+H)$^+$.

EXAMPLE 152

4-{[Ethyl(methyl)amino]methyl}-6-fluoro-1-(phenylsulfonyl)-1H-indol-5-ol

Paraformaldehyde (20.6 mg, 0.686 mmol) and N-ethylmethylamine (0.059 ml, 0.686 mmol) in EtOH (1 ml) was heated until a clear solution was obtained. The solution was added to 6-fluoro-1-(phenylsulfonyl)-1H-indol-5-ol (100 mg, 0.343 mmol; Intermediate 95) in EtOH (1 ml) and the mixture was heated in microwave oven at 90 oC for 10 min. Solvent was evaporated and 20% of material was purified on Gilson HPLC using 15-45% MeCN in 50 nM ammonium hydrogencarbonate buffer. Yield: 13 mg; white solid. MS (ESI+) for $C_{18}H_{19}FN_2O_3S$ m/z 363 (M+H)$^+$.

EXAMPLE 153

N-{[6-Fluoro-5-methoxy-1-(phenylsulfonyl)-1H-indol-4-yl]methyl}-N-methylethanamine trifluoroacetate Paraformaldehyde (20.6 mg, 0.686 mmol) and N-ethylmethylamine (0.059 ml, 0.686 mmol) in EtOH (1 ml) was heated until a clear solution was obtained. The solution was added 6-fluoro-1-(phenylsulfonyl)-1H-indol-5-ol (100 mg, 0.343 mmol; Intermediate 95) in EtOH (1 ml) and the mixture was heated in microwave oven at 90 oC for 10 min. Solvent was evaporated and 20% of material was purified on Gilson HPLC using 15-45% MeCN in 50 nM ammonium hydrogencarbonate buffer. Yield: 13 mg; white solid.

80% of the crude material from above was dissolved in DMF (2.5 ml) and DMF-DMA (500 µl) the mixture was heated at 180° C. for 180 s Solvent was evaporated and residue purified on Waters HPLC using 20-60% MeCN in 0.1% TFA twice. Yield: 2.8 mg; brown oil. MS (ESI+) for $C_{19}H_{21}FN_2O_3S$ m/z 377 (M+H)$^+$.

N-{[6-fluoro-5-methoxy-1-(phenylsulfonyl)-1H-indol-4-yl]methyl}-N-methylethanamine trifluoroacetate Intermediate 96

6-Fluoro-5-hydroxy-1-(phenylsulfonyl)-1H-indole-4-carbaldehyde

A solution of 6-fluoro-1-(phenylsulfonyl)-1H-indol-5-ol (200 mg, 687 µmol; Intermediate 95) in MeOH (2.14 mL) was treated with 2M NaOH (860 µL) and formaldehyde (2 mL of a 37 wt. % solution in H$_2$O, 26.8 mmol) and heated in an Emrys optimizer (MW) at 120° C. for 5 min. The solvent was removed in vacuo, the residue taken up with H$_2$O and 1M HCl (pH 1), extracted with EtOAc (3×), washed with sat. NaHCO$_3$, brine, dried (Na$_2$SO$_4$) and the solvent removed in vacuo to yield a brownish syrup (265 mg), which was directly used in the oxidation step. A solution of crude 6-fluoro-4-(hydroxymethyl)-1-(phenylsulfonyl)-1H-indol-5-ol (858 µmol) in CH$_2$Cl$_2$/MeOH (4.5+0.1 mL) was treated with MnO$_2$ (1.12 g, 12.9 mmol) and stirred at rt for 30 min. The reaction mixture was filtrated over a plug of SiO$_2$ and it was washed with CH$_2$Cl$_2$ (40 mL) to give the title compound as yellow solid (72 mg). This material was directly used in the next steps.

EXAMPLE 154

6-Fluoro-4-[(methylamino)methyl]-1-(phenylsulfonyl)-1H-indol-5-ol trifluoroacetate Crude 6-fluoro-5-hydroxy-1-(phenylsulfonyl)-1H-indole-4-carbaldehyde (25 mg, 78.3 µmol; Intermediate 96), methylamine (49 µL of a 8M sol. in EtOH, 392 µmol) and sodium triacetoxyborohydride (66.4 mg, 313 µmol) were mixed in 1,2-dichloroethane (3 mL) and stirred at rt for 4 h. The solvent was removed in vacuo, the residue taken up with MeOH and purified by prep. HPLC/UV (System A, 5-35% MeCN, 0.1% TFA) to yield the title compound as a brown glass (4.3 mg, 12%). MS (ESI+) for C$_{16}$H$_{16}$FN$_2$O$_3$S m/z 335 (M+H)$^+$.

EXAMPLE 155

{[6-Fluoro-5-methoxy-1-(phenylsulfonyl)-1H-indol-4-yl]methyl}methylamine trifluoroacetate The crude 6-fluoro-5-hydroxy-1-(phenylsulfonyl)-1H-indole-4-carbaldehyde (40.1 mg, 126 µmol; Intermediate 96) was suspended in acetone (3.5 mL) and treated with K$_2$CO$_3$ (34.7 mg, 251 µmol) and MeI (15.6 µL, 251 µmol) and stirred in a sealed tube at 65° C. for 1 h 45 min. The reaction mixture was cooled to rt and diluted with CH$_2$Cl$_2$, washed with H$_2$O, dried (Na$_2$SO$_4$) and the solvent removed in vacuo to give an intense yellow, vitreous solid (41.4 mg), which was directly used in the reductive amination. Crude 6-fluoro-5-methoxy-1-(phenylsulfonyl)-1H-indole-4-carbaldehyde (41.4 mg, 124 µmol), methylamine (78.6 µL of a 8M sol. in EtOH, 629 µmol) and sodium triacetoxyborohydride (66.5 mg, 314 µmol) were mixed in 1,2-dichloroethane (4 mL) and stirred at rt for 18.5 h. The solvent was removed in vacuo, the residue taken up with MeOH and purified by prep. HPLC/UV (System A, 9-39% MeCN, 0.1% TFA) to yield the title compound as an off-white solid (26.1 mg, 45%). MS (ESI+) for C$_{17}$H$_{18}$FN$_2$O$_3$S m/z 349 (M+H)$^+$.

Intermediate 97

1-(5-Methoxy-1H-indol-4-yl)-N,N-dimethylmethanamine

To 5-methoxy-1-(phenylsulfonyl)-1H-indol-4-yl]methyl}dimethylamine (1.50 g, 4.36 mmol) dissolved in EtOH (100 mL) 2M NaOH (40 mL) was added and the reaction mixture was warmed to 70° C. for 7 h. The reaction mixture was concentrated under reduced pressure and the residue was washed with DCM. The organic layer was collected, dried (MgSO$_4$), filtered and evaporated. The title compound (830 mg, 93%) was obtained as a brown solid. MS (ESI+) for C$_{12}$H$_{16}$N$_2$O m/z 205 (M+H)$^+$.

EXAMPLE 156

1-{5-Methoxy-1-[(4-methoxyphenyl)sulfonyl]-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 4-methoxybenzene-1-sulfonyl chloride (23 mg, 0.11 mmol) was added. The reaction mixture was allowed to stir at rt over night. The reaction was quenched by addition of water. Purification using preparative HPLC/UV (System B) afforded the title product (2 mg, 6%) as a white solid. MS (ESI+) for C$_{19}$H$_{22}$N$_2$O$_4$S m/z 375 (M+H)$^+$.

EXAMPLE 157

1-{1-[(3-Chlorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 3-chlorobenzene-1-sulfonyl chloride (23 mg, 0.11 mmol) was added. The reaction mixture was allowed to stir at rt over night. The reaction was quenched by addition of water. Purification using preparative HPLC/UV (System B) afforded the title product (3 mg, 10%) as a white solid. MS (ESI+) for C$_{18}$H$_{19}$ClN$_2$O$_3$S m/z 379 (M+H)$^+$.

EXAMPLE 158

1-{1-[(2,5-Difluorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2,5-difluorobenzenesulfonyl chloride (23 mg, 0.11 mmol) was added. The reaction mixture was allowed to stir at rt over night. The reaction was quenched by addition of water. Purification by preparative HPLC/UV (System B) afforded the title product (3 mg, 10%) as a white solid. MS (ESI+) for C$_{18}$H$_{18}$F$_2$N$_2$O$_3$S m/z 381 (M+H)$^+$.

EXAMPLE 159

1-(1-{[4-Fluoro-3-(trifluoromethyl)phenyl]sulfonyl}-5-methoxy-1H-indol-4-yl)-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 4-fluoro-3-(trifluoromethyl)benzenesulphonyl chloride (29 mg, 0.11 mmol) was added. The reaction mixture was allowed to stir at rt over night. The reaction was quenched by addition of water. Purification by preparative HPLC/UV (System B) afforded the title product (3 mg, 8%) as a white solid. MS (ESI+) for C$_{19}$H$_{18}$F$_4$N$_2$O$_3$S m/z 431 (M+H)$^+$.

EXAMPLE 160

1-[5-Methoxy-1-(quinolin-8-ylsulfonyl)-1H-indol-4-yl]-N,N-dimethylmethanamine

To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 8-quinolinesulfonyl chloride (25 mg, 0.11 mmol) was added. The reaction mixture was allowed to stir at rt over night. The reaction was quenched by addition of water. Purification by preparative HPLC/UV (System B) afforded the title product (3 mg, 11%) as a white solid. MS (ESI+) for $C_{21}H_{21}N_3O_3S$ m/z 396 $(M+H)^+$.

EXAMPLE 161

1-{1-[(2-Chlorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-chlorobenzene-1-sulfonyl chloride (23 mg, 0.11 mmol) was added. The reaction mixture was allowed to stir at rt over night. The reaction was quenched by addition of water. Purification by preparative HPLC/UV (System B) afforded the title product (5 mg, 17%) as a brown solid. MS (ESI+) for $C_{18}H_{19}ClN_2O_3S$ m/z 379 $(M+H)^+$.

EXAMPLE 162

1-{1-[(2-Chloro-6-methylphenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-chloro-5-methylbenzene-1-sulfonyl chloride (25 mg, 0.11 mmol) was added. The reaction mixture was allowed to stir at rt over night. The reaction was quenched by addition of water. Purification by preparative HPLC/UV (System B) afforded the title product (7 mg, 24%) as a white solid. MS (ESI+) for $C_{19}H_{21}ClN_2O_3S$ m/z 394 $(M+H)^+$.

EXAMPLE 163

1-{1-[(3-Chloro-4-fluorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 3-chloro-4-fluorobenzene-1-sulfonyl chloride (25 mg, 0.11 mmol) was added. The reaction mixture was allowed to stir at rt over night. The reaction was quenched by addition of water. Purification by preparative HPLC/UV (System B) afforded the title product (4 mg, 14%) as a white solid. MS (ESI+) for $C_{18}H_{18}ClFN_2O_3S$ m/z 397 $(M+H)^+$.

EXAMPLE 164

1-{5-Methoxy-1-[(2-methylphenyl)sulfonyl]-1H-indol-4-yl}-N,N-dimethylmethanamine To a solution of 1-(5-methoxy-11H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-methylbenzene-1-sulfonyl chloride (21 mg, 0.11 mmol) was added. The reaction mixture was allowed to stir at rt over night. The reaction was quenched by addition of water. Purification by preparative HPLC/UV (System B) afforded the title product (7 mg, 28%) as a white solid. MS (ESI+) for $C_{19}H_{22}N_2O_3S$ m/z 359 $(M+H)^+$.

EXAMPLE 165

2-({4-[(Dimethylamino)methyl]-5-methoxy-1H-indol-1-yl}sulfonyl)benzonitrile

To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-cyanobenzenesulphonyl chloride (22 mg, 0.11 mmol) was added. The reaction mixture was allowed to stir at rt over night. The reaction was quenched by addition of water. Purification by preparative HPLC/UV (System B) afforded the title product (6 mg, 22%) as a white solid. MS (ESI+) for $C_{19}H_{19}N_3O_3S$ m/z 370 $(M+H)^+$.

EXAMPLE 166

1-{1-[(2,6-Difluorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2,6-difluorobenzenesulphonyl chloride (23 mg, 0.11 mmol) was added. The reaction mixture was allowed to stir at rt over night. The reaction was quenched by addition of water. Purification by preparative HPLC/UV (System B) afforded the title product (6 mg, 24%) as a white solid. MS (ESI+) for $C_{18}H_{18}F_2N_2O_3S$ m/z 381 $(M+H)^+$.

EXAMPLE 167

1-{1-[(1,2-Dimethyl-1H-imidazol-4-yl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 1,2-dimethyl-1H-imidazole-4-sulfonyl chloride (21 mg, 0.11 mmol) was added. The reaction mixture was allowed to stir at rt over night. The reaction was quenched by addition of water. Purification by preparative HPLC/UV (System B) afforded the title product (4 mg, 14%) as a brown solid. MS (ESI+) for $C_{17}H_{22}N_4O_3S$ m/z 386 $(M+H)^+$.

EXAMPLE 168

1-{5-Methoxy-1-[(5-methyl-1-benzothien-2-yl)sulfonyl]-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 5-methyl-1-benzothiophene-2-sulfonyl chloride (27 mg, 0.11 mmol) was added. The reaction mixture was allowed to stir at rt over night. The reaction was quenched by addition of water. Purification by preparative HPLC/UV (System B) afforded the title product (8 mg, 27%) as a white solid. MS (ESI+) for $C_{21}H_{22}N_2O_3S_2$ m/z 415 (M+H)$^+$.

EXAMPLE 169

1-{5-Methoxy-1-[(2-methoxy-4-methylphenyl)sulfonyl]-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-methoxy-4-methylbenzenesulfonyl chloride (24 mg, 0.11 mmol) was added. The reaction mixture was allowed to stir at rt over night. The reaction was quenched by addition of water. Purification by preparative HPLC/UV (System B) afforded the title product (5 mg, 17%) as a white solid. MS (ESI+) for $C_{20}H_{24}N_2O_4S$ m/z 389 (M+H)$^+$.

EXAMPLE 170

1-{1-[(2,4-Dichlorophenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2,4-dichlorobenzenesulphonyl chloride (27 mg, 0.11 mmol) was added. The reaction mixture was allowed to stir at rt over night. The reaction was quenched by addition of water. Purification by preparative HPLC/UV (System B) afforded the title product (5 mg, 17%) as a white solid. MS (ESI+) for $C_{18}H_{18}Cl_2N_2O_3S$ m/z 414 (M+H)$^+$.

EXAMPLE 171

1-{1-[(5-Bromo-2-methoxyphenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 5-bromo-2-methoxybenzenesulphonyl chloride (31 mg, 0.11 mmol) was added. The reaction mixture was allowed to stir at rt over night. The reaction was quenched by addition of water. Purification by preparative HPLC/UV (System B) afforded the title product (9 mg, 27%) as a white solid. MS (ESI+) for $C_{19}H_{21}BrN_2O_4S$ m/z 454 (M+H)$^+$.

EXAMPLE 172

1-[1-(2,1,3-Benzothiadiazol-4-ylsulfonyl)-5-methoxy-1H-indol-4-yl]-N,N-dimethylmethanamine To a solution of 1-(5-methoxy-11H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2,1,3-benzothiadiazole-4-sulfonyl chloride (26 mg, 0.11 mmol) was added. The reaction mixture was allowed to stir at rt over night. The reaction was quenched by addition of water. Purification by preparative HPLC/UV (System B) afforded the title product (3 mg, 11%) as a yellow solid. MS (ESI+) for $C_{18}H_{18}N_4O_3S_2$ m/z 403 (M+H)$^+$.

EXAMPLE 173

1-[1-(3,4-Dihydro-2H-1,5-benzodioxepin-7-ylsulfonyl)-5-methoxy-1H-indol-4-yl]-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 3,4-dihydro-2H-1,5-benzodioxepine-7-sulfonyl chloride (27 mg, 0.11 mmol) was added. The reaction mixture was allowed to stir at rt over night. The reaction was quenched by addition of water. Purification by preparative HPLC/UV (System B) afforded the title product (5 mg, 17%) as a yellow solid. MS (ESI+) for $C_{21}H_{24}N_2O_5S$ m/z 417 (M+H)$^+$.

EXAMPLE 174

1-{1-[(2,5-Dimethoxyphenyl)sulfonyl]-5-methoxy-1H-indol-4-yl}-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2,5-dimethoxybenzenesulfonyl chloride (26 mg, 0.11 mmol) was added. The reaction mixture was allowed to stir at rt over night. The reaction was quenched by addition of water. Purification by preparative HPLC/UV (System B) afforded the title product (5 mg, 17%) as a beige solid. MS (ESI+) for $C_{20}H_{24}N_2O_5S$ m/z 405 (M+H)$^+$.

EXAMPLE 175

1-(5-Methoxy-1-{[2-(trifluoromethyl)phenyl]sulfonyl}-1H-indol-4-yl)-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 2-(trifluoromethyl)benzenesulfonyl chloride (27 mg, 0.11 mmol) was added. The reaction mixture was allowed to stir at rt over night. The reaction was quenched by addition of water. Purification by preparative HPLC/UV (System B) afforded the title product (5 mg, 17%) as a colorless solid. MS (ESI+) for $C_{19}H_{19}F_3N_2O_3S$ m/z 413 (M+H)$^+$.

EXAMPLE 176

1-(5-Methoxy-1-{[4-(trifluoromethoxy)phenyl]sulfonyl}-1H-indol-4-yl)-N,N-dimethylmethanamine To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 4-(trifluoromethoxy)benzenesulfonyl chloride (29 mg, 0.11 mmol) was added. The reaction mixture was allowed to stir at rt over night. The reaction was quenched by addition of water. Purification by preparative HPLC/UV (System B) afforded the title product (6 mg, 21%) as a white solid. MS (ESI+) for $C_{19}H_{19}F_3N_2O_4S$ m/z 429 (M+H)$^+$.

EXAMPLE 177

3-({4-[(Dimethylamino)methyl]-5-methoxy-1H-indol-1-yl}sulfonyl)benzonitrile

To a solution of 1-(5-methoxy-1H-indol-4-yl)-N,N-dimethylmethanamine (15 mg, 0.07 mmol; Intermediate 97) in DMF (1 mL) NaH (4 mg, 0.15 mmol) was added at rt. The reaction mixture was stirred at rt for 15 min and 3-cyanobenzenesulphonyl chloride (22 mg, 0.11 mmol) was added. The reaction mixture was allowed to stir at rt over night. The reaction was quenched by addition of water. Purification by preparative HPLC/UV (System B) afforded the title product (4 mg, 13%) as a white solid. MS (ESI+) for $C_{19}H_{19}N_3O_3S$ m/z 370 (M+H)$^+$.

EXAMPLE 178

1-[5-Methoxy-1-(pyridin-3-ylsulfonyl)-1H-indol-4-yl]-N,N-dimethylmethanamine

To a solution of 1-(5-methoxy-1H-indol-4-yl)-N,N-dimethylmethanamine (30 mg, 0.15 mmol; Intermediate 97) and pyridine-3-sulfonyl chloride hydrochloride (43 mg, 0.20 mmol) in DCM (1 mL) 5 M NaOH (2 mL) was added. The reaction mixture was stirred at rt over night. The organic phase was collected and the solvent was removed under reduced pressure. Purification by preparative HPLC/UV (System B) afforded the title product (2 mg, 4%) as a white solid. MS (ESI+) for $C_{17}H_{19}N_3O_3S$ m/z 346 (M+H)$^+$.

Intermediate 98

1-[1-(Phenylsulfonyl)-1H-indol-4-yl]ethanol

A solution of indole-4-carboxaldehyde (1.00 g, 6.89 mmol) in DMF (60 mL) under N$_2$ was treated with NaH (95%; 20.7 mmol, 496 mg) at rt for 15 min. benzenesulfonyl chloride (972 µL, 7.58 mmol) was added and stirring continued for 1 min. it was cooled to 0° C. and quenched with H$_2$O. The reaction mixture was extracted with EtOAc (3×), the combined org. phases washed with H$_2$O (3×), brine and dried (Na$_2$SO$_4$). conc. in vacuo gave an orange glue (1.79 g), which was directly used in the Grignard addition. The solution of crude 1-(phenylsulfonyl)-1H-indole-4-carbaldehyde in THF (60 mL) was treated with MeMgBr (9.84 mL of a 1.4 M solution in Toluene/THF, 13.78 mmol) at rt for 20 min upon which another 9.84 mL (2 eq) of Grignard reagent were added and stirring continued for another 5 min. The reaction mixture was quenched with sat. NH$_4$Cl, extracted with EtOAc (3×), the combined org. phases washed with brine, dried (Na$_2$SO$_4$) and the solvent removed in vacuo to give a yellow-brownish glue (2.21 g). The crude product was subjected to flash chromatography (SiO$_2$, CH$_2$Cl$_2$:MeOH=100:1) to yield the title compound as a yellow/orange foam (1.687 g, 81% over 2 steps). MS (ESI+) for $C_{16}H_{15}NO_3S$ m/z 284 (M-OH)$^+$.

Intermediate 99

4-(1-Iodoethyl)-1-(phenylsulfonyl)-1H-indole

To a solution of PPh$_3$ (457 mg, 1.74 mmol) in CH$_2$Cl$_2$ (7.5 mL) at rt was added I2 (442 mg, 1.74 mmol; Intermediate 99) and it was stirred for 5 min, upon which a solution of 1-[1-(phenylsulfonyl)-1H-indol-4-yl]ethanol (500 mg, 1.66 mmol; Intermediate 98) in CH$_2$Cl$_2$ (7.5 mL) was added and stirring continued for 3.5 h at rt. The reaction mixture was washed with Na$_2$S$_2$O$_3$ (to remove excess I2), dried (Na$_2$SO$_4$), the solvent removed in vacuo and the obtained residue purified by column chromatography (SiO$_2$, CH$_2$Cl$_2$=100%) to give a yellow/brownish solid (235.5 mg) which was directly used in the next steps.

EXAMPLE 179

Methyl{1-[1-(phenylsulfonyl)-1H-indol-4-yl]ethyl}amine

A solution of 4-(1-iodoethyl)-1-(phenylsulfonyl)-1H-indole (50 mg, 122 µmol; Intermediate 99) in CH$_2$Cl$_2$ (1.5 mL) was treated with MeNH$_2$ (153 µL of a 8 M solution in EtOH, 1.22 mmol) at rt for 2 h. The reaction mixture was concentrated in vacuo, the obtained residue taken up with MeOH/THF and purified by prep. HPLC (System B, 22-52% MeCN, 50 mM NH$_4$HCO$_3$) to yield the title compound as a white, waxy solid (13.2 mg, 12% over two steps). MS (ESI+) for $C_{17}H_{18}N_2O_2S$ m/z 284 (M-NHMe)$^+$, 315 (M+H)$^+$.

EXAMPLE 180

{1-[1-(Phenylsulfonyl)-1H-indol-4-yl]ethyl}aminetrifluoroacetate

A solution of 4-(1-iodoethyl)-1-(phenylsulfonyl)-1H-indole (50 mg, 122 µmol; Intermediate 99) in DMF (1.5 mL) was treated with phthalimide potassium salt (113 mg, 610 µmol) at rt for 6 h. Hydrazine monohydrate (296 µL, 6.10 mmol) was added, the reaction mixture warmed to 75° C. and stirring continued for 1 h. The crude mixture was taken up with H$_2$O, extracted with EtOAc (3×), the combined org. phases washed with brine, dried (Na$_2$SO$_4$) and the solvent removed in vacuo. The obtained residue was taken up with THF and purified by prep. HPLC (System A, 5-35% MeCN, 0.1% TFA) to yield the title compound as an off-white solid (15.1 mg, 10% over two steps). MS (ESI+) for $C_{16}H_{16}N_2O_2S$ m/z 284 (M-NH$_2$)$^+$.

EXAMPLE 181

Dimethyl{1-[1-(phenylsulfonyl)-1H-indol-4-yl]ethyl}amine

A solution of 4-(1-iodoethyl)-1-(phenylsulfonyl)-1H-indole (40 mg, 97.3 µmol; Intermediate 99) in CH$_2$Cl$_2$ (1.5 mL) was treated with Me$_2$NH (174 µL of a 5.6 M solution in EtOH, 973 µmol) at rt for 1 h. The reaction mixture was concentrated in vacuo, the obtained residue taken up with MeOH/THF and purified by prep. HPLC (System B, 30-60% MeCN, 50 mM NH$_4$HCO$_3$) to yield the title compound as a white, waxy solid (10.6 mg, 11% over two steps). MS (ESI+) for $C_{18}H_{20}N_2O_2S$ m/z 329 (M+H)$^+$.

EXAMPLE 182

4-(Azetidin-1-ylmethyl)-2,3-dichloro-5-methoxy-1-(phenylsulfonyl)-1H-indole trifluoroacetate 4-(Azetidin-1-ylmethyl)-5-methoxy-1-(phenylsulfonyl)-1H-indole hydrochloride, (250 mg, 0.64 mmol; Example 112) was converted to its free base by extraction between CHCl$_3$/1 M NaOH. The free base was dissolved in dry THF (4 mL), NCS, 425 mg (3.2 mmol) was added and the clear solution was stirred at 40° C. for 30 minutes. The solvent was evaporated at reduced pressure and the resulting oil was taken up between 0.1 M NaOH/CHCl$_3$. The dried (MgSO$_4$) organic phase was evaporated at reduced pressure and the resulting brown oil was purified by preparative HPLC (ACE C8 5 mm, water containing 0.1% TFA-CH$_3$CN) to give 33 mg (9.6%) of the title compound as a light yellow solid together with 64 mg (20%) of the 3-chlorinated product. MS (ESI+) for C$_{19}$H$_{18}$Cl$_2$N$_2$O$_3$SMS m/z 425 (M+H)$^+$.

EXAMPLE 183

{[1-(Phenylsulfonyl)-1H-indol-4-yl]methyl}amine

{[1-(phenylsulfonyl)-1H-indol-4-yl]methyl}amine hydrochloride 4-(Bromomethyl)-1-(phenylsulfonyl)-1H-indole (30 mg, 0.09 mmol; Intermediate 2) was dissolved in DMF (2 ml) and potassium phthalimide (5 eq) was added. The mixture was stirred at RT overnight. Water was added and the reaction mixture was extracted with EtOAc. The EtOAc phase was evaporated. Ethanol (3 ml) and hydrazine hydrate (235 µl) was added to the residue. The mixture was stirred at 78° for 30 min. Water was added and the slurry was extracted with EtOAc. The ethyl acetate phase was evaporated and 100 µl of HCl (1M) in diethyl ether was added. A solid was formed. The diethyl ether was evaporated from the solid and the solid was washed with EtOAc. Obtained 19.3 mg of the product as the HCl salt. MS (ESI$^+$) m/z 270 (M+H—NH3)$^+$ Intermediate 100

5-(Benzyloxy)-6-methoxy-1-(phenylsulfonyl)-1H-indole

To 5-benzyloxy-6-methoxyindole (5.0 g, 20 mmol), benzenesulfonyl chloride (5.2 g, 30 mmol) and tetrabutylammonium hydrogen sulfate (2.0 g, 6 mmol) DCM (200 mL) and 4M NaOH (50 mL) were added. The reaction mixture was allowed to stir at room temperature over night. The organic layer was collected and the aqueous phase was washed with DCM (2×30 mL). The combined organic layers were then washed with brine (2×50 mL). Drying, (MgSO$_4$), filtration and evaporation afforded a brown oil. The product precipitated when adding diethyl ether. Recrystallization from MeOH afforded the title compound in 84% yield (6.55 g) as light yellow crystals. MS (ESI+) for C$_{22}$H$_{19}$NO$_4$S m/z 394 (M+H)$^+$.

Intermediate 101

6-Methoxy-1-(phenylsulfonyl)-1H-indol-5-ol

To 5-(benzyloxy)-6-methoxy-1-(phenylsulfonyl)-1H-indole (6.6 g, 17 mmol; Intermediate 100) and Pd/C (2 g, 30 wt %), EtOH (30 mL), cyclohexene (9 mL) and HCl (9 mL) were added. The reaction mixture was warmed to 150° C. for 5 min using microwave heating. The Pd/C was filtered off and the solvent was removed under reduced pressure to afford the title compound in quantitative yield (5 g) as a black gum. The product was used without any further purification in the next step. MS (ESI+) for C$_{15}$H$_{13}$NO$_4$S m/z 304 (M+H)$^+$.

EXAMPLE 184

4-[(Dimethylamino)methyl]-6-methoxy-1-(phenylsulfonyl)-1H-indol-5-ol

Paraformaldehyde (28 mg, 0.932 mmol) and 2 M Me$_2$NH in MeOH (0.47 ml, 0.932 mmol) was heated until clear solution was obtained. The solution was added to 6-methoxy-1-(phenylsulfonyl)-1H-indol-5-ol (61 mg, 0.201 mmol; Intermediate 101) in EtOH (1.5 ml) and the mixture was heated in microwave oven at 80° C. for 10 min. A small part was purified on Gilson HPLC using 25-55% MeCN in 50 nM ammonium hydrogencarbonate as eluent. Yield: 3.8 mg; white solid. MS (ESI+) for C$_{18}$H$_{20}$N$_2$O$_4$S m/z 361 (M+H)$^+$.

EXAMPLE 185

1-[5,6-Dimethoxy-1-(phenylsulfonyl)-1H-indol-4-yl]-N,N-dimethylmethanamine

4-[(Dimethylamino)methyl]-6-methoxy-1-(phenylsulfonyl)-1H-indol-5-ol (60 mg, 0.166 mmol; Example 184) was dissolved in DMF (2 ml) and DMF-DMA (300 µl) was added. The mixture was heated in microwave oven at 180 oC for 180 s. Solvent was evaporated and the residue purified on Gilson HPLC using 30-60% MeCN in 50 nM ammonium hydrogencarbonate buffer as eluent. Yield: 13.2 mg (21%); brown oil. MS (ESI+) for C$_{19}$H$_{22}$N$_2$O$_4$S m/z 375 (M+H)$^+$.

EXAMPLE 186

{[3-Chloro-5-methoxy-1-(phenylsulfonyl)-1H-indol-4-yl]methyl}dimethylamine trifluoroacetate {[5-methoxy-1-(phenylsulfonyl)-1H-indol-4-yl]methyl}dimethylamine (80.0 mg, 0.23 mmol; Example 108) was dissolved in dry THF (4 ml) and NCS (93.4 mg, 0.7 mmol) was added. The mixture was stirred for 3 hours and evaporated. The crude product was purified by flash chromatography using 2.5% MeOH in dichloromethane to 5% MeOH in dichloromethane with 1% NEt$_3$ as the eluent and then by preparative HPLC ACE C8 5 µm (21.2×100 mm) column. Water containing 0.1% TFA and acetonitrile were used as mobile phases at a flow rate of 20 ml/min with gradient times of 11.5 min to give the title compound. Yield: 7 mg (6%). Light yellow oil. MS (ESI+) for C$_{18}$H$_{19}$ClN$_2$O$_3$S m/z 379 (M+H)$^+$.

Intermediate 102 tert-Butyl {[5-methoxy-1-(phenylsulfonyl)-1H-indol-4-yl]methyl}methylcarbamate

{[5-methoxy-1-(phenylsulfonyl)-1H-indol-4-yl]methyl}methylamine (0.627 g, 1.9 mmol; Example 144) was dissolved in dichloromethane (25 ml) and boc-anhydride (0.62 g, 2.8 mmol) was added. The mixture was stirred for 2 hours, washed with brine, dried (MgSO$_4$) and evaporated. The crude product was purified through a plug of silica using 5% MeOH in dichloromethane as the eluent. Yield 0.628 g (78%). White solid. MS (ESI+) for C$_{22}$H$_{26}$N$_2$O$_5$S m/z 375 (M+H)$^+$.

EXAMPLE 187

{[3-Chloro-5-methoxy-1-(phenylsulfonyl)-1H-indol-4-yl]methyl}methylamine trifluoroacetate Tert-butyl [(5-methoxy-1H-indol-4-yl)methyl]methylcarbamate (30.0 mg, 0.103 mmol; Intermediate 102) was dissolved in THF (2 ml) and NCS (25.0 mg, 0.19 mmol) was added. The mixture was stirred for 3 hours and diluted with dichloromethane. The organic phase was washed with water, dried (MgSO$_4$) and evaporated. This chlorinated crude intermediate (33.0 mg, 0.10 mmol) was dissolved in DMF (2 ml) and NaH (10.1 mg, 0.25 mmol) was added. The mixture was stirred for 10 minutes before benzenesulfonyl chloride (35.9 mg, 0.20 mmol) was added. The mixture was stirred for 20 minutes and diluted with dichloromethane and water. The organic phase was separated, dried (MgSO$_4$) and evaporated. The residue was dissolved in dichloromethane (2 ml) and trifluoroacetic acid (0.5 ml) was added. The mixture was stirred for 1 hour and evaporated.

The crude product was purified using preparative HPLC with ACE C8 5 µm (21.2×100 mm) column. Water containing 0.1% TFA and acetonitrile were used as mobile phases at a flow rate of 20 ml/min with gradient times of 11.5 min. Yield: 1.2 mg (2.5%). Dark gum. MS (ESI+) for $C_{17}H_{17}ClN_2O_3S$ 364.0648 m/z 365 (M+H)$^+$.

EXAMPLE 188

{[5-Methoxy-1-(phenylsulfonyl)-1H-indol-4-yl]methyl}amine trifluoroacetate

Ammonium acetate (0.146 g, 1.90 mmol) was added to a solution of 5-methoxy-1-(phenylsulfonyl)-1H-indole-4-carbaldehyde (30 mg, 0.095 mmol; Intermediate 75) in MeOH (3 ml) and stirred for 20 minutes at 50° C. before NaCNBH$_3$ (6 mg, 0.095 mmol) was added. The mixture was stirred for 1 h, quenched with 3 drops of water and evaporated. The crude product was purified by flash chromatography using 1% MeOH to 2.5% MeOH in dichloromethane with 1% NEt$_3$ as the eluent and then purified using preparative HPLC with ACE C8 5 µm (21.2×100 mm) column. Water containing 0.1% TFA and acetonitrile were used as mobile phases at a flow rate of 20 ml/min with gradient times of 11.5 min to give the title compound. Yield: 4.6 mg (15%). White solid. HPLC purity 99%. MS (ESI+) for $C_{16}H_{16}N_2O_3S$ 316.0882 (M−16)$^+$ m/z 300.

Intermediate 103

6-Fluoro-4-(1-hydroxyethyl)-1-(phenylsulfonyl)-1H-indol-5-ol

A solution of crude 6-fluoro-5-hydroxy-1-(phenylsulfonyl)-1H-indole-4-carbaldehyde (86.4 mg, 271 µmol; Intermediate 96) in THF (3 mL) was treated with MeMgBr (774 µL of a 1.4 M solution in Toluene/THF, 4 eq) at rt and stirred for 30 min. After 30 min another 2 eq and after 45 min another 4 eq. of Grignard solution were added and stirring continued for 15 min. The reaction mixture was quenched with sat. NH$_4$Cl, extracted with EtOAc (3×), the combined org. phases washed with brine, dried and the solvent removed in vacuo to give a yellow-brownish solid (95.6 mg). This material was purified by prep. HPLC (15-45% MeCN/50 mM NH$_4$HCO$_3$) to yield the title compound as an yellowish solid (31.8 mg, 11% over 3 steps). MS (ESI+) for $C_{16}H_{14}FNO_4S$ m/z 318 (M-OH)$^+$, 358 (M+Na)$^+$.

Intermediate 104

6-Fluoro-4-(1-iodoethyl)-1-(phenylsulfonyl)-1H-indol-5-ol

To a solution of PPh$_3$ (24.6 mg, 93.9 µmol) in CH$_2$Cl$_2$ (1 mL) at rt was added 12 (23.8 mg, 93.9 µmol) and it was stirred for 5 min, upon which a solution of 6-fluoro-4-(1-hydroxyethyl)-1-(phenylsulfonyl)-1H-indol-5-ol (30.0 mg, 89.5 µmol; Intermediate 103) in CH$_2$Cl$_2$ (1 mL) was added and stirring continued for 1 h at rt. The reaction mixture was concentrated in vacuo and the obtained crude product directly used in the subsequent amination steps.

EXAMPLE 189

6-Fluoro-4-[1-(methylamino)ethyl]-1-(phenylsulfonyl)-1H-indol-5-ol trifluoroacetate A solution of crude 6-fluoro-4-(1-iodoethyl)-1-(phenylsulfonyl)-1H-indol-5-ol (ca. 44.5 mmol; Intermediate 104) in CH$_2$Cl$_2$ (1 mL) was treated with MeNH$_2$ (111 µL of a 8 M solution in EtOH, 888 µmol) at rt for 1.5 h. The reaction mixture was concentrated in vacuo, the obtained residue taken up with MeOH and purified by prep. HPLC (6-36% MeCN, 0.1% TFA) to yield the title compound as a white, waxy solid (7.1 mg, 34% over two steps). MS (ESI+) for $C_{17}H_{17}FN_2O_3S$ m/z 349 (M+H)$^+$.

EXAMPLE 190

4-[1-(Dimethylamino)ethyl]-6-fluoro-1-(phenylsulfonyl)-1H-indol-5-ol

A solution of crude 6-fluoro-4-(1-iodoethyl)-1-(phenylsulfonyl)-1H-indol-5-ol (ca. 44.5 µmol; Intermediate 104) in CH$_2$Cl$_2$ (1 mL) was treated with Me$_2$NH (159 µL of a 5.6 M solution in EtOH, 890 µmol) at rt for 1.5 h. The reaction mixture was concentrated in vacuo, the obtained residue taken up with MeOH and purified by prep. HPLC (25-55% MeCN, 50 mM NH$_4$HCO$_3$) to yield the title compound as an off-white solid (10.0 mg, 62% over two steps). MS (ESI+) for $C_{18}H_{19}FN_2O_3S$ m/z 363 (M+H)$^+$.

Intermediate 105

1-[6-Fluoro-5-methoxy-1-(phenylsulfonyl)-1H-indol-4-yl]ethanol

Crude 6-fluoro-5-hydroxy-1-(phenylsulfonyl)-1H-indole-4-carbaldehyde (85 mg, 266 µmol; Intermediate 96) was suspended in acetone (5 mL) and treated with K$_2$CO$_3$ (73.6 mg, 532 µmol) and MeI (49.7 µL, 798 µmol) and stirred in a sealed tube at 65° C. for 1 h 30 min. The reaction mixture was cooled to rt and diluted with CH$_2$Cl$_2$, washed with H$_2$O, dried (Na$_2$SO$_4$) and the solvent removed in vacuo to give 6-fluoro-5-methoxy-1-(phenylsulfonyl)-1H-indole-4-carbaldehyde as an intense yellow, vitreous solid (72.3 mg), 65% pure according to LC/MS, which was directly used in the subsequent Grignard addition.

A solution of crude 6-fluoro-5-methoxy-1-(phenylsulfonyl)-1H-indole-4-carbaldehyde (72.3 mg, 217 µmol) in THF (2 mL) was treated with MeMgBr (310 µL of a 1.4 M solution in Toluene/THF, 2 eq) at rt and stirred for 20 min (50% conversion). After 20 min another 2 eq Grignard solution were added and stirring continued for 15 min. The reaction mixture was quenched with sat. NH$_4$Cl, extracted with EtOAc (3×), the combined org. phases were washed with brine, dried and the solvent removed in vacuo to give a yellow-brownish foam (81.9 mg), 56% pure according to LC/MS. This material was purified by prep. HPLC (25-55% MeCN/50 mM NH$_4$HCO$_3$) to yield the title compound as an off-white solid (26.5 mg, 9% over 4 steps). MS (ESI+) for $C_{17}H_{16}FNO_4S$ m/z 332 (M-OH)$^+$.

Intermediate 106

6-Fluoro-4-(1-iodoethyl)-5-methoxy-1-(phenylsulfonyl)-1H-indole

To a solution of $PPh_3$ (20.9 mg, 79.6 µmol) in $CH_2Cl_2$ (0.5 mL) at rt was added I2 (20.2 mg, 79.6 µmol) and it was stirred for 5 min, upon which a solution of 1-[6-fluoro-5-methoxy-1-(phenylsulfonyl)-1H-indol-4-yl]ethanol (26.5 mg, 75.8 µmol; Intermediate 105) in $CH_2Cl_2$ (1 mL) was added and stirring continued for 4.5 h at rt. The reaction mixture was concentrated in vacuo and the obtained crude product directly used in the subsequent amination steps.

EXAMPLE 191

{1-[6-Fluoro-5-methoxy-1-(phenylsulfonyl)-1H-indol-4-yl]ethyl}methylamine trifluoroacetate A solution of crude 6-fluoro-4-(1'-iodoethyl)-5-methoxy-1-(phenylsulfonyl)-1H-indole (ca. 37.9 µmol; Intermediate 106) in $CH_2Cl_2$ (1 mL) was treated with $MeNH_2$ (95 µL of a 8 M solution in EtOH, 758 µmol) at rt for 3 h. The reaction mixture was concentrated in vacuo, the obtained residue taken up with MeOH and purified by prep. HPLC (113-43% MeCN, 0.1% TFA) to yield the title compound as yellow-brown solid (9.4 mg, 52% over two steps). MS (ESI+) for $C_{18}H_{19}FN_2O_3S$ m/z 363 $(M+H)^+$.

EXAMPLE 192

{1-[6-Fluoro-5-methoxy-1-(phenylsulfonyl)-1H-indol-4-yl]ethyl}dimethylamine trifluoroacetate A solution of crude 6-fluoro-4-(1-iodoethyl)-5-methoxy-1-(phenylsulfonyl)-1H-indole (ca. 37.9 µmol; Intermediate 106) in $CH_2Cl_2$ (1 mL) was treated with $Me_2NH$ (135 µL of a 5.6 M solution in EtOH, 758 µmol) at rt for 1 h. The reaction mixture was concentrated in vacuo, the obtained residue taken up with MeOH and purified by prep. HPLC (12-42% MeCN, 0.1% TFA) to yield the title compound as white, waxy solid (9.5 mg, 51% over two steps). MS (ESI+) for $C_{19}H_{21}FN_2O_3S$ m/z 377 $(M+H)^+$.

Biological Tests

The ability of a compound according to the invention to bind to a 5-$HT_6$ receptor, and to be pharmaceutically useful, can be determined using in vivo and in vitro assays known in the art.

(a) 5-$HT_6$ Receptor Binding Assay

Binding affinity experiment for the human 5-$HT_6$ receptor are performed in HEK293 cells transfected with 5-$HT_6$ receptor using [$^3$H]-LSD as labeled ligand according to the general method as described by Boess F. G et al. Neuropharmacology 36(4/5) 713-720, 1997.

Materials

Cell Culture

The HEK-293 cell line transfected with the human 5-$HT_6$ receptor was cultured in Dulbeccos Modified Eagles Medium containing 5% dialyzed foetal bovine serum, (Gibco BRL 10106-169), 0.5 mM sodium pyruvate and 400 µg/mL Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England) was in ethanol and stored at –20° C. The compounds were dissolved in 100% DMSO and diluted with binding buffer.

Disposable

Compounds were diluted in Costar 96 well V-bottom polypropylene plates (Corning Inc. Costar, N.Y., USA). Samples were incubated in Packard Optiplate (Packard Instruments B.V., Groningen, The Netherlands). The total amount of added radioligand was measured in Packard 24-well Barex plates (Packard Instruments B.V., Groningen, The Netherlands) in the presence of Microscint™ 20 scintillation fluid (Packard Bioscience, Meriden, Conn., USA).

Buffer

The binding buffer consisted of 20 mM HEPES, 150 mM NaCl, 10 mM $MgCl_2$, and 1 mM, EDTA, pH 7.4.

Methods

Membrane Preparation

Cells were grown to approximately 90% confluence on 24.5×24.5 mm culture dishes. The medium was aspirated, and after rinsing with ice-cold PBS, the cells were scraped off using 25 mL Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20 000×g), suspended in binding buffer, and frozen in aliquots at –70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 mL of binding buffer per 96-well plate The binding reaction was then initiated by adding radioligand and test compounds to the bead-membrane suspension. Following incubation at room temperature, the assay plates were subjected to scintillation counting.

The original SPA method was followed except for that membranes were prepared from HEK293 cells expressing the human 5-$HT_6$ receptor instead of from HeLa cells (Dinh D M, Zaworski P G, Gill G S, Schlachter S K, Lawson C F, Smith M W. Validation of human 5-$HT_6$ receptors expressed in HeLa cell membranes: saturation binding studies, pharmacological profiles of standard CNS agents and SPA development. (The Upjohn Company Technical Report 7295-95-064 1995; 27 December). The specific binding of [$^3$H]-LSD was saturable, while the non-specific binding increased linearly with the concentration of added radioligand. [$^3$H]-LSD bound with high affinity to 5-$HT_6$ receptors. The $K_d$ value was estimated to 2.6±0.2 nM based on four separate experiments.

The total binding at 3 nM of [$^3$H]-LSD, the radioligand concentration used in the competition experiments, was typically 6000 dpm, and the specific binding more than 70%. 5-HT caused a concentration dependent inhibition of [$^3$H]-LSD binding with an over all average Ki value of 236 µM when tested against two different membrane preparations. The inter assay variability over three experiments showed a CV of 10% with an average $K_i$ values of 173 nM (SD 30) and a Hill coefficient of 0.94 (SD 0.09). The intra assay variation was 3% (n=4). All unlabelled ligands displaced the specific binding of [$^3$H]-LSD in a concentration-dependent manner, albeit at different potencies. The rank order of affinity for the 5-$HT_6$ receptor of reference compounds was methiothepin (Ki 2 nM)>mianserin (190 mM)≈5-HT (236 nM)>methysergide (482 nM)>mesulergine (1970 nM).

Protein Determination

Protein concentrations were determined with BioRad Protein Assay (Bradford MM. A rapid and sensitive method for the quantitation of microgram quantities of protein utilizing the principle of protein-dye binding. Anal. Biochem. 1976; 72:248-54). Bovine serum albumin was used as standard.

Scintillation Counting

The radioactivity was determined in a Packard Top-Count™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H]-LSD) were used in saturation experiments. The specific binding was calculated as the difference between total binding and non-specific binding, which was determined as the binding of radioligand in the presence of 5 µM lisuride. $B_{max}$ and the dissociation constant, $K_d$, were determined from the non-linear regression analysis using equation 1. $L_u$ is the unbound concentration of radioligand, and is y is the amount bound.

$$y = \frac{B_{max} \cdot Lu}{Lu + Kd} \quad \text{(equation 1)}$$

Competition Experiments

Total- and non-specific binding of radioligand was defined in eight replicates of each. Samples containing test compound were run in duplicate at 11 concentrations. Incubations were carried out at room temperature for 3 hours. The $IC_{50}$ value, i.e. the concentration of test compound that inhibited 50% of the specific binding of radioligand, was determined with non linear regression analysis and the $K_i$ value was calculated using equation 2 [Cheng Y. C. Biochem. Pharmacol. 22, 3099-3108, 1973].

$$Ki = \frac{IC_{50}}{1 + \frac{L}{K_d}} \quad \text{(equation 2)}$$

L=concentration of radioligand
$K_d$=Affinity of radioligand

Antagonists to the human 5-HT$_6$ receptor were characterized by measuring inhibition of 5-HT induced increase in cAMP in HEK 293 cells expressing the human 5-HT$_6$ receptor (see Boess et al. (1997) Neuropharmacology 36: 713-720). Briefly, HEK293/5-HT$_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% CO$_2$ incubator. The medium was then aspirated and replaced by 0.1mL assay medium (Hanks Balance Salt Solution containing 20 mM HEPES, 1.5 mM isobutylmethylxanthine and 1 mg/mL bovine serum albumin). After addition of test substances, 50 µl dissolved in assay medium, the cells were incubated for 10 min at 37° C. in a 5% CO$_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times EC$_{50}$) evoked increase in cAMP, using the formula $IC_{50,corr}=IC_{50}/(1+[5HT]/EC_{50})$.

The compounds in accordance with the invention have a selective affinity to human 5-HT$_6$ receptors with $K_i$ and $IC_{50,corr}$ values between 0.5 nM and 5 µM or display a % inhibition of [$^3$H]-LSD≧20% at 50 nM and are antagonists, agonists or partial agonists at the human 5-HT$_6$ receptor. The compounds show good selectivity over human 5-HT$_{1a}$, 5-HT$_{1b}$, 5-HT$_{2a}$, 5-HT$_{2b}$, and 5-HT$_{2c}$ receptors.

TABLE 2

Binding affinity ($K_i$) at the h5-HT$_6$ receptor

| Example | $K_i$ (nM) |
|---|---|
| 1 | 1.8 |
| 47 | 3.3 |
| 87 | 0.9 |

TABLE 3

Antagonist potency at the h5-HT$_6$ receptor

| Example | Ki (nM) |
|---|---|
| 1 | 6 |
| 15 | 403 |
| 21 | 96 |
| 42 | 59 |
| 48 | 436 |
| 69 | 96 |
| 77 | 66 |
| 82 | 17 |
| 87 | 0.6 |
| 91 | 63 |
| 95 | 106 |
| 96 | 216 |
| 103 | 19 |

(c) In Vivo Assay of Reduction of Food Intake

For a review on serotonin and food intake, see Blundell, J. E. and Halford, J. C. G. 1998) Serotonin and Appetite Regulation. Implications for the Pharmacological Treatment of Obesity. CNS Drugs 9:473-495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57BL/6JBom; Bomholtsgaard, Denmark) 8-9 weeks with an average body weight of 50 g (obese) and 25 g (lean) are used in all the studies. The animals are housed singly in cages at 23±1° C., 40-60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulphonic acid, polyethylene glycol/methane sulphonic acid, saline. Fresh solutions are made for each study. Doses of 30, 50 and 100 mg kg$^{-1}$day$^{-1}$ are used. The purity of the test compounds is of analytical grade.

The animals are weighed at the start of the study and randomized based on body weight. Alzet osmotic minipumps (Model 2001D; infusion rate 8 µl/h) are used and loaded essentially as recommended by the Alzet technical information manual (Alza Scientific Products, 1997; Theeuwes, F. and Yam, S. I. Ann. Biomed. Eng. 4(4). 343-353, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean ±SD and ±SEM from eight animals per dose group. Statistical evaluation is performed by Kruskal-Wallis one-way ANOVA using the percent basal values. If statistical significance is reached at the level of $p<0.05$, Mann-Whitney U-test for statistical comparison between control and treatment groups is performed.

The invention claimed is:
1. A compound of the formula (I):

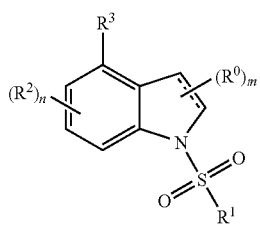

wherein:

----- represents a single bond or a double bond;
n is 0, 1, 2 or 3;
m is 0, 1 or 2;
each $R^0$ is independently selected from:
(a) hydrogen,
(b) halogen,
(c) $C_{1-6}$-alkyl,
(d) $C_{3-7}$-cycloalkyl,
(e) hydroxy-$C_{1-4}$-alkyl,
(f) —$COOR^6$,
(g) —$CONR^5R^5$,
(i) —CN,
(j) aryl, and
(k) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio,
(d) $C_{1-4}$-alkoxy,
(e) —$CF_3$,
(f) —CN, and
(g) hydroxymethyl;
$R^1$ is a group selected from:
(a) $C_{1-6}$-alkyl,
(b) $C_{3-7}$-cycloalkyl,
(c) $C_{3-6}$-alkenyl,
(d) aryl,
(e) aryl-$C_{2-6}$-alkenyl,
(f) aryl-$C_{1-6}$-alkyl,
(g) heteroaryl,
(h) heteroaryl-$C_{2-6}$-alkenyl, and
(i) heteroaryl-$C_{1-6}$-alkyl,
wherein any heteroaryl or aryl residue, alone or as part of another group, is optionally independently substituted in one or more positions with a substituent selected from:
(a) halogen,
(b) $C_{1-6}$-alkyl,
(c) fluoro-$C_{1-6}$-alkyl,
(d) $C_{3-7}$-cycloalkyl,
(e) $C_{2-6}$-alkenyl,
(f) fluoro-$C_{2-6}$-alkenyl,
(g) ethynyl,
(h) hydroxy-$C_{1-4}$-alkyl,
(i) hydroxy,
(j) $C_{1-6}$-alkoxy,
(k) fluoro-$C_{1-6}$-alkoxy,
(l) —$SCF_3$,
(m) —$SCF_2H$,
(n) —$SO_2NR^5R^5$,
(o) —$S(O)_eR^8$, wherein e is 0, 1, 2 or 3,
(p) —CN,
(q) —$NR^5R^5$,
(r) —$NHSO_2R^8$,
(s) —$NR^6COR^8$,
(t) —$NO_2$,
(u) —$CONR^5R^5$,
(v) —$C(=O)R^8$,
(w) —COOH,
(x) $C_{1-6}$-alkoxycarbonyl,
(y) $C_{3-7}$-cycloalkoxy,
(z) phenyl, optionally substituted with one or more of halogen, $C_{1-4}$-alkyl, $C_{1-4}$-alkylthio, $C_{1-4}$-alkoxy, cyano, or trifluoromethyl,
(aa) phenoxy, optionally substituted with one or more of halogen, $C_{1-4}$-alkyl, $C_{1-4}$-alkylthio, $C_{1-4}$-alkoxy, cyano, or trifluoromethyl,
(ab) benzyloxy, optionally substituted with one or more of halogen, $C_{1-4}$-alkyl, $C_{1-4}$-alkylthio, $C_{1-4}$-alkoxy, cyano, or trifluoromethyl,
(ac) benzoyl, optionally substituted with one or more of halogen, $C_{1-4}$-alkyl, $C_{1-4}$-alkylthio, $C_{1-4}$-alkoxy, cyano, or trifluoromethyl; and
(ad) heteroaryl, optionally substituted with trifluoromethyl and methyl;

each $R^2$ is independently selected from:
  (a) hydrogen,
  (b) halogen,
  (c) $C_{1-6}$-alkyl,
  (d) fluoro-$C_{1-6}$-alkyl,
  (e) $C_{3-7}$-cycloalkyl,
  (f) $C_{2-6}$-alkenyl,
  (g) fluoro-$C_{2-6}$-alkenyl,
  (h) ethynyl,
  (i) hydroxy-$C_{1-4}$-alkyl,
  (j) hydroxy,
  (k) $C_{1-6}$-alkoxy,
  (l) fluoro-$C_{1-6}$-alkoxy,
  (m) $C_{3-7}$-cycloalkoxy,
  (n) fluoro-$C_{3-7}$-cycloalkoxy,
  (o) —$SCF_3$,
  (p) —$SCF_2H$,
  (q) —$SO_2NR^5R^5$,
  (r) —$S(O)_eR^8$, wherein e is 0, 1, 2 or 3,
  (s) —CN,
  (t) —$NR^5R^5$,
  (u) —$NHSO_2R^8$,
  (v) —$NR^6COR^8$,
  (w) —$NO_2$,
  (x) —$CONR^5R^5$,
  (y) —$OCONR^5R^5$,
  (z) —$C(=O)R^8$,
  (aa) —COOH,
  (ab) $C_{1-6}$-alkoxycarbonyl, and
  (ac) —$OR^{11}$;
$R^3$ is a group selected from:

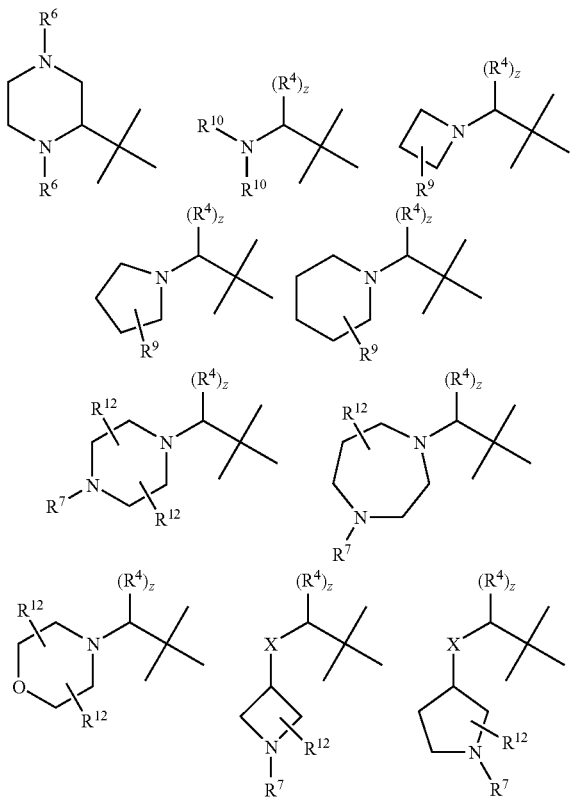
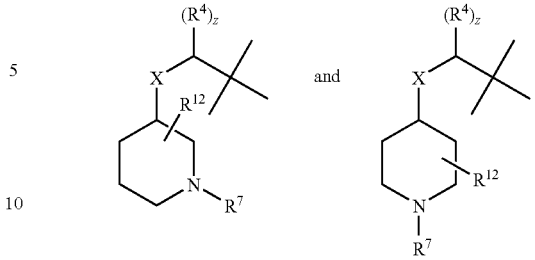

-continued wherein:
  X is selected from O and —$NR^6$;
  z is 2; and
    (i) both of the $R^4$ substituents are hydrogen; or
    (ii) one of the two $R^4$ substituents is hydrogen, and the other of the two $R^4$ substituents is $C_{1-4}$alkyl, fluoro-$C_{1-4}$-alkyl, hydroxy-$C_{1-4}$-alkyl, or cyano; or
    (iii) both of the $R^4$ substituents are $CH_3$;
each $R^5$ is independently selected from:
  (a) hydrogen,
  (b) $C_{1-6}$-alkyl,
  (c) fluoro-$C_{1-6}$-alkyl,
  (d) heteroaryl-$C_{1-2}$-alkyl, and
  (e) $C_{3-7}$-cycloalkyl, or
  two $R^5$ groups together with the nitrogen to which they are attached form a heterocyclic ring;
each $R^6$ is independently selected from:
  (a) hydrogen,
  (b) $C_{1-4}$-alkyl, and
  (b) fluoro-$C_{2-4}$-alkyl, and
  (c) hydroxy-$C_{1-3}$-alkyl;
$R^7$ is selected from:
  (a) hydrogen,
  (b) $C_{1-4}$-alkyl,
  (b) fluoro-$C_{2-4}$-alkyl,
  (c) 2-cyanoethyl,
  (d) hydroxy-$C_{2-4}$-alkyl,
  (e) $C_{3-4}$-alkenyl,
  (f) $C_{3-4}$-alkynyl,
  (g) $C_{3-7}$-cycloalkyl,
  (h) $C_{3-4}$-cycloalkyl-$C_{1-4}$-alkyl, and
  (i) $C_{1-4}$-alkoxy-$C_{2-4}$-alkyl;
each $R^8$ is independently selected from:
  (a) $C_{1-6}$-alkyl,
  (a) fluoro-$C_{1-6}$-alkyl,
  (b) $C_{3-7}$-cycloalkyl,
  (c) aryl, and
  (d) heteroaryl,
  wherein any heteroaryl or aryl residue is optionally independently substituted in one or more positions with a substituent selected from:
    (a) halogen,
    (b) $C_{1-4}$-alkyl,
    (c) $C_{1-4}$-alkylthio,
    (d) $C_{1-4}$-alkoxy,
    (e) —$CF_3$,
    (f) —$OCF_3$,
    (g) —CN, and
    (h) hydroxymethyl;
$R^9$ is selected from:
  (a) hydrogen,
  (b) fluorine, provided that the said fluorine is not attached to a carbon atom adjacent to a ring nitrogen atom, (c) $C_{1-4}$-alkyl,
(d) —$NR^6R^6$, provided that the said —$NR^6R^6$ group is not attached to a carbon atom adjacent to a ring nitrogen atom,
(e) hydroxy, provided that the said hydroxy group is not attached to a carbon atom adjacent to a ring nitrogen atom, and
(f) hydroxy-$C_{1-4}$-alkyl;
each $R^{10}$ is independently selected from:
(a) hydrogen,
(b) hydroxy-$C_{2-4}$-alkyl,
(c) $C_{1-3}$-alkoxy-$C_{2-4}$-alkyl,
(d) cyclopropyl,
(e) cyclobutyl,
(f) benzyl, and
(g) $C_{1-4}$-alkyl, provided that when both $R^{10}$ represent ethyl, then

----- represents a double bond;
$R^{11}$ is selected from:
(a) —$CH_2CN$ and
(b) benzyl; and
each $R^{12}$ is independently selected from:
(a) hydrogen,
(b) $C_{1-4}$-alkyl,
(c) fluoro-$C_{1-4}$-alkyl,
(d) hydroxy-$C_{1-3}$-alkyl, and
(e) $C_{1-6}$-alkoxycarbonyl;
or a pharmaceutically acceptable salt thereof,
with the proviso that the compound of formula (I) is not {[1-(phenylsulfonyl)-1H-indol-4-yl]methyl}amine, N-methyl-1-(phenylsulfonyl)-1H-indole-4-methanamine or N,N-dimethyl-1-[1-(phenylsulfonyl)-1H-indol-4-yl]methanamine.

2. A compound according to claim 1, or a pharmaceutically acceptable salt thereof, wherein:

----- represents a single bond or a double bond;
n is 1;
m is 1;
$R^0$ is a group selected from:
(a) hydrogen,
(b) $C_{1-6}$-alkyl,
(c) $C_{3-7}$-cycloalkyl,
(d) hydroxy-$C_{1-4}$-alkyl,
(e) —$COOR^6$,
(f) —$CONR^5R^{5'}$
(h) —CN,
(i) aryl, and
(j) heteroaryl,
wherein when $R^0$ is or includes a heteroaryl or aryl residue, each heteroaryl or aryl residue can be optionally substituted in one or more positions with a substituent independently selected from:
(a) halogen,
(b) $C_{1-4}$-alkyl,
(c) $C_{1-4}$-alkylthio,
(d) $C_{1-4}$-alkoxy,
(e) —$CF_3$, (f) —CN, and
(g) hydroxymethyl; and
$R^3$ is a group selected from:

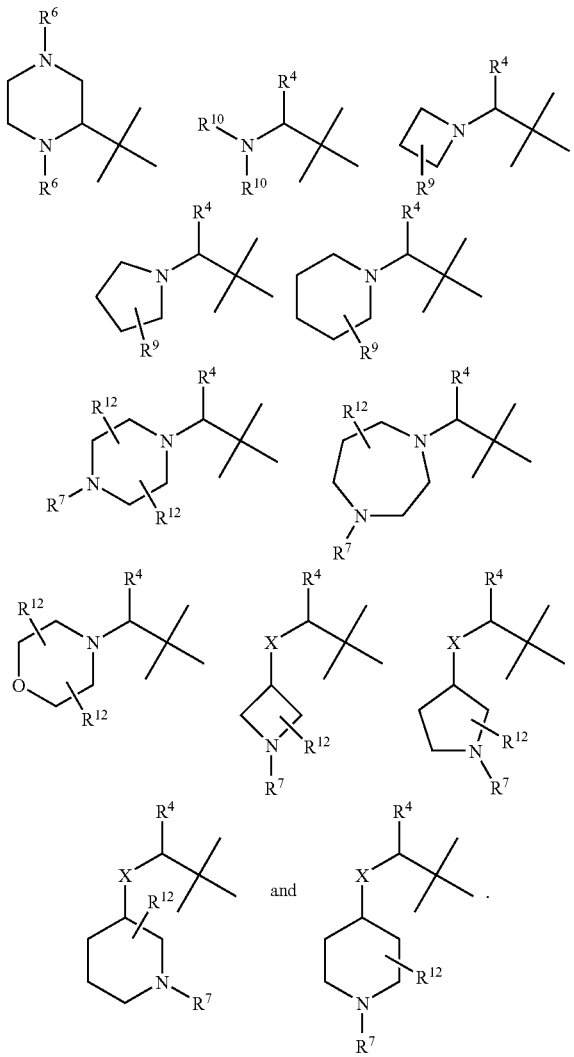

3. A compound according to claim 1, or a pharmaceutically acceptable salt thereof, wherein X is —$NR^6$.

4. A compound according to claim 1, or a pharmaceutically acceptable salt thereof, wherein

----- represents a double bond;
$R^0$ is a group selected from:
(a) hydrogen,
(b) $C_{1-6}$-alkyl,
(c) $C_{3-7}$-cycloalkyl,
(d) hydroxy-$C_{1-4}$-alkyl,
(f) —CN,
(g) aryl, and
(h) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkylthio, (d) $C_{1-4}$-alkoxy,
(e) —$CF_3$,
(f) —CN, and
(g) hydroxymethyl;

$R^1$ is a group selected from:
(a) aryl, and
(b) heteroaryl,
wherein any heteroaryl or aryl residue is optionally independently substituted in one or more positions with a substituent selected from:
(a) halogen,
(b) $C_{1-6}$-alkyl,
(c) fluoro-$C_{1-6}$-alkyl,
(d) $C_{3-7}$-cycloalkyl,
(e) $C_{2-6}$-alkenyl,
(f) fluoro-$C_{2-6}$-alkenyl,
(g) ethynyl,
(h) hydroxy-$C_{1-4}$-alkyl,
(i) hydroxy,
(j) $C_{1-6}$-alkoxy,
(k) fluoro-$C_{1-6}$-alkoxy,
(l) —$SCF_3$,
(m) —$SCF_2H$,
(n) —$SO_2NR^5R^5$,
(o) —$S(O)_eR^8$, wherein e is 0, 1, or 2,
(p) —CN,
(q) —$NR^5R^5$,
(r) —$NHSO_2R^8$,
(s) —$NR^6COR^8$,
(t) —$NO_2$,
(u) —$CONR^5R^5$, and
(v) —$C(=O)R^8$;

$R^2$ is a group selected from:
(a) hydrogen,
(b) halogen,
(c) $C_{1-6}$-alkyl,
(d) $C_{3-7}$-cycloalkyl,
(e) hydroxy-$C_{1-4}$-alkyl,
(f) hydroxy,
(g) $C_{1-6}$-alkoxy,
(h) —$SCF_3$,
(i) —$SCF_2H$,
(j) —$SO_2NR^5R^5$,
(k) —$S(O)_eR^8$, wherein e is 0, 1, 2 or 3,
(l) —CN,
(m) —$NR^5R^5$,
(n) —$NHSO_2R^8$,
(o) —$NR^6COR^8$,
(p) —$CONR^5R^5$,
(q) —$OCONR^5R^5$,
(r) —$C(=O)R^8$, and
(s) —$OR^{11}$;

$R^3$ is a group selected from:

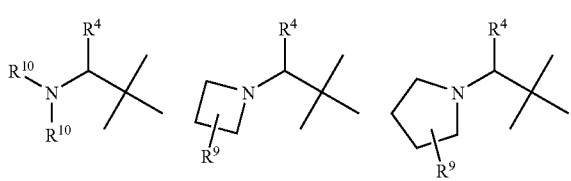

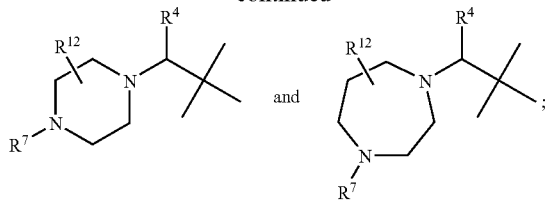

and $R^4$ is a group selected from:
(a) hydrogen,
(b) $C_{1-4}$-alkyl, and
(c) hydroxy-$C_{1-4}$-alkyl;

each $R^5$ is independently selected from:
(a) hydrogen, and
(b) $C_{1-3}$-alkyl,
or two $R^5$ groups together with the nitrogen to which they are attached form a heterocyclic ring;

each $R^6$ is independently selected from:
(a) hydrogen,
(b) methyl, and
(c) ethyl;

$R^7$ is selected from:
(a) hydrogen,
(b) $C_{1-4}$-alkyl,
(c) 2-cyanoethyl,
(d) 2-hydroxyethyl,
(e) $C_{3-4}$-alkenyl,
(f) $C_{3-7}$-cycloalkyl,
(h) $C_{3-4}$-cycloalkyl-$C_{1-4}$-alkyl, and
(i) $C_{1-4}$-alkoxy-$C_{2-4}$-alkyl;

each $R^8$ is independently selected from:
(a) $C_{1-3}$-alkyl,
(b) $C_{3-7}$-cycloalkyl,
(c) aryl, and
(d) heteroaryl,
wherein any heteroaryl or aryl residue is optionally independently substituted in one or more positions with a substituent selected from:
(a) fluorine,
(b) chlorine,
(c) bromine,
(d) $C_{1-4}$-alkyl,
(e) $C_{1-4}$-alkylthio,
(f) $C_{1-4}$-alkoxy,
(g) —$CF_3$,
(h) —CN, and
(i) hydroxymethyl;

$R^9$ is selected from:
(a) hydrogen,
(b) $C_{1-4}$-alkyl,
(c) —$NR^6R^6$, provided that the said —$NR^6R^6$ group is not attached to a carbon atom adjacent to a ring nitrogen atom,
(d) hydroxy, provided that the said hydroxy group is not attached to a carbon atom adjacent to a ring nitrogen atom, and
(e) hydroxymethyl;

each $R^{10}$ is independently selected from:
(a) hydrogen,
(b) hydroxy-$C_{2-4}$-alkyl,
(c) $C_{1-3}$-alkoxy-$C_{2-4}$-alkyl,
(d) $C_{1-4}$-alkyl,
(e) cyclopropyl, and
(f) cyclobutyl;

$R^{11}$ is selected from
(a) —CH$_2$CN, and
(b) benzyl; and
each $R^{12}$ is independently selected from:
(a) hydrogen,
(b) C$_{1-2}$-alkyl, and
(c) hydroxy-C$_{1-2}$-alkyl.

5. A compound according to claim 4, or a pharmaceutically acceptable salt thereof, wherein:
$R^6$ is a group selected from:
(a) hydrogen,
(b) methyl, and
(c) hydroxymethyl;
$R^1$ is a group selected from:
(a) aryl, and
(b) heteroaryl;
wherein any heteroaryl or aryl residue is optionally independently substituted in one or more positions with a substituent selected from:
(a) halogen,
(b) methyl,
(c) trifluoromethyl,
(d) methoxy,
(e) t-butyl, and
(f) —CN;
$R^2$ is a group selected from:
(a) hydrogen,
(b) fluorine,
(c) chlorine,
(d) bromine,
(e) hydroxy,
(f) methoxy,
(g) ethoxy,
(h) iso-propoxy,
(i) —OCON(Me)$_2$, and
(j) —OR$^{11}$;
$R^4$ is hydrogen;
$R^7$ is selected from:
(a) hydrogen,
(b) methyl,
(c) n-propyl,
(d) i-propyl, and
(e) 2-methoxyethyl;
$R^9$ is selected from:
(a) hydrogen,
(b) methyl,
(c) —NH$_2$, provided that the said —NH$_2$ group is not attached to a carbon atom adjacent to a ring nitrogen atom,
(d) hydroxy, provided that the said hydroxy group is not attached to a carbon atom adjacent to a ring nitrogen atom, and
(e) hydroxymethyl;
each $R^{10}$ is independently selected from:
(a) hydrogen,
(b) methyl,
(c) ethyl,
(d) i-propyl,
(e) 2-hydroxyethyl,
(f) 2-methoxyethyl,
(g) cyclopropyl, and
(h) cyclobutyl;
$R^{11}$ is selected from
(a) —CH$_2$CN,
(b) benzyl; and
each $R^{12}$ is independently selected from:
(a) hydrogen,
(b) methyl, and
(c) hydroxymethyl.

6. A compound according to claim 5, or a pharmaceutically acceptable salt thereof, wherein:
$R^1$ is a group selected from:
(a) phenyl,
(b) pyridyl, and
(c) 2-thienyl,
wherein any heteroaryl or aryl residue is optionally independently substituted in one or more positions with a substituent selected from:
(a) chlorine,
(b) fluorine,
(c) methyl,
(d) trifluoromethyl,
(e) methoxy, and
(f) —CN;
$R^2$ is a group selected from:
(a) hydrogen,
(b) fluorine,
(c) hydroxy,
(d) methoxy,
(e) ethoxy,
(f) iso-propoxy,
(g) —OCON(Me)$_2$, and
(h) —OR$^{11}$; and
$R^{11}$ is selected from
(a) —CH$_2$CN,
(b) benzyl.

7. A compound according to claim 1, or a pharmaceutically acceptable salt thereof, wherein:
$R^3$ is a group selected from:

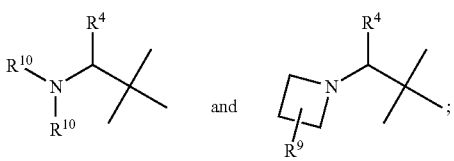

$R^4$ is hydrogen or methyl;
$R^9$ is hydrogen; and
$R^{10}$ is each independently selected from:
(a) hydrogen, and
(b) methyl.

8. A compounds according to claim 1, or a pharmaceutically acceptable salt thereof, wherein:
$R^3$ is

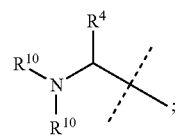

$R^4$ is H or methyl; and
each $R^{10}$ is independently selected from:
(a) hydrogen, and
(b) methyl.

9. A compound according to claim 1, or a pharmaceutically acceptable salt thereof, of formula (Ib):

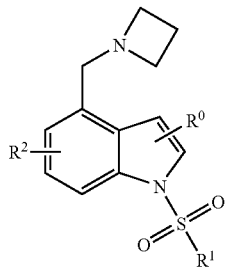

wherein
$R^0$ is a group selected from:
 (a) hydrogen,
 (b) methyl, and
 (c) hydroxymethyl;
$R^1$ is a group selected from:
 (a) phenyl,
 (b) 2-naphthyl,
 (c) 2-thienyl, and
 (d) 6-chloroimidazo[2,1-b][1,3]thiazol-5-yl;
 wherein any heteroaryl or aryl residue is optionally independently substituted in one, two or three positions with a substituent selected from:
 (a) chlorine,
 (b) fluorine,
 (c) bromine,
 (d) methyl,
 (e) trifluoromethyl,
 (f) methoxy, and
 (g) —CN;
$R^2$ is a group selected from:
 (a) hydrogen,
 (b) fluorine,
 (c) hydroxy,
 (d) methoxy,
 (e) ethoxy,
 (f) iso-propoxy,
 (g) —OCON(Me)$_2$, and
 (h) —OR$^{11}$; and
$R^{11}$ is selected from
 (a) —CH$_2$CN, and
 (b) benzyl.

10. A compound according to claim 1, wherein or a pharmaceutically acceptable salt thereof, wherein:

----- represents a single bond;
$R^1$ is a group selected from:
 (a) phenyl,
 (b) pyridyl, and
 (c) 2-thienyl,
 wherein any heteroaryl or aryl residue is optionally independently substituted in one or more positions with a substituent selected from:
 (a) chlorine,
 (b) fluorine,
 (c) methyl,
 (d) trifluoromethyl,
 (e) methoxy, and
 (f) —CN;
$R^2$ is a group selected from:
 (a) hydrogen,
 (b) fluorine,
 (c) hydroxy,
 (d) methoxy,
 (e) ethoxy,
 (f) iso-propoxy,
 (g) —OCON(Me)$_2$, and
 (h) —OR$^{11}$; and
$R^{11}$ is selected from:
 (a) —CH$_2$CN and
 (b) benzyl.

11. A compound according to claim 1, or a pharmaceutically acceptable salt thereof, which is a compound selected from:
1-(Phenylsulfonyl)-4-(piperazin-1-ylmethyl)-1H-indole,
4-(1,4-Diazepan-1-ylmethyl)-1-(phenylsulfonyl)-1H-indole,
1-{[1-(Phenylsulfonyl)-1H-indol-4-yl]methyl}pyrrolidin-3-amine,
1-{[1-(Phenylsulfonyl)-1H-indol-4-yl]methyl}pyrrolidin-3-amine,
1-[(4-Methylphenyl)sulfonyl]-4-(piperazin-1-ylmethyl)-1H-indole,
1-[(4-Methylphenyl)sulfonyl]-4-[(3-methylpiperazin-1-yl)methyl]-1H-indole,
4-(1,4-Diazepan-1-ylmethyl)-1-[(4-methylphenyl)sulfonyl]-1H-indole,
4-[(4-Methyl-1,4-diazepan-1-yl)methyl]-1-[(4-methylphenyl)sulfonyl]-1H-indole,
1-[(4-Methylphenyl)sulfonyl]-4-[(4-methylpiperazin-1-yl)methyl]-1H-indole,
4-[(4-Isopropylpiperazin-1-yl)methyl]-1-[(4-methylphenyl)sulfonyl]-1H-indole,
1-[(4-Methylphenyl)sulfonyl]-4-[(4-propylpiperazin-1-yl)methyl]-1H-indole,
1-[(4-Methylphenyl)sulfonyl]-4-(pyrrolidin-1-ylmethyl)-1H-indole,
1-[(2-Methoxy-5-methylphenyl)sulfonyl]-4-(piperazin-1-ylmethyl)-1H-indole,
1-[(2-Methoxy-5-methylphenyl)sulfonyl]-4-[(3-methylpiperazin-1-yl)methyl]-1H-indole,
N-({1-[(2-Methoxy-5-methylphenyl)sulfonyl]-1H-indol-4-yl}methyl)piperidin-4-amine,
1-Isopropyl-N-({1-[(2-methoxy-5-methylphenyl)sulfonyl]-1H-indol-4-yl}methyl)piperidin-4-amine,
1-[(2-Methoxy-5-methylphenyl)sulfonyl]-4-[(2-methylpyrrolidin-1-yl)methyl]-1 H-indole,
1-[(2-Methoxy-5-methylphenyl)sulfonyl]-4-[(3-methylpiperazin-1-yl)methyl]indoline,
1-[(2-Methoxy-5-methylphenyl)sulfonyl]-4-[(4-methylpiperazin-1-yl)methyl]indoline,
1-[(2-Methoxy-5-methylphenyl)sulfonyl]-4-(pyrrolidin-1-ylmethyl)indoline,
({1-[(2-Methoxy-5-methylphenyl)sulfonyl]-2,3-dihydro-1H-indol-4-yl}methyl)dimethylamine,
1-[(4-Fluorophenyl)sulfonyl]-4-[(3-methylpiperazin-1-yl)methyl]-1H-indole,
4-(1,4-Diazepan-1-ylmethyl)-1-[(4-fluorophenyl)sulfonyl]-1H-indole,
1-[(4-Fluorophenyl)sulfonyl]-4-(pyrrolidin-1-ylmethyl)-1H-indole,
({1-[(4-Fluorophenyl)sulfonyl]-1H-indol-4-yl}methyl)dimethylamine, 1-[(4-Fluorophenyl)sulfonyl]-4-(piperazin-1-ylmethyl)-1H-indole,
1-[(2-Methylphenyl)sulfonyl]-4-(piperazin-1-ylmethyl)-1H-indole,
1-[(2-Methylphenyl)sulfonyl]-4-[(4-methylpiperazin-1-yl)methyl]-1H-indole,
1-({1-[(2-Methylphenyl)sulfonyl]-1H-indol-4-yl}methyl)pyrrolidin-3-ol,
1-[(2-Methylphenyl)sulfonyl]-4-(pyrrolidin-1-ylmethyl)-1H-indole,
2-[Methyl({1-[(2-methylphenyl)sulfonyl]-1H-indol-4-yl}methyl)amino]ethanol,
N,N-Dimethyl-1-{1-[(2-methylphenyl)sulfonyl]-1H-indol-4-yl}methanamine,
4-(piperazin-1-ylmethyl)-1-{[3-(trifluoromethyl)phenyl]sulfonyl}-1H-indole,
{(2R)-1-[(1-{[3-(Trifluoromethyl)phenyl]sulfonyl}-1H-indol-4-yl)methyl]pyrrolidin-2-yl}methanol,
4-(Pyrrolidin-1-ylmethyl)-1-{[3-(trifluoromethyl)phenyl]sulfonyl}-1H-indole,
2-{Methyl[(1-{[3-(trifluoromethyl)phenyl]sulfonyl}-1H-indol-4-yl)methyl]amino}ethanol,
N,N-Dimethyl-1-(1-{[3-(trifluoromethyl)phenyl]sulfonyl}-1H-indol-4-yl)methanamine,
4-(piperazin-1-ylmethyl)-1-(2-thienylsulfonyl)-1H-indole,
N-Ethyl-N-{[1-(2-thienylsulfonyl)-1H-indol-4-yl]methyl}ethanamine,
4-(Pyrrolidin-1-ylmethyl)-1-(2-thienylsulfonyl)-1H-indole,
4-[(4-Propylpiperazin-1-yl)methyl]-1-(2-thienylsulfonyl)-1H-indole,
N,N-Dimethyl-1-[1-(2-thienylsulfonyl)-1H-indol-4-yl]methanamine,
4-(piperazin-1-ylmethyl)-1-(pyridin-3-ylsulfonyl)-1H-indole,
N,N-Dimethyl-1-[1-(pyridin-3-ylsulfonyl)-1H-indol-4-yl]methanamine,
1-(Pyridin-3-ylsulfonyl)-4-(pyrrolidin-1-ylmethyl)-1H-indole,
1-(Phenylsulfonyl)-4-(pyrrolidin-1-ylmethyl)-1H-indole,
N,N-Dimethyl-1-[1-(phenylsulfonyl)-1H-indol-4-yl]methanamine,
3-Methyl-1-(phenylsulfonyl)-4-(piperazin-1-ylmethyl)-1H-indole,
3-Methyl-4-[(4-methylpiperazin-1-yl)methyl]-1-(phenylsulfonyl)-1H-indole,
3-Methyl-1-(phenylsulfonyl)-4-(pyrrolidin-1-ylmethyl)-1H-indole,
N,N-Dimethyl-1-[3-methyl-1-(phenylsulfonyl)-1H-indol-4-yl]methanamine,
6-Methoxy-1-(phenylsulfonyl)-4-(piperazin-1-ylmethyl)-1H-indole,
{[6-Methoxy-1-(phenylsulfonyl)-1H-indol-4-yl]methyl}dimethylamine,
6-Methoxy-4-{[(3R)-3-methylpiperazin-1-yl]methyl}-1-(phenylsulfonyl)-1H-indole,
6-Methoxy-4-{[(3S)-3-methylpiperazin-1-yl]methyl}-1-(phenylsulfonyl)-1H-indole,
6-Methoxy-4-[(4-methylpiperazin-1-yl)methyl]-1-(phenylsulfonyl)-1H-indole,
4-(1,4-Diazepan-1-ylmethyl)-6-methoxy-1-(phenylsulfonyl)-1H-indole,
6-Methoxy-1-(phenylsulfonyl)-4-(pyrrolidin-1-ylmethyl)-1H-indole,
2-[{[6-Methoxy-1-(phenylsulfonyl)-1H-indol-4-yl]methyl}(methyl)amino]ethanol,
6-Fluoro-1-(phenylsulfonyl)-4-(piperazin-1-ylmethyl)-1H-indole,
4-(1,4-Diazepan-1-ylmethyl)-6-fluoro-1-(phenylsulfonyl)-1H-indole,
6-Fluoro-4-{[(3S)-3-methylpiperazin-1-yl]methyl}-1-(phenylsulfonyl)-1H-indole,
6-Fluoro-4-{[(3R)-3-methylpiperazin-1-yl]methyl}-1-(phenylsulfonyl)-1H-indole,
6-Fluoro-1-(phenylsulfonyl)-4-(pyrrolidin-1-ylmethyl)-1H-indole,
2-[{[6-Fluoro-1-(phenylsulfonyl)-1H-indol-4-yl]methyl}(methyl)amino]ethanol,
{[6-Fluoro-1-(phenylsulfonyl)-1H-indol-4-yl]methyl}dimethylamine,
6-Fluoro-4-[(4-methylpiperazin-1-yl)methyl]-1-(phenylsulfonyl)-1H-indole,
1-(Phenylsulfonyl)-4-(pyrrolidin-1-ylmethyl)-1H-indol-6-yl dimethylcarbamate,
4-(1,4-Diazepan-1-ylmethyl)-1-(phenylsulfonyl)-1H-indol-6-ol,
1-[(4-Fluorophenyl)sulfonyl]-6-methoxy-4-(piperazin-1-ylmethyl)-1H-indole,
6-Methoxy-4-(piperazin-1-ylmethyl)-1-{[3-(trifluoromethyl)phenyl]sulfonyl}-1H-indole,
1-[(2-Chlorophenyl)sulfonyl]-6-methoxy-4-(piperazin-1-ylmethyl)-1H-indole,
1-[(3-Chloro-2-methylphenyl)sulfonyl]-6-methoxy-4-(piperazin-1-ylmethyl)-1H-indole,
1-[(2,5-Dimethoxyphenyl)sulfonyl]-6-methoxy-4-(piperazin-1-ylmethyl)-1H-indole,
2-{[6-Methoxy-4-(piperazin-1-ylmethyl)-1H-indol-1-yl]sulfonyl}benzonitrile,
({1-[(4-Fluorophenyl)sulfonyl]-1H-indol-4-yl}methyl)amine,
N-({1-[(4-Fluorophenyl)sulfonyl]-1H-indol-4-yl}methyl)ethanamine,
7-Methoxy-1-(phenylsulfonyl)-4-(piperazin-1-ylmethyl)-1H-indole,
2-Methyl-1-(phenylsulfonyl)-4-(piperazin-1-ylmethyl)-1H-indole,
Methyl 4-{[1-(phenylsulfonyl)-1H-indol-4-yl]methyl}piperazine-2-carboxylate,
(4-{[1-(Phenylsulfonyl)-1H-indol-4-yl]methyl}piperazin-2-yl)methanol,
(2-Methoxyethyl){[1-(phenylsulfonyl)-1H-indol-4-yl]methyl}amine,
N-{[1-(Phenylsulfonyl)-1H-indol-4-yl]methyl}propan-2-amine,
4-{[4-(2-Methoxyethyl)piperazin-1-yl]methyl}-1-(phenylsulfonyl)-1H-indole,
((2R)-1-{[1-(Phenylsulfonyl)-1H-indol-4-yl]methyl}pyrrolidin-2-yl)methanol,
4-(Azetidin-1-ylmethyl)-1-(phenylsulfonyl)-1H-indole,
Ethyl 5-methoxy-1-(phenylsulfonyl)-4-(piperazin-1-ylmethyl)-1H-indole-2-carboxylate,
5-Methoxy-N-methyl-1-(phenylsulfonyl)-4-(piperazin-1-ylmethyl)-1H-indole-2-carboxamide,
N-Ethyl-5-methoxy-1-(phenylsulfonyl)-4-(piperazin-1-ylmethyl)-1H-indole-2-carboxamide,
5-Ethoxy-1-(phenylsulfonyl)-4-(piperazin-1-ylmethyl)-N-(2-thienylmethyl)-1H-indole-2-carboxamide,
4-(Azetidin-1-ylmethyl)-6-methoxy-1-(phenylsulfonyl)-1H-indole, 1-(Phenylsulfonyl)-4-(piperazin-1-ylmethyl)-1H-indol-5-ol,
1-(Phenylsulfonyl)-4-piperazin-2-yl-1H-indole,
4-(1,4-Dimethylpiperazin-2-yl)-1-(phenylsulfonyl)-1H-indole,

[7-Methoxy-1-(phenylsulfonyl)-1H-indol-4-yl](piperazin-1-yl)acetonitrile,
4-(Azetidin-1-ylmethyl)-7-methoxy-1-(phenylsulfonyl)-1H-indole,
{[1-(Phenylsulfonyl)-4-(piperazin-1-ylmethyl)-1H-indol-5-yl]oxy}acetonitrile,
5-Isopropoxy-1-(phenylsulfonyl)-4-(piperazin-1-ylmethyl)-1H-indole,
5-(Benzyloxy)-1-(phenylsulfonyl)-4-(piperazin-1-ylmethyl)-1H-indole,
4-{[(2-Hydroxyethyl)(methyl)amino]methyl}-1-(phenylsulfonyl)-1H-indol-5-ol,
4-[(3-Hydroxypyrrolidin-1-yl)methyl]-1-(phenylsulfonyl)-1H-indol-5-ol,
[1-(Phenylsulfonyl)-4-(piperazin-1-ylmethyl)-6-(trifluoromethyl)-1H-indol-2-yl]methanol,
5-Methoxy-1-(phenylsulfonyl)-4-(piperazin-1-ylmethyl)-1H-indole,
5-Ethoxy-1-(phenylsulfonyl)-4-(piperazin-1-ylmethyl)-1H-indole,
1-Phenyl-N-{[1-(phenylsulfonyl)-1H-indol-4-yl]methyl}methanamine,
N-{[5-Methoxy-1-(phenylsulfonyl)-1H-indol-4-yl]methyl}cyclopropanamine,
{[5-Methoxy-1-(phenylsulfonyl)-1H-indol-4-yl]methyl}dimethylamine,
N-{[5-Methoxy-1-(phenylsulfonyl)-1H-indol-4-yl]methyl}cyclobutanamine,
N-{[5-Methoxy-1-(phenylsulfonyl)-1H-indol-4-yl]methyl}-N-methylcyclobutanamine,
1-{[1-(Phenylsulfonyl)-1H-indol-4-yl]methyl}azetidin-3-ol,
4-(Azetidin-1-ylmethyl)-5-methoxy-1-(phenylsulfonyl)-1H-indole,
4-{[4-(Azetidin-1-ylmethyl)-1H-indol-1-yl]sulfonyl}benzonitrile,
2-((2S)-1-{[1-(Phenylsulfonyl)-1H-indol-4-yl]methyl}azetidin-2-yl)propan-2-ol,
4-(Azetidin-1-ylmethyl)-2-methyl-1-(phenylsulfonyl)-1H-indole,
4-(Azetidin-1-ylmethyl)-1-[(2-chlorophenyl)sulfonyl]-1H-indole,
4-(Azetidin-1-ylmethyl)-1-[(5-chloro-2-thienyl)sulfonyl]-1H-indole,
4-(Azetidin-1-ylmethyl)-1-(2-naphthylsulfonyl)-1H-indole,
4-(Azetidin-1-ylmethyl)-1-[(2-methoxy-5-methylphenyl)sulfonyl]-1H-indole,
4-(Azetidin-1-ylmethyl)-1-[(6-chloroimidazo[2,1-b][1,3]thiazol-5-yl)sulfonyl]-1H-indole,
4-(Azetidin-1-ylmethyl)-1-[(4-tert-butylphenyl)sulfonyl]-1H-indole,
4-(Azetidin-1-ylmethyl)-1-[(2,6-difluorophenyl)sulfonyl]-1H-indole,
4-(Azetidin-1-ylmethyl)-1-{[2-(trifluoromethyl)phenyl]sulfonyl}-1H-indole,
3-{[4-(Azetidin-1-ylmethyl)-1H-indol-1-yl]sulfonyl}benzonitrile,
4-(Azetidin-1-ylmethyl)-1-{[4-bromo-2-(trifluoromethyl)phenyl]sulfonyl}-1H-indole,
4-(Azetidin-1-ylmethyl)-1-(2-thienylsulfonyl)-1H-indole,
4-(Azetidin-1-ylmethyl)-1-[(2,5-difluorophenyl)sulfonyl]-1H-indole,
[(5-Methoxy-1-{[3-(trifluoromethyl)phenyl]sulfonyl}-1H-indol-4-yl)methyl]dimethylamine,
4-(Azetidin-1-ylmethyl)-7-(benzyloxy)-1-(methylsulfonyl)-1H-indole,
({1-[(6-Chloroimidazo[2,1-b][1,3]thiazol-5-yl)sulfonyl]-5-methoxy-1H-indol-4-yl}methyl)dimethylamine,
4-[(Dimethylamino)methyl]-1-(phenylsulfonyl)-1H-indol-5-ol,
{[5-Ethoxy-1-(phenylsulfonyl)-1H-indol-4-yl]methyl}dimethylamine,
({5-Ethoxy-1-[(2-methoxy-5-methylphenyl)sulfonyl]-1H-indol-4-yl}methyl)dimethylamine,
{[5-Ethoxy-1-(1-naphthylsulfonyl)-1H-indol-4-yl]methyl}dimethylamine,
{[5-Ethoxy-1-(2-naphthylsulfonyl)-1H-indol-4-yl]methyl}dimethylamine,
({1-[(2-Chlorophenyl)sulfonyl]-5-ethoxy-1H-indol-4-yl}methyl)dimethylamine,
({1-[(3-Chloro-2-methylphenyl)sulfonyl]-5-ethoxy-1H-indol-4-yl}methyl)dimethylamine,
({5-Methoxy-1-[(2-methoxy-5-methylphenyl)sulfonyl]-1H-indol-4-yl}methyl)dimethylamine,
({1-[(2,3-Dichlorophenyl)sulfonyl]-5-methoxy-1H-indol-4-yl}methyl)dimethylamine,
{[5-Ethoxy-1-(quinolin-8-ylsulfonyl)-1H-indol-4-yl]methyl}dimethylamine,
{[5-Ethoxy-1-({5-[1-methyl-3-(trifluoromethyl)-1H-pyrazol-5-yl]-2-thienyl}sulfonyl)-1H-indol-4-yl]methyl}dimethylamine,
({1-[(2,5-Dichlorophenyl)sulfonyl]-5-ethoxy-1H-indol-4-yl}methyl)dimethylamine,
({5-Ethoxy-1-[(2,4,6-trichlorophenyl)sulfonyl]-1H-indol-4-yl}methyl)dimethylamine,
1-[5-Methoxy-1-(phenylsulfonyl)-1H-indol-4-yl]-N-methylmethanamine,
({1-[(2-Methoxy-5-methylphenyl)sulfonyl]-1H-indol-4-yl}methyl)methylamine,
4-[(Dimethylamino)methyl]-6-fluoro-1-(phenylsulfonyl)-1H-indol-5-ol,
1-[6-Fluoro-5-methoxy-1-(phenylsulfonyl)-1H-indol-4-yl]-N,N-dimethylmethanamine,
6-Fluoro-1-(phenylsulfonyl)-4-(pyrrolidin-1-ylmethyl)-1H-indol-5-ol,
6-Fluoro-5-methoxy-1-(phenylsulfonyl)-4-(pyrrolidin-1-ylmethyl)-1H-indole,
4-(Azetidin-1-ylmethyl)-6-fluoro-1-(phenylsulfonyl)-1H-indol-5-ol,
4-(Azetidin-1-ylmethyl)-6-fluoro-5-methoxy-1-(phenylsulfonyl)-1H-indole,
4-{([Ethyl(methyl)amino]methyl}-6-fluoro-1-(phenylsulfonyl)-1H-indol-5-ol,
N-{[6-Fluoro-5-methoxy-1-(phenylsulfonyl)-1H-indol-4-yl]methyl}-N-methylethanamine,
6-Fluoro-4-[(methylamino)methyl]-1-(phenylsulfonyl)-1H-indol-5-ol,
{[6-Fluoro-5-methoxy-1-(phenylsulfonyl)-1H-indol-4-yl]methyl}methylamine,
1-{5-Methoxy-1-[(4-methoxyphenyl)sulfonyl]-1H-indol-4-yl}-N,N-dimethylmethanamine,
1-{1-[(3-Chlorophenyl)sulfonyl]-5-methoxy-1H-indol-4-yl}-N,N-dimethylmethanamine,
1-{1-[(2,5-Difluorophenyl)sulfonyl]-5-methoxy-1H-indol-4-yl}-N,N-dimethylmethanamine,
1-(1-{[4-Fluoro-3-(trifluoromethyl)phenyl]sulfonyl}-5-methoxy-1H-indol-4-yl)-N,N-dimethylmethanamine,
1-[5-Methoxy-1-(quinolin-8-ylsulfonyl)-1H-indol-4-yl]-N,N-dimethylmethanamine,
1-{1-[(2-Chlorophenyl)sulfonyl]-5-methoxy-1H-indol-4-yl}-N,N-dimethylmethanamine,
1-{1-[(2-Chloro-6-methylphenyl)sulfonyl]-5-methoxy-1H-indol-4-yl}-N,N-dimethylmethanamine,
1-{1-[(3-Chloro-4-fluorophenyl)sulfonyl]-5-methoxy-1H-indol-4-yl}-N,N-dimethylmethanamine,
1-{5-Methoxy-1-[(2-methylphenyl)sulfonyl]-1H-indol-4-yl}-N,N-dimethylmethanamine, 2-({4-[(Dimethylamino)methyl]-5-methoxy-1H-indol-1-yl}sulfonyl)benzonitrile,
1-{1-[(2,6-Difluorophenyl)sulfonyl]-5-methoxy-1H-indol-4-yl}-N,N-dimethylmethanamine,
1-{1-[(1,2-Dimethyl-1H-imidazol-4-yl)sulfonyl]-5-methoxy-1H-indol-4-yl}-N,N-dimethylmethanamine,
1-{5-Methoxy-1-[(5-methyl-1-benzothien-2-yl)sulfonyl]-1H-indol-4-yl}-N,N-dimethylmethanamine,
1-{5-Methoxy-1-[(2-methoxy-4-methylphenyl)sulfonyl]-1H-indol-4-yl}-N,N-dimethylmethanamine,
1-{1-[(2,4-Dichlorophenyl)sulfonyl]-5-methoxy-1H-indol-4-yl}-N,N-dimethylmethanamine,
1-{1-[(5-Bromo-2-methoxyphenyl)sulfonyl]-5-methoxy-1H-indol-4-yl}-N,N-dimethylmethanamine,
1-[1-(2,1,3-Benzothiadiazol-4-ylsulfonyl)-5-methoxy-1H-indol-4-yl]-N,N-dimethylmethanamine,
1-[1-(3,4-Dihydro-2H-1,5-benzodioxepin-7-ylsulfonyl)-5-methoxy-1H-indol-4-yl]-N,N-dimethylmethanamine,
1-{1-[(2,5-Dimethoxyphenyl)sulfonyl]-5-methoxy-1H-indol-4-yl}-N,N-dimethylmethanamine,
1-(5-Methoxy-1-{[2-(trifluoromethyl)phenyl]sulfonyl}-1H-indol-4-yl)-N,N-dimethylmethanamine,
1-(5-Methoxy-1-{[4-(trifluoromethoxy)phenyl]sulfonyl}-1H-indol-4-yl)-N,N-dimethylmethanamine,
3-({4-[(Dimethylamino)methyl]-5-methoxy-1H-indol-1-yl}sulfonyl)benzonitrile,
1-[5-Methoxy-1-(pyridin-3-ylsulfonyl)-1H-indol-4-yl]-N,N-dimethylmethanamine,
Methyl {1-[1-(phenylsulfonyl)-1H-indol-4-yl]ethyl}amine,
{1-[1-(Phenylsulfonyl)-1H-indol-4-yl]ethyl}amine,
Dimethyl {1-[1-(phenylsulfonyl)-1H-indol-4-yl]ethyl}amine,
4-(Azetidin-1-ylmethyl)-2,3-dichloro-5-methoxy-1-(phenylsulfonyl)-1H-indole,
4-[(dimethylamino)methyl]-6-methoxy-1-(phenylsulfonyl)-1H-indol-5-ol,
1-[5,6-dimethoxy-1-(phenylsulfonyl)-1H-indol-4-yl]-N,N-dimethylmethanamine,
{[3-chloro-5-methoxy-1-(phenylsulfonyl)-1H-indol-4-yl]methyl}dimethylamine,
{[3-Chloro-5-methoxy-1-(phenylsulfonyl)-1H-indol-4-yl]methyl}methylamine,
{[5-Methoxy-1-(phenylsulfonyl)-1H-indol-4-yl]methyl}amine,
6-Fluoro-4-[1-(methylamino)ethyl]-1-(phenylsulfonyl)-1H-indol-5-ol,
4-[1-(Dimethylamino)ethyl]-6-fluoro-1-(phenylsulfonyl)-1H-indol-5-ol,
{1-[6-Fluoro-5-methoxy-1-(phenylsulfonyl)-1H-indol-4-yl]ethyl}methylamine, and
{1-[6-Fluoro-5-methoxy-1-(phenylsulfonyl)-1H-indol-4-yl]ethyl}dimethylamine,
or a pharmaceutically acceptable salt thereof.

12. A pharmaceutical composition comprising a compound according to claim 1 or a pharmaceutically acceptable salt thereof, in combination with a pharmaceutically acceptable diluent or carrier.

13. A method for reducing body weight or reducing body weight gain, the method comprising administering to a subject in need thereof an effective amount of a compound according to claim 1 or a pharmaceutically acceptable salt thereof.

14. A method for inhibititing 5-HT$_6$ receptor activity, comprising administering to a subject in need of such treatment an effective amount of a compound according to claim 1 or a pharmaceutically acceptable salt thereof.

15. A cosmetic composition comprising a compound according to claim 1 or a pharmaceutically acceptable salt thereof as an active ingredient, in combination with a cosmetically acceptable diluent or carrier.

16. A method for preparing a compound according to claim 1, comprising:
 a) reacting 4-methyl-1-R$^1$-substituted sulfonyl-1H-indole with N-bromosuccinimide;
 b) reacting the product from step a) under conditions sufficients to introduce a group selected from

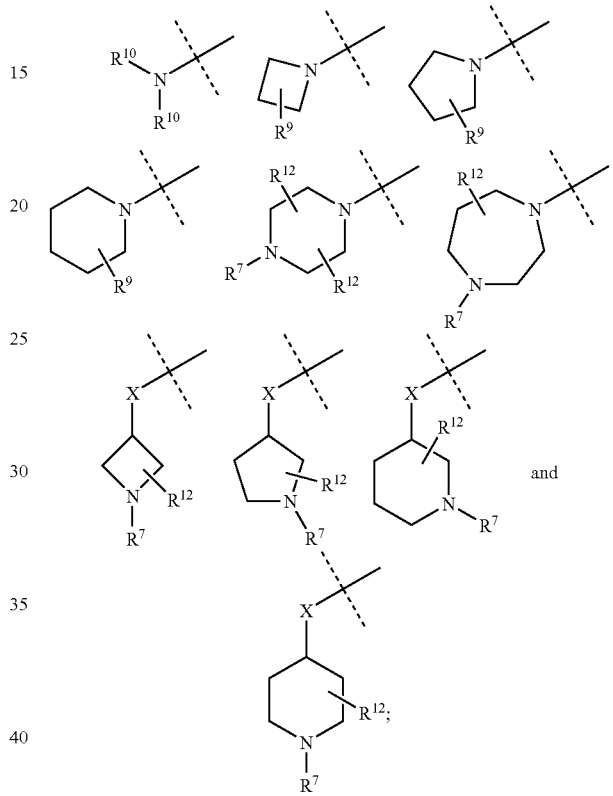

wherein the groups R$^1$, R$^7$, R$^9$, R$^{10}$, and R$^{12}$ and X are as defined for formula (I), or a salt or a protected derivative thereof; and optionally thereafter forming a pharmaceutically acceptable salt of the compound of formula (I).

17. A method for preparing the compound of claim 1, wherein

----- represents a double bond, comprising:
 aa) reacting a 4-bromoindole derivative of formula (III),

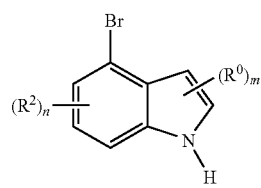

(III)

wherein m, n, R$^0$, R$^1$ and R$^2$ are as defined in claim 1, with a sulfonyl chloride of the formula R¹SO₂Cl wherein R¹ is as defined in claim 1, to give a compound of formula (IV):

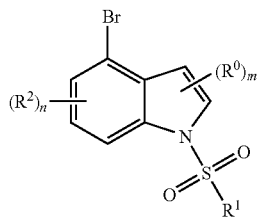

(IV)

wherein m, n, R⁰, R¹ and R² are as defined in claim 1;

bb) reacting the compound of formula (IV) with tributyl (vinyl)stannane in the presence of a palladium complex as a catalyst, to give a compound of formula (V):

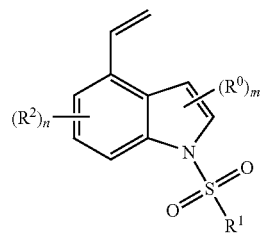

(V)

wherein m, n, R⁰, R¹ and R² are as defined in claim 1;

cc) reacting the compound of formula (V) with osmium tetroxide (OsO₄) and sodium periodate, to produce the aldehyde derivative of formula (VI):

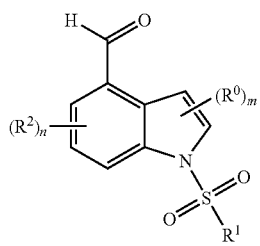

(VI)

wherein m, n, R⁰, R¹ and R² are as defined in claim 1; and dd) reacting the compound of formula (VI) with an appropriate amine selected from:

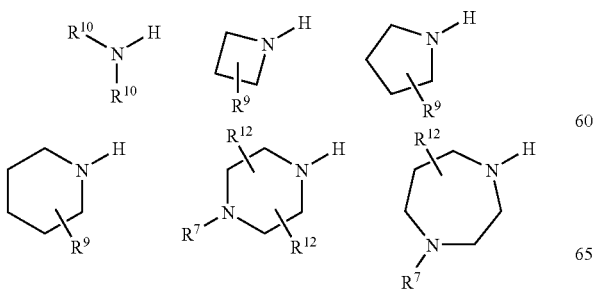

-continued

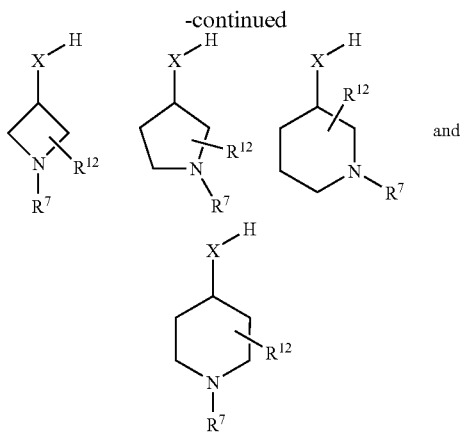

and wherein X is NR⁶, and R⁶, R⁷, R⁹, R¹⁰, and R¹² are as defined in claim 1, or a salt or a protected derivative thereof, in the presence of a suitable reducing agent, to produce a compound of formula (I) as defined in claim 1 wherein

- - - - - represents a double bond; and optionally thereafter forming a pharmaceutically acceptable salt of the compound of formula (I).

18. A method for preparing the compound of claim 1, wherein

- - - - - represents a single bond, comprising:

aaa) reacting a compound of formula (IV):

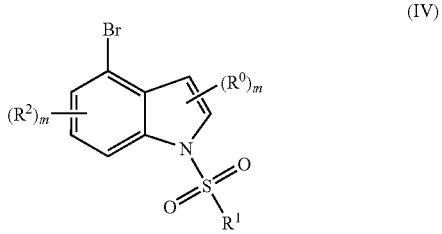

(IV)

wherein m, n, R⁰, R¹ and R² are as defined in claim 1;

with a reducing agent to give a compound of formula (VII):

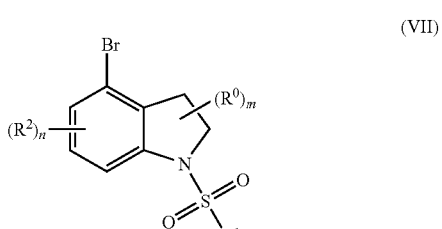

(VII)

wherein m, n, R⁰, R¹ and R² are as defined in claim 1;

bbb) reacting a compound of formula (VII) with tributyl (vinyl)stannane in the presence of a palladium complex as a catalyst, to give a compound of formula (XII):

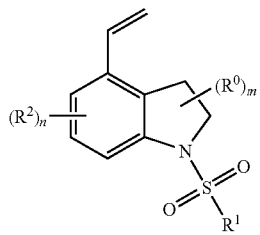

(XII)

wherein m, n, $R^0$, $R^1$ and $R^2$ are as defined in claim 1;

ccc) reacting the compound of formula (V) with osmium tetroxide ($OsO_4$) and sodium periodate, to produce the aldehyde derivative of formula (XIII):

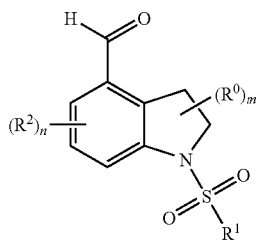

(XIII)

wherein m, n, $R^0$, $R^1$ and $R^2$ are as defined in claim 1; and ddd) reacting the compound of formula (XIII) with an appropriate amine selected from:

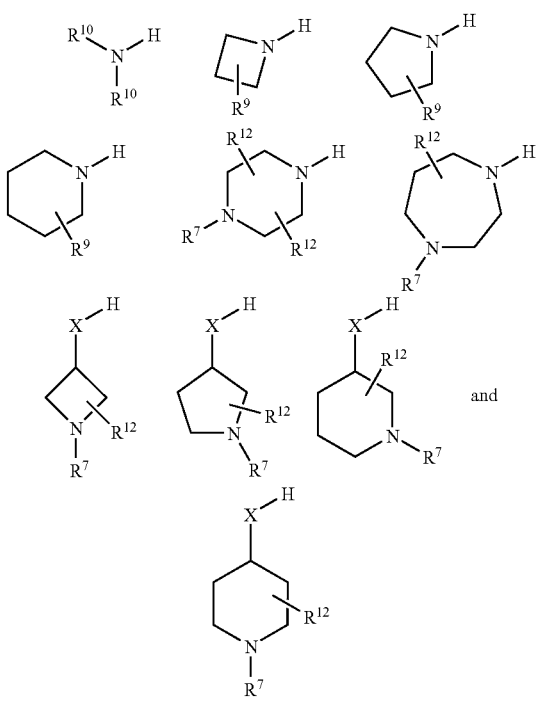

and wherein X is $NR^6$, and $R^6$, $R^7$, $R^{10}$, and $R^{12}$ are as defined in claim 1, or a salt or a protected derivative thereof,
in the presence of a suitable reducing agent,
to produce a compound of formula (I) as defined in claim 1 wherein

----- represents a single bond; and optionally thereafter forming a pharmaceutically acceptable salt of the compound of formula (I).

19. A compound according to claim 2, or a pharmaceutically acceptable salt thereof, wherein:
  $R^0$ is a group selected from:
    (b) $C_{1-6}$-alkyl,
    (c) $C_{3-7}$-cycloalkyl,
    (d) hydroxy-$C_{1-4}$-alkyl,
    (e) —$COOR^6$,
    (f) —$CONR^5R^5$,
    (h) —CN,
    (i) aryl, and
    (j) heteroaryl,
    wherein when $R^0$ is or includes a heteroaryl or aryl residue, each heteroaryl or aryl residue can be optionally substituted in one or more positions with a substituent independently selected from:
      (a) halogen,
      (b) $C_{1-4}$-alkyl,
      (c) $C_{1-4}$-alkylthio,
      (d) $C_{1-4}$-alkoxy,
      (e) —$CF_3$,
      (f) —CN, and
      (g) hydroxymethyl.

20. A compound according to claim 2, or a pharmaceutically acceptable salt thereof, wherein
  each $R^2$ is independently selected from:
    (b) halogen,
    (c) $C_{1-6}$-alkyl,
    (d) fluoro-$C_{1-6}$-alkyl,
    (e) $C_{3-7}$-cycloalkyl,
    (f) $C_{2-6}$-alkenyl,
    (g) fluoro-$C_{2-6}$-alkenyl,
    (h) ethynyl,
    (i) hydroxy-$C_{1-4}$-alkyl,
    (j) hydroxy,
    (k) $C_{1-6}$-alkoxy,
    (l) fluoro-$C_{1-6}$-alkoxy,
    (m) $C_{3-7}$-cycloalkoxy,
    (n) fluoro-$C_{3-7}$-cycloalkoxy,
    (o) —$SCF_3$,
    (p) —$SCF_2H$,
    (q) —$SO_2NR^5R^5$,
    (r) —$S(O)_eR^8$, wherein e is 0, 1, 2 or 3,
    (s) —CN,
    (t) —$NR^5R^5$,
    (u) —$NHSO_2R^8$,
    (v) —$NR^6COR^8$,
    (w) —$NO_2$,
    (x) —$CONR^5R^5$,
    (y) —$OCONR^5R^5$,
    (z) —$C(=O)R^8$,
    (aa) —COOH,
    (ab) $C_{1-6}$-alkoxycarbonyl, and
    (ac) —$OR^{11}$.

21. A compound according to claim 1, or a pharmaceutically acceptable salt thereof, wherein $R^0$ is halogen.

22. A compound according to claim 21, or a pharmaceutically acceptable salt thereof, wherein m is 1 or 2.

23. A compound according to claim 2, or a pharmaceutically acceptable salt thereof, wherein $R^2$ is hydroxy.

24. A compound according to claim 2, or a pharmaceutically acceptable salt thereof, wherein $R^2$ is $C_{1-6}$-alkoxy.

25. A compound according to claim 1, or a pharmaceutically acceptable salt thereof, wherein each $R^{10}$ is ethyl.

26. A method according to claim 17 wherein the palladium catalyst in step bb) is bis(triphenylphosphine)palladium(II) diacetate and the reducing agent in step dd) is $NaBH_4$, $NaBH_3CN$ or sodium triacetoxyborohydride.

27. A method according to claim 18 wherein the reducing agent in step aaa) is $NaBH_3CN$ in trifluoroacetic acid (TFA), the palladium complex in step bbb) is bis(triphenylphosphine)palladium(II) diacetate, and the reducing agent in step ddd) is $NaBH_4$, $NaBH_3CN$ or sodium triacetoxyborohydride.

* * * * *

UNITED STATES PATENT AND TRADEMARK OFFICE
CERTIFICATE OF CORRECTION

PATENT NO. : 7,812,017 B2  
APPLICATION NO. : 11/824939  
DATED : October 12, 2010  
INVENTOR(S) : Johan Angbrant et al.

Page 1 of 2

It is certified that error appears in the above-identified patent and that said Letters Patent is hereby corrected as shown below:

Title page, Col. 2, (Other Publications), Line 7, delete "Sep. 23, 2009]." and insert -- Sep. 23, 2003]. --.

In the Claims:

Col. 167, Line 55, Claim 2, delete "—$CONR^5R^5$," and insert -- —$CONR^5R^5$, --.

Col. 169, Line 51, Claim 4, after "—$NHSO_2R^8$" insert -- , --.

Col. 171, Line 62, Claim 5, after "—$CH_2CN$," insert -- and --.

Col. 173, Line 17, Claim 9, after "wherein" insert -- : --.

Col. 173, Line 49, Claim 10, after "claim 1," delete "wherein".

Col. 174, Line 49, Claim 11, delete "4-yl }" and insert -- 4-yl} --.

Col. 174, Line 51, Claim 11, delete "1 H-indole," and insert -- 1H-indole, --.

Col. 175, Line 15, Claim 11, delete "4-(piperazin" and insert -- 4-(Piperazin --.

Col. 175, Line 25, Claim 11, delete "4-(piperazin" and insert -- 4-(Piperazin --.

Col. 175, Line 42, Claim 11, below "1H-indole," delete "N,N-Dimethyl-1-[1-(phenylsulfonyl)-1H-indol-4-yl]methanamine,".

Col. 179, Line 64, Claim 13, after "claim 1" insert -- , --.

Col. 179, Line 66, Claim 14, delete "inhibititing" and insert -- inhibiting --.

Signed and Sealed this  
Twenty-eighth Day of May, 2013

Teresa Stanek Rea  
*Acting Director of the United States Patent and Trademark Office*

CERTIFICATE OF CORRECTION (continued)
U.S. Pat. No. 7,812,017 B2

Col. 180, Line 1, Claim 14, after "claim 1" insert -- , --.

Col. 180, Line 4, Claim 15, after "claim 1" insert -- , --.

Col. 180, Line 5, Claim 15, after "thereof" insert -- , --.

Col. 182, Line 43-51, Claim 18, delete " 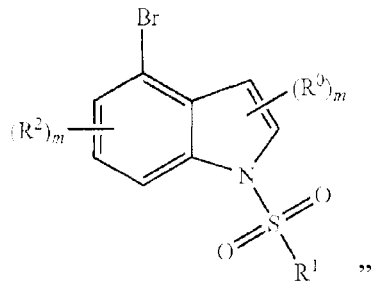 "

and insert -- 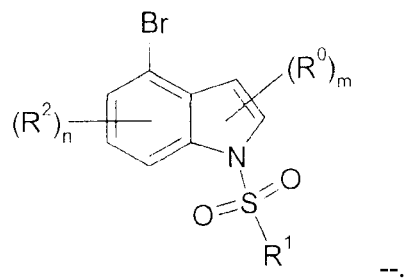 --.

Col. 184, Line 1, Claim 18, after "$R^7$," insert -- $R^9$, --.